US010973872B2

(12) United States Patent
Kelly

(10) Patent No.: US 10,973,872 B2
(45) Date of Patent: Apr. 13, 2021

(54) PIRIN POLYPEPTIDE AND IMMUNE MODULATION

(71) Applicant: 4D PHARMA RESEARCH LIMITED, Aberdeen (GB)

(72) Inventor: Denise Kelly, Aberdeen (GB)

(73) Assignee: 4D PHARMA RESEARCH LIMITED, Aberdeen (GB)

( * ) Notice: Subject to any disclaimer, the term of this patent is extended or adjusted under 35 U.S.C. 154(b) by 0 days.

(21) Appl. No.: 16/560,381

(22) Filed: Sep. 4, 2019

(65) Prior Publication Data

US 2020/0164027 A1 May 28, 2020

Related U.S. Application Data

(60) Division of application No. 15/631,952, filed on Jun. 23, 2017, now Pat. No. 10,456,444, which is a continuation of application No. PCT/GB2015/054113, filed on Dec. 22, 2015.

(30) Foreign Application Priority Data

Dec. 23, 2014 (GB) ..................................... 1423083

(51) Int. Cl.
| A61K 39/02 | (2006.01) |
| A61K 35/741 | (2015.01) |
| A61K 35/00 | (2006.01) |
| A61K 38/16 | (2006.01) |
| A23L 33/135 | (2016.01) |
| A23L 33/17 | (2016.01) |
| A23L 33/18 | (2016.01) |

(52) U.S. Cl.
CPC .......... *A61K 38/164* (2013.01); *A23L 33/135* (2016.08); *A23L 33/17* (2016.08); *A23L 33/18* (2016.08); *A61K 35/741* (2013.01); *A61K 39/0216* (2013.01); *A23V 2002/00* (2013.01); *A61K 2035/115* (2013.01)

(58) Field of Classification Search
None
See application file for complete search history.

(56) References Cited

U.S. PATENT DOCUMENTS

| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio et al. |
| 4,366,241 A | 12/1982 | Tom et al. |
| 4,683,202 A | 7/1987 | Mullis |
| 4,816,567 A | 3/1989 | Cabilly et al. |
| 5,589,168 A | 12/1996 | Allen et al. |
| 5,599,795 A | 2/1997 | McCann et al. |
| 5,674,707 A | 10/1997 | Hintz et al. |
| 5,741,665 A | 4/1998 | Kato et al. |
| 5,925,657 A | 7/1999 | Seed et al. |
| 5,951,977 A | 9/1999 | Nisbet et al. |
| 6,348,452 B1 | 2/2002 | Brown et al. |
| 6,468,964 B1 | 10/2002 | Rowe et al. |
| 6,645,530 B1 | 11/2003 | Borody |
| 7,101,565 B2 | 9/2006 | Monte |
| 7,485,325 B2 | 2/2009 | Swain |
| 7,625,704 B2 | 12/2009 | Fredricks et al. |
| 7,749,494 B2 | 7/2010 | Renaud et al. |
| 7,998,474 B2 | 8/2011 | Kelly |
| 8,197,805 B2 | 6/2012 | Lin et al. |
| 8,287,932 B2 | 10/2012 | Rosales et al. |
| 8,460,648 B2 | 6/2013 | Borody |
| 8,557,233 B2 | 10/2013 | MacSharry et al. |
| 9,011,834 B1 | 4/2015 | McKenzie et al. |
| 9,314,489 B2 | 4/2016 | Kelly et al. |
| 9,371,510 B2 | 6/2016 | Moore |

(Continued)

FOREIGN PATENT DOCUMENTS

| CA | 2768301 A1 | 1/2011 |
| CN | 1863540 A | 11/2006 |

(Continued)

OTHER PUBLICATIONS

"Amedei, A. et al. Multiple sclerosis: the role of cytokines in pathogenesis and in therapies. Int J Mol Sci. Oct. 19, 2012;13(10):13438-60. doi: 10.3390/ijms131013438."

(Continued)

*Primary Examiner* — Sarvamangala Devi

(74) *Attorney, Agent, or Firm* — Wilson Sonsini Goodrich & Rosati

(57) ABSTRACT

The present invention relates to polypeptide HP, or a polynucleotide sequence encoding polypeptide HP, or a host cell comprising said polynucleotide sequence, or a host cell comprising an expression vector comprising said polynucleotide sequence, for use in the treatment and/or prevention of a disorder in a subject; wherein said disorder is an inflammatory disorder and/or an autoimmune disorder; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

19 Claims, 13 Drawing Sheets

Specification includes a Sequence Listing.

(56) References Cited

U.S. PATENT DOCUMENTS

| | | | |
|---|---|---|---|
| 9,376,473 B2 | 6/2016 | Gleiberman et al. |
| 9,539,293 B2 | 1/2017 | Kelly et al. |
| 9,610,307 B2 | 4/2017 | Berry et al. |
| 9,662,381 B2 | 5/2017 | Honda et al. |
| 9,796,762 B2 | 10/2017 | Kelly et al. |
| 9,808,519 B2 | 11/2017 | Honda et al. |
| 9,839,655 B2 | 12/2017 | Mulder et al. |
| 9,855,302 B2 | 1/2018 | Gajewski et al. |
| 9,937,211 B2 | 4/2018 | Kelly et al. |
| 9,974,815 B2 | 5/2018 | Mulder et al. |
| 9,987,311 B2 | 6/2018 | Mulder et al. |
| 10,046,015 B2 | 8/2018 | Mulder et al. |
| 10,058,574 B2 | 8/2018 | Grant et al. |
| 10,080,772 B2 | 9/2018 | Crouzet et al. |
| 10,086,020 B2 | 10/2018 | Bernalier-Donadille et al. |
| 10,086,021 B2 | 10/2018 | Jeffery et al. |
| 10,086,022 B2 | 10/2018 | Bernalier-Donadille et al. |
| 10,086,023 B2 | 10/2018 | Bernalier-Donadille et al. |
| 10,183,046 B2 | 1/2019 | Kelly |
| 10,226,489 B2 | 3/2019 | Patterson et al. |
| 2003/0147858 A1 | 8/2003 | Renaud et al. |
| 2004/0005304 A1 | 1/2004 | Brudnak |
| 2004/0106564 A1 | 6/2004 | Nilius et al. |
| 2006/0062774 A1 | 3/2006 | Davis et al. |
| 2006/0073161 A1 | 4/2006 | Breton |
| 2006/0115465 A1 | 6/2006 | MacFarlane et al. |
| 2007/0167423 A1 | 7/2007 | Bergauer et al. |
| 2007/0258953 A1 | 11/2007 | Duncan et al. |
| 2007/0286913 A1 | 12/2007 | Swain et al. |
| 2008/0069861 A1 | 3/2008 | Brown et al. |
| 2008/0206212 A1 | 8/2008 | McMahon et al. |
| 2008/0260906 A1 | 10/2008 | Stojanovic |
| 2008/0299098 A1 | 12/2008 | Se et al. |
| 2009/0217401 A1 | 8/2009 | Korman et al. |
| 2010/0028449 A1 | 2/2010 | Prakash et al. |
| 2010/0047209 A1 | 2/2010 | Stanton et al. |
| 2010/0247489 A1 | 9/2010 | Saur-Brosch |
| 2010/0284973 A1 | 11/2010 | Schiffer-Mannioui et al. |
| 2010/0303782 A1 | 12/2010 | Cobb et al. |
| 2010/0311686 A1 | 12/2010 | Kasper et al. |
| 2010/0316617 A1 | 12/2010 | Renaud et al. |
| 2011/0053829 A1 | 3/2011 | Baumhof et al. |
| 2011/0086011 A1 | 4/2011 | Kasper et al. |
| 2011/0280840 A1 | 11/2011 | Blaser et al. |
| 2012/0020943 A1 | 1/2012 | Lin |
| 2012/0107279 A1 | 5/2012 | Arigoni et al. |
| 2013/0022575 A1 | 1/2013 | Cassity |
| 2013/0130988 A1 | 5/2013 | Blareau et al. |
| 2013/0195802 A1 | 8/2013 | Moore |
| 2013/0280724 A1 | 10/2013 | Ramadan et al. |
| 2013/0316032 A1 | 11/2013 | Itoh et al. |
| 2013/0336931 A1 | 12/2013 | Wadstroem et al. |
| 2014/0037716 A1 | 2/2014 | Nowill et al. |
| 2014/0056852 A1 | 2/2014 | Guglielmetti et al. |
| 2014/0112897 A1 | 4/2014 | Pyne et al. |
| 2014/0147425 A1 | 5/2014 | Henn et al. |
| 2014/0154218 A1 | 6/2014 | Kohno et al. |
| 2014/0179770 A1 | 6/2014 | Zhang et al. |
| 2014/0193464 A1 | 7/2014 | Lin et al. |
| 2014/0199281 A1 | 7/2014 | Henn et al. |
| 2014/0227227 A1 | 8/2014 | Qin et al. |
| 2014/0328803 A1 | 11/2014 | McKenzie et al. |
| 2014/0335131 A1 | 11/2014 | Mazmanian et al. |
| 2014/0341921 A1 | 11/2014 | Honda et al. |
| 2014/0363397 A1 | 12/2014 | Allen-Vercoe et al. |
| 2015/0044173 A1 | 2/2015 | Jones et al. |
| 2015/0071957 A1 | 3/2015 | Kelly et al. |
| 2015/0104418 A1 | 4/2015 | Flint et al. |
| 2015/0132264 A1 | 5/2015 | Kelly et al. |
| 2015/0284781 A1 | 10/2015 | Klumpp et al. |
| 2016/0058804 A1 | 3/2016 | Jones et al. |
| 2016/0067188 A1 | 3/2016 | Cade et al. |
| 2016/0184370 A1 | 6/2016 | McKenzie et al. |
| 2016/0199424 A1 | 7/2016 | Berry et al. |
| 2016/0223553 A1 | 8/2016 | Sears et al. |
| 2017/0143772 A1 | 5/2017 | Mulder et al. |
| 2017/0143773 A1 | 5/2017 | Mulder et al. |
| 2017/0143774 A1 | 5/2017 | Mulder et al. |
| 2017/0143775 A1 | 5/2017 | Mulder et al. |
| 2017/0319634 A1 | 11/2017 | Grant et al. |
| 2017/0354695 A1 | 12/2017 | Grant et al. |
| 2017/0360856 A1 | 12/2017 | Grant et al. |
| 2017/0368110 A1 | 12/2017 | Grant et al. |
| 2018/0072778 A1 | 3/2018 | Kelly et al. |
| 2018/0078585 A1 | 3/2018 | Mulder et al. |
| 2018/0078587 A1 | 3/2018 | Crott et al. |
| 2018/0133265 A1 | 5/2018 | Stevenson |
| 2018/0207207 A1 | 7/2018 | Bernalier-Donadille et al. |
| 2018/0207208 A1 | 7/2018 | Jeffery et al. |
| 2018/0214496 A1 | 8/2018 | Bernalier-Donadille |
| 2018/0221421 A1 | 8/2018 | Bernalier-Donadille |
| 2018/0250346 A1 | 9/2018 | Mulder et al. |
| 2018/0271918 A1 | 9/2018 | Kelly et al. |
| 2018/0344780 A1 | 12/2018 | Grant et al. |
| 2018/0369292 A1 | 12/2018 | Bernalier-Donadille et al. |
| 2018/0369293 A1 | 12/2018 | Jeffery et al. |
| 2018/0369294 A1 | 12/2018 | Bernalier-Donadille et al. |
| 2019/0000892 A1 | 1/2019 | Mulder et al. |
| 2019/0008908 A1 | 1/2019 | Crouzet et al. |
| 2019/0015459 A1 | 1/2019 | Grant et al. |
| 2019/0099458 A1 | 4/2019 | Grant et al. |

FOREIGN PATENT DOCUMENTS

| | | |
|---|---|---|
| CN | 1917946 A | 2/2007 |
| CN | 1954066 A | 4/2007 |
| CN | 101590081 A | 12/2009 |
| CN | 102304483 A | 1/2012 |
| CN | 102031235 B | 7/2012 |
| CN | 102093967 B | 1/2013 |
| CN | 102905558 A | 1/2013 |
| CN | 102940652 A | 2/2013 |
| CN | 102373172 B | 3/2013 |
| CN | 103037876 A | 4/2013 |
| CN | 103142656 A | 6/2013 |
| CN | 103146620 A | 6/2013 |
| CN | 103156888 A | 6/2013 |
| CN | 103652322 A | 3/2014 |
| CN | 103781487 A | 5/2014 |
| CN | 103820363 A | 5/2014 |
| CN | 103849590 A | 6/2014 |
| CN | 103865846 A | 6/2014 |
| CN | 103930117 A | 7/2014 |
| CN | 103981115 A | 8/2014 |
| CN | 103981117 A | 8/2014 |
| CN | 104160014 A | 11/2014 |
| CN | 104195075 A | 12/2014 |
| CN | 103509741 B | 2/2015 |
| CN | 102940652 B | 3/2015 |
| CN | 104435000 A | 3/2015 |
| CN | 103037876 B | 4/2015 |
| CN | 104546932 A | 4/2015 |
| CN | 104546933 A | 4/2015 |
| CN | 104546934 A | 4/2015 |
| CN | 104546935 A | 4/2015 |
| CN | 104546940 A | 4/2015 |
| CN | 104546942 A | 4/2015 |
| CN | 104560820 A | 4/2015 |
| CN | 105112333 A | 12/2015 |
| CN | 103820363 B | 2/2016 |
| CN | 103865846 B | 3/2016 |
| CN | 105982919 A | 10/2016 |
| DE | 19826928 A1 | 12/1999 |
| DE | 10206995 A1 | 9/2003 |
| EP | 0120516 A2 | 10/1984 |
| EP | 0238023 A2 | 9/1987 |
| EP | 0433299 A1 | 6/1991 |
| EP | 0449375 A2 | 10/1991 |
| EP | 0581171 A1 | 2/1994 |
| EP | 0778778 A1 | 6/1997 |
| EP | 0888118 A1 | 1/1999 |
| EP | 1141235 A2 | 10/2001 |
| EP | 1227152 A1 | 7/2002 |
| EP | 1383514 A1 | 1/2004 |

(56) References Cited

FOREIGN PATENT DOCUMENTS

| | | |
|---|---|---|
| EP | 1448995 A1 | 8/2004 |
| EP | 1481681 A1 | 12/2004 |
| EP | 1765391 A1 | 3/2007 |
| EP | 1675481 B1 | 11/2008 |
| EP | 1997499 A1 | 12/2008 |
| EP | 1997905 A1 | 12/2008 |
| EP | 1997906 A1 | 12/2008 |
| EP | 1997907 A1 | 12/2008 |
| EP | 2044436 A2 | 4/2009 |
| EP | 2103226 A1 | 9/2009 |
| EP | 2133088 A3 | 1/2010 |
| EP | 1280541 B2 | 3/2010 |
| EP | 2236598 A1 | 10/2010 |
| EP | 2286832 A1 | 2/2011 |
| EP | 2308498 A1 | 4/2011 |
| EP | 2217253 B1 | 6/2011 |
| EP | 1940243 B1 | 8/2011 |
| EP | 2359838 A1 | 8/2011 |
| EP | 1855550 B1 | 10/2011 |
| EP | 1871400 B1 | 10/2011 |
| EP | 2124972 B1 | 6/2012 |
| EP | 1773361 B2 | 9/2012 |
| EP | 1945234 B1 | 12/2012 |
| EP | 2323493 B8 | 12/2012 |
| EP | 2323494 B8 | 12/2012 |
| EP | 1629850 B2 | 5/2013 |
| EP | 2203551 B1 | 8/2013 |
| EP | 2140771 B1 | 12/2013 |
| EP | 2687227 A1 | 1/2014 |
| EP | 2179028 B1 | 8/2014 |
| EP | 2650002 A4 | 8/2014 |
| EP | 2164349 B1 | 9/2014 |
| EP | 2134835 B1 | 10/2014 |
| EP | 2810652 A2 | 12/2014 |
| EP | 2305838 B1 | 1/2015 |
| EP | 2832859 A1 | 2/2015 |
| ES | 2408279 A2 | 6/2013 |
| JP | H08259450 A | 10/1996 |
| JP | 2003261453 A | 9/2003 |
| JP | 2005097280 A | 4/2005 |
| JP | 2006265212 A | 10/2006 |
| JP | 2007084533 A | 4/2007 |
| JP | 2007116991 A | 5/2007 |
| JP | 2008195635 A | 8/2008 |
| JP | 2009507023 A | 2/2009 |
| JP | 2010246523 A | 11/2010 |
| JP | 5031249 B2 | 9/2012 |
| JP | 2013005759 A | 1/2013 |
| JP | 5183848 B2 | 4/2013 |
| JP | 2013527240 A | 6/2013 |
| JP | 2013201912 A | 10/2013 |
| JP | 2014196260 A | 10/2014 |
| JP | 2014534957 A | 12/2014 |
| JP | 2015500792 A | 1/2015 |
| JP | 5710876 B2 | 4/2015 |
| JP | 5792105 B2 | 10/2015 |
| KR | 100468522 B1 | 1/2005 |
| KR | 20100128168 A | 12/2010 |
| KR | 1020100128168 | 12/2010 |
| KR | 101017448 B1 | 2/2011 |
| KR | 101057357 B1 | 8/2011 |
| KR | 20130021764 A | 3/2013 |
| KR | 101250463 B1 | 4/2013 |
| KR | 20140037544 A | 3/2014 |
| KR | 20140061328 A | 5/2014 |
| PL | 229020 B1 | 5/2018 |
| RU | 2078815 C1 | 5/1997 |
| TW | I417054 B | 12/2013 |
| WO | WO-8807865 A1 | 10/1988 |
| WO | WO-9117243 A1 | 11/1991 |
| WO | WO-9611014 A1 | 4/1996 |
| WO | WO-9720577 A1 | 6/1997 |
| WO | WO-9730717 A1 | 8/1997 |
| WO | WO-9735956 A1 | 10/1997 |
| WO | WO-9843081 A1 | 10/1998 |
| WO | WO-9855131 A1 | 12/1998 |
| WO | WO-9857631 A1 | 12/1998 |
| WO | WO-9919459 A1 | 4/1999 |
| WO | WO-9942568 A1 | 8/1999 |
| WO | WO-9945955 A1 | 9/1999 |
| WO | WO-0116120 A1 | 3/2001 |
| WO | WO-0158275 A2 | 8/2001 |
| WO | WO-0185187 A1 | 11/2001 |
| WO | WO-0193904 A1 | 12/2001 |
| WO | WO-0207741 A1 | 1/2002 |
| WO | WO-0242328 A2 | 5/2002 |
| WO | WO-02070670 A1 | 9/2002 |
| WO | WO-02085933 A1 | 10/2002 |
| WO | WO-02094296 A1 | 11/2002 |
| WO | WO-03010297 A1 | 2/2003 |
| WO | WO-03022255 A2 | 3/2003 |
| WO | WO-03045317 A2 | 6/2003 |
| WO | WO-03046580 A1 | 6/2003 |
| WO | WO-03053220 A2 | 7/2003 |
| WO | WO-2004003235 A3 | 6/2004 |
| WO | WO-2004085628 A1 | 10/2004 |
| WO | WO-2005007834 A1 | 1/2005 |
| WO | WO-2005030133 A2 | 4/2005 |
| WO | WO-2005032567 A2 | 4/2005 |
| WO | WO-2005058335 A1 | 6/2005 |
| WO | WO-2005032567 A3 | 7/2005 |
| WO | WO-2005093049 A1 | 10/2005 |
| WO | WO-2005107381 A2 | 11/2005 |
| WO | WO-2005121130 A2 | 12/2005 |
| WO | WO-2006012586 A2 | 2/2006 |
| WO | WO-2006033949 A1 | 3/2006 |
| WO | WO-2006033950 A1 | 3/2006 |
| WO | WO-2006033951 A1 | 3/2006 |
| WO | WO-2006102350 A1 | 9/2006 |
| WO | WO-2006102536 A2 | 9/2006 |
| WO | WO-2006091103 A3 | 10/2006 |
| WO | WO-2006110406 A2 | 10/2006 |
| WO | WO-2006130205 A1 | 12/2006 |
| WO | WO-2007027761 A2 | 3/2007 |
| WO | WO-2007056218 A2 | 5/2007 |
| WO | WO-2007064732 A1 | 6/2007 |
| WO | WO-2007064749 A1 | 6/2007 |
| WO | WO-2007098371 A2 | 8/2007 |
| WO | WO-2007136719 A2 | 11/2007 |
| WO | WO-2007140230 A3 | 2/2008 |
| WO | WO-2008031438 A3 | 5/2008 |
| WO | WO-2008055702 A1 | 5/2008 |
| WO | WO-2008055703 A2 | 5/2008 |
| WO | WO-2008064489 A1 | 6/2008 |
| WO | WO-2008073148 A2 | 6/2008 |
| WO | WO-2008076696 A2 | 6/2008 |
| WO | WO-2008053444 A3 | 7/2008 |
| WO | WO-2008083157 A2 | 7/2008 |
| WO | WO-2008134450 A2 | 11/2008 |
| WO | WO-2008153377 A1 | 12/2008 |
| WO | WO-2009027753 A1 | 3/2009 |
| WO | WO-2009030481 A1 | 3/2009 |
| WO | WO-2009055362 A1 | 4/2009 |
| WO | WO-2009059284 A2 | 5/2009 |
| WO | WO-2009072889 A1 | 6/2009 |
| WO | WO-2009079564 A2 | 6/2009 |
| WO | WO-2009043856 A3 | 7/2009 |
| WO | WO-2009080862 A1 | 7/2009 |
| WO | WO-2009100331 A2 | 8/2009 |
| WO | WO-2009116864 A1 | 9/2009 |
| WO | WO-2009128949 A2 | 10/2009 |
| WO | WO-2009138220 A1 | 11/2009 |
| WO | WO-2009149149 A1 | 12/2009 |
| WO | WO-2009151315 A1 | 12/2009 |
| WO | WO-2009154463 A2 | 12/2009 |
| WO | WO-2009156301 A1 | 12/2009 |
| WO | WO-2010002241 A1 | 1/2010 |
| WO | WO-2010036876 A2 | 4/2010 |
| WO | WO-2010037402 A1 | 4/2010 |
| WO | WO-2010037408 A1 | 4/2010 |
| WO | WO-2010037539 A1 | 4/2010 |
| WO | WO-2010048481 A1 | 4/2010 |
| WO | WO-2010063601 A1 | 6/2010 |
| WO | WO-2010081126 A3 | 9/2010 |

(56) References Cited

FOREIGN PATENT DOCUMENTS

| | | |
|---|---|---|
| WO | WO-2010129839 A1 | 11/2010 |
| WO | WO-2010130659 A1 | 11/2010 |
| WO | WO-2010130660 A1 | 11/2010 |
| WO | WO-2010130662 A1 | 11/2010 |
| WO | WO-2010130663 A1 | 11/2010 |
| WO | WO-2010130697 A1 | 11/2010 |
| WO | WO-2010130699 A1 | 11/2010 |
| WO | WO-2010130700 A1 | 11/2010 |
| WO | WO-2010130701 A1 | 11/2010 |
| WO | WO-2010130702 A1 | 11/2010 |
| WO | WO-2010130704 A1 | 11/2010 |
| WO | WO-2010130710 A1 | 11/2010 |
| WO | WO-2010130713 A1 | 11/2010 |
| WO | WO-2010/143940 A1 | 12/2010 |
| WO | WO-2010139531 A1 | 12/2010 |
| WO | WO-2010142504 A1 | 12/2010 |
| WO | WO-2010143961 A1 | 12/2010 |
| WO | WO-2010147714 A1 | 12/2010 |
| WO | WO-2010133475 A3 | 1/2011 |
| WO | WO-2011000620 A1 | 1/2011 |
| WO | WO-2011000621 A1 | 1/2011 |
| WO | WO-2011005756 A1 | 1/2011 |
| WO | WO-2010133472 A3 | 2/2011 |
| WO | WO-2011020748 A1 | 2/2011 |
| WO | WO-2011036539 A1 | 3/2011 |
| WO | WO-2011043654 A1 | 4/2011 |
| WO | WO-2011044208 A1 | 4/2011 |
| WO | WO-2011058535 A1 | 5/2011 |
| WO | WO-2011075138 A1 | 6/2011 |
| WO | WO-2011096808 A1 | 8/2011 |
| WO | WO-2011096809 A1 | 8/2011 |
| WO | WO-2011110918 A1 | 9/2011 |
| WO | WO-2011121379 A1 | 10/2011 |
| WO | WO-2011149335 A1 | 12/2011 |
| WO | WO-2011152566 A2 | 12/2011 |
| WO | WO-2011153226 A2 | 12/2011 |
| WO | WO-2011157816 A1 | 12/2011 |
| WO | WO-2012012874 A1 | 2/2012 |
| WO | WO-2012016287 A2 | 2/2012 |
| WO | WO-2012024638 A2 | 2/2012 |
| WO | WO-2011153226 A3 | 3/2012 |
| WO | WO-2012055408 A1 | 5/2012 |
| WO | WO-2012062780 A1 | 5/2012 |
| WO | WO-2012071380 A1 | 5/2012 |
| WO | WO-2012076739 A1 | 6/2012 |
| WO | WO-2012105312 A1 | 8/2012 |
| WO | WO-2012122478 A1 | 9/2012 |
| WO | WO-2012140636 A1 | 10/2012 |
| WO | WO-2012142605 A1 | 10/2012 |
| WO | WO-2012145491 A2 | 10/2012 |
| WO | WO-2012158517 A1 | 11/2012 |
| WO | WO-2012165843 A2 | 12/2012 |
| WO | WO-2012170478 A2 | 12/2012 |
| WO | WO-2013005836 A1 | 1/2013 |
| WO | WO-2013008039 A2 | 1/2013 |
| WO | WO-2013008102 A2 | 1/2013 |
| WO | WO-2013037068 A1 | 3/2013 |
| WO | WO-2013050792 A1 | 4/2013 |
| WO | WO-2013053836 A1 | 4/2013 |
| WO | WO-2013063849 A1 | 5/2013 |
| WO | WO-2013080561 A1 | 6/2013 |
| WO | WO-2013124725 A1 | 8/2013 |
| WO | WO-2013144701 A1 | 10/2013 |
| WO | WO-2013153358 A1 | 10/2013 |
| WO | WO-2013154725 A1 | 10/2013 |
| WO | WO-2013171515 A1 | 11/2013 |
| WO | WO-2013175038 A1 | 11/2013 |
| WO | WO-2013181694 A1 | 12/2013 |
| WO | WO-2013182038 A1 | 12/2013 |
| WO | WO-2014001368 A1 | 1/2014 |
| WO | WO-2014019271 A1 | 2/2014 |
| WO | WO-2014020004 A1 | 2/2014 |
| WO | WO-2014032108 A1 | 3/2014 |
| WO | WO-2014036182 A2 | 3/2014 |
| WO | WO-2014043593 A2 | 3/2014 |
| WO | WO-2014053608 A1 | 4/2014 |
| WO | WO-2014064359 A1 | 5/2014 |
| WO | WO-2014067976 A1 | 5/2014 |
| WO | WO-2014070014 A1 | 5/2014 |
| WO | WO-2014070225 A1 | 5/2014 |
| WO | WO-2014075745 A1 | 5/2014 |
| WO | WO-2014078911 A1 | 5/2014 |
| WO | WO-2014082050 A1 | 5/2014 |
| WO | WO-2014093622 A2 | 6/2014 |
| WO | WO-2014093635 A1 | 6/2014 |
| WO | WO-2014093655 A2 | 6/2014 |
| WO | WO-2014121298 A2 | 8/2014 |
| WO | WO-2014121301 A1 | 8/2014 |
| WO | WO-2014121302 A2 | 8/2014 |
| WO | WO-2014121304 A1 | 8/2014 |
| WO | WO-2014130540 A1 | 8/2014 |
| WO | WO-2014137211 A1 | 9/2014 |
| WO | WO-2014145958 A2 | 9/2014 |
| WO | WO-2014150094 A1 | 9/2014 |
| WO | WO-2014152338 A1 | 9/2014 |
| WO | WO-2014153194 A2 | 9/2014 |
| WO | WO-2014121302 A3 | 10/2014 |
| WO | WO-2014167338 A1 | 10/2014 |
| WO | WO-2014182966 A1 | 11/2014 |
| WO | WO-2014200334 A1 | 12/2014 |
| WO | WO-2014201037 A2 | 12/2014 |
| WO | WO-2015003001 A1 | 1/2015 |
| WO | WO-2015006355 A2 | 1/2015 |
| WO | WO-2015013214 A2 | 1/2015 |
| WO | WO-2015017625 A1 | 2/2015 |
| WO | WO-2015021936 A1 | 2/2015 |
| WO | WO-201503305 A1 | 3/2015 |
| WO | WO-2015038731 A1 | 3/2015 |
| WO | WO-2015057151 A1 | 4/2015 |
| WO | WO-2015077794 A1 | 5/2015 |
| WO | WO-2015095241 A2 | 6/2015 |
| WO | WO-2015077794 A4 | 7/2015 |
| WO | WO-2015156419 A1 | 10/2015 |
| WO | WO-2015156519 A1 | 10/2015 |
| WO | WO-2015168534 A1 | 11/2015 |
| WO | WO-2015169944 A1 | 11/2015 |
| WO | WO-2015095241 A4 | 12/2015 |
| WO | WO-2016019506 A1 | 2/2016 |
| WO | WO-2016033439 A2 | 3/2016 |
| WO | WO-2016036615 A1 | 3/2016 |
| WO | WO-2016057671 A1 | 4/2016 |
| WO | WO-2016065324 A1 | 4/2016 |
| WO | WO-2016069795 A2 | 5/2016 |
| WO | WO-2016069801 A1 | 5/2016 |
| WO | WO-2016070151 A1 | 5/2016 |
| WO | WO-2016086161 A1 | 6/2016 |
| WO | WO-2016086205 A2 | 6/2016 |
| WO | WO-2016086206 A1 | 6/2016 |
| WO | WO-2016086208 A1 | 6/2016 |
| WO | WO-2016086209 A1 | 6/2016 |
| WO | WO-2016086210 A1 | 6/2016 |
| WO | WO-2016102950 A1 | 6/2016 |
| WO | WO-2016102951 A1 | 6/2016 |
| WO | WO-2016118730 A1 | 7/2016 |
| WO | WO-2016139217 A1 | 9/2016 |
| WO | WO-2016149449 A1 | 9/2016 |
| WO | WO-2016149687 A1 | 9/2016 |
| WO | WO-2016203218 A1 | 12/2016 |
| WO | WO-2016203220 A1 | 12/2016 |
| WO | WO-2017085520 A1 | 5/2017 |
| WO | WO-2017091753 A1 | 6/2017 |
| WO | WO-2017148596 A1 | 9/2017 |
| WO | WO-2018011594 A1 | 1/2018 |
| WO | WO-2018/112365 A2 | 6/2018 |
| WO | WO-2018112363 | 6/2018 |
| WO | WO-2018112363 A1 | 6/2018 |
| WO | WO-2018112365 A2 | 6/2018 |
| WO | WO-2018215782 A1 | 11/2018 |

OTHER PUBLICATIONS

"Campeau, J.L. et al., Intestinal Epithelial Cells Modulate Antigen-Presenting Cell Responses to Bacterial DNA. Infectionand Immunity. Aug. 2012; 80(8): 2632-2644."

(56) References Cited

OTHER PUBLICATIONS

Jan. 17, 2019 First Office Action for CN201680041407.6 (Translated).
Jan. 17, 2019 Notice of Allowance for U.S. Appl. No. 15/803,721.
Jan. 30, 2019 Notice of Corrected Allowability for U.S. Appl. No. 15/803,721.
Jan. 30, 2019 Final Rejection for U.S. Appl. No. 15/842,635.
Dec. 21, 2018 Notice of Allowance U.S. Appl. No. 15/700,700.
Feb. 1, 2019 Non-Final Office Action U.S. Appl. No. 16/040,356.
Mar. 4, 2019 Final Office Action for U.S. Appl. No. 15/704,245.
4d Pharma Plc: "Clinical Update—RNS—London Stock Exchange", Jul. 19, 2016.
4D Pharma:"4Dpharma PLC clinical update on blautix (TM), a novel treatment to irritable bowel syndrome," 4DPharma, Jan. 19, 2016, XP002769874, Retrieved from: https://www.directorstalkinterviews.com/4d-pharma-plc-clinical-update-on-blautix-a-novel-treatment-for-irritable-bowel-syndrome/412689588. [Retrieved on May 5, 2017].
Ahanchian, Hamic, A multi-strain synbiotic may reduce viral respiratory infections in asthmatic children: a randomized controlled trial; Sep. 2016, vol. 8, Issue 9, pp. 2833-2839, DOI: http://dxdoi.or/10.19082/2833.
Alp, G., and Aslim, B. (2010). Relationship between the resistance to bile salts and low pH with exopolysaccharide (EPS) production of *Bifidobacterium* spp. isolated from infants feces and breast milk. Anaerobe 16(2), 101-105. doi: 10.1016/j.anaerobe.2009.06.006.
Altschul et al. 'Basic local alignment search tool.' Journal of Molecular Biology. 1990, vol. 215, No. 3, pp. 403-410.
Álvarez-Martín, P., O'Connell-Motherway, M., van Sinderen, D., and Mayo, B. (2007). Functional analysis of the pBC1 replicon from Bifidobacterium catenulatum L48. Applied Microbiology and Biotechnology 76(6), 1395. doi: 10.1007/s00253-007-1115-5.
Aminov et al. Molecular diversity, cultivation, and improved detection by fluorescent in situ hybridization of a dominant group of human gut bacteria related to *Roseburia* spp. or *Eubacterium rectale*. Applied and environmental microbiology. 2006, vol. 72, No. 9, pp. 6371-6376.
An et al. (1985) "New cloning vehicles for transformation of higher plants," EMBO J. 4:277-284.
An et al. (1988) "Binary Vectors," Plant Molecular Biology Manual. A3:1-19.
An et al. Transformation of Tobacco, Tomato, Potato, and *Arabiodopsis thaliana* Using a Binary Ti Vector System,Plant Physiol. May 1986; 81:301-305.
Anonymous: "4D pharma's Blautix for Irritable Bowel Syndrome shows positive impact—pharmaceutical daily news", Dec. 13, 2016.
Appleyard, Caroline B. et al., Pretreatment with the probiotic VSL#3 delays transition from inflammation to dysplasia in rate model of colitis-associated cancer; Am J. Physiol. Gastrointest. Liver Physiol. 301:G1004-G1013, 2011, Sep. 8, 2011:DOI:10.1152. ajpg.00167.2011.
Archer et al. (1997) "The Molecular Biology of Secreted Enzyme Production by Fungi," Critical Reviews Biotechnology. 17(4):273-306.
Arenberg, et al., Interferon-y-inducible Protein 10 (IP-10) Is an Angiostatic Factor That Inhibits Human Non-small Cell Lung Cancer (NSCLC) Tumorigenesis and Spontaneous Metastases. 1996. J. Exp.Med. 184:981-92.
Atarashi et al. Induction of colonic regulatory T cells by indigenous *Clostridium* species. Science 331(6015):337-341 (2011).
Atarashi et al., Th17 Cell Induction by Adhesion of Microbes to Intestinal Epithelial Cells. Cell, vol. 163, No. 2, Oct. 8, 2015. pp. 367-380.
Atarashi, et al., Treg induction by a rationally selected mixture of Clostridia strains from the human microbiota. Supplementary Information. Nature 500, 232-236 (Aug. 8, 2013) doi:10.1038/nature12331.
Atarashi, K. et al., Treg induction by a rationally selected mixture of Clostridia strains from the human microbiota. Nature. 2013; 500(7461):232-236.

ATCC Catalog, https://www.atcc.org/search_results.aspx?dsNav=Ntk:primarysearch%7cbacteroides+thetaiotaomicron%7c3%7c,Ny:true,ro:0,N:1000552&searchterms=bacteroides+thetaiotaomicron&redir=1, Accessed on May 2, 2018.
Atlas, R. Handbook of Microbiological Media, Fourth Edition. CRC Press. 2010.
Ausubel et al. (1999) Short Protocols in Molecular Biology. 4th edition. pp. 7-58 to 7-60, and Chapter 18. pp. 18-1 to 18-23.
Ausubel et al., Short protocols in molecular biology. Fifth edition, 2002.
Ausubel, et al. Current Protocols in Molecular Biology. 1987. Supplement 30.
Awadel-Kariem, Mustafa et al., First report of Parabacteroides goldsteinii bacteraemia in a patient with complicated intra-abdominal infection, Anaerobe, vol. 16, Issue 3, Jun. 2010, pp. 223-225.
Azad, M.B. et al., Probiotic supplementation during pregnancy or infancy for the prevention of asthma and wheeze: systematic review and meta-analysis BMJ 2013; 347 :f6471.
Aziz et al. The RAST Server: rapid annotations using subsystems technology. BMC Genomics. 2008, vol. 9, No. 1, pp. 75.
Aziz, R.K., Bartels, D., Best, A.A., DeJongh, M., Disz, T., Edwards, R.A., et al. (2008). The RAST Server: Rapid Annotations using Subsystems Technology. BMC Genomics 9, 75. doi: 10.1186/1471-2164-9-75.
Bagge, et al., Diversity of spore-forming bacteria in cattle manure, slaughterhouse waste and samples from biogas plants. Journal of applied microbiology. 2010;109: 1549-1565.
Balato, et al., Effects of adalimumab therapy in adult subjects with moderate-to-severe psoriasis on Th17 pathway. (2014) J Eur Acad Dermatol Venereol. 28(8):1016-24.
Banfield, J. & Murphy, K.R., Non-Th2, Late-onset, non-allergic asthma. Copd & Asthma for NPs, A peer-reviewed newsletter, Aug. 2016; 14: 8 Pages.
Barcenilla et al. "Phylogenetic relationships of butyrate-producing bacteria from the human gut" Applied and environmental microbiology. 2000, vol. 66, No. 4, pp. 1654-1661.
Barry, et al., Criteria for Disksusceptibility tests and quality control guidelines for the cefoperazone-sulbactam combination, Journal of clinical microbiology, Jan. 1988;26(1):13-17.
Beaucage, et al. Deoxynucleoside phosphoramidites—A new class of key intermediates for deoxypolynucleotide synthesis. Tetrahedron Letters, vol. 22, 1981, pp. 1859-1869.
Beggs (1978) "Transformation of yeast by a replicating hybrid plasmid," Nature. 275:104-109.
Begley, M., Hill, C., and Gahan, C.G.M. (2006). Bile Salt Hydrolase Activity in Probiotics. Applied and Environmental Microbiology 72(3), 1729-1738. doi: 10.1128/AEM.72.3.1729-1738.2006.
Berg et al. (1996) "Enterocolitis and colon cancer in interleukin-10-deficient mice are associated with aberrant cytokine production and CD4(+) TH1-like responses," The Journal of Clinical Investigation. 98(4):1010-1020.
Berger, B., Moine, D., Mansourian, R., and Arigoni, F. (2010). HspR Mutations Are Naturally Selected in Bifidobacterium longum When Successive Heat Shock Treatments Are Applied. Journal of Bacteriology 192(1), 256-263. doi: 10.1128/jb.01147-09.
Berger, S. Gideon guide to medically important bacteria. Gideon E-book Series. 2017 edition. 4 pages.
Bergonzelli, G.E., Granato, D., Pridmore, R.D., Marvin-Guy, L.F., Donnicola, D., and Corthesy-Theulaz, I.E. (2006). GroEL of Lactobacillus johnsonii La1 (NCC 533) is cell surface associated: potential role in interactions with the host and the gastric pathogen *Helicobacter pylori*. Infect Immun 74(1), 425-434. doi: 10.1128/IAI.74.1.425-434.2006.
Bernalier et al. *Ruminococcus hydrogenotrophicus* sp. nov., a new H2/CO2-utilizing acetogenic bacterium isolated from human feces. 1996 Arch. Microbiol. 166 (3), 176-183.
Bernalier et al., "Acetogenesis from H02 and C0-2 by Methane and Non-Methane-Producing Human Colonic Bacterial Communities" Fems Microbiology Ecology. vol. 19. No. 3. 1996. pp. 193-202. XP000979130.

(56) References Cited

OTHER PUBLICATIONS

Bernalier, A., et al., "Diversity of H2/C02-utilizing acetogenic Bacteria from Feces of Non-Methane-Producing Humans", Current Microbiology vol. 33 (Aug. 1996), pp. 94-99, Springer-Vertag New York Inc., USA.
Bertram, J. et al. Establishment of a cloned line of Lewis lung carcinoma cells adapted to cell culture. (1980) Cancer let. 11:63-73.
Birdi, K.S. Handbook of Surface and Colloid Chemistry, 2nd Edition. CRC Press. 1997.
Blandino, G., Fazio, D., DiMarco, R. Probiotics: Overview of microbiological and immunological characteristics (2008). Expert Review of Anti-Infective Therapy, 6 (4), pp. 497-508.
Bond, John H., Jr., et al., "Factors Influencing Pulmonary Medicine Excretion in Man: An indirect method of studying the in situ metabolism of the methane-producing colonic bacteria"; Journal of Experimental Medicine, Oct. 29, 1970, pp. 572-388.
Born, P., et al., "Fecal bacterial activity in symptomatic carbohydrate malabsorption: Effect on the fecal short-chain fatty acid ratio", intervention during the week "Digestive Diseases Week" from May 16 to May 19, 1999, Orlando, Z. Gasteroenterol2000: 38:623-626, Georg Thieme Verlag Stuttgart, New York, USA.
Born, P., et al., English Abstract "Carbohydrate substitutes: comparative study of intestinal absorption of fructose, sorbitol and xylitol", "Zuckeraustauschstoffe: Vergleichende Untersuchung zur intestinalen Resorption von Fructose, Sorbit and Xylit", Medizinische Klinik 89, Technischen Universitat Munchen (Munich) Nov. 15, 1994; 89 (11): 575-8 (Article in German), Urban & Vogel, Munich, Germany.
Bottacini, et al., Comparative genomics of the Bifidobacterium brevetaxon. BMC Genomics, 2014; 15:170. DOI:10.1186/1471-1471-2164-15-170.
Bottacini, F., Morrissey, R., Esteban-Torres, M., James, K., van Breen, J., Dikareva, E., et al. (2018). Comparative genomics and genotype-phenotype associations in Bifidobacterium breve. Scientific Reports 8(1), 10633. doi: 10.1038/s41598-018-28919-4.
Bottacini, F., O'Connell Motherway, M., Kuczynski, J., O'Connell, K.J., Serafini, F., Duranti, S., et al. (2014). Comparative genomics of the Bifidobacterium breve taxon. BMC Genomics 15(1), 170. doi: 10.1186/1471-2164-15-170.
Brand et al., Collagen-induced arthritis, 2007; Protocol 2(5):1269-1275.
Brasel et al. (2000) "Generation of murine dendritic cells from ftl3-ligand-supplemented bone marrow cultures," Blood. 96(9):3029-3039.
Bressa, et al., Differences in gut microbiota profile between women with active lifestyle and sedentary women. Plos One, 2017; 12(2): 1-20.
Bry et al. A model of host-microbial interactions in an open mammalian ecosystem. Science 273(5280):1380-1383 (1996).
Buffie et al., Precision microbiome restoration of bile acid-mediated resistance to Clostridium difficile. Nature, 517(7533):205-208 (2015).
Busing, K. et al., Effects of oral Enterococcus faecium strain DSM 10663 NCIMB 10415 on diarrhoea patterns and performance of sucking piglets. Benef Microbes. Mar. 2015;6(1):41-4. doi: 10.3920/BM2014.0008.
Butcher et al. (1980) The role of tissue culture in the study of crown-gall tumorigenesis. Tissue Culture Methods for Plant Pathologists. Eds.: Ingrams, D. S.; Helgeson, J.P. pp. 203-208.
Candela et al. 'Interaction of probiotic Lactobacillus and Bifidobacterium strains with human intestinal epithelial cells:Adhesion properties, competition against enteropathogens and modulation of IL-8 production'. International Journal of Food Microbiology. 2008, vol. 125, No. 3, pp. 286-292.
Candela, M., Bergmann, S., Vici, M., Vitali, B., Turroni, S., Eikmanns, B.J., et al. (2007). Binding of human plasminogen to Bifidobacterium. J Bacteriol 189(16), 5929-5936. doi: 10.1128/JB.00159-07.
Candela, M., Biagi, E., Centanni, M., Turroni, S., Vici, M., Musiani, F., et al. (2009). Bifidobacterial enolase, a cell surface receptor for human plasminogen involved in the interaction with the host. Microbiology 155(Pt 10), 3294-3303. doi: 10.1099/mic.0.028795-0.
Candela, M., Centanni M Fau—Fiori, J., Fiori J Fau—Biagi, E., Biagi E Fau—Turroni, S., Turroni S Fau—Orrico, C., Orrico C Fau—Bergmann, S., et al. (2010). DnaK from Bifidobacterium animalis subsp. lactis is a surface-exposed human plasminogen receptor upregulated in response to bile salts. Microbiology 156(6), 1609-1618.
Caruthers, et al. New chemical methods for synthesizing polynucleotides. Nucleic Acids Symp Ser. 1980;(7):215-23.
Carvalho et al. (Jan. 2011) "TLR5 activation induces secretory interleukin-1 receptor antagonist (sII-1 Ra) and reduces inftammasome-associated tissue damage," Nature. 4(1):1 02-111.
Casey et al. 'Isolation and characterization of anti-*Salmonella* lactic acid bacteria from the porcine gastrointestinal tract'. Letters in Applied Microbiology. 2004, vol. 39, No. 5, pp. 431-438.
Caspi, P.R. Experimental autoimmune uveoretinitis in the rat and mouse. Curr Protoc Immunol. May 2003;Chapter 15:Unit 15.6. doi: 10.1002/0471142735.im1506s53.
Cekanaviciute, et al., Gut bacteria from multiple sclerosis patients modulate human T cells and exacerbate symptoms in mouse models. PNAS. Jun. 30, 2017; 1-6.
Cereghino et al. (2000) "Heterologous protein expression in the methylotrophic yeast Pichia pastoris," FEMS Microbiol Review. 24(1):45-66.
Charriot, et al., Future treatment for asthma, Eur Respir Rev 2016; 25: 77-92.
Cheluvappa, R. et al., T helper type 17 pathway suppression by appendicitis and appendectomy protects against colitis. Clin Exp Immunol. Feb. 2014;175(2):316-22. doi: 10.1111/cei.12237.
Chen, S. et al., Live combined bacillus subtilis and enterococcus faecium ameliorate murine experimental colitis by immunosuppression. International journal of inflammation. 2014(878054). 7 Pages.
Chevreux et al. 'Genome sequence assembly using trace signals and additional sequence information.' German Conference on Bioinformatics. 1999.
Chi, W. et al. Upregulated IL-23 and IL-17 in Behçet patients with active uveitis. Invest Ophthalmol Vis Sci. Jul. 2008;49(7):3058-64. doi: 10.1167/iovs.07-1390.
Chi, W. et al., IL-23 promotes CD4+ T cells to produce IL-17 in Vogt-Koyanagi-Harada disease. J Allergy Clin Immunol. May 2007;119(5):1218-24. Epub Mar. 1, 2007.
Chiu, et al., Monocolonization of germ-free mice with bacteroides fragilis protects against dectran sulfate sodium-induced acute colitis. Biomed Research International 2014. vol. 2014. Article ID 675786. 9 Pages.
Choji Kaneuchi et al., "*Clostridium coccoides*, a New Species from the Feces of Mice", International Journal of Systematic Bacteriology, vol. 26, No. 4, Oct. 1976, p. 482-486.
Chothia et al. The relation between the divergence of sequence and structure in proteins. EMBO Journal. 1986, 5(4):823-826.
Christiaen, S.E., O'Connell Motherway, M., Bottacini, F., Lanigan, N., Casey, P.G., Huys, G., et al. (2014). Autoinducer-2 plays a crucial role in gut colonization and probiotic functionality of Bifidobacterium breve UCC2003. PLoS One 9(5), e98111. doi: 10.1371/journal.pone.0098111.
Christmann, et al., Human seroreactivity to gut microbiota antigens. J Allergy Clin Immunol 136(5):1378-1386; available online May 23, 2015.
Christou (1994) "Genetic engineering of crop legumes and cereals: current status and recent advances," Agro-Food Industry Hi-Tech. pp. 17-27.
Chung et al. 'Microbiota-stimulated immune mechanisms to maintain gut homeostasis.' Current Opinion in Immunology. 2010, vol. 22, No. 4, pp. 455-460.
Cintas LM, Casaus MP, Herranz C, Nes IF, Hernandez PE. Review: bacteriocins of lactic acid bacteria (2001). Food Sci Technol 7(4):281-305.
Claesson, et al. Gut microbiota composition correlates with diet and health in the elderly. 2012. Nature, 488, 178-184.
Claims to be granted in European Application No. 15817513.3 amended Jun. 6, 2016.

(56) References Cited

OTHER PUBLICATIONS

Clarridge III, J.E. Impact of 16S rRNA gene sequence analysis for identification of bacteria on clinical microbiology and infectious diseases (2004). Clinical Microbiology Reviews, 17 (4), pp. 840-862.
Clinical Trials for Thetanix, EU Clinical Trials Register, Date of commencement of clinical trial: Oct. 16, 2015. Available at: https://clinicaltrialsregister.eu/ctr-search/search?query=Thetanix.
CN Office Action dated Jan. 17, 2019, for CN 201680041407.6 (translation not yet available).
Coakley M et al: Intestinal bifidobacteria that produce trans-9, trans-11 conjugated linoleicacid: A fatty acid with antiproliferative activity against human colon SW480and HT-29 cancer cells, Nutrition and Cancer, Taylor & Francis Group, US vol. 56, No. 1, Jan. 1, 2006 (Jan. 1, 2006), pp. 95-102, XP008087265, ISSN: 0163-5581, DOI:10.1207/515327914NC5601 13 cf. abstract, p. 101, last para. of the right-hand col.
Colin, et al., GIC-1001, A Clinical Stage, Orally Administered Colonic Analgesic Drug Proposed As a Cost-Effective Alternative to I.V. Sedation Used in Colonoscopy. Canadian Digestive Diseases Week, 2014; 2 pages.
Collins, M.D., et al., *Enterococcus avium* nom. rev., comb. nov.; *E. casseliflavus* nom. rev., comb. nov.; *E. durans* nom. rev., comb. nov.; *E. gallinarum* comb. nov.; and *E. malodoratus* sp. nov. (1984) Int J Syst Evol Microbiol. 34: 220-223.
Colowick, S. and Kaplan, N., Methods of Enzymology. Academic Press, Inc. 1996.
Constantinescu et al. Experimental autoimmune encephalomyelitis (EAE) as a model for multiple sclerosis (MS). 2011. Br J Pharmacol. 164(4):1079-1106.
Co-pending U.S. Appl. No. 15/359,144, filed Nov. 22, 2016.
Co-pending U.S. Appl. No. 15/916,205, filed Mar. 8, 2018.
Co-pending U.S. Appl. No. 16/147,551, filed Sep. 28, 2018.
Co-pending U.S. Appl. No. 16/206,250, filed Nov. 30, 2018.
Co-pending U.S. Appl. No. 16/240,644, filed Jan. 4, 2019.
Co-pending U.S. Appl. No. 16/247,834, filed Jan. 15, 2019.
Co-pending U.S. Appl. No. 16/248,857, filed Jan. 16, 2019.
Co-pending U.S. Appl. No. 16/251,462, filed Jan. 18, 2019.
Co-pending U.S. Appl. No. 16/265,238, filed Feb. 1, 2019.
Cotter, P.O., Hill, C., Ross, R.P. Food microbiology: Bacteriocins: Developing imlate immunity for food (2005). Nature Reviews Microbiology, 3 (10), pp. 777-788.
Crellin et al. (2005) "Human CD4+ T cells express TLR5 and its ligand ftagellin enhances the suppressive capacity and expression of FOXP3 in CD4+ CD25+ T regulatory cells," Journal of Immunology. 175(12):8051-8059.
Cronin, M., Knobel, M., O'Connell-Motherway, M., Fitzgerald, G.F., and van Sinderen, D. (2007). Molecular Dissection of a Bifidobacterial Replicon. Applied and Environmental Microbiology 73(24), 7858-7866.
Cummings, M., Breitling, R., and Takano, E. (2014). Steps towards the synthetic biology of polyketide biosynthesis. Fems Microbiology Letters 351(2), 116-125. doi: 10.1111/1574-6968.12365.
Dahya V. et al., Clostridium ramosum Osteomyelitis in an immunocompetent patient after traumatic injury, Infectious Diseases in Clinical Practice Mar. 12, 2015 Lippincott Williams and Wilkins USA, vol. 23, No. 2, Mar. 12, 2015, pp. 102-104, XP009193312, ISSN: 1056-9103 the whole document.
Daniel Garrido et al., "Utilization of galactooligosaccharides by *Bifidobacterium longum* subsp. *infantis* isolates", Food Microbiology, 33 (2013) 262-270.
Darfeuille-Michaud et al. High prevalence of adherent-invasive *Escherichia coli* associated with ileal mucosa in Crohn's disease. .2004. Gastroenterology 127(2):412-21.
Darlington, G.J., Liver Cell Lines. (1987) Meth Enzymol. 151:19-38.
Database UniProt [Online] Jun. 1, 2003 (Jun. 1, 2003), "subname:Full= possible pirin family protein {ECO:0000313|EMBL:AAO75294. 1};", XP00275366,retrieved from EBI accession No. UniProt:Q8ABC3 Database accession No. Q8ABC3.
Database WPI, Week Jan. 2018, Thomson Scientific, London, GB; AN 2017-834299, XP002787097, & WO 2017/209156 AI (Morinaga Milk IND Co. Ltd) Dec. 7, 2017 (Dec. 7, 2017) * abstract * of WO2017/2019156, Kobayashi, Youdai et al.
Database WPI,Week Jan. 2018, Thomson Scientific, London, GB; AN 2017-834299, XP002787097,& WO 2017/209156 AI (Morinaga Milk IND Co Ltd) Dec. 7, 2017 (Dec. 7 , 2017)* abstract *.
Davis et al. (1971) "Genetic and Microbiological Research Technqiues," Methods Enzymol. 17A:79-143.
Davis et al., Genetic and Microbiological Research Techniques, Methods Enzymol. 1970; 17A:79-143.
Day, J.G. et al., Cryopreservation and Freeze-Drying Protocols. Springer. 2007. 2nd edition.
De Paepe et al. 'Trade-off between bile resistance and nutritional competence drives *Escherichia coli* diversification in the mouse gut.' PLoS Genetics. 2011, vol. 7, No. 6, e1002107.
De Ruyter, P.G., Kuipers, O.P., and de Vos, W.M. (1996). Controlled gene expression systems for Lactococcus lactis with the food-grade inducer nisin. Applied and Environmental Microbiology 62(10), 3662-3667.
Deangelis, M., et al., Selection of potential probiotic lactobacilli from pig feces to be used as additives in pelleted feeding (2006). Research in Microbiology, 157 (8), pp. 792-801.
Delgado, S., Ruiz, L., Hevia, A., Ruas-Madiedo, P., Margolles, A., and Sánchez, B. (2018). "Evidence of the In Vitro and In Vivo Immunological Relevance of Bifidobacteria," in The Bifidobacteria and Related Organisms.), 295-305.
Demarche, et al., Detailed analysis of sputum and systemic inflammation in asthma phenotypes: are paucigranulocytic asthmatics really non-inflammatory?, BMC Pulmonary Medicine, 2016; (16)46: 1-13.
Dennis et al. 'DAVID: database for annotation, visualization, and integrated discovery.' Genome Bioi. 2003, vol. 4, No. 5, pp. 3.
Dheeraj Mohania et al., "Modulation of expression of Programmed Death-1 by administration of probiotic Dahi in DMH-induced colorectal carcinogenesis in rats", Acta Biomed 2013; 84: 102-109.
Distrutti, et al., 5-Amino-2-hydroxybenzoic Acid 4-(5-Thioxo-5H-[1,2]dithiol-3yl)-phenyl Ester (ATB-429), a Hydrogen Sulfide-Releasing Derivative of Mesalamine, Exerts Antinociceptive Effects in a Model of Postinflammatory Hypersensitivity. The Journal of pharmacology and experimental therapeutics, 2006;319(1):447-458.
Distrutti, et al., Gut Microbiota role in irritable bowel syndrome: New therapeutic strategies. World Journal of Gastroenterology. Feb. 21, 2016; 22(7): p. 2219-2241, XP002769875.
Distrutti, et al., Hydrogen sulphide induces u opioid receptor-dependent analgesia in a rodent model of visceral pain. Molecular Pain, 2010; 6(36):1-16.
Divyashri et al. Probiotic attributes, antioxidant, anti-inflammatory and neuromodulatory effects of Enterococcus faecium CFR 3003: in vitro and in vivo evidence. (2015) J Med Microbiol. doi: 10.1099/jmm.0.000184.
DMSZ: Opening of Ampoules and Rehydration of Dried Cultures; (http://web.archive.org/web/20000 52411541 O/www.dsmz.de/open. htm); updated of website on Mar. 2000.
Dong, H., Rowland I Fau—Yacioob, P., and Yaqoob, P. (2012). Comparative effects of six probiotic strains on immune function in vitro. Br J Nutr 108(3), 459-470. doi: 10.1017/S0007114511005824.
Dong-Hyun Kim and Young-Ho Jin, "Intestinal Bacterial B-Glucuronidase Activity of Patients with Colon Cancer", Arch Pharm Res vol. 24, No. 6, 564-567, 2001.
Drago, Lorenzo et al., Immunodulatory Effects of Lactobucillus salivarius LS01 and Bifidobacterium breve, Alone and in Combination on Peripheral Blood Mononuclear Cells of Allergic Asthmatics; Allergy Asthma Immunol. Res. Jul. 2015: 7(4):409-413.
Duck et al. 'Isolation of flagellated bacteria implicated in Crohn's disease.' Inflammatory Bowel Diseases. 2007, vol. 13, No. 10, pp. 1191-1201.
Duncan et al. "Lactate-utilizing bacteria, isolated from human feces, that produce butyrate as a major fermentation product" Applied and environmental microbiology. 2004, vol. 70, No. 10, pp. 5810-5817.

(56) References Cited

OTHER PUBLICATIONS

Duncan et al. (2002) "*Roseburia intestinalis* sp. nov., a novel saccharolytic, butyrate-producing bacterium from human faeces," International Journal Systematic Evolutionary Microbiology. 52:1615-1620.
Duncan et al. (2006) "Proposal of *Roseburia faecis* sp. nov., *Roseburia hominis* sp. nov. and *Roseburia inulinivorans* sp. nov., based on isolates from human faeces," International Journal of Systematic and Evolutionary Microbiology. vol. 56, No. Pt 10, pp. 2437-2441.
Duncan, et al. *Roseburia intestinalis* sp. nov., a novel saccharolytic, butyrate-producing bacterium from human faeces. Int J Syst Evol Microbiol. Sep. 2002;52(Pt 5):1615-20.
Durand et al., "Reductive Acetogenesis in Animal and Human Gut." Physiological and Clinical Aspects of Short-Chain Fatty Acids, 1995. pp. 107-117, XP000979817 Cambridge University Press ISBN 0-521-44048-3.
Eckburg, PB. et al., Diversity of the human intestinal microbial flora.Science. Jun. 10, 2005;308(5728):1635-8. Epub Apr. 14, 2005.
Elhenawy et al., Preferential packing of acidic glycosidases and proteases into bacteroides Outer membrane vesicles. mBio 5:e00909-14, pp. 1-12, 2014.
Elkins et al. 'Genes encoding bile salt hydrolases and conjugated bile salt transporters in *Lactobacillus johnsonii* 100-100 and other *Lactobacillus* species.' Microbiology. 2001, vol. 147, No. 12, pp. 3403-3412.
Elmadfa, I., Klein, P., Meyer, AL. Immune-stimulating effects oflactic acid bacteria in vivo and in vitro (2010). Proceedings of the Nutrition Society, 69 (3), pp. 416-420.
Ely et al. (2000) "A family of six flagellin genes contributes to the Caulobacter crescentus flagellar filament," Journal of Bacteriology. 182(17):5001-5004.
Embl sequence AA075294.1 (2003)—provided within the Office Action dated Feb. 16, 2018 in U.S. Appl. No. 15/631,952. 2 Pages.
Eren, A. Murat et al., "A single genus in the gut microbiome reflects host preference and specificity," The ISME Journal (2015) 9, 9-100 (2015).
ESR dated Dec. 17, 2018, Appl. 18189521.0.
Estelle Devillard et al., Metabolism of Linoleic Acid by Human Gut Bacteria: Different Routes for Biosynthesis of Conjugated Linoleic Acid, Journal of Bacteriology, Mar. 2007, vol. 189, No. 4, pp. 2566-2570.
European Communication dated Jun. 14, 2017 for EP Application No. 15817513.3.
Evelo Biosciences, Inc. Clinical Trials (Rank 1): A Study of EDP1503 in Patients With Colorectal Cancer, Breast Cancer, and Checkpoint Inhibitor Relapsed Tumors, https://clinicaltrials.gov/ct2/show/NCT03775850?spons=evelo&rank=1.
Evelo Biosciences, Inc. Clinical Trials (Rank 2): A Study of EDP1815 in Healthy Participants and Participants With Mild to Moderate Psoriasis and Atopic Dermatitis, https://clinicaltrials.gov/ct2/show/NCT03733353?spons=evelo&rank=2.
Evelo Biosciences, Inc. Clinical Trials (Rank 3): A Study of EDP1066 in Healthy Participants and Participants With Mild to Moderate Psoriasis and Atopic Dermatitis, https://clinicaltrials.gov/ct2/show/NCT03542994?spons=evelo&rank=3.
Evelo Biosciences, Inc. Clinical Trials (Rank 4): Pembrolizumab and EDP1503 in Advanced Melanoma, https://clinicaltrials.gov/ct2/show/NCT03595683?spons=evelo&rank=4.
Evelo Biosciences, Inc. Portfolio: https://evelobio.com/portfolio/.
Evelo Biosciences, Inc. website: https://evelobio.com/science/.
Extended European search report and opinion dated Aug. 23, 2016 for EP Application No. 16166001.4.
Fabro, A. et al., The Th17 pathway in the peripheral lung microenvironment interacts with expression of collagen V in the late state of experimental pulmonary fibrosis. (2015) Immunobiology. 220(1):124-35.
Faghih, Z. et a., IL-17 and IL-4 Producing CD8+ T Cells in Tumor Draining Lymph Nodes of Breast Cancer Patients: Positive Association with Tumor Progression. (2013). Iranian Journal of Immunology. 10(4):193-204.
Fahy, J.V. Eosinophilic and neutrophilic inflammation in asthma: insights from clinical studies. Proc Am Thorac Soc. May 1, 2009;6(3):256-9. doi: 10.1513/pats.200808-087RM.
Faith et al. Identifying gut microbe-host phenotype relationships using combinatorial communities in gnotobiotic mice. Sci Transl Med 6(220):220ra11 (2014).
Faith et al. The long-term stability of the human gut microbiota. 2013. Science, 341(6141): 1237439.
Falony et al. In vitro kinetics of prebiotic inulin-type fructan fermentation by butyrate-producing colon bacteria: Implementation of online gas chromatography for quantitative analysis of carbon dioxide and hydrogen gas production. Applied and Environmental Microbiology. 2009, vol. 75, No. 18, pp. 5884-5892.
Falony, et al., Coculture Fermentations of *Bifidobacterium* species and bacteroides thetaiotaomicron Reveal a mechanistic insight into the prebiotic effect of inulin-type Fructans. Applied and environmental microbiology, Apr. 2009;75(8):2312-2319.
Fanning, S., Hall, L.J., Cronin, M., Zomer, A., MacSharry, J., Goulding, D., et al. (2012). Bifidobacterial surface-exopolysaccharide facilitates commensal-host interaction through immune modulation and pathogen protection. Proc Natl Acad Sci U S A 109(6), 2108-2113. doi: 10.1073/pnas.1115621109.
Farmer, et al., Gut pain & visceral hypersensitivity. British journal of pain, 2013;7(1):39-47.
Farooq, P.D. et al., Pseudomembranous colitis, Disease-A-Month 2015 Mosby Inc. USA, vol. 61, No. 5, May 1, 2015, pp. 181-206, XP009193313, ISSN: 0011-5029 p. 195.
FDA Orphan Drug Designations. Total Orphan Drugs website. Aug. 2014. Available at http://www.orphan-drugs.org/2014/09/01/fda-orphandrug- designations-august-2014. Accessed on Apr. 13, 2016.
Federico E. Rey et al., "Dissecting the in Vivo Metabolic Potential of Two Human Gut Acetogens",The Journal of Biological Chemistry, vol. 285, No. 29, pp. 22082-22090, Jul. 16, 2010.
Fenner, et al., *Bacteroides massiliensis* sp. nov., isolated from blood culture of a newborn. International Journal of systematic and evolutionary microbiology, 2005. 55: 1335-1337.
Ferrario, C., Milani, C., Mancabelli, L., Lugli, G.A., Duranti, S., Mangifesta, M., et al. (2016). Modulation of the eps-ome transcription of bifidobacteria through simulation of human intestinal environment. FEMS Microbiol Ecol 92(4), fiw056. doi: 10.1093/femsec/fiw056.
Flores-Langarica et al. (2012) "Systemic flagellin immunization stimulates mucosal CD1 03+ dendritic cells and drives Foxp3+ regulatory T Cell and IgA responses in the mesenteric lymph node," Journal of Immunology. 189 (12):57 45-5754.
Fraley et al. (1986) "Genetic Transformation in Higher Plants," Critical Reviews Plant Science. 4:1-46.
Frame et al., Production of fertile transgenic maize plants by silicon carbide whisker-mediated transformation, The Plant Journal. 1994; 6:941-948.
Frank, D. et al., Molecular-phylogenetic characterization of microbial community imbalances in human inflammatory bowel diseases. 2007. PNAS. 104(34):13780-5.
Frick, et al., Identification of commensal bacterial strains that modulate Yersinia enterocolitica and Dextran sodium sulfate-induced inflammatory responses: implications for the development of probiotics. Infection and immunity, Jul. 2007;75(7):3490-3497.
Gaboriau-Routhiau et al. 'The key role of segmented filamentous bacteria in the coordinated maturation of gut helper T cell responses.' Immunity. 2009, vol. 31, No. 4, pp. 677-689.
Gait, M.J., (1984) Oligonucleotide Synthesis: A Practical Approach. Irl Press. pp. vii-xiii.
GB Exam and search report dated Aug. 30, 2016 for GB Application No. 1520638.6.
GB Search and Exam report dated Mar. 31, 2016 for GB application 1510469.8.
GB Search and Exam report dated Mar. 31, 2016 for GB application 1510470.6.

(56) References Cited

OTHER PUBLICATIONS

GB Search and Exam report dated Apr. 15, 2016 for GB application 1510467.2.
GB Search and Exam report dated Apr. 20, 2016 for GB application 1510466.4.
GB Search and Exam report dated Apr. 20, 2016 for GB application 1510468.0.
GB Search and Exam report dated Aug. 30, 2016 for GB application No. 1520631.1.
GB Search and Exam report dated Nov. 17, 2016 for GB application 1520502.4.
GB Search and Exam report dated Sep. 13, 2016 for GB application 1520497.7.
GB1612190.7 International Search Report dated Apr. 12, 2017.
GB1809729.5 Examination Report dated Oct. 15, 2018.
GenBank Accession No. ABI48297.1 (Jul. 20, 2007) "Fial flagellin [Roseburia hominis]".
GenBank Accession No. ABY J02000000 (Nov. 8, 2013) Version 2. "Roseburia intestinal is L 1-82, whole genome shotgun sequencing project".
GenBank accession No. AJ312385 (Oct. 9, 2002) "Roseburia intestinalis 16S rRNA gene, strain L 1-82".
GenBank Accession No. CP003040 (Aug. 5, 2011) Version 1. "Roseburia Hominis A2-183, complete genome".
GenBank Accession No. DQ789141. (Jul. 20, 2007) "Roseburia hom in is Fla2 flagellin gene".
GenBank Accession No. M20983. (Apr. 26, 1993) "*R.cecicola* ftagellin gene".
GenBank Accession No. NR_044054.1 (Feb. 3, 2015) Blautia wexlerae strain SSM 19850 16S ribsomal RNA gene, partial sequence.
GenBank Accession No. NR_117867.1 (Feb. 3, 2015) Blautia stercoris strain Game-1 16S ribsomal RNA gene, partial sequence.
GenBank Accession Nos. ABY J02000001—ABY J02000409 search results page (Last Updated Apr. 24, 2015).
Genbank NCBI Reference Sequence: NR_026314, Blautia hydrongentrophica strain S5a36 16S ribosomal RNA gene, partial sequence.
Genbank NCBI Reference Sequence: NR_117867.1, Blautia stercoris strain GAMC6-1 16S ribosomal RNA gene, partial sequence.
Genbank NCBI Reference Sequence: NR-044054.1, Blautia wexlerae strain DSM 19850 16S ribosomal RNA gene, partial sequence.
Gennaro, A.R. "Quality Assurance and Control," from Remington: The Science and Practice of Pharmacy, 2000, Lippincott Williams & Wilkins, 20th ed., pp. 980-983.
Gennaro, A.R., Remington's Pharmaceutical sciences, Mack publishin co. 1985.
Geraedts et al. 'Release of satiety hormones in response to specific dietary proteins is different between human and murine small intestinal mucosa.' Annals of Nutrition and Metabolism. 2010, vol. 56, No. 4, pp. 3018-313.
Geuking et al. 'Intestinal bacterial colonization induces mutualistic regulatory T cell responses.' Immunity. 2011, vol. 34, No. 5, pp. 794-806.
Gewirtz et al. (2001) Cutting edge: bacterial flagellin activates basolaterally expressed TLR5 to induce epithelial proinflammatory gene expression. The Journal of Immunology. 167:(4)1882-1885.
Ghadimi, D. et al., Epigenetic imprinting by commensal probiotics inhibits the IL-23/IL-17 axis in an in vitro model of the intestinal mucosal immune system. JLB. 2012;92(4):895-911.
Giraud et al. 'Dissecting the genetic components of adaptation of *Escherichia coli* to the mouse gut.' PLoS Genetics.2008, vol. 4, No. 1, pp. e2.
Goldin, B.R. et al., Clinical indications for probiotics: an overview. Clin Infect Dis. Feb. 1, 2008;46 Suppl 2:S96-100; discussion S144-51. doi: 10.1086/523333.
Gonzalez-Rodriguez, I., Sanchez, B., Ruiz, L., Turroni, F., Ventura, M., Ruas-Madiedo, P., et al. (2012). Role of extracellular transaldolase from Bifidobacterium bifidum in mucin adhesion and aggregation. Appl Environ Microbiol 78(11), 3992-3998. doi: 10.1128/AEM.08024-11.
Gopal, P.K., Sullivan, P.A., Smart, J.B. Utilization of galacto-oligosaccharides as selective substrates for growth by lactic acid bacteria including Bifidobacterium lactis DR10 and Lactobacillus rhamnosus DR20 (200 1 ). International Dairy Journal, 11 (1-2), pp. 19-25.
Gousia, P., et al., Antimicrobial resistance of major foodbome pathogens from major meat products (20II). Foodborne Pathogens and Disease, 8 (1), pp. 27-38.
Greenspan et al., Defining epitopes: It's not as easy as it seems. Nature Biotechnology 7: 936-937, 1999.
Groeger, D., O'Mahony, L., Murphy, E.F., Bourke, J.F., Dinan, T.G., Kiely, B., et al. (2013). Bifidobacterium infantis 35624 modulates host inflammatory processes beyond the gut. Gut Microbes 4(4), 325-339. doi: 10.4161/gmic.25487.
GT Biologics obtains FDA orphan drug designation for paediatric crohn's drug, pharmaceutical-technology.com news, Oct. 8, 2013. Available at: http://www.pharmaceutical-technology.com/news/newsgt-biologics-obtains-fda-orphan-drug-designation-for-paediatric-crohns-drug?WT.mc_id=DN_News.
Guide for the care and use of laboratory animals: 8th edition. The national academic press; 2011.
Haabeth et al. A model for cancer-suppressive inflammation. (2012) Oncolmmunology 1(1):1146-1152.
Hammerich, L. et al., Interleukins in chronic liver disease: lessons learned from experimental mouse models. (2014) Clin Exp Gastroenterol. 7:297-306.
Handbook of Experimental Immunology, vols. I IV (D.M. Weir and C.C. Blackwell, eds, 1986, Blackwell Scientific Publications).
Handbook of Pharmaceutical Excipients, 2nd Edition, (1994), Edited by A Wade and PJ Weller.
Hansen, et al., The role of mucosal immunity and host genetics in defining intestinal commensal bacteria. 2010. Curr. Opin. Gastroenterol., 26(6): 564-571.
Hapfelmeier et al. 'Reversible microbial colonization of germ-free mice reveals the dynamics of IgA immune responses.' Science. 2010, vol. 328, No. 5986, pp. 1705-1709.
Hayashi et al. The innate immune response to bacterial ftagellin is mediated by Toll-like receptor 5. Nature. 2001, vol. 410, No. 6832, pp. 1099-1103.
Heberle, H., Meirelles, G.V., da Silva, F.R., Telles, G.P., and Minghim, R. (2015). InteractiVenn: a web-based tool for the analysis of sets through Venn diagrams. BMC Bioinformatics 16(1), 169. doi: 10.1186/s12859-015-0611-3.
Hedayat et al. (Mar. 1, 2012) "Prophylactic and therapeutic implications of toll-like receptor ligands," Medicinal Research Reviews. 32(2):294-325.
Heuvelin, E., Lebreton, C., Grangette, C., Pot, B., Cerf-Bensussan, N., and Heyman, M. (2009). Mechanisms Involved in Alleviation of Intestinal Inflammation by Bifidobacterium Breve Soluble Factors. PLoS One 4(4), e5184. doi: 10.1371/journal.pone.0005184.
Hidalgo-Cantabrana, C., Lopez, P., Gueimonde, M., de Los Reyes-Gavilan, C.G., Suarez, A., Margolles, A., et al. (2012). Immune Modulation Capability of Exopolysaccharides Synthesised by Lactic Acid Bacteria and Bifidobacteria. Probiotics Antimicrob Proteins 4(4), 227-237. doi: 10.1007/s12602-012-9110-2.
Hidalgo-Cantabrana, C., Sanchez, B., Alvarez-Martin, P., Lopez, P., Martinez-Alvarez, N., Delley, M., et al. (2015). A single mutation in the gene responsible for the mucoid phenotype of *Bifidobacterium animalis* subsp. lactis confers surface and functional characteristics. Appl Environ Microbiol 81(23), 7960-7968. doi: 10.1128/AEM.02095-15.
Hidalgo-Cantabrana, C., Sanchez, B., Milani, C., Ventura, M., Margolles, A., and Ruas-Madiedo, P. (2014). Genomic overview and biological functions of exopolysaccharide biosynthesis in *Bifidobacterium* spp. Appl Environ Microbiol 80(1), 9-18. doi: 10.1128/AEM.02977-13.
Higgins, et al. CLUSTAL: A Package for Performing Multiple Sequence Alignment on a Microcomputer. Gene. 73 (1988): 237-244.
Hinchliffe (1993) "Yeast as a vehicle for the expression of heterologous genes," Yeasts. 2nd edition. Rose, A. R.; Harrison, J. H.: Eds. Academic Press Ltd. 5(9). pp. 325-356.

(56) References Cited

OTHER PUBLICATIONS

Hinnen et al., Transformation of yeast, Proc. Natl. Acad. Sci. USA. Apr. 1978; 75:1929-1933.

Hoarau et al: "TLR2 Activation by Supernatant From Bifidobacterium Breve Modulates Maturation and Survival of Human DCs Via Differential Effects on PI3Kinase, p38 and ERK Pathways",Journal of Allergy and Clinical Immuno, Elsevier, Amsterdam, NL, vol. 119, No. 1, Jan. 1, 2007 (Jan. 1, 2007), p. S258, XP005756921, ISSN: 0091-6749, DOI: 10.1016/J.JACI.2006.12.377 *cf. abs.No. 1008 at p. S258*.

Hoarau, Cyrille et al., Supernatant from Bifidobacterium Differentially Modulates Transduction Signaling Pathways for Biological Functions of Human Dendritic Cells, PLoS One, Public Library of Science, US, vol. 3, No. 7, Jul. 1, 2008 (Jul. 1, 2008), pp. e2753-1, XP009139666,ISSN: 1932-6203 *cf. abstract and conclusion, furthermore discussion part at p. 3, col. at the right side*.

Hoekema (1985) The Binary Plant Vector System Offset-drukkerij Kanters BB, Alblasserdam. Chapter V. pp. 63-71.

Hold et al. 'Oligonucleotide probes that detect quantitatively significant groups of butyrate-producing bacteria in human feces.' Applied and environmental microbiology. 2003, vol. 69, No. 7, pp. 4320-4324.

Holdeman, et al., *Eubacterium contortum* (Prevot) comb. nov.: Emendation of description and designation of the type strain. International journal of systematic bacteriology. Oct. 1971;21(4): 304-306.

Holland et al. (1990) "Secretion of Heterologous Proteins in *Escherichia coli*," Methods Enzymology. 182:132-143.

Hollenberg et al. (1997) "Production of recombinant proteins by methulotrophic yeasts," Current Opinion Biotechnology. 8(5):554-560.

Hooper at al. 'Molecular analysis of commensal host-microbial relationships in the intestine.' Science. 2001; vol. 291, No. 5505, pp. 881-884.

Horn, et al., Synthesis of Oligonucleotides on Cellulose. Part II: Design and Synthetic Strategy to the Synthesis of 22 Oligodeoxynucleotides Coding for Gastric Inhibitory Polypeptide (GIP). 1980. Nuc Acids Res Symp Ser 225-232.

Horwell, et al., The 'peptoid' approach to the design of non-peptide, small molecule agonists and antagonists of neuropeptides. 1995. Trends Biotechnol. 13(4):132-134.

Hossain et al. "Flagellin, a TLR5 agonist, reduces graft-versus-host disease in allogeneic hematopoietic stem cell transplantation recipients while enhancing antiviral immunity," Journal of Immunology. Nov. 2011; 187(10): p. 5130-5140.

Hougee, et al., Oral treatment with probiotics reduces allergic symptoms in ovalbumin-sensitized mice:a bacterial strain comparative study. Int Arch Allergy Immunol. 2010; 151:107-117.

Hoyles L. et al. Gastrointestinal Tract, Chapter 56. Handbook of Hydrocarbon and Lipid Microbiology Springer Verlag Berlin 2010, 3120-32.

Hughes, K.R., Harnisch, L.C., Alcon-Giner, C., Mitra, S., Wright, C.J., Ketskemety, J., et al. (2017). Bifidobacterium breve reduces apoptotic epithelial cell shedding in an exopolysaccharide and MyD88-dependent manner. Open Biol 7(1). doi: 10.1098/rsob. 160155.

Hytönen, J., Haataja, S., and Finne, J. (2003). *Streptococcus pyogenes* Glycoprotein-Binding Strepadhesin Activity Is Mediated by a Surface-Associated Carbohydrate-Degrading Enzyme, Pullulanase. Infection and Immunity 71(2), 784-793.

Hytonen, J., Haataja, S., and Finne, J. (2006). Use of flow cytometry for the adhesion analysis of *Streptococcus pyogenes* mutant strains to epithelial cells: investigation of the possible role of surface pullulanase and cysteine protease, and the transcriptional regulator Rgg. BMC Microbiol 6, 18. doi: 10.1186/1471-2180-6-18.

Ibrahim et al., "Method for the isolation of highly purified *Salmonella flagellins*," Journal of Clinical Microbiology. Dec. 1985; 22(6):1040-1044.

Inaba et al., "Generation of large numbers of dendritic cells from mouse bone marrow cultures supplemented with granulocyte/macrophage colony-stimulating factor," J. Exp. Med. Dec. 1992; 176(6):1693-1702.

Interational Search Report for International Application No. PCT/GB2012/052495, dated Mar. 25, 2013.

International Preliminary Report dated Mar. 1, 2017 for International Application No. PCT/GB2015/054113.

International Preliminary Report on Patentability corresponding to International Patent Application No. PCT/GB2014/051123, dated Oct. 13, 2015.

International Preliminary Report on Patentability for International Application No. PCT/GB2012/051686 dated Jan. 14, 2014.

International Search Report dated Jan. 27, 2017 for International Application No. PCT/GB2016/053622.

International Search Report dated Feb. 10, 2016 for International Application No. PCT/GB2015/054113.

International Search Report dated Feb. 17, 2017 for International Application No. PCT/GB2016/053676.

International Search Report dated Mar. 7, 2016 for International Application No. PCT/GB2015/054112.

International Search report dated Mar. 15, 2003 for International Application No. PCT/GB2002/05255.

International Search Report dated Aug. 21, 2014 for International Application No. PCT/GB2014/051123.

International Search Report dated Aug. 26, 2016 for International application No. PCT/GB2016/051774.

International Search Report dated Aug. 26, 2016 for International application No. PCT/GB2016/051776.

International Search Report dated Sep. 6, 2016 for International application No. PCT/GB2016/051768.

International Search Report dated Sep. 6, 2016 for International application No. PCT/GB2016/051773.

International Search Report dated Sep. 6, 2016 for International application No. PCT/GB2016/051770.

International Search Report dated Feb. 2, 2017 for International application No. PCT/GB2016/053620.

International Search Report dated Mar. 6, 2017 for International Application No. PCT/GB2016/053677.

International Search Report for International Application No. PCT/GB2012/051686 dated Jan. 31, 2013.

International search report with written opinion dated Feb. 26, 2018 for PCT/GB2017/053722.

International search report with written opinion dated Jun. 8, 2017 for GB Application No. 1616016.

International search report with written opinion dated Sep. 29, 2017 for GB Application No. 1621123.

International search report with written opinion dated Oct. 16, 2017 for PCT/GB2017/052076.

Inturri, R., Molinaro, A., Di Lorenzo, F., Blandino, G., Tomasello, B., Hidalgo-Cantabrana, C., et al. (2017). Chemical and biological properties of the novel exopolysaccharide produced by a probiotic strain of Bifidobacterium longum. Carbohydr Polym 174, 1172-1180. doi: 10.1016/j.carbpol.2017.07.039.

Ishikawa, et al., Effect of bifidobacteria to suppress Th17, Food Science and technology institute, 2008, 5 Pages.

Ispirli, H. et al., Characterization of functional properties of Enterococcus faecium strains isolated from human gut.Can. J. Microbiol. 61: 861-870 (2015) dx.doi.org/10.1139/cjm-2015-0446.

Israel, E. et al., Supplementary Appendix, Severe and difficult-to-treat asthma in adults. N. Engl J Med 2017;p. 377:965-76. DOI: 10.1056/NEJMra1608969 . . . .

Israel, et al., Severe and difficult-to-treat asthma in adults, The New England Journal of Medicine, Sep. 2017; 377(10):965-976.

Issue Notification dated Feb. 20, 2019 for Co-Pending U.S. Appl. No. 15/631,945.

Ito et al. (1983) "Transformation of Intact Yeast Cells Treated with Alkali Cations," J. Bacteriology. 153:163-168.

Ivanov et al. 'Induction of intestinal Th17 cells by segmented filamentous bacteria.' Cell. 2009, vol. 139, No. 3, pp. 485-498.

Ivanov, D., Emonet, C., Foata, F., Affolter, M., Delley, M., Fisseha, M., et al. (2006). A serpin from the gut bacterium Bifidobacterium

(56) References Cited

OTHER PUBLICATIONS longum inhibits eukaryotic elastase-like serine proteases. J Biol Chem 281(25), 17246-17252. doi: 10.1074/jbc.M601678200.
Jackson MS, Bird AR, McOrist AL. Comparison of two selective media for the detection and enumeration of Lactobacilli in human faeces (2002). J Microbial Methods. 51 (3), pp. 313-321.
Jagveer Singh et al., "Bifidobacterium longum, a lactic acid-producing intestinal bacterium inhibits colon cancer and modulates the intermediate biomarkers of colon carcinogenesis", Carcinogenesis vol. 18 No. 4 pp. 833-841, 1997.
Jarchum et al., "Toll-Like Receptor 5 Stimulation Protects Mice from Acute Clostridium difficile Colitis," Infection and Immunity. Apr. 2011; 79(4):1498-1503.
Jawad, S. et al., Elevated serum levels of interleukin-17A in uveitis patients. Ocul Immunol Inflamm. Dec. 2013;21(6):434-9. doi: 10.3109/09273948.2013.815786. Epub Aug. 19, 2013.
Jenq, Robert R., Intestinal Bluatia is associated with reduced death from graft versus-host disease, Bio Blood Marro Transplant. Aug. 2015; 21(8): 1373-1383. doi:10.1016/j.bbmt.2015.04.016.
Jeon, S.G., Kayama, H., Ueda, Y., Takahashi, T., Asahara, T., Tsuji, H., et al. (2012). Probiotic Bifidobacterium breve induces IL-10-producing Tr1 cells in the colon. PLoS Pathog 8(5), e1002714. doi: 10.1371/journal.ppat.1002714.
Jiao et al., Blockade of Notch Signaling Ameliorates Murine Collagen-Induced Arthritis via Suppressing Th1 and Th17 Cell Responses. 2014; Pathology, 184(4):1085-1093.
Joblin K N., "Ruminal Acetogens and Their Potential to Lower Remnant Methane Emissions." Australian Journal of Agricultural Research. vol. 50. No. 8. 1999, pp. 1307-1313. XP001010439.
Kailasapathy, K. Microencapsulation of Probiotic Bacteria:Technology and Potential Applications. Curr. Issues Intest. Microbiol. (2002) 3: 39-48.
Kanauchi, et al., Eubacterium limosum ameliorates experimental colitis and metabolite of microbe attenuates colonic inflammatory action with increase of mucosal integrity introduction, China World J Gastroenterol February, Jan. 1, 2006. pp. 1071-1077.
Kanauchi, et al., Eubacterium limosum (probiotic) and its metabolites showed anti-inflammatory effects and increased mucosal barrier function in colitis. Gastroenterology, 2005;128: p. A281, XP009193489.
Kang et al. (2010) "Dysbiosis of fecal microbiota in Crohn's disease patients as revealed by a custom phylogenetic microarray," Inflammatory Bowel Diseases. 16(12):2034-2042.
Kang, S. et al., Dysbiosis of fecal microbiota in Crohn's disease patients as revealed by a custom phylogenetic microarray.Inflamm Bowel Dis. Dec. 2010;16(12):2034-42. doi: 10.1002/ibd.21319.
Karaffova, et al., Interaction of TGF-B4 and IL-17 with IgA secretion in the intestine of chickens fed with E. faecium AL41 and challenged with S. Enteritidis. Research in Veterinary science. 2015:75-79.
Kari Shoaf et al., "Prebiotic Galactooligosaccharides Reduce Adherence of Enteropathogenic *Escherichia coli* to Tissue Culture Cells", Infection and Immunity, Dec. 2006, vol. 74. No. 12, p. 6920-6928.
Karin, M. Nuclear factor-kappaB in cancer development and progression. Nature. May 25, 2006;441(7092):431-6.
Keller et al.. "DNA Probes", 1994. Stockton Press. New York. XP002158943 108660 pp. 594-596.
Kelly et al. 'Commensal anaerobic gut bacteria attenuate inflammation by regulating nuclear-cytoplasmic shuttling of PPAR-y and ReiA.' Nature Immunology. 2003, vol. 5, No. 1, pp. 104-112.
Kelly, et al., Commensal gut bacteria: mechanisms of immune modulation. TRENDS in immunology, 2005;26(6):326-333.
Kingsley M. A Personalized Approach to Managing 18D. Gastroenterology and Hepatology 12(5)308-315, May 2016.
Kinnebrew et al., Interleukin 23 production by intestinal CD1 03(+)CD11 b(+) dendritic cells in response to Interleukin 23 production by intestinal CD1 03(+)CD11 b(+) dendritic cells in response to bacterial flagellin enhances mucosal innate immune defense, Immunity. 2012; 36(2): 276-287.
Kinoshita, H., Uchida, H., Kawai, Y., Kawasaki, T., Wakahara, N., Matsuo, H., et al. (2008). Cell surface Lactobacillus plantarum LA 318 glyceraldehyde-3-phosphate dehydrogenase (GAPDH) adheres to human colonic mucin. J Appl Microbiol 104(6), 1667-1674. doi: 10.1111/j.1365-2672.2007.03679.x.
Kirsty Minton: Mucosal immunology: The ins and outs of gut inflammation, The journal of immunology, 4(2), Feb. 1, 2004: pp. 81-81, XP055252701.
Kishimoto, M., Nomoto, R., Mizuno, M., and Osawa, R. (2017). An in vitro investigation of immunomodulatory properties of Lactobacillus plantarum and L. delbrueckii cells and their extracellular polysaccharides. Bioscience of Microbiota, Food and Health 36(3), 101-110. doi: 10.12938/bmfh.17-001.
Kitahara et al., *Bacteroides plebeius* sp. nov. and *Bacteroides coprocola* sp. nov., isolated from human faeces, 2005; Int J Syst Ev Microbiol 55: 2143-47.
Kitahara, M. et al., *Bacteroides plebeius* sp. nov. and *Bacteroides coprocola* sp. nov., isolated from human faeces. International journal of systematic and evolutionary microbiology. 2005; 55: 2143-2147.
Koenders, M.I. et al., Interleukin-17 Acts Independently of TNF-a under Arthritic Conditions. (2006) J. Immunol. 176:6262-6269.
Kogyo, S. Lactic Acid Bacteria, Intestinal Flora ad Health II; Physiological effects of heat-treated lactococcus "EF-2001" and application to food. Mar. 30, 2001, vol. 44, No. 6, pp. 35-39.
Koh, Gar Yee et al., Parabacteroides distasonis attenuate toll-like receptor 4 signalling and Akt activation and blocks colon tumor formulation in high-fat-diet-fed azoxymethane-treated mice, International Journal of Cancer, pp. 1-30. Accepted Article, doi: 10.1002/ijc.31559.
Korhonen, J.M., Sclivagnotis, Y., Von Wright, A Characterization of dominant cultivable lactobacilli and their antibiotic resistance profiles from faecal samples of weaning piglets (2007). Journal of Applied Microbiology, 103 (6), pp. 2496-2503.
Kumolosasi, E., Salim, E., Jantan, I., and Ahmad, W. (2014). Kinetics of Intracellular, Extracellular and Production of Pro-Inflammatory Cytokines in Lipopolysaccharide-Stimulated Human Peripheral Blood Mononuclear Cells. Tropical Journal of Pharmaceutical Research 13(4), 536-543. doi: 10.4314/tjpr.v13i4.8.
Kverka, M. et al., Oral administration of Parabacteroides distasonis antigens attenuates experimental murine colitis through modulation of immunity and microbiota composition. Clinical & Experimental Immunology. 2010; 163:250-259.
Laetitia Rodes et al., "Microencapsulated *Bifidobacterium longum* subsp. *infantis* ATCC 15697 Favorably Modulates Gut Microbiota and Reduces Circulating Endotoxins in F344 Rats", BioMed Research International, vol. 2014, Article ID 602832, 11 pages.
Lahteinen, T., et al., A Pro biotic properties of Lactobacillus isolates originating from porcine intestine and feces (20 10) Anaerobe, 16 (3), pp. 293-300.
Lakhdari, et al. Identification of NF-KB Modulation Capabilities within Human Intestinal Commensal Bacteria. J Biomed Biotechnol. 2011; 2011: 282356.
Laukova, A. et al. Benefits of Combinative Application of Probiotic, Enterocin M-Producing Strain Enterococcus Faecium AL41 and Eleutherococcus Senticosus in Rabbits. Folia Microbiol (Praha) 61 (2), 169-177. Sep. 9, 2015.
Laureen Crouzet et al., "The altered gut microbiota of IBS patients plays a key role in visceral hypersensitivity: specific role of sulphate-reducing bacteria", INRA Symposium, 2012.
Lavallie et al. (1995) "Gene fusion expression systems in *Escherichia coli*," Current Opinion Biotechnology. 6 (5):501-506.
Law, J., Buist, G., Haandrikman, A., Kok, J., Venema, G., and Leenhouts, K. (1995). A system to generate chromosomal mutations in Lactococcus lactis which allows fast analysis of targeted genes. Journal of Bacteriology 177(24), 7011-7018.
Lebeer, S., Claes, I.J., Verhoeven, T.L., Vanderleyden, J., and De Keersmaecker, S.C. (2011). Exopolysaccharides of Lactobacillus rhamnosus GG form a protective shield against innate immune factors in the intestine. Microb Biotechnol 4(3), 368-374. doi: 10.1111/j.1751-7915.2010.00199.x.
Lebeer, S., Verhoeven, T.L., Francius, G., Schoofs, G., Lambrichts, I., Dufrene, Y., et al. (2009). Identification of a Gene Cluster for the

(56) References Cited

OTHER PUBLICATIONS

Biosynthesis of a Long, Galactose-Rich Exopolysaccharide in Lactobacillus rhamnosus GG and Functional Analysis of the Priming Glycosyltransferase. Appl Environ Microbiol 75(11), 3554-3563. doi: 10.1128/AEM.02919-08.
Lee, et al. Intestinal microbiota in pathophysiology and management of irritable bowel syndrome . 2014. World J Gastroenterol. 20(27): 8886-8897.
Lejeune, FJ. et al., Efficiency of Recombinant Human TNF in Human Cancer Therapy. (2006) Cancer Immun. 6:6.
Leser et al. 'Culture-independent analysis of gut bacteria: the pig gastrointestinal tract microbiota revisited'. Applied and Environmental Microbiology. 2002, vol. 68, No. 2, pp. 673-690.
Leslie, et al., Trehalose and sucrose protect both membranes and proteins in intact bacteria during drying. (1995) Appl. Environ. Microbiol. 61, 3592-3597.
Letran et al. 'TLR5-deficient mice lack basal inflammatory and metabolic defects but exhibit impaired CD4 T cell responses to a flagellated pathogen.' The Journal of Immunology. 2011, vol. 186, No. 9, pp. 5406-5412.
Li, C.Y., Lin Hc Fau—Lai, C.-H., Lai Ch Fau—Lu, J.J.-Y., Lu Jj Fau—Wu, S.-F., Wu Sf Fau—Fang, S.-H., and Fang, S.H. (2011). Immunomodulatory effects of lactobacillus and Bifidobacterium on both murine and human mitogen-activated T cells. Int Arch Allergy Immunol 156(2), 128-136. doi: 10.1159/000322350.
Li, et al,. Screening and Identification of Lactobacillus animalis strain and characteristics of its bacteriostatic protein, Weishengwuxue Tongbao 2009; 36(7): 1001-1007.
Lilley et al., Methods in Enzymology; DNA Structure Part A: Synthesis and Physical Analysis of DNA. 1992; vol. 2011. pp. v-vii.
Liu et al. Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces. 2008. Int J Syst Evol Microbiol 58,1896-1902.
Liu, Chang-jian et al., Antioxidant and Cholesterol-Reducing Properties of Enterococcus gallinarum m661, Bioengineering (Food Science), vol. 34, No. 7, Dec. 31, 2013, pp. 157-161.
Liu, Y., et al., Human-derived probiotic Lactobacillus reuteri strains differentially reduce intestinal inflannuation (20 10). American Journal of Physiology—Gastrointestinal and Liver Physiology, 299 (5), pp. G1087-G1096.
Ljungh, A, Wadstrorn, T. Lactic acid bacteria as probiotics (2006). Current Issues in Intestinal Microbiology, 7 (2), pp. 73-90.
Lodemann, U. et al., Effects of the Probiotic enterococcus faecium and pathogenic *Escherichia coli* strains in a pig and human epithelial intestinal cell model. Hindawi publishing corporation scientifica. 2015(235184) 10 pages.
Lopetuso et al. Commensal Clostridia: leading players in the maintenance of gut homeostasis. 2013. Gut Pathogens, 5: 23.
López, P., González-Rodríguez, I., Gueimonde, M., Margolles, A., and Suárez, A. (2011). Immune Response to Bifidobacterium bifidum Strains Support Treg/Th17 Plasticity. PLoS One 6(9), e24776. doi: 10.1371/journal.pone.0024776.
Lopez, P., Gonzalez-Rodriguez, I., Sanchez, B., Ruas-Madiedo, P., Suarez, A., Margolles, A., et al. (2012). Interaction of Bifidobacterium bifidum LMG13195 with HT29 cells influences regulatory-T-cell-associated chemokine receptor expression. Appl Environ Microbiol 78(8), 2850-2857. doi: 10.1128/AEM.07581-11.
López, P., Gueimonde, M., Margolles, A., and Suárez, A. (2010). Distinct Bifidobacterium strains drive different immune responses in vitro. International Journal of Food Microbiology 138(1), 157-165. doi: https://doi.org/10.1016/j.ijfoodmicro.2009.12.023.
Lopez-Boado, Y. S. et al., Bacterial Exposure Induces and Activates Matrilysin in Mucosal Epithelial Cells. J Cell Biol148, 1305-1315 (2000).

Louis et al. 'Diversity of human colonic butyrate-producing bacteria revealed by analysis of the butyryl-GoA: acetate GoA-transferase gene.' Environmental Microbiology. 2010, vol. 12, No. 2, pp. 304-314.
Louis et al. 'Diversity, metabolism and microbial ecology of butyrate-producing bacteria from the human large Intestine.' FEMS Microbiology Letters. 2009, vol. 294, No. 1, pp. 1-8.
Louis et al. 'Organization of butyrate synthetic genes in human colonic bacteria: phylogenetic conservation and horizontal gene transfer.' FEMS Microbiology Letters. 2007, vol. 269, No. 2, pp. 240-247.
Lozupone. Diversity, stability and resilience of the human gut microbiota. 2012. Nature. Sep. 13, 2012; 489 (7415): 220-230.
Luger, D. and Caspi, R.R., New perspectives on effector mechanisms in uveitis. (2008) Semin. Immunopathol. 30(2): 134-143.
Lyons, et al., Bacterial strain-specific induction of Foxp3 T regulatory cells is protective in murine allergy models. Clinical & Experimental Allergy. 2010; 40:811-819.
Machiels, et al., Predominant dysbiosis in patients with ulcerative colitis is different from Crohn's disease patients, Inflammatory Bowel Diseases, Microbiology 2012. 8th Congress of ECCO. (This Abstract Is in 7th Congress 2012).
Machiels, K. A decrease of the butyrate-producing species *Roseburia hominis* and *Faecalibacterium prausnitzii* defines dysbiosis in patients with ulcerative colitis.Gut. Aug. 2014;63(8):1275-83. doi: 10.1136/gutjnl-2013-304833. Epub Sep. 10, 2013.
MacPherson et al. 'IgA adaptation to the presence of commensal bacteria in the intestine.' Gut-Associated Lymphoid Tissues. Springer Berlin Heidelberg, 2006. 117-136.
MacPherson, AJ. et al., IgA responses in the intestinal mucosa against pathogenic and non-pathogenic microorganisms. Oct. 2001. 3(12). 1021-1035.
MacPherson, AJ., et al., The functions of mucosal T cells in containing the indigenous commensal flora of the intestine.Cell Mol Life Sci. Dec. 2002;59(12):2088-96.
MacSharry et al., Immunomodulatory effects of feeding with bifidobacterium longum on allergen-induced lung inflammation in the mouse. Pulmonary pharmacology & Therapeutics. 2012; 25:325-334.
Mahowald et al. 'Characterizing a model human gut microbiota composed of members of its two dominant bacterial phyla.' Proceedings of the National Academy of Sciences. 2009, vol. 106, No. 14, pp. 5859-5864.
Maintaining Cultures for Biotechnology and Industry (1996) Jennie C. Hunter-Cevera, Academic Press.
Mallya et al. 'Characterization of the five novel Ly—6 superfamily members encoded in the MHC, and detection of cells expressing their potential ligands.' Protein Science. 2006, vol. 15, No. 10, pp. 2244-2256.
Manni et al., A tale of two cytokines: IL-17 and IL-22 in asthma and infection. Expert Rev Respir Med. Feb. 2014 ; 8(1): 25-42. doi:10.1586/17476348.2014.854167.
Mansour et al. Isolation of Enterococcus faecium NM113, Enterococcus faecium NM213 and Lactobacillus casei NM512 as novel probiotics with immunomodulatory properties. (2014) Microbiol Immunol. 58(10):559-69.
Martin et al., Cloning, Nucleotide Sequence, and Taxonomic Implications of the Flagellin Gene of Roseburia cecicola, Journal of Bacteriology. Jun. 1988; 170(6):2612-2617.
Martin R. et al., Isolation of lactobacilli from sow milk and evaluation of their probiotic potential. J of dairy research 76(4)418-425. Nov. 2009.
Masco, L., et al., Identification of *Bifidobacterium* Species Using rep-PCR Fingerprinting. Systematic and Applied Microbiology 26(4):557-63 • Dec. 2003.
Matsuda F et al: Evaluation of a probiotics,BBG-01, for enhancement of immunogenicity of an oral inactivated cholera vaccine and safety: A randomized, double-blind, placebo-controlled trial in Bangladeshi children under 5 years of age,Vaccine, Elsevier, Amsterdam, NL, vol. 29, No. 10, Dec. 26, 2010 (Dec. 26, 2010), pp. 1855-1858, XP028147184, ISSN: 0264-410X, DOI: 10.1016/J.VACCINE.2010.12.133 [retrieved on Jan. 7, 2011] *cf. abstract*.

(56) References Cited

OTHER PUBLICATIONS

Matthes, et al., Simultaneous rapid chemical synthesis of over one hundred oligonucleotides on a microscale. Apr. 1984. EMBO Journal, 3(4): p. 801-805.
Maya, J.R. et al., Emerging Therapies for Noninfectious Uveitis: What May Be Coming to the Clinics. (2014) J. Ophthalmology. 310329.
Mazmanian et al. 'An immunomodulatory molecule of symbiotic bacteria directs maturation of the host immune system.' Cell. 2005, vol. 122, No. 1, pp. 107-118.
Mazmanian, SK., An immunomodulatory molecule of symbiotic bacteria directs maturation of the host immune system.Cell. Jul. 15, 2005;122(1):107-18.
McCarville, J.L., Dong, J., Caminero, A., Bermudez-Brito, M., Jury, J., Murray, J.A., et al. (2017). A Commensal Bifidobacterium longum Strain Prevents Gluten-Related Immunopathology in Mice through Expression of a Serine Protease Inhibitor. Applied and Environmental Microbiology 83(19), e01323-01317. doi: 10.1128/AEM.01323-17.
McClymont, S.A., Putnam Al Fau—Lee, M.R., Lee Mr Fau—Esensten, J.H., Esensten Jh Fau—Liu, W., Liu W Fau—Hulme, M.A., Hulme Ma Fau—Hoffmuller, U., et al. (2011). Plasticity of human regulatory T cells in healthy subjects and patients with type 1 diabetes. Journal of Immunology 186(7), 3918-3926. doi: 10.4049/jimmunol.1003099.
McIntosh et al. 'Mechanism of conjugated linoleic acid and vaccenic acid formation in human faecal suspensions and pure cultures of intestinal bacteria.' Microbiology. 2009, vol. 155, No. 1, pp. 285-294.
McLaughlin., "McLaughlin et al. Fatty acid chain length determines cholecystokinin secretion and effect on human gastric motility. Gastroenterology. 1999, vol. 116, No. 1, pp. 46-53".
Menard, S., Laharie D Fau—Asensio, C., Asensio C Fau—Vidal-Martinez, T., Vidal-Martinez T Fau—Candalh, C., Candalh C Fau—Rullier, A., Rullier A Fau—Zerbib, F., et al. (2005). Bifidobacterium breve and *Streptococcus thermophilus* secretion products enhance T helper 1 immune response and intestinal barrier in mice. Experimental Biology and Medicine (Maywood) 230(10), 749-756.
Meyer et al. (1992) "The use of cassava mosaic virus as a vector system for plants," Gene. 110:213-217.
Meyza, et al. The BTBR mouse model of idiopathic autism—Current view on mechanisms. 2017. Neurosci Biobehav Rev.;76(Pt A):99-110.
Mikayama, et al., Molecular cloning and functional expression of a cDNA encoding glycosylation-inhibiting factor. Proc.Nati.Acad. Sci. USA, Nov. 1993; vol. 90: 10056-1 0060.
Milani, C., Mangifesta, M., Mancabelli, L., Lugli, G.A., Mancino, W., Viappiani, A., et al. (2017). The Sortase-Dependent Fimbriome of the Genus *Bifidobacterium*: Extracellular Structures with Potential to Modulate Microbe-Host Dialogue. Appl Environ Microbiol 83(19). doi: 10.1128/AEM.01295-17.
Mincheol Kim et al., "Towards a taxonomic coherence between average nucleotide identity and 16S rRNA gene sequence similarity for species demarcation of prokaryotes", International Journal of Systematic and Evolutionary Microbiology (2014), 64, 346-351.
Miossec et al., Targeting IL-17 and TH17 cells in chronic inflammation, 2012; Nature Drug Discovery 11, 763-776.
Miossec, P. et al. Targeting IL-17 and TH17 cells in chronic inflammation. Nat Rev Drug Discov. Oct. 2012;11(10):763-76. doi: 10.1038/nrd3794.
Miraglia Del Giudice, M., Indolfi, C., Capasso, M., Maiello, N., Decimo, F., and Ciprandi, G. (2017). Bifidobacterium mixture (B longum BB536, B infantis M-63, B breve M-16V) treatment in children with seasonal allergic rhinitis and intermittent asthma. Italian Journal of Pediatrics 43(1), 25. doi: 10.1186/s13052-017-0340-5.
Mitropoulou, G. et al. Immobilization Technologies in Probiotic Food Production. (2013) Journal Nutr Metab. (2013) 716861.
Miyake, et al., Phylogenetic analysis of the genus *Bifidobacterium* and related genera based on 16S rDNA sequences. Microbiol. Immunol. 1998; 42(10): 661-667.
Miyake, T. et al., Phylogenetic Analysis of the Genus *Bifidobacterium* and Related Genera Based on 16S rDNA Sequences. Microbiol. Immunol. 1998; 42(10):661-667.
Miyamoto-Shinohara et al. Survival of freeze-dried bacteria. J Gen Appl Microbiol 54(1):9-24 (2008).
Miyauchi, E., Control of multiple sclerosis by gut microbiota. Journal of clinical and experimental medicine. 2015. vol. 253 No. 5.2, pp. 445-450.
Molecular Biology Techniques, 1st edition. An intensive laboratory course. 1998.
Molecular Biology Techniques: An Intensive Laboratory Course, (Ream et al., eds., 1998, Academic Press).
Monteleone et al., IL-10-dependent partial refractoriness to Toll-like receptor stimulation modulates gut mucosal dendritic cell function, European Journal of Immunology. 2008; 38(6):1533-1547.
Monteleone, I. et al., Th17-related cytokines: new players in the control of chronic intestinal inflammation. (2011) BMC Medicine. 2011, 9:122.
Mortaz, E. et, al., Anti-Inflammatory Effects of Lactobacillus Rahmosus and Bifidobacterium Breve on Cigarette Smoke Activated Human Mcrophiages, PLoS One, Apr. 21, 20i15, 10(8):e0136455.DOI:10.1371, Journal.pone.0136455.
Mucientes, A. et al., Specific association of IL17A genetic variants with panuveitis. (2015) Br J Ophthalmol. 99(4):566-70.
Mukai et al., SH3BP2 Gain-Of-Function Mutation Exacerbates Inflammation and Bone Loss in a Murine Collagen-Induced Arthritis Model, 2014 PLoS One 9(8): e105518.
Mulder et al. 'Environmentally-acquired bacteria influence microbial diversity and natural innate immune responses at gut surfaces'. Bmc Biology. 2009, vol. 7, No. 1, pp. 79.
Murofushi, Y., Villena, J., Morie, K., Kanmani, P., Tohno, M., Shimazu, T., et al. (2015). The toll-like receptor family protein RP105/MD1 complex is involved in the immunoregulatory effect of exopolysaccharides from Lactobacillus plantarum N14. Mol Immunol 64(1), 63-75. doi: 10.1016/j.molimm.2014.10.027.
Narushima, et al., Characterization of the 17 strains of regulatory T cell-inducing human-derived Clostridia. Gut Microbes Mar. 18, 2014; 5:3, 333-339.
Naughton PJ; Grant G. (2005) Modelling of salmonellosis In: Microbial Ecology of the Growing Animal Holzapfel WH, Naughton PJ. (Eds). London, Elsevier. pp. 235-257.
NCBI Reference Sequence: NR_026314.1, *Blautia hydrogenotrophica* strain S5a36 16S ribosomal RNA gene, partial sequence (Feb. 3, 2015), 3 pages.
Neeser, J.R., et al., Lactobacillus johnsonii Lal shares carbohydrate-binding specificities with several enteropathogenic bacteria (2000). Glycobiology, 10 (II), pp. II93-II99.
Neish et al., TLRS in the Gut. II. Flagellin-induced inftammation and antiapoptosis, American Journal of Physiology-Gastrointestinal and Liver Physiology. 2007;292:G462-466.
Neish, A. S. et al., Prokaryotic Regulation of Epithelial Responses by Inhibition of IκB-α Ubiquitination. Science 289, 1560 (2000).
Nemeth et al. 'Inhibition of *Salmonella*-induced IL-8 synthesis and expression of Hsp70 in enterocyte-like Caco-2 cells after exposure to non-starter lactobacilli'. International Journal of Food Microbiology. 2006, vol. 112, No. 3, pp. 266-274.
Neville, B.A., Functional genomics of motile commensal intestinal bacteria. PhD Thesis. University College Cork. 2013. 281 Pages.
Neville, et al., Characterization of pro-inflammatory flagellin proteins produced by Lactobacillus ruminis and related motile Lactobacilli. PloS one. Jul. 2012;7(7):e40592.
Neyrinck et al. 'Dietary modulation of clostridial cluster XIVa gut bacteria (*Roseburia* spp.) by chitin-glucan fiber improves host metabolic alterations induced by high-fat diet in mice.' The Journal of Nutritional Biochemistry. 2012, vol. 23, No. 1, pp. 51-59.
Ng et al., Archaeal flagella, bacterial flagella and type IV pili: a comparison of genes and posttranslation modification, Journal of Molecular Microbiology and Biotechnology. 2006;11:167-191.

(56) References Cited

OTHER PUBLICATIONS

Nicolau, D.P. Current challenges in the management of the infected patient (20II). Current Opinion in Infectious Diseases, 24 (SupplI), pp. SI-S10.
Notice of Allowance dated Feb. 3, 2016 for U.S. Appl. No. 14/349,907.
Notice of Allowance dated Mar. 6, 2017 for U.S. Appl. No. 14/249,710.
Notice of Allowance dated Mar. 30, 2011 for U.S. Appl. No. 10/285,224.
Notice of Allowance dated Apr. 25, 2016 for U.S. Appl. No. 14/232,475.
Notice of allowance dated Jun. 16, 2017 for U.S. Appl. No. 14/249,710.
Notice of Allowance dated Aug. 23, 2016 for U.S. Appl. No. 14/232,475.
Notice of allowance dated Sep. 1, 2017 for U.S. Appl. No. 15/357,850.
Notice of allowance dated Sep. 6, 2017 for U.S. Appl. No. 14/249,710.
Notice of Allowance dated Nov. 17, 2016 for U.S. Appl. No. 14/249,710.
Notice of Allowance dated Nov. 22, 2017 for U.S. Appl. No. 15/359,988.
Notice of Allowance dated Nov. 24, 2017 for U.S. Appl. No. 15/070,605.
Notice of Publication dated Dec. 27, 2018 for U.S. Appl. No. 16/022,256.
Nuala Moran: 'Microbial wealth', chemistry and industry, 78(6), Jun. 1, 2014, pp. 20-23, XP055252922.
Numasaki, M. et al., IL-17 Enhances the Net Angiogenic Activity and In Vivo Growth of Human Non-Small Cell Lung Cancer in SCID Mice through Promoting CXCR-2-Dependent Angiogenesis. (2005) J. Immunol. 175: 6177-6189.
Numasaki, M. et al., Interleukin-17 promotes angiogenesis and tumor growth. Blood. Apr. 1, 2003;101(7):2620-7. Epub Oct. 31, 2002.
Nutsch et al., T cell tolerance and immunity to commensal bacteria. Current Opinion in Immunology. Aug. 2012; 24 (4):385-391.
O'Connell Motherway, M., Kinsella, M., Fitzgerald, G.F., and Sinderen, D. (2013). Transcriptional and functional characterization of genetic elements involved in galacto-oligosaccharide utilization by Bifidobacterium breve UCC2003. Microbial biotechnology 6(1), 67-79. doi: 10.1111/1751-7915.12011.
O'Connell Motherway, M., O'Driscoll, J., Fitzgerald Gerald, F., and Van Sinderen, D. (2009). Overcoming the restriction barrier to plasmid transformation and targeted mutagenesis in Bifidobacterium breve UCC2003. Microbial Biotechnology 2(3), 321-332. doi: 10.1111/j.1751-7915.2008.00071.x.
O'Connell Motherway, M., Zomer, A., Leahy, S.C., Reunanen, J., Bottacini, F., Claesson, M.J., et al. (2011). Functional genome analysis of Bifidobacterium breve UCC2003 reveals type IVb tight adherence (Tad) pili as an essential and conserved host-colonization factor. Proc Natl Acad Sci USA 108(27), 11217-11222. doi: 10.1073/pnas.1105380108.
Odamaki, Toshitaka et al., "Age-related changes in gut microbiota composition from newborn to centenarian: a cross-sectional study," BMC Microbiology (2016) 16:90, pp. 1-12, DOI 10.1186/S12866-016-0708-5.
Odile Menard et al, "Gnotobiotic Mouse Immune Response Induced by Bifidobacterium sp. Strains Isolated from Infants", Applied and Environmental Microbiology, Feb. 2008, p. 660-666.
Office Action dated Jan. 2, 2018 for U.S. Appl. No. 15/357,936.
Office Action dated Jan. 11, 2005 for U.S. Appl. No. 10/285,224.
Office Action dated Jan. 26, 2009 for U.S. Appl. No. 10/275,706.
Office Action dated Feb. 18, 2010 for U.S. Appl. No. 10/285,224.
Office Action dated Mar. 13, 2013 for U.S. Appl. No. 12/760,926.
Office Action dated Mar. 26, 2007 for U.S. Appl. No. 10/275,706.
Office Action dated Apr. 4, 2008 for U.S. Appl. No. 10/285,224.
Office Action dated May 2, 2007 for U.S. Appl. No. 10/285,224.
Office Action dated May 2, 2008 for U.S. Appl. No. 10/275,706.
Office Action dated May 25, 2016 for U.S. Appl. No. 14/249,710.
Office Action dated May 26, 2009 for U.S. Appl. No. 10/285,224.
Office Action dated May 26, 2017 for U.S. Appl. No. 15/357,850.
Office Action dated May 30, 2006 for U.S. Appl. No. 10/285,224.
Office Action dated Jun. 26, 2017 for U.S. Appl. No. 15/357,936.
Office Action dated Jul. 6, 2017 for U.S. Appl. No. 15/070,605.
Office action dated Jul. 8, 2015 for U.S. Appl. No. 14/349,907.
Office Action dated Jul. 31, 2017 for U.S. Appl. No. 15/359,988.
Office Action dated Aug. 10, 2017 for U.S. Appl. No. 15/357,850.
Office Action dated Aug. 21, 2013 for U.S. Appl. No. 12/760,926.
Office Action dated Sep. 4, 2015 for U.S. Appl. No. 14/249,710.
Office Action dated Sep. 17, 2010 for U.S. Appl. No. 10/285,224.
Office Action dated Oct. 12, 2005 for U.S. Appl. No. 10/285,224.
Office Action dated Oct. 28, 2009 for U.S. Appl. No. 10/275,706.
Office Action dated Oct. 30, 2008 for U.S. Appl. No. 10/285,224.
Office Action dated Nov. 2, 2017 for U.S. Appl. No. 15/700,007.
Office Action dated Nov. 6, 2006 for U.S. Appl. No. 10/285,224.
Office Action dated Nov. 23, 2015 for U.S. Appl. No. 14/232,475.
Office Action dated Nov. 24, 2017 for U.S. Appl. No. 15/359,972.
Office Action dated Nov. 24, 2017 for U.S. Appl. No. 15/679,857.
Office Action dated Dec. 6, 2017 for U.S. Appl. No. 15/592,178.
Office Action dated Dec. 13, 2012 for U.S. Appl. No. 12/760,926.
Office Action dated Dec. 19, 2005 for U.S. Appl. No. 10/275,706.
Office Action dated Mar. 19, 2019 for U.S. Appl. No. 16/031,024.
Ohashi, Y., Ushida, K. Health-beneficial effects ofprobiotics: Its mode of action (2009). Animal Science Journal, 80 (4), pp. 361-371.
Oladipo, et al., Bioprotective potential of bacteriocinogenic enterococcus gallinarum strains isolated from some Nigerian fermented foods, and of their bacteriocins. Polish Journal of Microbiology. 2014; 63(4): 415-422.
Olivares, M., Castillejo, G., Varea, V., and Sanz, Y. (2014). Double-blind, randomised, placebo-controlled intervention trial to evaluate the effects of Bifidobacterium longum CECT 7347 in children with newly diagnosed coeliac disease. British Journal of Nutrition 112(1), 30-40. doi: 10.1017/S0007114514000609.
Olivera et al. 'Nutritional and physiological responses of young growing rats to diets containing raw cowpea seed meal, protein isolate (globulins), or starch.' Journal of agricultural and food chemistry. 2003, vol. 51, No. 1, pp. 319-325.
O'Sullivan et al., "Bacterial Supplementation in the Irritable Bowel Syndrome. A Randomised Double-Blind Placebo-Controlled Crossover Study", Digest Liver Dis. 2000. pp. 294-301.
Overbeek, R., Begley, T., Butler, R.M., Choudhuri, J.V., Chuang, H.-Y., Cohoon, M., et al. (2005). The Subsystems Approach to Genome Annotation and its Use in the Project to Annotate 1000 Genomes. Nucleic Acids Research 33(17), 5691-5702. doi: 10.1093/nar/gki866.
Overstreet et al. 'Dysbiosis Characterized by Reduced Abundance of Roseburia is Associated With Increased Severity of Colitis in IL-10-/-Mice'. Gastroenterology. 2011, vol. 140, No. 5, Suppl. 1, pp. S-S696.
Pace et al. Macrophage activiation: Priming activity from a T-cell hybridoma is attributable to interferon. (1983) PNAS. 80:3782-6.
Pang, et al., Crystal structure of human pirin: an iron-binding nuclear protein and transcription cofactor. Journal of Biological Chemistry, 279(2); Jan. 9, 2004:1491-1498.
Parabacteroides distasonis (Eggerth and Gagnon) Sakamoto and Benno (ATCC 8503). Sep. 19, 2017. 2 Pages.
Parfenov A.I., "Pain syndrome in the practice of a gastroenterologist", "Breast Cancer" N°0 from Jan. 25, 2008, 5 pages, https://www.rmj.ru/articles/bolevoy_sindrom/Bolevoy_sindrom_v_praktike_gastroenterologa-.
Park, S.K. et al., Blautia stercoris sp. nov., isolated from human faeces. International journal of systematic and evolutionary microbiology. 2012; 62(4): 776-779.
Patel., R. et al., Determination of 16S rRNA sequences of enterococci and application to species identification of nonmotile enterococcus gallinarum isolates. Journal of clinical microbiology, 1998; 36(11):3399-3407.
Paustian, C., Taylor, P., Johnson, T., Xu, M., Ramirez, N., Rosenthal, K.S., et al. (2013). Extracellular ATP and Toll-like receptor 2 agonists trigger in human monocytes an activation program that favors T helper 17. PLoS One 8(1), e54804. doi: 10.1371/journal.pone.0054804.

(56) References Cited

OTHER PUBLICATIONS

PCR (Introduction to Biotechniques Series), 2nd ed. (Newton & Graham eds., 1997, Springer Verlag).
PCT/EP2017/025038 International Preliminary Report on Patentability dated Jun. 6, 2018, 8 Pages.
PCT/EP2017/025038 International Search Report and Written Report dated Jun. 12, 2017.
PCT/EP2017/025038 Written Opinion of the International Preliminary Examining Authority dated Jan. 1, 2018.
PCT/EP2017/025038 Written Opinion of the International Preliminary Examining Authority dated Jan. 25, 2018.
PCT/GB2017/052076 Written Opinion of the International Preliminary Examining Authority dated Jun. 21, 2018, 11 Pages.
PCT/GB2017/052077 International Search Report dated Oct. 16, 2017.
PCT/GB2017/052077 Written Opinion dated Oct. 16, 2017.
PCT/GB2017/052077 Written Opinion of the International Preliminary Examining Authority dated Jun. 21, 2018, 10 Pages.
Pearson, WR. An introduction to sequence similarity ("Homology") searching. Current protocols in bioinformatics/editoral board, Andreas D Baxevanis. [et al]. 2013; 0 3:10. 1002/0471250953. bi0301s42. doi:10.1002/0471250953.bi0301s42.
Pedro Berraondo et al., "Cytokines in clinical cancer immunotherapy", British Journal of Cancer, 2019, 120:6-15.
Petersen et al. Intestinal colonization with phylogenetic group B2 *Escherichia coli* related to inflammatory bowel disease: a systematic review and meta-analysis. 2015. Scand J Gastroenterol. ;50(10):1199-207.
Peterson et al. 'Catecholamines increase conjugative gene transfer between enteric bacteria.' Microbial Pathogensis. 2011, vol. 51, No. 1, pp. 1-8.
Petsuriyawong et al. 'Screening of probiotic lactic acid bacteria from piglet feces'. Nature Science. 2011, vol. 45, pp. 245-253.
Ping Dong et al., "The role of intestinal bifidobacteria on immune system development in young rats", Early Human Development 86 (2010) 51-58.
Pinto-Sánchez, M.I., Smecuol, E.C., Temprano, M.P., Sugai, E., González, A., Moreno, M.L., et al. (2017). *Bifidobacterium infantis* NLS Super Strain Reduces the Expression of α-Defensin-5, a Marker of Innate Immunity, in the Mucosa of Active Celiac Disease Patients. Journal of Clinical Gastroenterology 51(9), 814-817. doi: 10.1097/mcg.0000000000000687.
Polak J.M. and McGee J.O., In Situ Hybridization: Principles and Practice, Oxford University Press. 1990; pp. vii-viii.
Potrykus (1991) "Gene Transfer to Plants: Assessment of Published Approaches and Results," Annu. Rev. Plant Physiol. Plant Mol. Bioi. 42:205-225.
Prakash, et al., Complete genome sequences of rat and mouse segmented filamentous bacteria, a potent inducer of th17 cell differentiation. Cell Host & Microbe. Sep. 2011 ;10(3):273-284.
Pryde et al. 'The microbiology of butyrate formation in the human colon.' FEMS Microbiology Letters. 2002. vol. 217,No. 2, pp. 133-139.
Punt et al. (2002) "Filamentous fungi as cell factories for heterologous protein production," Trends Biotechnol. 20 (5):200-206.
Qin et al. 'A human gut microbial gene catalogue established by metagenomic sequencing.' Nature. 2010, vol. 464, No. 7285, pp. 59-65.
Rajilic-Stojanovic, et al. The first 1000 cultures species of the human gastrointestinal micriobiota. FEMS Mlcriobiol Rev, vol. 38, 2014. pp. 996-1047.
Reddy, K.B.P.K., et al., Role of cryoprotectants on the viability and functional properties of pro biotic lactic acid bacteria during freeze drying (2009). Food Biotechnology, 23 (3), pp. 243-265.
Reiff,C. and Kelly,D.,Inflammatory bowel disease, gut bacteria and probiotic therapy. International journal of medical microbiology, 2010;300:25-33.
Remington. Remington: The science and practice of pharmacy. 20th Edition. Gennaro, Eds. Lippincott Williams & Wilkins, 2003.
Reuter, G. (2001). The Lactobacillus and Bifidobacterium microflora of the human intestine: composition and succession. Current Issues in Intestinal Microbiology 2(2), 43-53.
Rhee et al.,Toll-Like Receptor 5 Engagement Modulates Tumor Development and Growth in a Mouse Xenograft Model of Human Colon Cancer. Gastroenterology. Aug. 2008;135(2):518-528.
Rhee, Young-Kyung et al.., Antihumor Activity of *Bifidobacterium* Spp. isolated from a healthy Korean, Arch Pharm Res vol. 23, No. t, 482-487 2000.
Riquelme. Will 4D Pharma be UK's next Microbiome leader? Feb. 2, 2015, LABIOTECH.eu [online].
Robertson, J.M.C., et al., Lack of flagella disadvantages *Salmonella enterica* serovar Enteritidis during the early stages of infection in the rat (2003). Journal of Medical Microbiology, 52 (1), pp. 91-99.
Robinson, et al. Inside information—The unique features of visceral sensation. 2008. Mol Interv, 8(5): 242-253.
Rockwell, S.C. et al., Characteristics of a Serially Transplanted Mouse Mammary Tumor and Its Tissue-Culture-Adapted Derivative. (1972) J Natl Cancer Inst. 49:735-49.
Roe, et al., DNA Isolation and Sequencing: Essential Techniques. John Wiley & Sons, New York, New York. 1996; pp. v-vii.
Rong, Y., Dong, Z., Hong, Z., Jin, Y., Zhang, W., Zhang, B., et al. (2017). Reactivity toward Bifidobacterium longum and Enterococcus hirae demonstrate robust CD8(+) T cell response and better prognosis in HBV-related hepatocellular carcinoma. Experimental Cell Research 358(2), 352-359. doi: 10.1016/j.yexcr.2017.07.009.
Roseburia. Ubiome, 2018. Accessed on Jun. 25, 2018; Available at: https://shop.ubiome.com/pages/roseburia-1.
Round et al. 'The Toll-like receptor 2 pathway establishes colonization by a commensal of the human microbiota.' Science. 2011, vol. 332, No. 6032, pp. 974-977.
Rudinger J, "Characteristics of the amino acids as components of a peptide hormone sequence," Peptide Hormones, JA Parsons Edition, University Park Press, Jun. 1976, pp. 1-7.
Ruiz, L., Delgado, S., Ruas-Madiedo, P., Margolles, A., and Sanchez, B. (2016). Proteinaceous Molecules Mediating Bifidobacterium-Host Interactions. Front Microbiol 7, 1193. doi: 10.3389/fmicb.2016.01193.
Ruiz, P.A., Hoffmann, M., Szcesny, S., Blaut, M., and Haller, D. (2005). Innate mechanisms for Bifidobacterium lactis to activate transient pro-inflammatory host responses in intestinal epithelial cells after the colonization of germ-free rats. Immunology 115(4), 441-450. doi: 10.1111/j.1365-2567.2005.02176.x.
Russell et al. 'High-protein, reduced-carbohydrate weight-loss diets promote metabolite profiles likely to be detrimental to colonic health.' The American Journal of Clinical Nutrition. 2011, vol. 93, No. 5, pp. 1062-1072.
Sagar, et al., Bifidobacterium breve and lactobacillus rhamnosus treatment is as effective as budesonide at reducing inflammation in a murine model for chronic asthma. Respiratory Research. 2014; 15(46):1-17.
Saiki, et al., Primer-directed enzymatic amplification of DNA with a thermostable DNA polymerase. 1988. Science, 239. pp. 487-491.
Sakamato, et al., *Parabacteroides faecis* sp. nov., isolated from human faeces. International Journal of Systematic and Evolutionary Microbiology (2015), 65, 1342-1346.
Sakamoto Mitsuo et al., Reclassfication of Baceroides distasonis, Bacteroides goldsteinii and Bacteroides merdae as *Parabacteroides distasonis* gen. nov., comb. nov., *Parabacteroides goldsteinii* comb. nov. and *Parabacteroides merdae* comb. nov., International Journal of Systematic and Evolutionary Microbiology (2006) 56, 15-99-1605. DOI 10.1099/ijs.0.0641920.
Sakamoto, et al., *Parabacteroides gordonii* sp. nov., isolated from human blood cultures. International Journal of Systematic and Evolutionary Microbiology (2009), 59, 2843-2847.
Sakamoto, et al., *Parabacteroides johnsonii* sp. nov., isolated from human faeces. International Journal of Systematic and Evolutionary Microbiology (2007), 57, 293-296.
Sakamoto, M. et al., Reclassification of Bacteroides distasonis, Bacteroides goldsteinii and Bacteroides merdae as *Parabacteroides distasonis* gen. nov., comb. nov., *Parabacteroides goldsteinii* comb. nov. and *Parabacteroides merdae* comb. nov. International journal of systematic and evolutionary microbiology. 2006; 56: 1599-1605.

(56) References Cited

OTHER PUBLICATIONS

Salix Pharmaceuticals, Inc. FDA Highlights of Prescribing Information—XIFAXAN (rifaximin tablet). Revised Nov. 2015.
Salminen et al. 'Probiotics: how should they be defined?.' Trends in Food Science & Technology. 1999, vol. 10, No. 3, pp. 107-110.
Salonen et al., Gastrointestinal microbia in irritable bowel syndrome: present state and perspectives. Microbiology. 2010; 156: 3205-3215.
Sambrook, J.F. et al., Molecular Cloning: A Laboratory Manual, 3rd ed. Cold spring harbor laboratory press. 2001.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Scher et al., Expansion of intestinal Prevotella copri correlates with enhanced susceptibility to arthritis. 2013; eLIFE 2, e01202, 20 Pages.
Schiavi, E., Gleinser, M., Molloy, E., Groeger, D., Frei, R., Ferstl, R., et al. (2016). The Surface-Associated Exopolysaccharide of Bifidobacterium longum 35624 Plays an Essential Role in Dampening Host Proinflammatory Responses and Repressing Local TH17 Responses. Appl Environ Microbiol 82(24), 7185-7196. doi: 10.1128/AEM.02238-16.
Schiavi, E., Plattner, S., Rodriguez-Perez, N., Barcik, W., Frei, R., Ferstl, R., et al. (2018). Exopolysaccharide from *Bifidobacterium longum* subsp. *longum* 35624 modulates murine allergic airway responses. Benef Microbes, 1-14. doi: 10.3920/BM2017.0180.
Schieck, M. et al., Genetic variation in TH17 pathway genes, childhood asthma, and total serum IgE levels.(2014) J Allergy Clin Immunol. 133(3):888-91.
Schleifer, K.H. et al., Transfer of *Streptococcus faecalis* and *Streptococcus faecium* to the Genus *Enterococcus* nom. rev. as *Enterococcus faecalis* comb. nov. and *Enterococcus faecium* comb. nov. Int J Syst Evol Microbiol, Jan. 1984 34: 31-34, doi:10.1099/00207713-34-1-31.
Schmitz, S. et al., A prospective, randomized, blinded, placebo-controlled pilot study on the effect of Enterococcus faecium on clinical activity and intestinal gene expression in canine food-responsive chronic enteropathy. J Vet Intern Med. Mar.-Apr. 2015;29(2):533-43. doi: 10.1111/jvim.12563. Epub Mar. 16, 2015.
Schouten, et al., Cow milk allergy symptoms are reduced in mice fed dietary synbiotics during oral sensitization with whey. Nutritional Immunology. 2015; 139(7):1390-403.
Schreiber, O, et al., Lactobacillus reuteri prevents colitis by reducing P-selectin-associated leukocyte- and plateletendothelial cell interactions (2009). American Journal of Physiology—Gastrointestinal and Liver Physiology, 296 (3), pp. G534-G542.
Schulke et al. (Aug. 26, 2011) "A fusion protein of ftagellin and ovalbumin suppresses the 25 TH2 response and prevents murine intestinal allergy," The Journal of Allergy and Clinical Immunology. 128(6):1340-1348.
Schwiertz, et al., Quantification of Different *Eubacterium* spp. in Human Fecal Samples with Species-Specific 16S rRNA-Targeted Oligonucleotide Probes. Applied and environmental biology, vol. 66, No. 1, Jan. 1, 2000; pp. 375-382.
Scott et al. 'Substrate-driven gene expression in Roseburia inulinivorans: importance of inducible enzymes in the utilization of inulin and starch.' Proceedings of the National Academy of Sciences. 2011, vol. 108, Supp. 1, pp. 672-4679.
Scuotto, Angelo et al., In silico mining and characterization of bifidobacterial lipoprotein with CHHP domain secreted in an aggregated form, International J. of Biol. Macromolecutes 82(2016), 653-662.
Sczesnak, et al., The genome of th17 cell-inducing segmented filamentous bacteria reveals extensive auxotrophy and adaptations to the intestinal environment. Cell Host Microbe. Sep. 2011;10 (3):260-272.
Severijnen, A. J. et al., Chronic Arthritis Induced in Rats by Cell Wall Fragments of *Eubacterium* Species from the Human Intestinal Flora. Infection and Immunity, 1990, vol. 58, No. 2, 523-528.
Severijnen, et al., Chronic Arthritis Induced in Rats by Cell Wall Fragments of *Eubacterium* Species from the Human Intestinal Flora. Infection and Immunity, Feb. 1990; 58(2): p. 523-528.
Sgadari et al. Mig, the Monokine Induced by Interferon-g, Promotes Tumor Necrosis In Vivo. (1997) Blood. 89:2635-43.
Sgadari, C. et al., Interferon-inducible protein-10 identified as a mediator of tumor necrosis in vivo. (1996) PNAS. 93:13791-6.
Shabgah, A.G. et al., Interleukin-17 in human inflammatory diseases. Postepy Dermatol Alergol. Aug. 2014; 31(4): 256-261.
Shevach et al., Current Protocols in Immunology. John Wiley & Sons. New York, New York. 1992. Table of Contents only, as accessed online at URL: http://www.4ulr.com/products/currentprotocols/immunology_toc.html. [Last Accessed Jun. 18, 2015].
Simon, et al., Peptoids: A modular approach to drug discover, Oct. 1992. PNAS, 89(20):9367-9371.
Simpson-Herren, L. et al., Kinetic parameters and growth curves for experimental tumor systems. Cancer Chemother Rep. Jun. 1970;54(3):143-74.
Sisson, G. et al., Randomised clinical trial: a liquid multi-strain probiotic vs. placebo in the irritable bowel syndrome—a 12 week double-blind study. Aliment Pharmacol Ther. 2014; 40: 51-62.
Sivan, A., Corrales, L., Hubert, N., Williams, J.B., Aquino-Michaels, K., Earley, Z.M., et al. (2015). Commensal Bifidobacterium promotes antitumor immunity and facilitates anti-PD-L1 efficacy. Science 350(6264), 1084-1089. doi: 10.1126/science.aac4255.
Sivieri, K. et al., Probiotic enterococcus faecium CRL 183 inhibit chemically induced colon cancer in male wistar rats. Eur Food Res Technol. 2008; 228:231-237.
Skolnick, et al. From genes to protein structure and function: novel applications of computational approaches in the genomic era. Trends Biotechnol. Jan. 2000;18(1):34-9. Review.
Skountzou, et al., *Salmonella flagellins* are potent adjuvants for intranasally administered whole inactivated influenza vaccine. Vaccine. May 2010; 28(24):4103-4112.
Smith, C.L., et al., Lactobacillus fermentum BRII and fmcto-oligosaccharide partially reduce jejunal inflammation in a model of intestinal mucositis in rats (2008). Nutrition and Cancer, 60 (6), pp. 757-767.
Smith, et al. Comparison of Biosequences. Advances in Applied Mathematics. 1981;2: 482-489.
Sokol et al. 'Faecalibacterium prausnitzii is an anti-inftammatory commensal bacterium identified by gut microbiota analysis of Crohn disease patients.' Proceedings of the National Academy of Sciences. 2008, vol. 105, No. 43, pp. 6731-16736.
Sokol et al. 'Low counts of Faecalibacterium prausnitzii in colitis microbiota.' Inflammatory bowel diseases. 2009, vol. 15, No. 8, pp. 1183-1189.
Song et al., Impact of Schistosoma japonicum Infection on Collagen-Induced Arthritis in DBA/1 Mice: A Murine Model of Human Rheumatoid Arthritis. 2011; PLoS One 6, e23453, 10 pages.
Song, Yuli et al., *Bacteroides goldsteinii* sp. nov. Isolated from Clinical Specimens of Human Intestinal Origin, J. Clinical Microbiology, Sep. 2005, p. 4522-4527. DOI:10.1128/JCM.43.9.4522-4527.2005.
Sonnenburg, et al., Genomic and Metabolic Studies of the Impact of Probiotics on a Model Gut Symbiont and Host. PLoS Biol 4(12): e413. https://doi.org/10.1371/journal.pbio.0040413.
Spor, A. et al., Unravelling the effects of the environment and host genotype on the gut microbiome. Nat Rev Microbiol. Apr. 2011;9(4):279-90. doi: 10.1038/nrmicro2540.
Srutkova, D. et al., Efficiency of PCR-based methods in discriminating *Bifidobacterium longum* ssp. *longum* and *Bifidobacterium longum* ssp. *infantis* strains of human origin.J Microbiol Methods. Oct. 2011;87(1):10-6. doi: 10.1016/j.mimet.2011.06.014. Epub Jul. 2, 2011.
Stanton et al. (1983) "*Roseburia cecicola* gen. nov., sp. nov., a Motile, Obligately Anaerobic Bacterium from a Mouse Cecum," Int. J. Syst. Bacterial. 33:618-627.
Stokholm, et al., Maturation of the gut microbiome and risk of asthma in childhood. Nature Communications, 2018; 9(141): 1-10.
Stoll et al., Altered microbiota associated with abnormal humoral immune responses to commensal organisms in enthesitis-related arthritis, 2014; Arthritis Res Ther. 16:486.

(56) References Cited

OTHER PUBLICATIONS

Strasser, S. et al., Influence of lyophilization, fluidized bed drying, addition of protectants, and storage on the viability oflactic acid bacteria (2009). Journal of Applied Microbiology, 107(1), pp. 167-177.
Strickertsson, J.A. et al., Enterococcus faecalis Infection and Reactive Oxygen Species Down-Regulates the miR-17-92 Cluster in Gastric Adenocarcinoma Cell Culture. Genes 2014, 5(3), 726-738.
Strobel, H.J. Basic laboratory culture methods for anaerobic bacteria. Methods Mol Biol. 2009;581:247-61. doi: 10.1007/978-1-60761-214-8_16.
Strus et al. Distinct effects of Lactobacillus plantarum KL30B and *Escherichia coli* 3A1 on the induction and development of acute and chronic inflammation. 2015. Cent EurJ Immunol.40(4):420-30.
Sudha B. Singh and Henry C. Lin, "Hydrogen Sulfide in Physiology and Diseases of the Digestive Tract", Microorganisms 2015, 3, 866-889; doi:10.3390/microorganisms3040866.
Sun, D. et al., The role of Th17-associated cytokines in the pathogenesis of experimental autoimmune uveitis (EAU). (2015) Cytokine. 74(1):76-80.
Sun, et al., Exploring gut microbes in human health and disease: Pushing the envelope. Genes Dis. Dec. 2014; 1(2):132-139.doi:10.1016/j.gendis.2014.08.001.
Supplement to: Israel, et al., Severe and difficult-to-treat asthma in adults. N Engl J Med 2017; 377:965-76.
Suzanne L. Topalian et al., "Survival, Durable Tumor Remission, and Long-Term Safety in Patients With Advanced Melanoma Receiving Nivolumab", Journal of Clinical Oncology, vol. 32, No. 10, Apr. 1, 2014, pp. 1-12.
Tahoun, A., Masutani, H., El-Sharkawy, H., Gillespie, T., Honda, R.P., Kuwata, K., et al. (2017). Capsular polysaccharide inhibits adhesion of Bifidobacterium longum 105-A to enterocyte-like Caco-2 cells and phagocytosis by macrophages. Gut Pathog 9, 27. doi: 10.1186/s13099-017-0177-x.
Takashi Nakamura et al., "Evaluation of the Effects of Dietary Organic Germanium, Ge-132, and Raffinose Supplementation on Caecal Flora in Rats", Bioscience of Microbiota, Food and Health vol. 31 (2), 37-45, 2012.
Tamanai-Shacoori, et al., *Roseburia* spp.: a marker of health?. Future Microbiology Review 12(2), 157-170 (2017).
Tan, Hai-Qin et al., *Parabacteroides chartae* sp. nov., an obligately anaerobic species from wastewater of a paper mill, International Journal of systematic and Evolutionary Microbiology (2012), 62-2613-2617, DOI 10.1099/ijs.0.038000-0.
Tanaka, K. and Watanabe, K., In Vitro tebipenem activity against anaerobic bacteria. Japanese Journal of Chemotherapy. Mar. 2009. vol. 57 S-1.
Tap et al. Towards the human intestinal microbiota phylogenetic core. 2009. Environ Microbiol, 11(10):2574-84.
Tatusova et al. (1999) "BLAST 2 Sequences, a new tool for comparing protein and nucleotide sequences," FEMS Microbial. Lett. 174(2):247-250.
Tatusova et al., BLAST 2 Sequences, a new tool for comparing protein and nucleotidesequences, FEMS Microbiology Letters 174 (1999) 247-250.
Tatusova et al., Erratum to BLAST 2 Sequences, a new tool for comparing protein and nucleotide sequences, FEMS Microbiology Letters 177 (1999) 187-188.
Tatusova, et al., Erratum to BLAST 2 Sequences, a new tool for comparing protein and nucleotide sequences [FEMS Microbiol. 174 (1999) 247-250], FEMS Microbial. Lett. 1999;177(1):187-188.
Teng, L. J. et al., PCR Assay for Species-Specific Identification ofBacteroides thetaiotaomicron. J Clin Microbiol38, 1672-1675 (2000).
Terciz, Janos et al., Inflammation and Colon Cancer, Gastroenterology, 2010: 138: 2101-2114.
Tesmer, LA. et al., Th17 cells in human disease. Immunol Rev. 2008;223:87-113.
Tilg, et al., Roseburia hominis: a novel guilty player in ulcerative colitis pathogenesis? Gut, Oct. 14, 2013;63(8)1204-1205.
Tomas, M.S.J., et al., Stability of freeze-dried vaginal Lactobacillus strains in the presence of different lyoprotectors (2009). Canadian Journal of Microbiology, 55 (5), pp. 544-552.
Tomosada, Y., Villena, J., Murata, K., Chiba, E., Shimazu, T., Aso, H., et al. (2013). Immunoregulatory Effect of Bifidobacteria Strains in Porcine Intestinal Epithelial Cells through Modulation of Ubiquitin-Editing Enzyme A20 Expression. PLoS One 8(3), e59259. doi: 10.1371/journal.pone.0059259.
Toomer, O. et al., Maternal and postnatal dietary probiotic supplementation enhances splenic regulatory T helper cell population and reduces peanut allergen-induced hypersensitivity responses in mice. Immunobiology. 209; 2014: 661-670.
Travis, et al. Complete genome sequence of the human gut symbiont Roseburia hominis. Genome announcements. 2015; 3(6):e01286-15.
Tremaroli, et al., A role for the gut microbiota in energy harvesting? Gut. Dec. 2010; 59(12):1589-1590.
Trueman (1995) "Heterologous Expression in Yeast," Methods Molecular Biology. 49:341-354.
Tsukinowa, et al., Fecal microbiota of a dugong (Dugong dugong) in captivity at Toba Aquarium. J. Gen. Appl. Microbiol., 54, 25-38 (2008).
Turnbaugh et al. A core gut microbiome in obese and lean twins. Jan. 22, 2009. Nature, 457(7228): 480-484.
Turnbaugh et al., Diet-induced obesity is linked to marked but reversible alterations in the mouse distal gut microbiome. Cell Host & Microbe. Apr. 2008;3(4):213-223.
Turnbaugh, et al., An obesity-associated gut microbiome with increased capacity for energy harvest. Nature. Dec. 2006;444(7122):1027-1031.
Turner (1994) "Vectors for genetic manipulation," In; Martinelli, S.D.; Kinghorn J. R.: Eds. Aspergillus: 50 years on. Progress in industrial microbiology. vol. 29. Elsevier. Amsterdam, The Netherlands. pp. 641-666.
Turroni, F., Taverniti V Fau—Ruas-Madiedo, P., Ruas-Madiedo p. Fau—Duranti, S., Duranti S Fau—Guglielmetti, S., Guglielmetti S Fau—Lugli, G.A., Lugli Ga Fau—Gioiosa, L., et al. (2014). Bifidobacterium bifidum PRL2010 modulates the host innate immune response. Appl Environ Microbiol 80(1098-5336 (Electronic)), 730-740.
Tzortzis, G., et al., Modulation of anti-pathogenic activity in canine-derived *Lactobacillus* species by carbohydrate growth substrate (2004). Journal of Applied Microbiology, 96 (3), pp. 552-559.
U.S. Appl. No. 15/357,936 Notice of Allowance dated Apr. 18, 2018.
U.S. Appl. No. 15/359,144 Notice of Allowance dated Sep. 4, 2018.
U.S. Appl. No. 15/359,972 Notice of Allowance dated Aug. 8, 2018.
U.S. Appl. No. 15/359,988 Notice of Allowance dated Mar. 2, 2018.
U.S. Appl. No. 15/359,988 Notice of Allowance dated Mar. 16, 2018.
U.S. Appl. No. 15/592,178 Notice of Allowance dated Apr. 12, 2018.
U.S. Appl. No. 15/592,178 Notice of Allowance dated Jul. 12, 2018.
U.S. Appl. No. 15/631,945 Notice of Allowance dated Oct. 18, 2018.
U.S. Appl. No. 15/700,007 Notice of Allowance dated Oct. 17, 2018.
U.S. Appl. No. 15/915,885 Notice of Allowance dated May 23, 2018.
U.S. Appl. No. 15/915,889 Notice of Allowance dated Jun. 4, 2018.
U.S. Appl. No. 15/916,167 Notice of Allowance dated May 31, 2018.
U.S. Appl. No. 15/916,202 Notice of Allowance dated Jun. 11, 2018.
U.S. Appl. No. 15/916,205 Notice of Allowance dated May 30, 2018.
U.S. Appl. No. 15/359,144 Office Action dated Apr. 10, 2018.
U.S. Appl. No. 15/359,972 Office Action dated Apr. 4, 2018.
U.S. Appl. No. 15/431,393 Office Action dated Jul. 30, 2018.
U.S. Appl. No. 15/631,945 Office Action dated Jul. 5, 2018.
U.S. Appl. No. 15/631,945 Office Action dated May 15, 2018.
U.S. Appl. No. 15/631,952 Office Action dated Feb. 16, 2018.
U.S. Appl. No. 15/631,952 Office Action dated Jul. 19, 2018.

(56) References Cited

OTHER PUBLICATIONS

U.S. Appl. No. 15/673,270 Office Action dated Apr. 10, 2018.
U.S. Appl. No. 15/679,857 Office Action dated Aug. 6, 2018.
U.S. Appl. No. 15/679,857 Office Action dated Feb. 14, 2018.
U.S. Appl. No. 15/700,007 Non-Final Office Action dated Jun. 10, 2019.
U.S. Appl. No. 15/700,007 Office Action dated Jun. 1, 2018.
U.S. Appl. No. 15/704,245 Non-Final Office Action dated Jul. 3, 2019.
U.S. Appl. No. 15/704,245 Office Action dated Sep. 17, 2018.
U.S. Appl. No. 15/803,723 Notice of Allowance dated Feb. 13, 2018.
U.S. Appl. No. 15/842,635 Office Action dated Aug. 27, 2018.
Udayappan et al., PS4—5. Administration of Eubacterium hallii improves insulin sensitivity and degree of liversteatosis in male db/db mice. Nederlands tijdschrift voor diabetologie, vol. 11, No. 4., Nov. 23, 2013.pp. 145.
Udayappan, et al., Oral treatment with Eubacterium hallii improves insulin sensitivity in db/db mice. NPJ Biofilms and microbiomes, vol. 2, Jul. 6, 2016; p. 16009.
Ukena, et al., Probiotic *Escherichia coli* Nissle 1917 inhibits leaky gut by enhancing mucosal integrity, PloS one. Dec. 2007;2(12):e1308.
Untergasser, A., Nijveen, H., Rao, X., Bisseling, T., Geurts, R., and Leunissen, J.A. (2007). Primer3Plus, an enhanced web interface to Primer3. Nucleic Acids Res 35(Web Server issue), W71-74. doi: 10.1093/nar/gkm306.
Untergasser, et al., Primer3Plus, an enhanced web interface to Primer3, Nucleic Acids Res. 2007;35(Web Server issue):W71-W74.
U.S. Appl. No. 15/842,635 Non-Final Office Action dated May 29, 2019.
U.S. Appl. No. 16/022,577 Non-Final Office Action dated Jul. 9, 2019.
Van De Bogert, et al., Immunomodulatory properties of *Streptococcus* and veillonella isolates from the human small intestine microbiota, PLoS One, Dec. 2014: 1-20, DOI:10.1371/journal.pone. 0114277.
Van de Pot, M.A. et al., Sybiotics reduce allergen-induced T-helper 2 respond and improve peak expiatory flow in allergic asthmatics, Allergy 2011;66:39-47.
Van De Veerdonk, et al., The Anti-CD20 antibody rituximab reduces the Th17 cell response. Arthritis & Rheumatism. Jun. 2011; 63(6):1507-1516.
Van Immerseel et al. 'Butyric acid-producing anaerobic bacteria as a novel probiotic treatment approach for inflammatory bowel disease.' Journal of medical microbiology. 2010, vol. 59, No. 2, pp. 141-143.
Van Nevel et al., "Control of Rumen Methanogenesis." Environmental Monitoring and Assessment. vol. 42, 1996, pp. 73097, XP000979267.
Van Tilburg, M. Can we treat visceral hypersensitivity in functional abdominal pain? Lancet Gastroenterolhepatol, 2017; 2 Pages.
Verheijden, K.A.T. et al., The development of allergic inflammation in a murine house dust mite asthma is suppressed by symbiotic mixtures of non-digestible oligosaccharides and Bifidobacterium breve M-16V; Eur. J. Nut. (2016) 55: 1141-1151, DOI 10.1007, 500394-015-0928-8.
Vetrovsky, T. and Baldrian, P., The variability of the 16S rRNA gene in bacterial genomes and its consequences for bacterial community analyses. Plos One. Feb. 2013; 8(2): e57923.
Viaud, Sophie et al. "The intestinal microbiota modulates the anticancer immune effects of cyclophosphamide." Science (New York, N.Y.) vol. 342,6161 (2013): 971-6. doi:10.1126/science. 1240537.
Vijay-Kumar et al., Flagellin Treatment Protects against Chemicals, Bacteria, Viruses, and Radiation. The Journal of Immunology. 2008;180(12):8280-8285.
Vijay-Kumar, et al., Deletion of TLR5 results in 10 spontaneous colitis in mice. The Journal of Clinical Investigation. Dec. 2007;117(12):3909-3921.

Walker et al. 'Dominant and diet-responsive groups of bacteria within the human colonic microbiota.' The ISME Journal. 2010, vol. 5, No. 2, pp. 220-230.
Wang et al. 16S rRNA gene-based analysis of fecal microbiota from preterm infants with and without necrotizing enterocolitis. 2009. ISME J. 3(8): 944-954.
Wang W., Lyophilization and development of solid protein pharmaceuticals. International J. Pharmaceutics 203: 1-60, 2000.
Wang, Chun-Sai-Er, et al., VSL#3 can prevent ulcerative colitis-associated carcinogenesis in mice, Oct. 7, 2018, vol. 24, Issue 37, pp. 4254-4262.
Wang, Feng, Bifidobacterium can mitigate intestinal immunopathology in the context of CTLA-4 blockade, PNA, Jan. 2, 2018 vol. 115, No. 1, pp. 157-161.
Wang, G., Xia, Y., Cui, J., Gu, Z., Song, Y., Q., C.Y., et al. (2014). The Roles of Moonlighting Proteins in Bacteria. Current Issues in Molecular Biology 16, 15-22.
Wang, R.F., and Kushner, S.R. (1991). Construction of versatile low-copy-number vectors for cloning, sequencing and gene expression in *Escherichia coli*. Gene 100, 195-199. doi: https://doi.org/10.1016/0378-1119(91)90366-J.
Watson, et al., Signal transduction in Campylobacter jejuni-induced cytokine production. Cellular Microbiology. 2005;7(5):655-665.
Wei, X., Yan, X., Chen, X., Yang, Z., Li, H., Zou, D., et al. (2014). Proteomic analysis of the interaction of Bifidobacterium longum NCC2705 with the intestine cells Caco-2 and identification of plasminogen receptors. J Proteomics 108, 89-98. doi: 10.1016/j.jprot.2014.04.038.
Weigel, et al., Comparative analysis of murine marrow-derived dendritic cells generated by Flt3L or GMCSF/IL-4 and matured with immune stimulatory agents on the in vivo induction of antileukemia responses. Blood. Dec. 2002;100(12):4169-4176.
Welman, A.D., and Maddox, I.S. (2003). Exopolysaccharides from lactic acid bacteria: perspectives and challenges. Trends in Biotechnology 21(6), 269-274. doi: https://doi.org/10.1016/S0167-7799(03)00107-0.
Wendler, et al., Identification of a pirin, a novel highly conserved nuclear protein. J. Biol Chem. Mar. 28, 1997; 272(13):8482-9.
Wenzel, S.E., Asthma phenotypes: the evolution from clinical to molecular approaches, Nature medicine, May 2012; 18(5):716-725.
Werth, et al., The transcription factor grainyhead-like 2 regulates the molecular composition of the epithelial apical junctional complex. Development. 2010;37(22):3835-3845.
Westermann, C., Gleinser, M., Corr, S.C., and Riedel, C.U. (2016). A Critical Evaluation of Bifidobacterial Adhesion to the Host Tissue. Front Microbiol 7, 1220. doi: 10.3389/fmicb.2016.01220.
Williams, N.T. Probiotics (2010). American Journal of Health-System Pharmacy, 67 (6), pp. 449-458.
Wilson, et al., The TLR5 ligand flagellin promotes asthma by priming allergic responses to indoor allergens. Nature Medicine. Nov. 2012;18(11):1705-1710.
Workman et al. Guidelines for the welfare and use of animals in cancer research (2010) Br. J. Cancer. 102:1555-77.
Written Opinion for PCT/US17/066709 (Published as WO2018/12363) owned by Evelo Biosciences, Inc.
Written Opinion for PCT/US2017/066709 (Published as WO2018/112365) owned by Evelo Biosciences, Inc.
Wrzosek, et al., Bacteroides thetaiotaomicron and Faecalibacterium prausnitzii influence the production of mucus glycans and the development of globlet cells in the colonic epithelium of a gnotobiotic model rodent. BMC biology, 2013;11(61):1-13.
Wunderlich, P.F. et al., Double-blind report on the efficacy of lactic acid-producing enterococcus SF68 in the prevention of antibiotic-associated diarrhoea and in the treatment of acute diarrhoea. The journal of international medical research. 1989; 17: 333-338.
Xie et al. Short communication: Modulation of the small intestinal microbial community composition over short-term or long-term administration with Lactobacillus plantarum ZDY2013. 2016. Journal Dairy Sci. 99:6913-6921.
Xu, et al., A genomic view of the human-Bacteroides thetaiotaomicron symbiosis. Science. Mar. 28, 2003; 299(5615):2074-6.

(56) References Cited

OTHER PUBLICATIONS

Xu, et al., Differential development of murine dendritic cells by GM-CSF versus Flt3 ligand has implications for inflammation and trafficking. J. Immunology. 2007;179(11):7577-7584.

Xu, et al., The endogenous hydrogen sulfide producing enzyme cystathionine-i synthase contributes to visceral hypersensitivity in a rat model of irritable bowel syndrome. Molecular Pain, Biomed central, London, GB. Aug. 6, 2009; 5(1):p. 44.

Xu, J. et al., "Message from a human gut symbiont: sensitivity is a prerequisite for sharing", Trends in microbiology, 12(1), Jan. 1, 2004: pp. 21-28, XP055253932.

Yang, Changa et al., Non-invasive imaging of toll-like receptor 5 expressing using 131 labelled mAb in the mice bearing H22 tumors, Oncol. Lett. 2014., 7(6).1919-1924., Published online Apr. 12, 2014. DOI: 10.3892/ol.2014.2025.

Yang, J. et al., Targeting Th17 cells in autoimmune diseases. Trends Pharmacol Sci. Oct. 2014;35(10):493-500. doi: 10.1016/j.tips.2014. 07.006. Epub Aug. 14, 2014.

Yao, W., et al., Cultivation-Independent Analysis of the Development of the *Lactobacillus* spp. Community in the Intestinal TractofNewbornPiglets (20II)Agricultural Sciences in China, 10 (3), pp. 438-447.

Ye, X. et al., The Role of IL-23/Th17 Pathway in Patients with Primary Immune Thrombocytopenia. (2015) PLoS One. 10(1):e0117704.

Yin, X. et al., Combined effect of five single nucleotide polymorphisms related to IL23/Th17 pathway in the risk of psoriasis. Immunogenetics. Mar. 2014;66(3):215-8. doi: 10.1007/s00251-013-0756-z. Epub Jan. 14, 2014.

Yoon, et al., Structural basis of TLR5-flagellin recognition and signaling. Science. Feb. 2012; 335(6070):859-864.

Yoshinori Kohwi et al., "Antitumor Effect of Bifidobacterium Infant's in Mice", Gann, 69, 613-618; Oct. 1978.

Yq et al. Therapeutic Modulation of the Gut Microbiota in IBD—More Questions to Be Answered. (2016). J. Dig. Dis., Oct. 15, 1751-2980, 12422, Epub ahead of print.

Yu, Dah-Shyong et al., Bacille Calmette-Guerin can induce cellular apoptosis of urothelial cancer directly through toll-like receptor 7 activation, Kaohsiung Journal of Medical Sciences (2015) 31,391-397.

Yu, et al., Utilization of major fucosylated and sialylated human milk oligosaccharides by isolated human gut microbes. Glycobiology, 2013; 23(11):1281-1292.

Yu, N.Y., Wagner, J.R., Laird, M.R., Melli, G., Rey, S., Lo, R., et al. (2010a). PSORTb 3.0: improved protein subcellular localization prediction with refined localization subcategories and predictive capabilities for all prokaryotes. Bioinformatics 26(13), 1608-1615. doi: 10.1093/bioinformatics/btq249.

Yun, J.H., et al., Isolation and characterization of potential pro biotic lactobacilli from pig feces (2009). Journal of Basic Microbiology, 49 (2), pp. 220-226.

Yurdusev, N. et al., Antagonistic Effect Exerted by Three Strictly Anaerobic Strains Against Various Strains of Clostridium Perfringens in Gnotobiotic Rodent Intestines. Can J Microbiol 33, 226-231 (1987).

Yurdusev, N. et al., InfectInunun 57,724-731 (1989).

Yutin, N. and Galperin, M.Y., A genomic update on clostridial phylogeny:Gram-negative spore formers and other misplaced clostridia. Environmental microbiology. Oct. 2013; 15(10): 2631-2641.

Zhang, B. et al., Oral administration of enterococcus faecalis FK-23 suppresses Th17 cell development and attenuates allergic airway responses in mice. International journal of molecular medicine. 2012; 30:248-254.

Zhang, B. et al., The Prevalence of Th17 Cells in Patients With Gastric Cancer. 2008. Biochem Biophys Res Commun 374 (3), 533-537.

Zhang, et al., The Activation of NF-κB in Infiltrated Mononuclear Cells Negatively Correlates with Treg Cell Frequency in Oral Lichen Planus. Inflammation. Aug. 2015;38(4):1683-9. doi: 10.1007/s10753-015-0145-x.

Zheng, B. et al., Bifidobacteriu breve attenuates murine dextran sodium sulfate-induced colitis and increases regulatory T cell responses. PLoS one. May 2014; 9(5).

Zheng, B., van Bergenhenegouwen, J., Overbeek, S., van de Kant, H.J., Garssen, J., Folkerts, G., et al. (2014). Bifidobacterium breve attenuates murine dextran sodium sulfate-induced colitis and increases regulatory T cell responses. PLoS One 9(5), e95441. doi: 10.1371/journal.pone.0095441.

Zheng, Bin et al., Bifodobacterium breve Attenuates Murine Dexran Doium Sulfate-Induced Colitis and Increases Regulatory T Cell Responses, PLoS One, vol. 9, Isue 5, e95441, May 2014.

Zhongyuan, T. et al., The inflammation regulation effects of enterococcus faecium HDRsEf1 on human enterocyte-like HT-29 cells. Animal cells and systems. Mar. 2016;20(2):70-76.

Zhou et al. Central and peripheral hypersensitivity in the irritable bowel syndrome. 2010. Pain. 148(3): 454-461.

Zhu, S. and Qian, Y., IL-17/IL-17 receptor system in autoimmune disease: mechanisms and therapeutic potential. Clinical Science (2012) 122, 487-511.

Zitomersky, N. et al., Characterization of Adherent Bacteroidales from Intestinal Biopsies of Children and Young Adults with Inflammatory Bowel Disease. PLoS one. 2013; 8(6).

Zitvogel, et al., Type I interferons in anticancer immunity. Nature Reviews. Jul. 2015:405-414.

Genbank Accession No. AA075294.1, possible Pirin family protein [Bacteroides thetaiotaomicron VPI-5482], accessed Oct. 5, 2020.

Baohua Liu et al., Jiezhichang Liangxing Jibing Waike Zhilia, Surgical treatment of benign colorectal diseases, 2012, 4 pages, ISBN 978-7-5091-6025-1.

Liu, Fange et al., "Pirin is an iron-dependent redox regulator of NF-κB", Proceedings of the National Academy of Sciences Jun. 11, 2013, 110 (24) 9722-9727; DOI: 10.1073/Pnas.1221743110 Epub May 28, 2013.

FIG. 1A

| | | |
|---|---|---|
| HP | 1 | --mkkvidrassrgyfnhgwlkthhtfsfanyynperihfgalrvlnddsvdpsmgfdthphknmevisiplkgylrhgd |
| Rec 1 HP | 1 | gtmkkvidrassrgyfnhgwlkthhtfsfanyynperihfgalrvlnddsvdpsmgfdthphknmevisiplkgylrhgd |
| Rec 2 HP | 1 | gtmkkvidrassrgyfnhgwlkthhtfsfanyynperihfgalrvlnddsvdpsmgfdthphknmevisiplkgylrhgd |
| HP | 235 | svqntktitpgdiqvmstgsgiyhseyndskeeqleflqiwvfprientkpeynnfdirpllkpnelslfispngktpas |
| Rec 1 HP | 241 | svqntktitpgdiqvmstgsgiyhseyndskeeqleflqiwvfprientkpeynnfdirpllkpnelslfispngktpas |
| Rec 2 HP | 241 | svqntktitpgdiqvmstgsgiyhseyndskeeqleflqiwvfprientkpeynnfdirpllkpnelslfispngktpas |
| HP | 475 | ikqdawfsmgdfdtertieycmhqegngaylfviegeisvadehlakrdgigiwdtksfsiratkgtkllvmevpm --- |
| Rec 1 HP | 481 | ikqdawfsmgdfdtertieycmhqegngaylfviegeisvadehlakrdgigiwdtksfsiratkgtkllvmevpm el |
| Rec 2 HP | 481 | ikqdawfsmgdfdtertieycmhqegngaylfviegeisvadehlakrdgigiwdtksfsiratkgtkllvmevpm el |

*FIG. 1B*

SEQUENCE LISTING

<160> NUMBER OF SEQ ID NOS: 8

<210> SEQ ID NO 1
<211> LENGTH: 705
<212> TYPE: DNA
<213> ORGANISM: Bacteroides thetaiotaomicron VPI-5482

<400> SEQUENCE: 1

| | | | | | |
|---|---|---|---|---|---|
| atgaaaaaag | taatcgacag | agcttcatca | agaggctatt | taatcatgg | ctggctcaaa | 60 |
| acccaccaca | cattcagttt | tgctaactat | tacaatccgg | aaagaatcca | tttcggagcc | 120 |
| ttgcgagtgc | tgaatgatga | cagtgtagac | ccgtcgatgg | gatttgatac | tcatccacat | 180 |
| aaaaatatgg | aagtaatttc | cattccgttg | aaagggtatc | tgagacatgg | cgacagtgta | 240 |
| caaaatacga | aaacgattac | tcccggtgat | atccaagtga | tgagtacggg | cagtggtatc | 300 |
| tatcatagtg | agtataacga | cagcaaggaa | gaacaattgg | aattcctgca | aatatgggta | 360 |
| ttcccccgaa | tcgagaatac | gaaacccgaa | tataacaatt | tcgatatacg | tccgctgctg | 420 |
| aaaccgaacg | agttatctct | gttcatttca | ccgaacggca | agacaccggc | tccatcaaa | 480 |
| caggatgcct | ggttctctat | gggagacttc | gatacgaaa | gaaccatcga | atattgtatg | 540 |
| catcaggaag | gtaacggagc | ttatctgttt | gtgatagaag | agagatcag | cgtggccgat | 600 |
| gaacatctgg | ccaaacgtga | cggcatcgga | atatgggata | ccaaaagctt | ctctatccgt | 660 |
| gctactaaag | ggaccaaaact | tctggtaatg | aagtaccca | tgtaa | | 705 |

<210> SEQ ID NO 2
<211> LENGTH: 234
<212> TYPE: PRT
<213> ORGANISM: Bacteroides thetaiotaomicron VPI-5482

<400> SEQUENCE: 2

Met Lys Lys Val Ile Asp Arg Ala Ser Ser Arg Gly Tyr Phe Asn His
1               5                   10                  15

Gly Trp Leu Lys Thr His His Thr Phe Ser Phe Ala Asn Tyr Tyr Asn
            20                  25                  30

Pro Glu Arg Ile His Phe Gly Ala Leu Arg Val Leu Asn Asp Asp Ser
        35                  40                  45

Val Asp Pro Ser Met Gly Phe Asp Thr His Pro His Lys Asn Met Glu
    50                  55                  60

Val Ile Ser Ile Pro Leu Lys Gly Tyr Leu Arg His Gly Asp Ser Val
65                  70                  75                  80

Gln Asn Thr Lys Thr Ile Thr Pro Gly Asp Ile Gln Val Met Ser Thr
                85                  90                  95

Gly Ser Gly Ile Tyr His Ser Glu Tyr Asn Asp Ser Lys Glu Glu Gln
            100                 105                 110

Leu Glu Phe Leu Gln Ile Trp Val Phe Pro Arg Ile Glu Asn Thr Lys
        115                 120                 125

Pro Glu Tyr Asn Asn Phe Asp Ile Arg Pro Leu Leu Lys Pro Asn Glu
    130                 135                 140

Leu Ser Leu Phe Ile Ser Pro Asn Gly Lys Thr Pro Ala Ser Ile Lys
145                 150                 155                 160

Gln Asp Ala Trp Phe Ser Met Gly Asp Phe Asp Thr Glu Arg Thr Ile
                165                 170                 175

Glu Tyr Cys Met His Gln Glu Gly Asn Gly Ala Tyr Leu Phe Val Ile
            180                 185                 190

Glu Gly Glu Ile Ser Val Ala Asp Glu His Leu Ala Lys Arg Asp Gly

```
                195                 200                 205
Ile Gly Ile Trp Asp Thr Lys Ser Phe Ser Ile Arg Ala Thr Lys Gly
    210                 215                 220

Thr Lys Leu Leu Val Met Glu Val Pro Met
225                 230
```

<210> SEQ ID NO 3
<211> LENGTH: 720
<212> TYPE: DNA
<213> ORGANISM: Artificial Sequence
<220> FEATURE:
<223> OTHER INFORMATION: B. thetaiotaomicron VPI-5482 sequence codon
      optimised for expression in E. coli

<400> SEQUENCE: 3

```
ggtaccatga aaaaagtgat tgatcgtgcg agcagccgtg gctatttta ccatggctgg      60
ctgaaaaccc atcatacctt tagcttcgcg aactattata atccggaacg cattcatttt     120
ggcgcgctgc gtgtgctgaa cgatgatagc gtggatccga gcatgggctt tgatacccat    180
ccgcacaaaa acatggaagt gattagcatt ccgctgaaag gctatctgcg tcatggcgat    240
agcgtgcaga caccaaaaac cattaccccg ggtgatattc aggtgatgag caccggcagc    300
ggcatttatc atagcgaata aacgatagc aaagaagaac agctggaatt tctgcagatt     360
tgggtgtttc gcgtattga aaacaccaaa ccggaatata caactttga tattcgcccg      420
ctgctgaaac cgaacgaact gagcctgttt attagcccga acggcaaaac cccggcgagc    480
attaaacagg atgcgtggtt tagcatgggc gatttgata ccgaacgcac cattgaatat     540
tgcatgcatc aggaaggcaa cggcgcgtac ctgtttgtga ttgaaggcga aattagcgtg    600
gcggatgaac atctggccaa acgtgatggc attggcattt gggataccaa aagcttcagc    660
attcgtgcga ccaaaggcac caaactgctg gtgatggaag tgccgatgta ataagagctc    720
```

<210> SEQ ID NO 4
<211> LENGTH: 238
<212> TYPE: PRT
<213> ORGANISM: Artificial Sequence
<220> FEATURE:
<223> OTHER INFORMATION: B. thetaiotaomicron VPI-5482 sequence codon
      optimised for expression in E. coli

<400> SEQUENCE: 4

```
Gly Thr Met Lys Lys Val Ile Asp Arg Ala Ser Ser Arg Gly Tyr Phe
1               5                   10                  15

Asn His Gly Trp Leu Lys Thr His His Thr Phe Ser Phe Ala Asn Tyr
            20                  25                  30

Tyr Asn Pro Glu Arg Ile His Phe Gly Ala Leu Arg Val Leu Asn Asp
        35                  40                  45

Asp Ser Val Asp Pro Ser Met Gly Phe Asp Thr His Pro His Lys Asn
    50                  55                  60

Met Glu Val Ile Ser Ile Pro Leu Lys Gly Tyr Leu Arg His Gly Asp
65                  70                  75                  80

Ser Val Gln Asn Thr Lys Thr Ile Thr Pro Gly Asp Ile Gln Val Met
                85                  90                  95

Ser Thr Gly Ser Gly Ile Tyr His Ser Glu Tyr Asn Asp Ser Lys Glu
            100                 105                 110

Glu Gln Leu Glu Phe Leu Gln Ile Trp Val Phe Pro Arg Ile Glu Asn
        115                 120                 125

Thr Lys Pro Glu Tyr Asn Asn Phe Asp Ile Arg Pro Leu Leu Lys Pro
```

```
                    130             135                 140
Asn Glu Leu Ser Leu Phe Ile Ser Pro Asn Gly Lys Thr Pro Ala Ser
145                 150                 155                 160

Ile Lys Gln Asp Ala Trp Phe Ser Met Gly Asp Phe Asp Thr Glu Arg
                165                 170                 175

Thr Ile Glu Tyr Cys Met His Gln Glu Gly Asn Gly Ala Tyr Leu Phe
            180                 185                 190

Val Ile Glu Gly Glu Ile Ser Val Ala Asp Glu His Leu Ala Lys Arg
        195                 200                 205

Asp Gly Ile Gly Ile Trp Asp Thr Lys Ser Phe Ser Ile Arg Ala Thr
    210                 215                 220

Lys Gly Thr Lys Leu Leu Val Met Glu Val Pro Met Glu Leu
225                 230                 235
```

<210> SEQ ID NO 5
<211> LENGTH: 720
<212> TYPE: DNA
<213> ORGANISM: Artificial Sequence
<220> FEATURE:
<223> OTHER INFORMATION: B. thetaiotaomicron VPI-5482 sequence codon
      optimised for expression in L. lactis

<400> SEQUENCE: 5

```
ggtaccatga aaaagttat tgatcgtgct tcatcacgtg gatattttaa tcatggatgg    60
cttaaaactc atcatacatt tagttttgcc aattattata tccagaacg tattcattt   120
ggtgctcttc gtgttcttaa tgatgattca gttgatccat caatgggatt tgatacacat   180
ccacataaaa atatggaagt tatttcaatt ccacttaaag gatatcttcg tcatggtgat   240
tcagttcaaa atacaaaaac aattacacct ggagatattc aagttatgtc tacaggatca   300
ggaatttatc attcagaata taatgattca aaagaagaac aacttgaatt tcttcaaatt   360
tgggtctttc cacgtattga aaatacaaaa ccagaatata taatttcga cattcgtcca   420
cttcttaaac caaatgaact ttcacttttt atctcaccaa atggaaaaac accagcttca   480
attaaacaag atgcttggtt ttcaatggga gattttgata cagaacgtac aattgaatat   540
tgtatgcatc aagaaggtaa cggcgcttat ctttttgtta ttgaaggtga aatttcagtt   600
gctgatgaac atcttgctaa acgtgatgga attggaattt gggatacaaa atcattttca   660
attcgtgcta caaaaggtac aaaacttctt gttatggaag ttccaatgta ataagagctc   720
```

<210> SEQ ID NO 6
<211> LENGTH: 238
<212> TYPE: PRT
<213> ORGANISM: Artificial Sequence
<220> FEATURE:
<223> OTHER INFORMATION: B. thetaiotaomicron VPI-5482 sequence codon
      optimised for expression in L. lactis

<400> SEQUENCE: 6

```
Gly Thr Met Lys Lys Val Ile Asp Arg Ala Ser Ser Arg Gly Tyr Phe
1               5                   10                  15

Asn His Gly Trp Leu Lys Thr His His Thr Phe Ser Phe Ala Asn Tyr
            20                  25                  30

Tyr Asn Pro Glu Arg Ile His Phe Gly Ala Leu Arg Val Leu Asn Asp
        35                  40                  45

Asp Ser Val Asp Pro Ser Met Gly Phe Asp Thr His Pro His Lys Asn
    50                  55                  60

Met Glu Val Ile Ser Ile Pro Leu Lys Gly Tyr Leu Arg His Gly Asp
```

```
              65                  70                  75                  80
Ser Val Gln Asn Thr Lys Thr Ile Thr Pro Gly Asp Ile Gln Val Met
                    85                  90                  95

Ser Thr Gly Ser Gly Ile Tyr His Ser Glu Tyr Asn Asp Ser Lys Glu
                100                 105                 110

Glu Gln Leu Glu Phe Leu Gln Ile Trp Val Phe Pro Arg Ile Glu Asn
                115                 120                 125

Thr Lys Pro Glu Tyr Asn Asn Phe Asp Ile Arg Pro Leu Leu Lys Pro
            130                 135                 140

Asn Glu Leu Ser Leu Phe Ile Ser Pro Asn Gly Lys Thr Pro Ala Ser
145                 150                 155                 160

Ile Lys Gln Asp Ala Trp Phe Ser Met Gly Asp Phe Asp Thr Glu Arg
                165                 170                 175

Thr Ile Glu Tyr Cys Met His Gln Glu Gly Asn Gly Ala Tyr Leu Phe
                180                 185                 190

Val Ile Glu Gly Glu Ile Ser Val Ala Asp Glu His Leu Ala Lys Arg
            195                 200                 205

Asp Gly Ile Gly Ile Trp Asp Thr Lys Ser Phe Ser Ile Arg Ala Thr
            210                 215                 220

Lys Gly Thr Lys Leu Leu Val Met Glu Val Pro Met Glu Leu
225                 230                 235

<210> SEQ ID NO 7
<211> LENGTH: 234
<212> TYPE: PRT
<213> ORGANISM: Bacteroides thetaiotaomicron VPI-5482

<400> SEQUENCE: 7

Met Lys Lys Val Ile His Lys Ala Asp Thr Arg Gly His Ser Gln Tyr
1               5                   10                  15

Asp Trp Leu Asp Ser Tyr His Thr Phe Ser Phe Asp Glu Tyr Phe Asp
            20                  25                  30

Ser Asp Arg Ile Asn Phe Gly Ala Leu Arg Val Leu Asn Asp Asp Lys
        35                  40                  45

Val Ala Pro Gly Glu Gly Phe Gln Thr His Pro His Lys Asn Met Glu
    50                  55                  60

Ile Ile Ser Ile Pro Leu Lys Gly His Leu Gln His Gly Asp Ser Lys
65                  70                  75                  80

Lys Asn Ser Arg Ile Ile Thr Val Gly Glu Ile Gln Thr Met Ser Ala
                85                  90                  95

Gly Thr Gly Ile Phe His Ser Glu Val Asn Ala Ser Pro Val Glu Pro
                100                 105                 110

Val Glu Phe Leu Gln Ile Trp Ile Met Pro Arg Glu Arg Asn Thr His
            115                 120                 125

Pro Val Tyr Lys Asp Phe Ser Ile Lys Glu Leu Glu Arg Pro Asn Glu
        130                 135                 140

Leu Ala Val Ile Val Ser Pro Asp Gly Ser Thr Pro Ala Ser Leu Leu
145                 150                 155                 160

Gln Asp Thr Trp Phe Ser Ile Gly Lys Val Glu Ala Gly Lys Lys Leu
                165                 170                 175

Gly Tyr His Leu His Gln Ser His Gly Gly Val Tyr Ile Phe Leu Ile
            180                 185                 190

Glu Gly Glu Ile Val Val Asp Gly Glu Val Leu Lys Arg Arg Asp Gly
        195                 200                 205
```

```
Met Gly Val Tyr Asp Thr Lys Ser Phe Glu Leu Glu Thr Leu Lys Asp
    210                 215                 220

Ser His Ile Leu Leu Ile Glu Val Pro Met
225                 230

<210> SEQ ID NO 8
<211> LENGTH: 234
<212> TYPE: PRT
<213> ORGANISM: Bacteroides thetaiotaomicron CAG:40

<400> SEQUENCE: 8

Met Lys Lys Val Ile His Lys Ala Asp Thr Arg Gly His Ser Gln Tyr
1               5                   10                  15

Asp Trp Leu Asp Ser Tyr His Thr Phe Ser Phe Asp Glu Tyr Phe Asp
                20                  25                  30

Ser Asp Arg Ile Asn Phe Gly Ala Leu Arg Val Leu Asn Asp Asp Lys
            35                  40                  45

Val Ala Pro Gly Glu Gly Phe Gln Thr His Pro His Lys Asn Met Glu
        50                  55                  60

Ile Ile Ser Ile Pro Leu Lys Gly His Leu Gln His Gly Asp Ser Lys
65                  70                  75                  80

Lys Asn Ser Arg Ile Ile Thr Val Gly Glu Ile Gln Thr Met Ser Ala
                85                  90                  95

Gly Thr Gly Ile Phe His Ser Glu Val Asn Ala Ser Pro Val Glu Pro
            100                 105                 110

Val Glu Phe Leu Gln Ile Trp Ile Met Pro Arg Glu Arg Asn Thr His
        115                 120                 125

Pro Val Tyr Lys Asp Phe Ser Ile Lys Glu Leu Glu Arg Pro Asn Glu
130                 135                 140

Leu Ala Val Ile Val Ser Pro Asp Gly Ser Thr Pro Ala Ser Leu Leu
145                 150                 155                 160

Gln Asp Thr Trp Phe Ser Ile Gly Lys Val Glu Ala Gly Lys Lys Leu
                165                 170                 175

Gly Tyr His Leu His Gln Ser His Gly Gly Val Tyr Ile Phe Leu Ile
            180                 185                 190

Glu Gly Glu Ile Val Val Asp Gly Glu Val Leu Lys Arg Arg Asp Gly
        195                 200                 205

Met Gly Val Tyr Asp Thr Lys Ser Phe Glu Leu Glu Thr Leu Lys Asp
    210                 215                 220

Ser His Ile Leu Leu Ile Glu Val Pro Met
225                 230
```

PIRIN POLYPEPTIDE AND IMMUNE MODULATION

CROSS-REFERENCE

This application is a division of U.S. application Ser. No. 15/631,952, filed Jun. 23, 2017, now U.S. Pat. No. 10,456,444, which is a continuation of International Application No. PCT/GB2015/054113, filed Dec. 22, 2015, which claims the benefit of Great Britain Application No. 1423083.3, filed Dec. 23, 2014, which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jan. 7, 2016, is named p067638WO_sequence_listing.txt and is 14,000 bytes in size.

FIELD OF INVENTION

The present invention relates to the polypeptide HP or a polynucleotide sequence encoding polypeptide HP or a host cell comprising said polynucleotide sequence or a host cell comprising an expression vector comprising said polynucleotide sequence for various therapeutic and nutritional uses.

BACKGROUND

*Bacteroides thetaiotaomicron* has potent anti-inflammatory effects in vitro and in vivo (Kelly et al. Commensal anaerobic gut bacteria attenuate inflammation by regulating nuclear-cytoplasmic shuttling of PPAR-gamma and RelA. Nat Immunol. 2004 January; 5(1):104-12). It modulates molecular signalling pathways of NF-κB (Kelly et al, Commensal anaerobic gut bacteria attenuate inflammation by regulating nuclear-cytoplasmic shuttling of PPAR-gamma and RelA. Nat Immunol. 2004 January; 5(1):104-12). In particular, it stops binding of the active component (RelA) of NF-κB to key genes in the nucleus, thereby preventing the activation of pro-inflammatory pathways (Kelly et al, Commensal anaerobic gut bacteria attenuate inflammation by regulating nuclear-cytoplasmic shuttling of PPAR-gamma and RelA. Nat Immunol. 2004 January; 5(1):104-12).

The full genome of *B. thetaiotaomicron* was sequenced and annotated by the Gordon Group (Washington University School of Medicine, USA) in 2003 [Xu et al, A genomic view of the human-*Bacteroides thetaiotaomicron* symbiosis. Science. 2003 Mar. 28; 299(5615):2074-6].

STATEMENTS OF INVENTION

Surprisingly, the present inventors found that HP (a hypothetical protein; gene ID 1075517; gene symbol BT_0187; accession number AAO75294) identified from the genome of *Bacteroides thetaiotaomicron* (VPI5482), a pirin-related protein; deposited as AAO75294.1, which reduces inflammation in cells.

The present invention provides polypeptide HP, or a polynucleotide sequence encoding polypeptide HP, or a host cell comprising said polynucleotide sequence, or a host cell comprising an expression vector comprising said polynucleotide sequence, for use in the treatment and/or prevention of a disorder in a subject; wherein said disorder is an inflammatory disorder and/or an autoimmune disorder; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In another aspect, the present invention provides polypeptide HP, or a polynucleotide sequence encoding polypeptide HP, or a host cell comprising said polynucleotide sequence, or a host cell comprising an expression vector comprising said polynucleotide sequence, for use in modulating the inflammation of a cell, a tissue or an organ in a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In a further aspect, the present invention provides polypeptide HP, or a polynucleotide sequence encoding polypeptide HP, or a host cell comprising said polynucleotide sequence, or a host cell comprising an expression vector comprising said polynucleotide sequence, for use in improving intestine barrier integrity in a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in another aspect, polypeptide HP, or a polynucleotide sequence encoding polypeptide HP, or a host cell comprising said polynucleotide sequence, or a host cell comprising an expression vector comprising said polynucleotide sequence, for use in modifying the bacterial composition in a tissue or organ to provide a more beneficial microbiota. For example, the invention may be of use in reducing the level of one or more types of lactose fermenting bacteria (such as *E. coli*) in a tissue or an organ in a subject and/or reducing the level of one or more types of non-lactose fermenting bacteria in a tissue or an organ in a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in a further aspect, polypeptide HP, or a polynucleotide sequence encoding polypeptide HP, or a host cell comprising said polynucleotide sequence, or a host cell comprising an expression vector comprising said polynucleotide sequence, for use in maintaining the length of the large intestine and/or small intestine of a subject, (e.g. said subject has IBD); wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In a further aspect, the present invention provides polypeptide HP, or a polynucleotide sequence encoding polypeptide HP, or a host cell comprising said polynucleotide sequence, or a host cell comprising an expression vector comprising said polynucleotide sequence, for use in reducing disruption to the intestine (such as the large intestine) of a subject, (e.g. said subject has IBD); wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In another aspect, the present invention provides polypeptide HP, or a polynucleotide sequence encoding polypeptide HP, or a host cell comprising said polynucleotide sequence, or a host cell comprising an expression vector comprising said polynucleotide sequence, for use in regulating the expression of one or more pro-inflammatory genes and/or one or more barrier integrity genes in a cell or cells of a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in another aspect, polypeptide HP, or a polynucleotide sequence encoding polypeptide HP, or a host cell comprising said polynucleotide sequence, or a host cell comprising an expression vector comprising said polynucleotide sequence, for use in regulating the expression in a cell or cells of a subject of one or more genes selected from the group consisting of regenerating islet-derived 3 beta gene (Reg3b), resistin-like gamma resistin like beta gene (Retnlg|Retnlb), sucrase-isomaltase (alpha-glucosidase) gene (Si), defensin alpha 24 gene (Defa24), hydroxysteroid 11-beta dehydrogenase 2 gene (Hsd11b2), hydroxysteroid (17-beta) dehydrogenase 2 gene (Hsd17b2), resistin-Like Molecule-beta (RELMb), and nuclear receptor 1D1 thyroid hormone receptor alpha gene (Nr1d1|Thra); (e.g. said subject has IBD); wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In a further aspect, the present invention provides polypeptide HP or a polynucleotide sequence encoding polypeptide HP, or a host cell comprising said polynucleotide sequence, or a host cell comprising an expression vector comprising said polynucleotide sequence, for use in reducing the activation of pro-inflammatory pathways in a cell or cells of a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in a further aspect, polypeptide HP, or a polynucleotide sequence encoding polypeptide HP, or a host cell comprising said polynucleotide sequence, or a host cell comprising an expression vector comprising said polynucleotide sequence, for use in reducing the activity and/or expression of NF-κβ in a cell or cells (such as epithelial cells, epidermal cells, neuronal cells, and/or pancreatic cells) of a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in another aspect, polypeptide HP, or a polynucleotide sequence encoding polypeptide HP, or a host cell comprising said polynucleotide sequence, or a host cell comprising an expression vector comprising said polynucleotide sequence, for use in improving alimentary canal health in a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in a further aspect, a pharmaceutical composition comprising polypeptide HP, or a polynucleotide sequence encoding polypeptide HP, or a host cell comprising said polynucleotide sequence, or a host cell comprising an expression vector comprising said polynucleotide sequence, and a pharmaceutically acceptable excipient, carrier or diluent; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In a further aspect, the present invention provides a nutritional supplement comprising polypeptide HP, or a polynucleotide sequence encoding polypeptide HP, or a host cell comprising said polynucleotide sequence, or a host cell comprising an expression vector comprising said polynucleotide sequence, and a nutritional acceptable excipient, carrier or diluent; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In another aspect, the present invention provides a feedstuff, food product, dietary supplement, or food additive comprising polypeptide HP, or a polynucleotide sequence encoding polypeptide HP, or a host cell comprising said polynucleotide sequence, or a host cell comprising an expression vector comprising said polynucleotide sequence; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides in a further aspect a process for producing a pharmaceutical composition according to the present invention, said process comprising admixing polypeptide HP, or a polynucleotide sequence encoding polypeptide HP, or a host cell comprising said polynucleotide sequence, or a host cell comprising an expression vector comprising said polynucleotide sequence with a pharmaceutically acceptable excipient, carrier or diluent; optionally said polypeptide or polynucleotide sequence or host cell is encapsulated in said process; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In a further aspect, the present invention provides a process for producing a nutritional supplement according to the present invention, said process comprising admixing polypeptide HP, or a polynucleotide sequence encoding polypeptide HP, or a host cell comprising said polynucleotide sequence, or a host cell comprising an expression vector comprising said polynucleotide sequence with a nutritionally acceptable excipient, carrier or diluent; optionally said polypeptide or polynucleotide is encapsulated in said process; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In another aspect, the present invention provides a process for producing a feedstuff, food product, dietary supplement, or food additive according to the present invention, said process comprising admixing polypeptide HP, or a polynucleotide sequence encoding polypeptide HP, or a host cell comprising said polynucleotide sequence, or a host cell comprising an expression vector comprising said polynucleotide sequence with a feedstuff, food product, dietary supplement, food additive or ingredient thereof; optionally said polypeptide or polynucleotide is encapsulated in said process; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in another aspect, a method for treating and/or preventing a disorder in a subject, wherein said method comprises administering to the subject polypeptide HP, or a polynucleotide sequence encoding polypeptide HP, or a host cell comprising said polynucleotide sequence, or a host cell comprising an expression vector comprising said polynucleotide sequence; wherein said polypeptide or polynucleotide sequence or host cell treats and/or prevents a disorder in the subject, wherein said disorder is an inflammatory disorder and/or an autoimmune disorder; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in a further aspect, a method for modulating the inflammation of a tissue or an organ in a subject wherein said method comprises administering to the subject polypeptide HP, or a polynucleotide sequence encoding polypeptide HP, or a host cell comprising said polynucleotide sequence, or a host cell comprising an expression vector comprising said polynucleotide sequence; wherein said polypeptide, polynucleotide sequence or host cell modulates the inflammation of a tissue or an organ in the subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In another aspect, the present invention provides a method for improving intestine barrier integrity in a subject wherein said method comprises administering to the subject polypeptide HP, or a polynucleotide sequence encoding polypeptide HP, or a host cell comprising said polynucleotide sequence, or a host cell comprising an expression vector comprising said polynucleotide sequence; wherein said polypeptide or polynucleotide sequence or host cell improves intestine barrier integrity in the subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in another aspect, a method for reducing the level of one or more types of lactose fermenting bacteria (such as *E. coli*) in a tissue or an organ in a subject and/or reducing the level of one or more types of non-lactose fermenting bacteria in a tissue or an organ in a subject, wherein said method comprises administering to the subject polypeptide HP, or a polynucleotide sequence encoding polypeptide HP, or a host cell comprising said polynucleotide sequence, or a host cell comprising an expression vector comprising said polynucleotide sequence; wherein said polypeptide, polynucleotide sequence or host cell reduces the level of one or more types of lactose fermenting bacteria (such as *E. coli*) in a tissue or an organ in the subject and/or reduces the level of one or more types of non-lactose fermenting bacteria in a tissue or an organ in the subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in a further aspect, a method for maintaining the length of the large intestine and/or small intestine of a subject wherein said method comprises administering to the subject polypeptide HP, or a polynucleotide sequence encoding polypeptide HP, or a host cell comprising said polynucleotide sequence, or a host cell comprising an expression vector comprising said polynucleotide sequence; (e.g. said subject has IBD); wherein said polypeptide or polynucleotide sequence or host cell maintains the length of the large intestine and/or small intestine of the subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In a further aspect, the present invention provides a method for reducing disruption to the intestine (e.g. the large intestine) of a subject wherein said method comprises administering to the subject polypeptide HP, or a polynucleotide sequence encoding polypeptide HP, or a host cell comprising said polynucleotide sequence, or a host cell comprising an expression vector comprising said polynucleotide sequence; (e.g. said subject has IBD); wherein said polypeptide or polynucleotide sequence or host cell reduces disruption to the intestine (e.g. large intestine) of the subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in another aspect, a method for regulating the expression of one or more pro-inflammatory or anti-inflammatory genes in a cell or cells of a subject wherein said method comprises administering to the subject polypeptide HP, or a polynucleotide sequence encoding polypeptide HP, or a host cell comprising said polynucleotide sequence, or a host cell comprising an expression vector comprising said polynucleotide sequence; wherein said polypeptide or polynucleotide sequence or host cell regulates the expression of one or more pro-inflammatory genes and/or anti-inflammatory genes in a cell or cells of the subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In another aspect, the present invention provides a method for regulating the expression of one or more genes in a cell or cells of a subject wherein said method comprises administering to the subject polypeptide HP, or a polynucleotide sequence encoding polypeptide HP, or a host cell comprising said polynucleotide sequence, or a host cell comprising an expression vector comprising said polynucleotide sequence, to said subject; wherein said polypeptide or polynucleotide sequence or host cell regulates the expression of one or more genes in a cell or cells of the subject; wherein the one or more genes are selected from the group consisting of regenerating islet-derived 3 beta gene (Reg3b), resistin-like gamma resistin like beta gene (Retnlg|Retnlb), sucrase-isomaltase (alpha-glucosidase) gene (Si), defensin alpha 24 gene (Defa24), hydroxysteroid 11-beta dehydrogenase 2 gene (Hsd11b2), hydroxysteroid (17-beta) dehydrogenase 2 gene (Hsd17b2), resistin-Like Molecule-beta (RELMb), and nuclear receptor 1D1 thyroid hormone receptor alpha gene (Nr1d1|Thra); (e.g. said subject has IBD); wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in a further aspect, a method for reducing the activation of pro-inflammatory pathways in a cell or cells of a subject wherein said method comprises administering to the subject polypeptide HP, or a polynucleotide sequence encoding polypeptide HP, or a host cell comprising said polynucleotide sequence, or a host cell comprising an expression vector comprising said polynucleotide sequence; wherein said polypeptide or polynucleotide sequence or host cell reduces the activation of pro-inflammatory pathways in a cell or cells of the subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In a further aspect, the present invention provides a method for reducing the activity and/or expression of NF-κβ in a cell or cells (such as epithelial cells, epidermal cells, neuronal cells, and/or pancreatic cells) of a subject wherein said method comprises administering to the subject polypeptide HP, or a polynucleotide sequence encoding polypeptide HP, or a host cell comprising said polynucleotide sequence, or a host cell comprising an expression vector comprising said polynucleotide sequence; wherein said polypeptide or polynucleotide or host cell reduces the activity and/or expression of NF-κβ in a cell or cells (such as epithelial cells, epidermal cells, neuronal cells, and/or pancreatic cells) of the subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In another aspect, the present invention provides a method for improving alimentary canal health in a subject wherein said method comprises administering to the subject polypeptide HP, or a polynucleotide sequence encoding polypeptide HP, or a host cell comprising said polynucleotide sequence, or a host cell comprising an expression vector comprising said polynucleotide sequence; wherein said polypeptide or polynucleotide sequence or host cell improves alimentary canal health in the subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in a further aspect, use of polypeptide HP, or a polynucleotide sequence encoding polypeptide HP, or a host cell comprising said polynucleotide sequence, or a host cell comprising an expression vector comprising said polynucleotide sequence, for the manufacture of a medicament for the treatment and/or prevention of a disorder in a subject, wherein said disorder is an inflammatory disorder and/or an autoimmune disorder; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in another aspect, use of polypeptide HP, or a polynucleotide sequence encoding polypeptide HP, or a host cell comprising said polynucleotide sequence, or a host cell comprising an expression vector comprising said polynucleotide sequence, for the manufacture of a medicament for modulating the inflammation of a tissue or an organ in a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In another aspect, the present invention provides use of polypeptide HP or a polynucleotide sequence encoding polypeptide HP, or a host cell comprising said polynucleotide sequence, or a host cell comprising an expression vector comprising said polynucleotide sequence, for the manufacture of a medicament for improving intestine barrier integrity in a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in a further aspect, use of polypeptide HP, or a polynucleotide sequence encoding polypeptide HP, or a host cell comprising said polynucleotide sequence, or a host cell comprising an expression vector comprising said polynucleotide sequence, for the manufacture of a medicament for maintaining the length of the large intestine and/or small intestine of a subject; (e.g. said subject has IBD); wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In a further aspect, the present invention provides use of a polypeptide HP, or a polynucleotide sequence encoding polypeptide HP, or a host cell comprising said polynucleotide sequence, or a host cell comprising an expression vector comprising said polynucleotide sequence, for the manufacture of a medicament for modifying the bacterial composition in a tissue or organ to provide a beneficial microbiota, preferably, for use in reducing the level of one or more types of lactose fermenting bacteria (such as *E. coli*) in a tissue or an organ in a subject and/or reducing the level of one or more types of non-lactose fermenting bacteria in a tissue or an organ in a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In another aspect, the present invention provides use of polypeptide HP, or a polynucleotide sequence encoding polypeptide HP, or a host cell comprising said polynucleotide sequence, or a host cell comprising an expression vector comprising said polynucleotide sequence, for the manufacture of a medicament for reducing disruption to the intestine (e.g. large intestine) of a subject; (e.g. said subject has IBD); wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in a further aspect, use of polypeptide HP, or a polynucleotide sequence encoding polypeptide HP, or a host cell comprising said polynucleotide sequence, or a host cell comprising an expression vector comprising said polynucleotide sequence, for the manufacture of a medicament for regulating the expression of one or more pro-inflammatory genes in a cell or cells of a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in another aspect, use of polypeptide HP, or a polynucleotide sequence encoding polypeptide HP, or a host cell comprising said polynucleotide sequence, or a host cell comprising an expression vector comprising said polynucleotide sequence, for the manufacture of a medicament for regulating the expression in a cell or cells of a subject of one or more genes selected from the group consisting of regenerating islet-derived 3 beta gene (Reg3b), resistin-like gamma resistin like beta gene (Retnlg|Retnlb), sucrase-isomaltase (alpha-glucosidase) gene (Si), defensin alpha 24 gene (Defa24), hydroxysteroid 11-beta dehydrogenase 2 gene (Hsd11b2), hydroxysteroid (17-beta) dehydrogenase 2 gene (Hsd17b2), resistin-Like Molecule-beta (RELMb), and nuclear receptor 1D1 thyroid hormone receptor alpha gene (Nr1d1|Thra) (e.g. said subject has IBD); wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In another aspect, the present invention provides use of polypeptide HP, or a polynucleotide sequence encoding polypeptide HP, or a host cell comprising said polynucleotide sequence, or a host cell comprising an expression vector comprising said polynucleotide sequence, for the manufacture of a medicament for reducing the activation of pro-inflammatory pathways in a cell or cells of a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

In a further aspect, the present invention provides use of a polypeptide HP, or a polynucleotide sequence encoding polypeptide HP, or a host cell comprising said polynucleotide sequence, or a host cell comprising an expression vector comprising said polynucleotide sequence, for the manufacture of a medicament for reducing the activity and/or expression of NF-κβ in a cell or cells (such as epithelial cells, epidermal cells, neuronal cells, and/or pancreatic cells) of a subject; wherein said polypeptide has at least 75% identity to SEQ ID NO 2, SEQ ID NO 4 or SEQ ID NO 6 or variants, homologues, fragments or derivatives thereof; and wherein said polynucleotide sequence encodes a polypeptide which has at least 75% identity to SEQ ID NO 2, SEQ ID NO 4 or SEQ ID NO 6 or variants, homologues, fragments or derivatives thereof and/or wherein said polynucleotide sequence has at least 75% identity to SEQ ID NO 1, SEQ ID NO 3 or SEQ ID NO 5 or variants, homologues, fragments or derivatives thereof.

The present invention provides, in another aspect, use of a polypeptide HP, or a polynucleotide sequence encoding polypeptide HP, or a host cell comprising said polynucleotide sequence, or a host cell comprising an expression vector comprising said polynucleotide sequence, for the manufacture of a medicament for improving alimentary canal health in a subject.

FIGURES

The invention is described with reference to the accompanying figures, wherein:

FIG. 1A shows an alignment of the polynucleotide sequences encoding HP (SEQ ID NO 1), *E. coli* optimised HP (Rec 1 HP—SEQ ID NO 3) and *L. lactis* optimised HP (Rec 2 HP—SEQ ID NO 5). HP is deposited with GenBank under accession number: AAO75294.1 and is described in GenBank as possible Pirin family protein [*Bacteroides thetaiotaomicron* VPI-5482].

FIG. 1B shows an alignment of the polypeptide sequences HP (SEQ ID NO 2), *E. coli* optimised HP (Rec 1 HP—SEQ ID NO 4) and *L. lactis* optimised HP (Rec 2 HP SEQ ID NO 6). HP is deposited with GenBank under accession number:

AAO75294.1 and is described in GenBank as possible Pirin family protein [*Bacteroides thetaiotaomicron* VPI-5482].

Figure 2A:
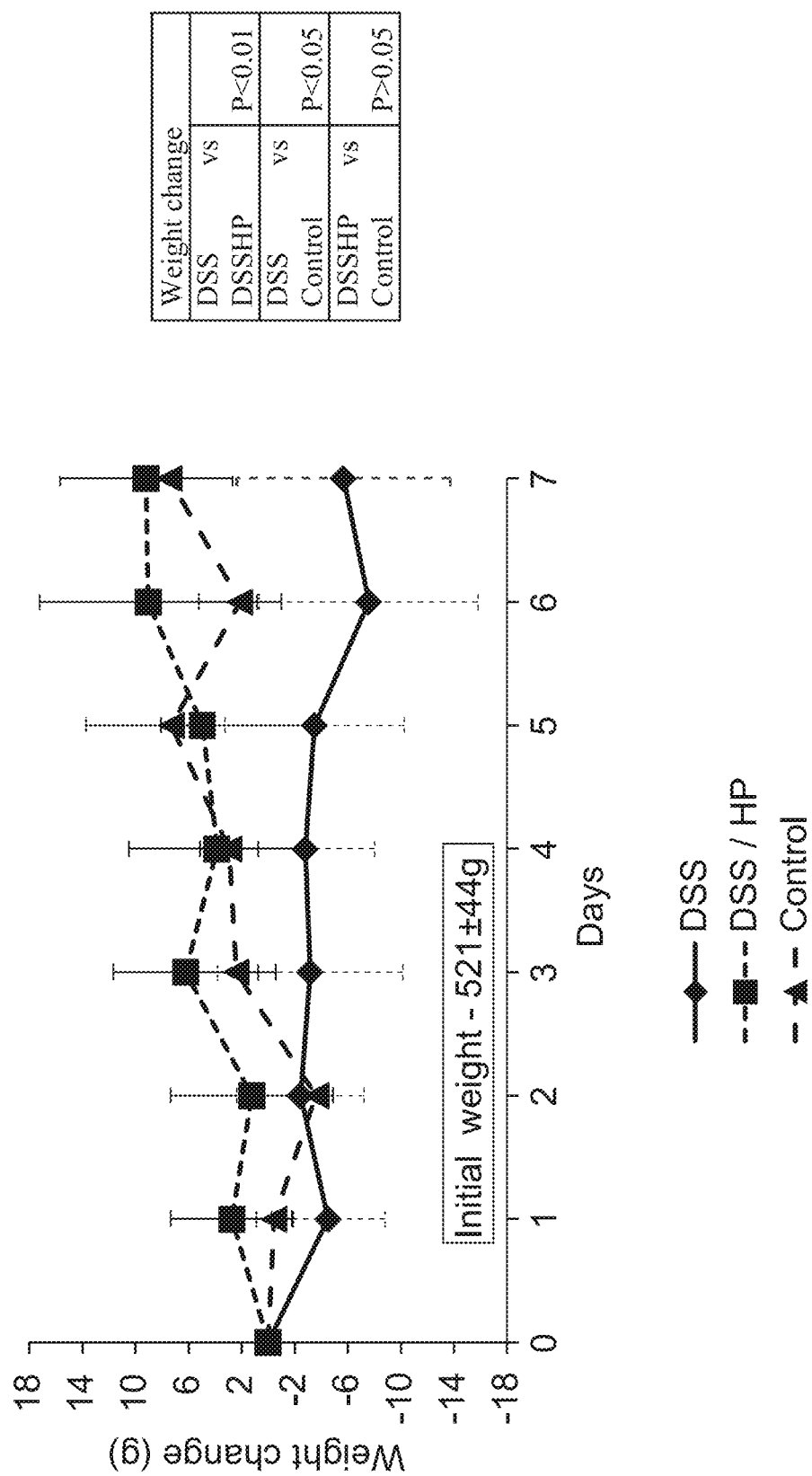

FIG. 2A shows the change in weight in rats given Dextran Sodium Sulphate (DSS) in water with (DSS/HP) or without (DSS) co-treatment with hypothetical protein (HP).

Figure 2B:
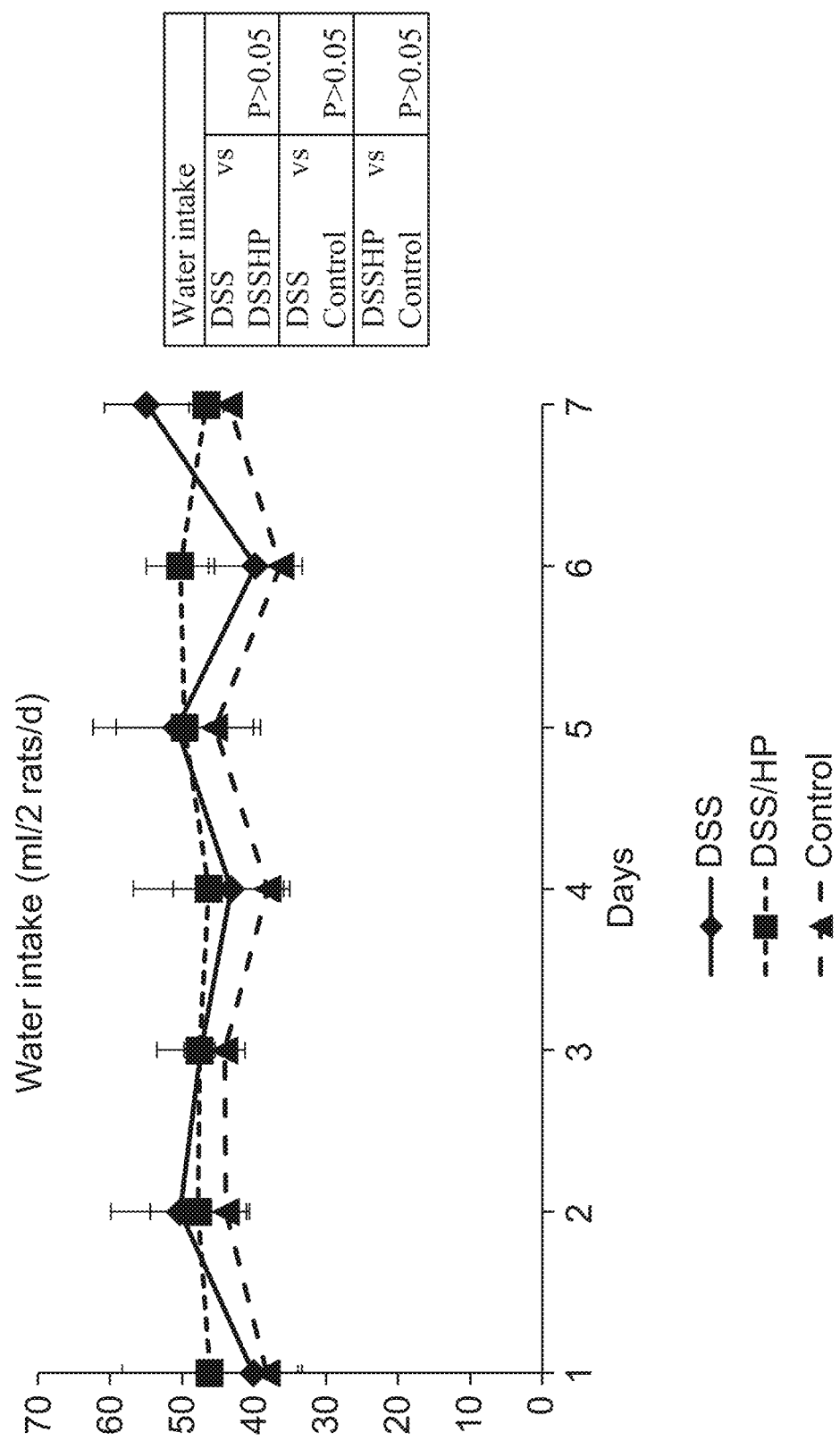

FIG. 2B shows the change in water intake by rats given Dextran Sodium Sulphate (DSS) in water with (DSS/HP) or without (DSS) co-treatment with hypothetical protein (HP).

Figure 2C:
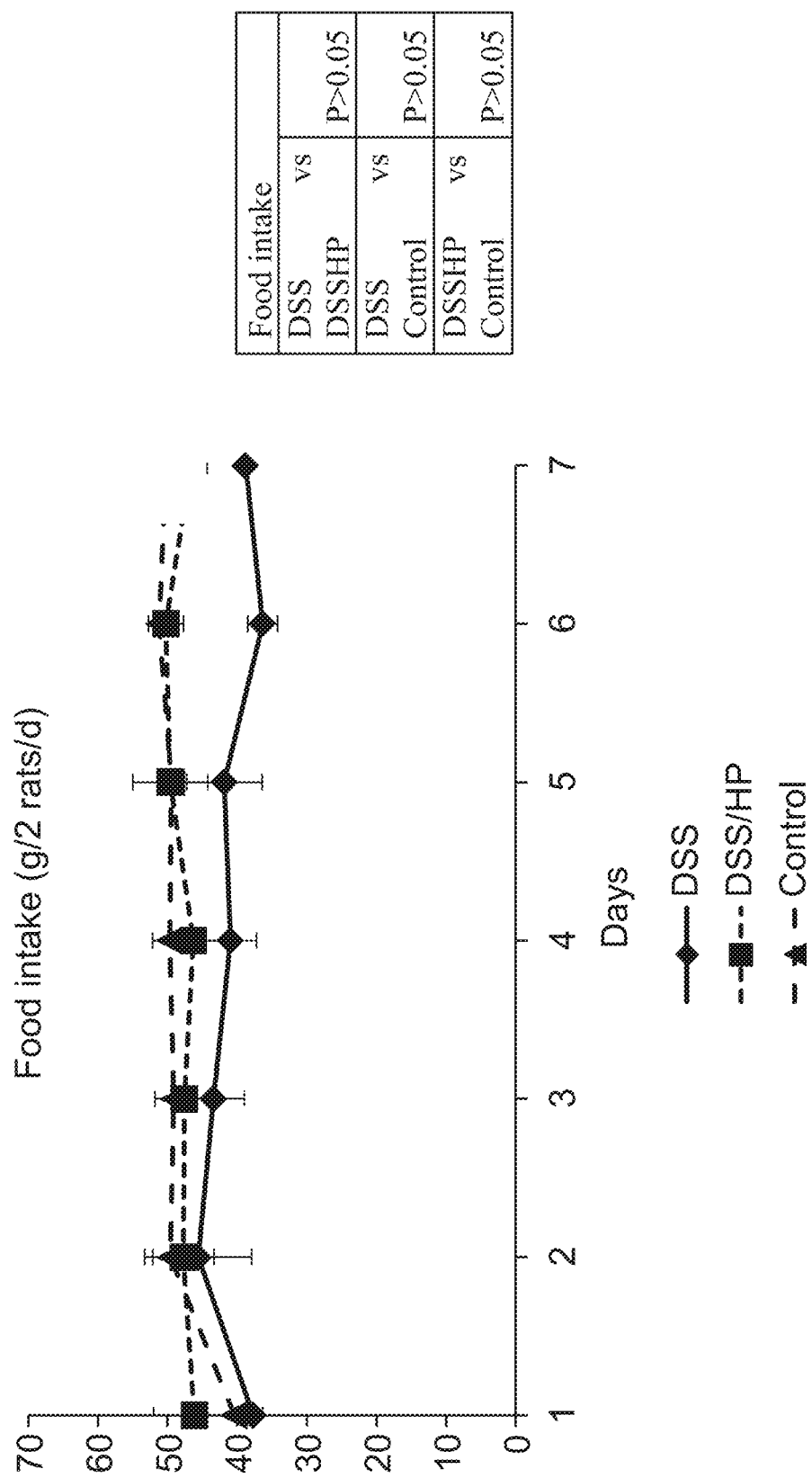

FIG. 2C shows the change in food intake by rats given Dextran Sodium Sulphate (DSS) in water with (DSS/HP) or without (DSS) co-treatment with hypothetical protein (HP).

Figure 3:
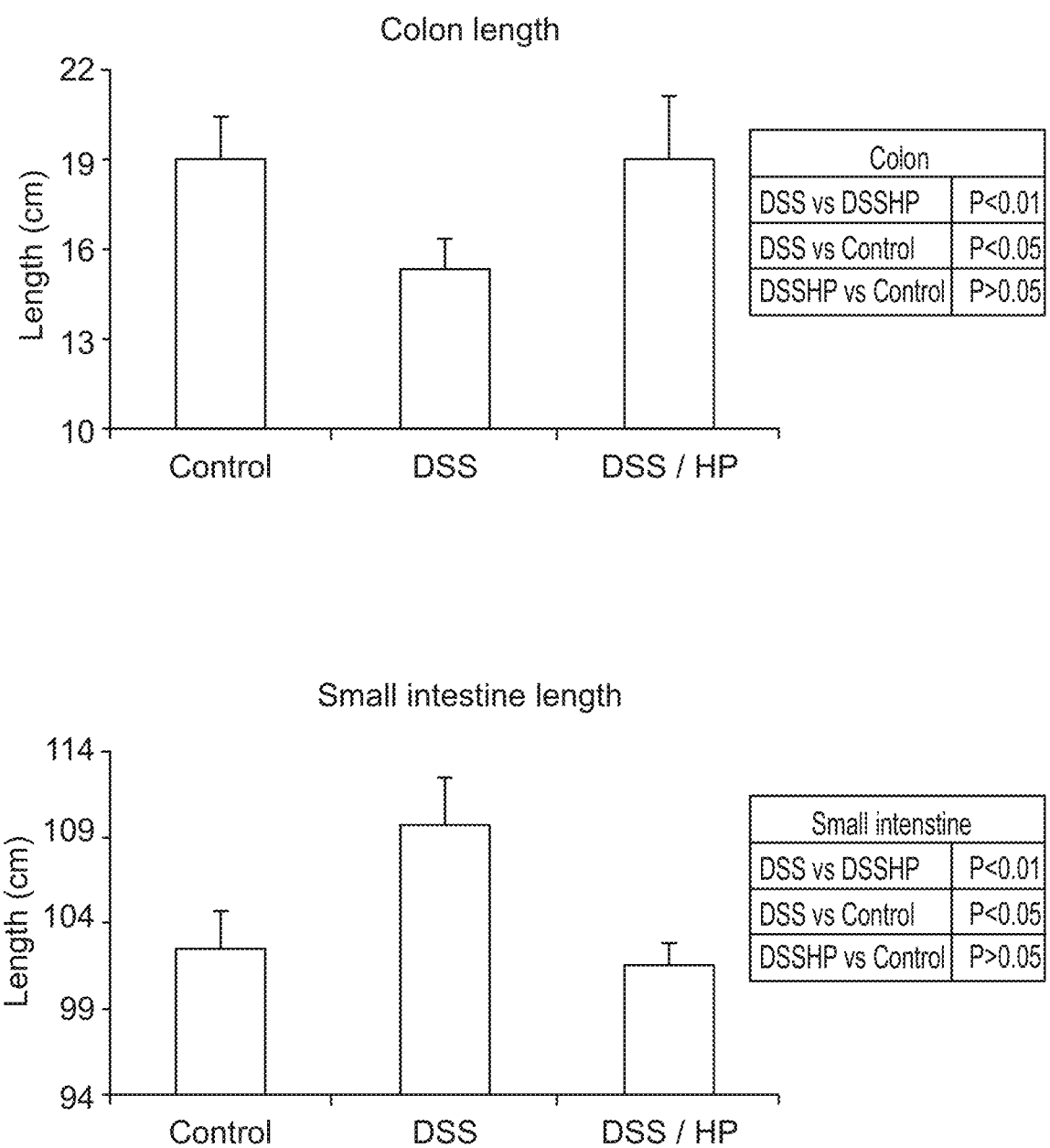

FIG. 3 shows the length of the colon and small intestine in rats given Dextran Sodium Sulphate in water with (DSS/HP) or without (DSS) co-treatment with hypothetical protein (HP).

Figure 4:
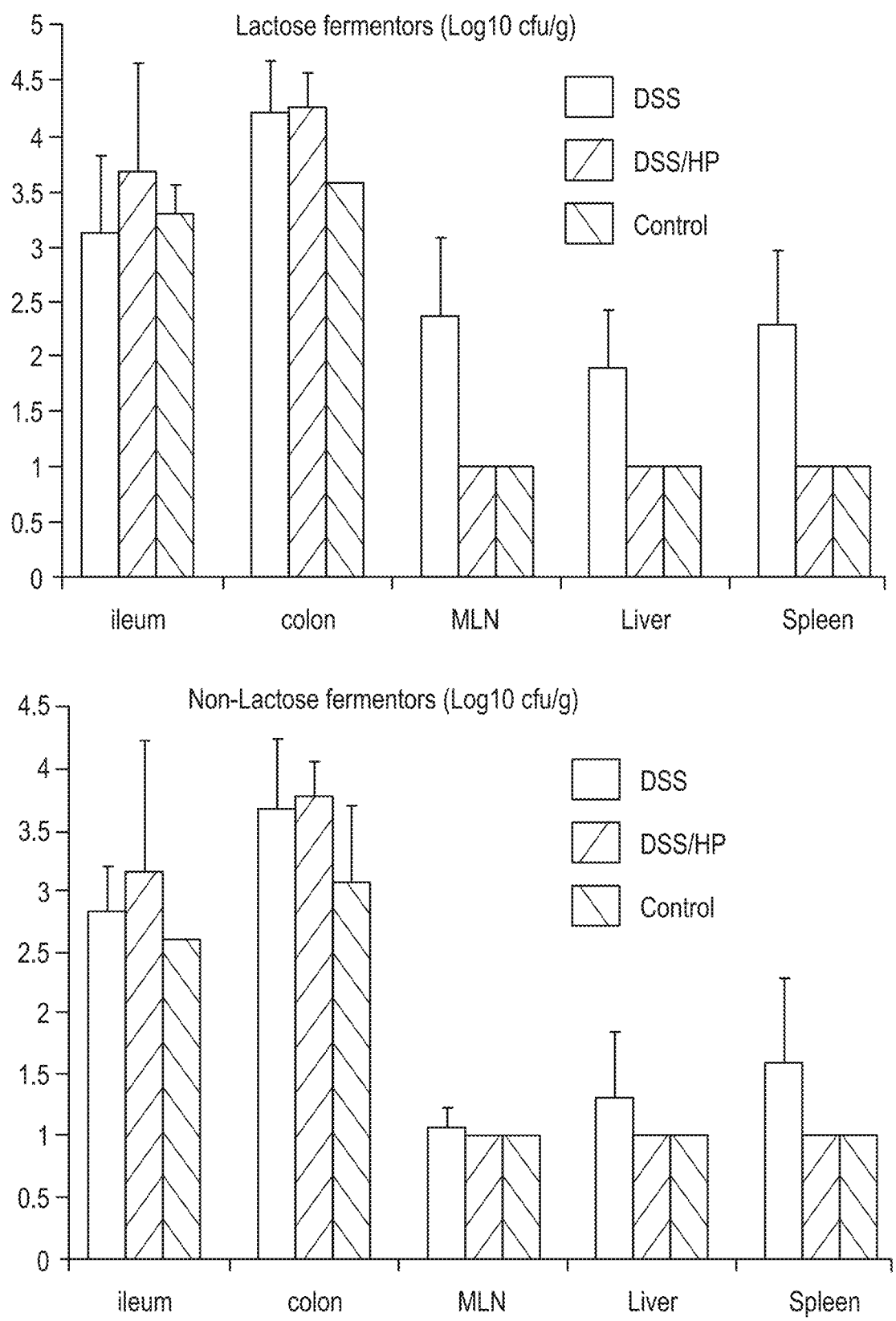

FIG. 4 shows the numbers of lactose-fermenting (predominantly *E. coli*) and non-lactose-fermenting bacteria in tissues from rats given Dextran Sodium Sulphate (DSS) in water with (DSS/HP) or without (DSS) co-treatment with hypothetical protein (HP). [When Log 10=1.0, no bacteria were detected].

Figure 5A:
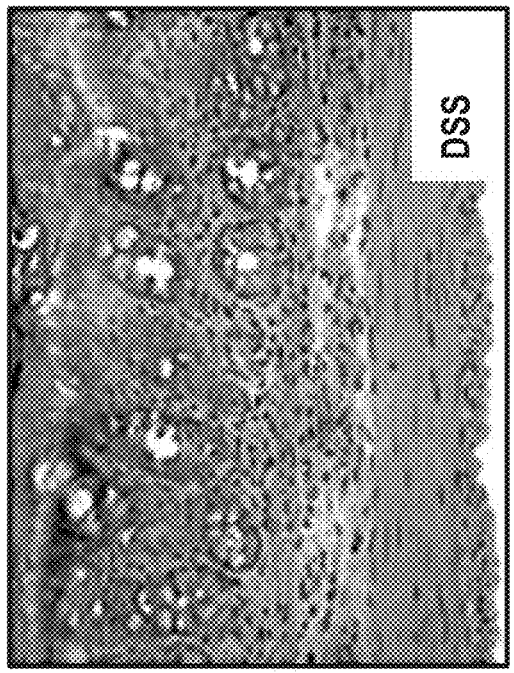
Figure 5A:
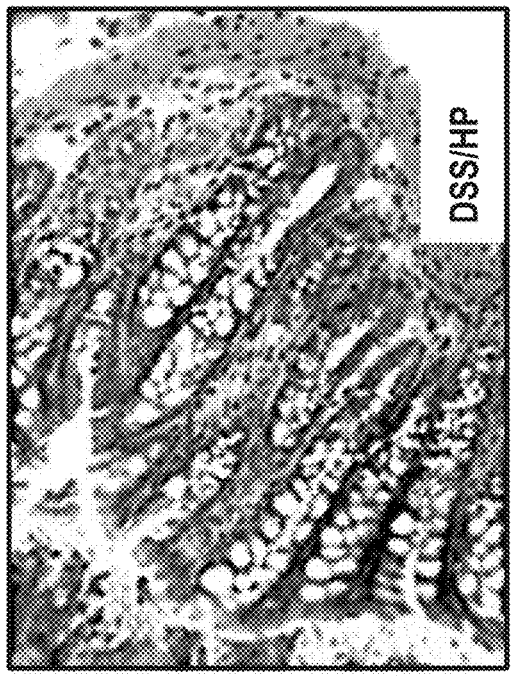
Figure 5A:
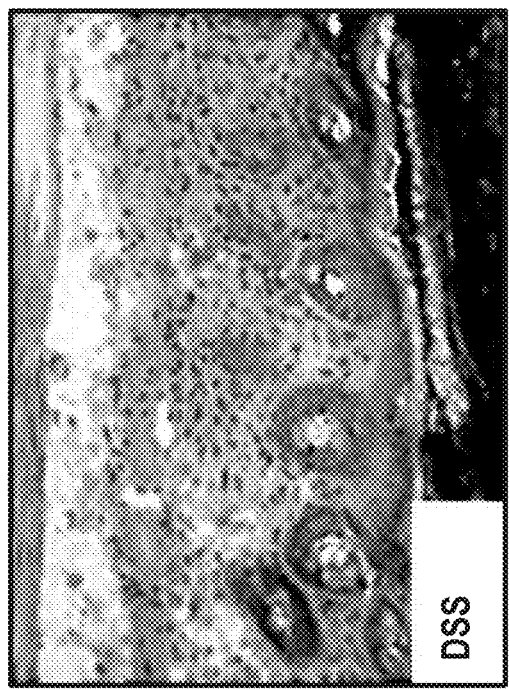
Figure 5A:
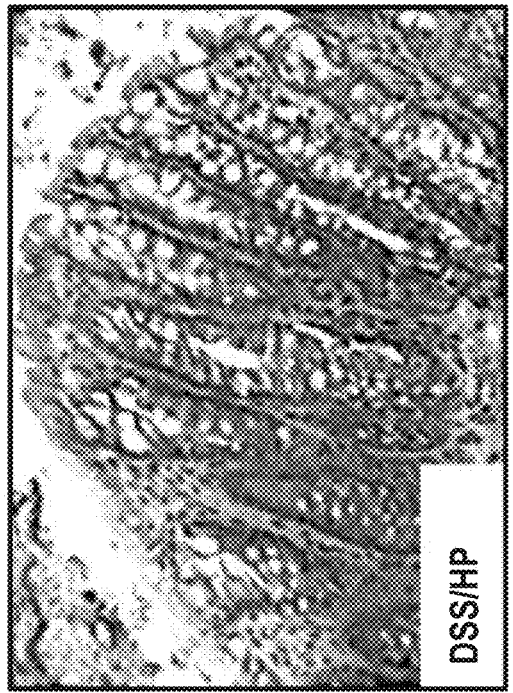

FIG. 5A shows the morphology of the descending colon from rats given Dextran Sodium Sulphate in water with (DSS/HP) or without (DSS) co-treatment with hypothetical protein (HP).

Figure 5B:
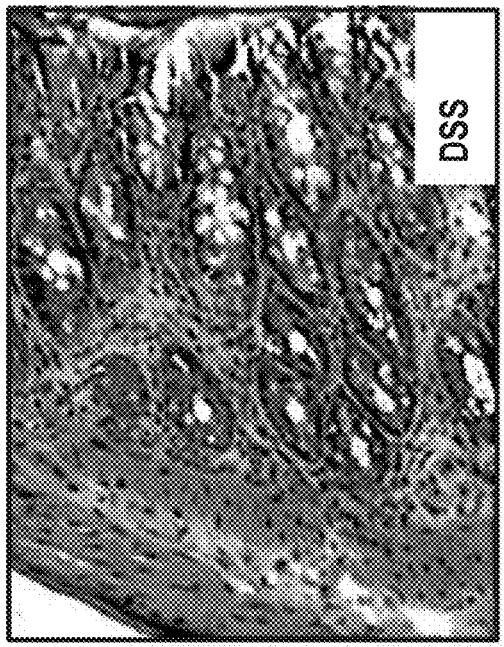
Figure 5B:
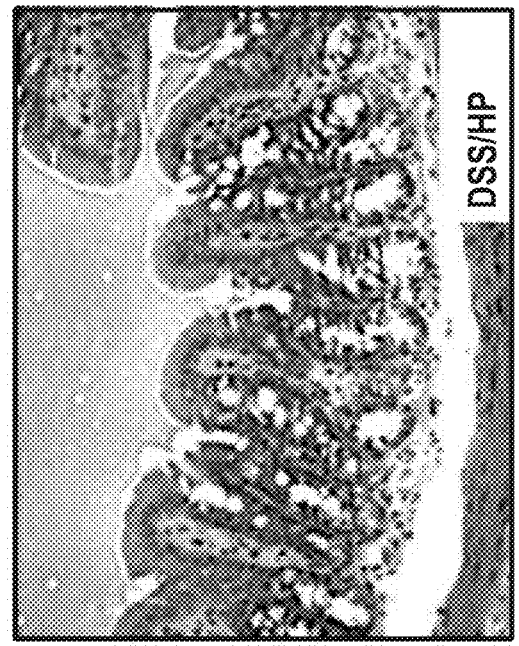
Figure 5B:
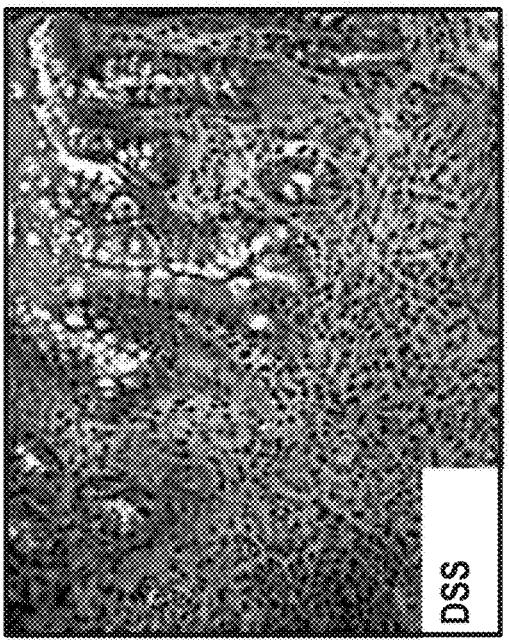
Figure 5B:
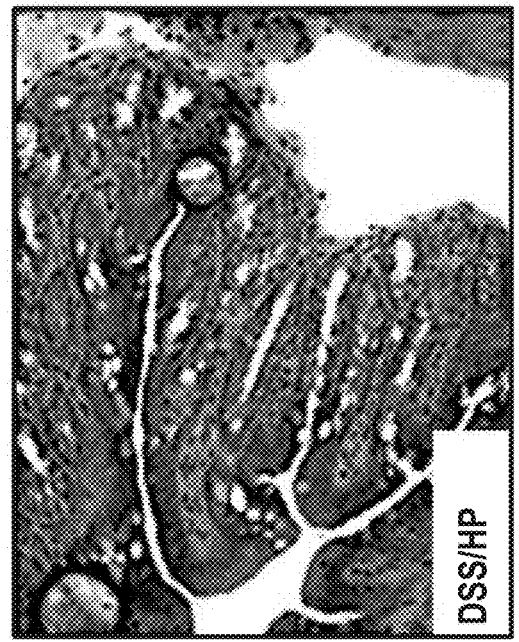

FIG. 5B shows the morphology of the ascending colon from rats given Dextran Sodium Sulphate in water with (DSS/HP) or without (DSS) co-treatment with hypothetical protein (HP).

Figure 6:
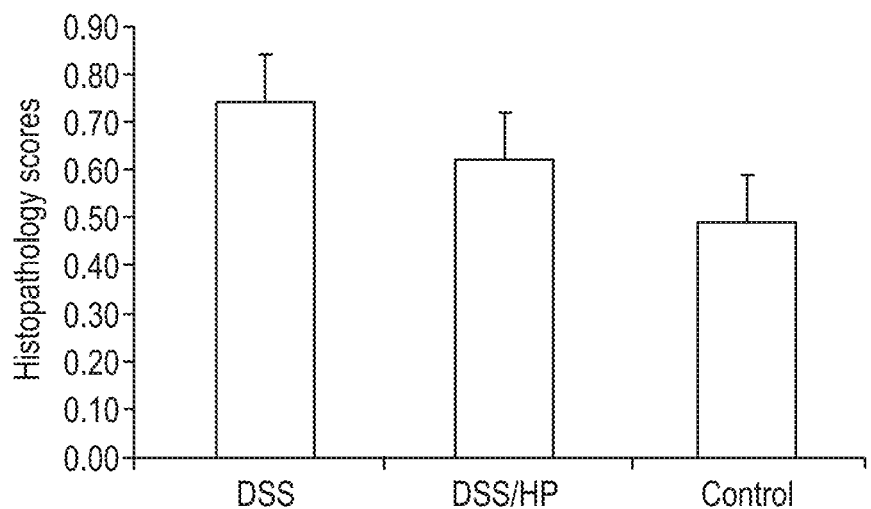
Figure 6:
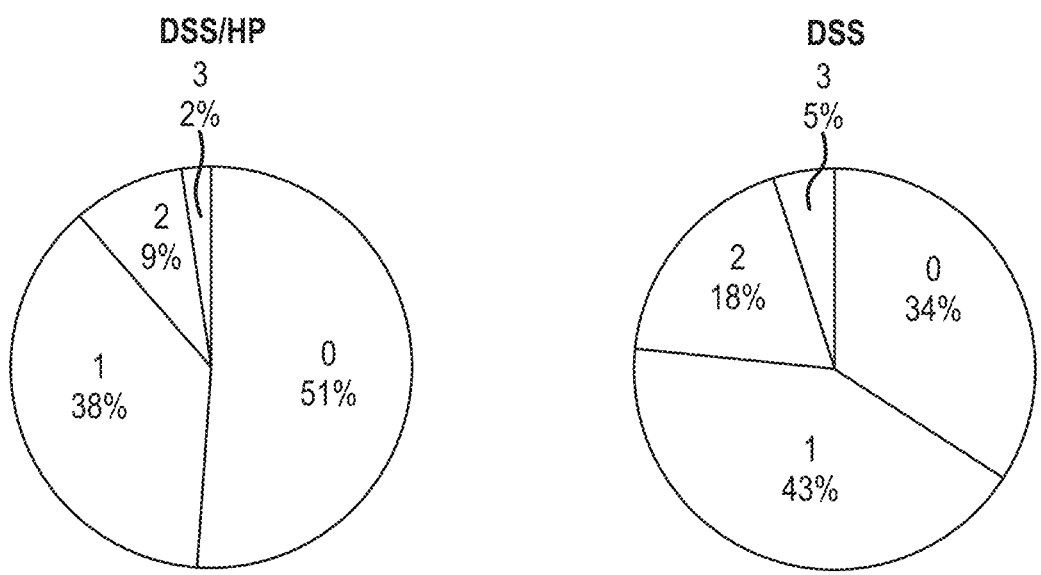

FIG. 6 shows the mean histopathology scores and histopathology scores as percentage fields of view with pathology of grades 0-3 for the ascending colon from rats given Dextran Sodium Sulphate in water with (DSS/HP) or without (DSS) co-treatment with hypothetical protein (HP).

Figure 7:
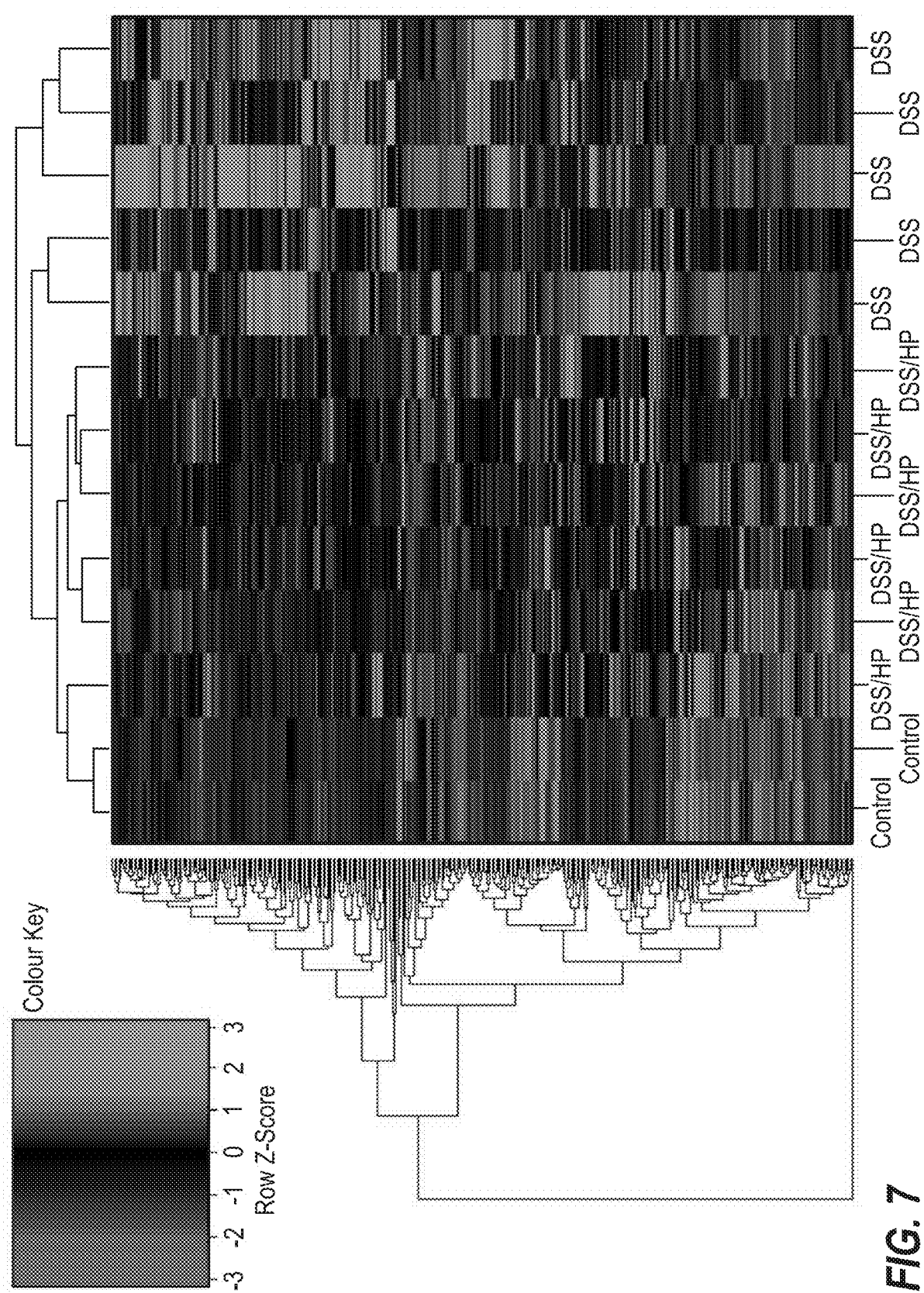

FIG. 7 shows the heatmap of 377 differentially expressed genes in tissue from rats given Dextran Sodium Sulphate in water with or without co-treatment with hypothetical protein (HP).

Figure 8A:
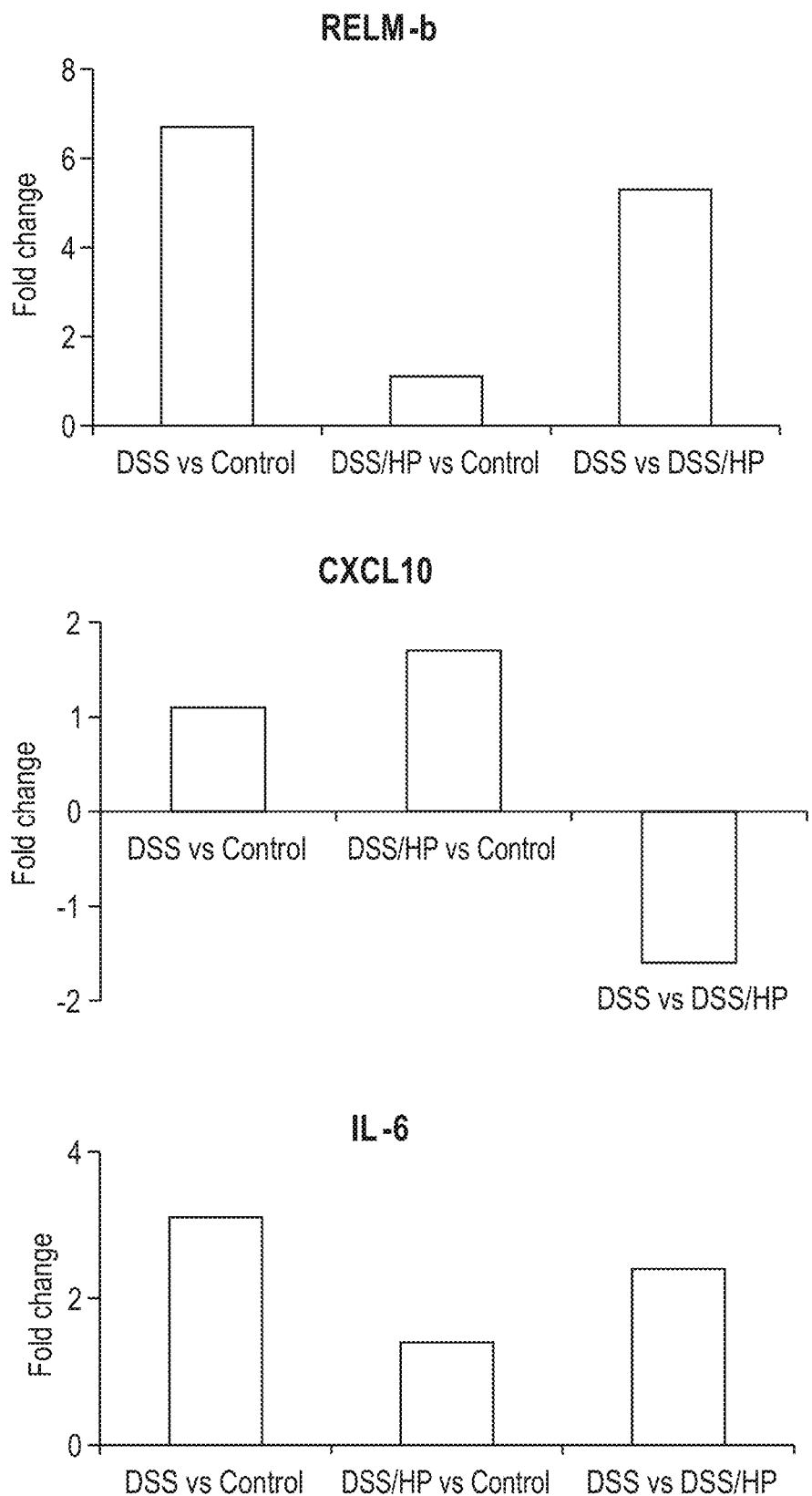

FIG. 8A shows the expression of inflammation-associated genes (Realtime PCR) in ascending colons from rats given Dextran Sodium Sulphate in water with (DSS/HP) or without (DSS) co-treatment with hypothetical protein (HP).

Figure 8B:
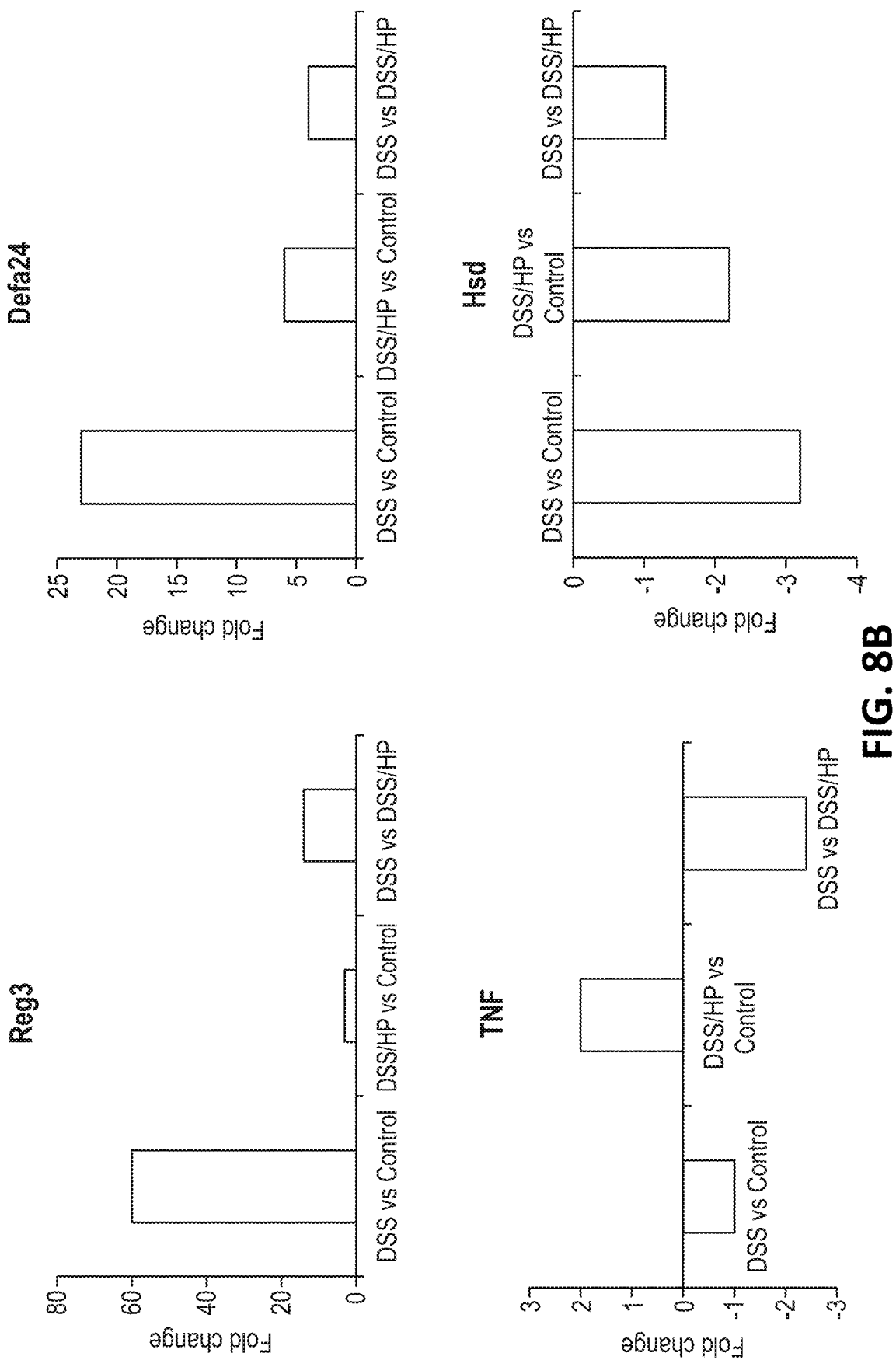

FIG. 8B shows the expression of inflammation-associated genes (Realtime PCR) in ascending colons from rats given Dextran Sodium Sulphate in water with (DSS/HP) or without (DSS) co-treatment with hypothetical protein (HP).

DETAILED DESCRIPTION

HP

Without wishing to be bound by theory, the polypeptide HP of the present invention is a pirin-related protein.

Polypeptide HP has at least 75%, 80%, 85%, 90%, 95%, 97%, 98%, 99% or 100% identity to the polypeptide sequence shown as SEQ ID NO 2, SEQ ID NO 4 or SEQ ID NO 6 or variants, homologues, fragments or derivatives thereof.

One example of polypeptide HP of the present invention is SEQ ID NO 2 deposited with GenBank as AAO75294.1; *Bacteroides thetaiotaomicron* comprising SEQ ID NO 1 can be found deposited as DSM2079 [E50(VPI5482), VPI5482] at DSMZ (Deutsche Sammlung von Mikroorganismen and Zellkulturen GmbH). The polypeptide sequence SEQ ID NO 2 has the following sequence:

```
            10         20         30         40
    MKKVIDRASS RGYFNHGWLK THHTFSFANY YNPERIHFGA 50         60         70         80
    LRVLNDDSVD PSMGFDTHPH KNMEVISIPL KGYLRHGDSV 90        100        110        120
    QNTKTITPGD IQVMSTGSGI YHSEYNDSKE EQLEFLQIWV 130        140        150        160
    FPRIENTKPE YNNFDIRPLL KPNELSLFIS PNGKTPASIK 170        180        190        200
    QDAWFSMGDF DTERTIEYCM HQEGNGAYLF VIEGEISVAD 210        220        230
    EHLAKRDGIG IWDTKSFSIR ATKGTKLLVM EVPM
```

AAO75294.1 is described as being a possible Pirin family protein. AAO75294.1 was identified from *Bacteroides thetaiotaomicron* VPI-5482.

The polypeptides sequences deposited in GenBank as AAO76683.1 and CDE80552.1 are examples of polypeptides having at least 75% identity to SEQ ID NO 2, SEQ ID NO 4 or SEQ ID NO 6.

The polypeptide sequence of AAO76683.1 is as follows:

```
            10         20         30         40
    MKKVIHKADT RGHSQYDWLD SYHTFSFDEY FDSDRINFGA 50         60         70         80
    LRVLNDDKVA PGEGFQTHPH KNMEIISIPL KGHLQHGDSK 90        100        110        120
    KNSRIITVGE IQTMSAGTGI FHSEVNASPV EPVEFLQIWI 130        140        150        160
    MPRERNTHPV YKDFSIKELE RPNELAVIVS PDGSTPASLL 170        180        190        200
    QDTWFSIGKV EAGKKLGYHL HQSHGGVYIF LIEGEIVVDG 210        220        230
    EVLKRRDGMG VYDTKSFELE TLKDSHILLI EVPM
```

The polypeptide sequence of AAO76683.1 is also referred to as SEQ ID NO 7 herein. AAO76683.1 is described in GenBank as being a putative Pirin family protein. AAO76683.1 was isolated from *Bacteroides thetaiotaomicron* VPI-5482. [E50(VPI5482), VPI5482]. *Bacteroides thetaiotaomicron* comprising SEQ ID NO 7 can be found deposited as DSM2079 BT 1576 at DSMZ (Deutsche Sammlung von Mikroorganismen und Zellkulturen GmbH).

The polypeptide sequence of CDE80552.1 is as follows:

```
           10         20         30         40         50         60
    MKKVIHKADT RGHSQYDWLD SYHTFSFDEY FDSDRINFGA LRVLNDDKVA PGEGFQTHPH 70         80         90        100        110        120
    KNMEIISIPL KGHLQHGDSK KNSRIITVGE IQTMSAGTGI FHSEVNASPV EPVEFLQIWI
```

```
            130       140       150       160       170       180
MPRERNTHPV YKDFSIKELE RPNELAVIVS PDGSTPASLL QDTWFSIGKV EAGKKLGYHL 190       200       210       220       230
HQSHGGVYIF LIEGEIVVDG EVLKRRDGMG VYDTKSFELE TLKDSHILLI EVPM
```

The polypeptide sequence of CDE80552.1 is also referred to as SEQ ID NO 8 herein. CDE80552.1 is described in GenBank as being a putative Pirin family protein. CDE80552.1 was isolated from *Bacteroides thetaiotaomicron* CAG:40.

The terms "polypeptide HP", "HP polypeptide" and "HP" are used interchangeably herein.

In one embodiment, the polypeptide HP is the polypeptide shown as SEQ ID NO 2.

In another embodiment, the polypeptide HP is the polypeptide shown as SEQ ID NO 4.

In further embodiment, the polypeptide HP is the polypeptide shown as SEQ ID NO 6.

HP polypeptides can be derived from certain microorganisms. In one aspect, the HP polypeptide is derived from an anaerobic, gram negative bacterium which can live in the alimentary canal. In a further aspect, the HP polypeptide is derived from a *Bacteroides* spp such as a *Bacteroides thetaiotaomicron*.

Examples of a polynucleotide sequence encoding polypeptide HP include the polynucleotide sequences shown as SEQ ID NO 1, SEQ ID NO 3 or SEQ ID NO 5; polynucleotide sequences encoding the polypeptide shown as SEQ ID NO 2, SEQ ID NO 4 or SEQ ID NO 6; polynucleotides sequences having at least 75%, 80%, 85%, 90%, 95%, 97%, 98%, or 99% identity to SEQ ID NO 1, SEQ ID NO 3 or SEQ ID NO 5 or variants, homologues, fragments or derivatives thereof; polynucleotides sequences encoding a polypeptide having at least 75%, 80%, 85%, 90%, 95%, 97%, 98%, or 99% identity to the polypeptide shown as SEQ ID NO 2, SEQ ID NO 4 or SEQ ID NO 6 or variants, homologues, fragments or derivatives thereof; and polynucleotide sequences encoding SEQ ID NO 7 or SEQ ID NO 8.

Figure 1A:
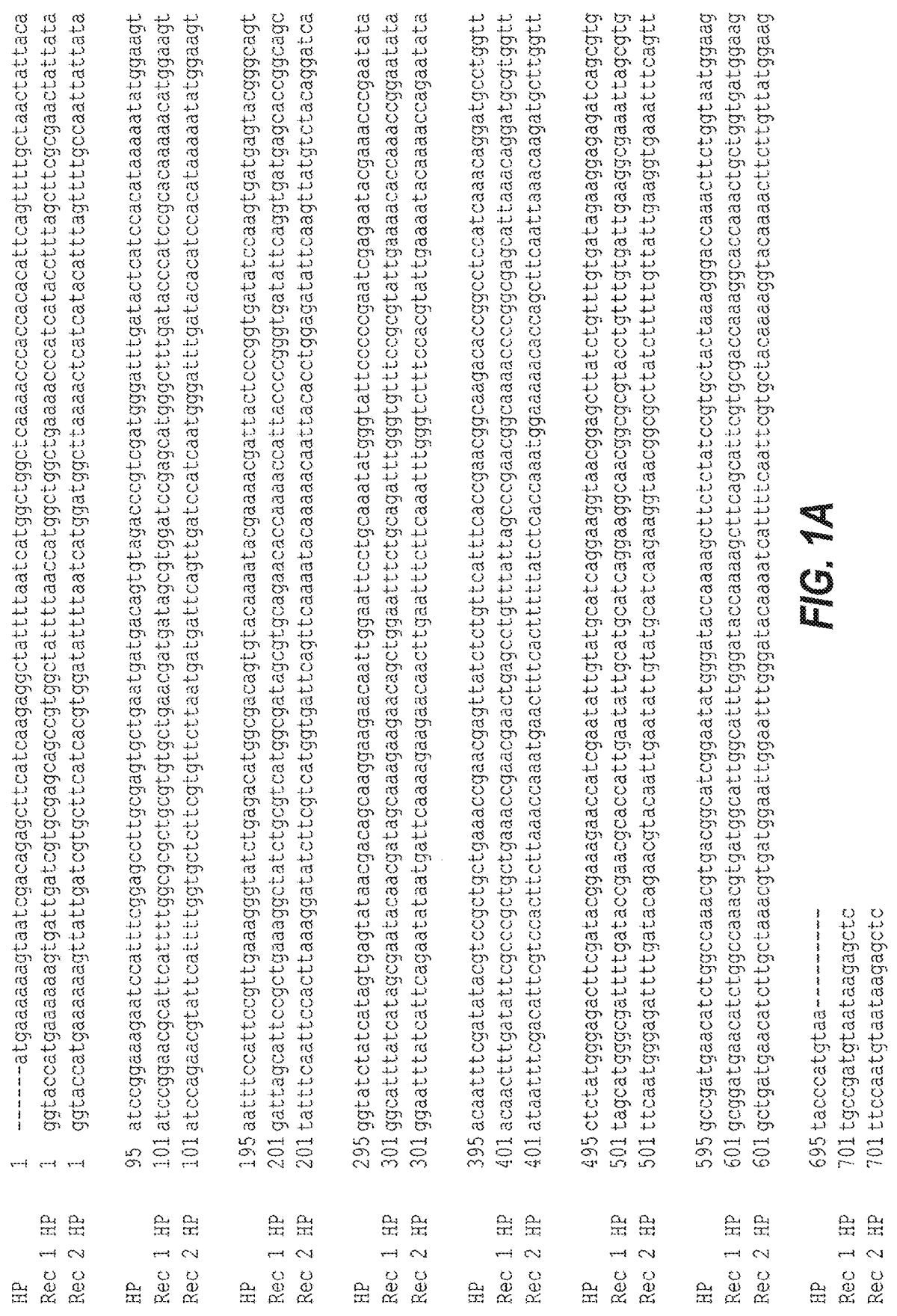

SEQ ID NOs 1, 3 and 5 are shown in FIG. 1A.

SEQ ID NO 1 has the following sequence:

```
Atgaaaaaagtaatcgacagagcttcatcaagaggctatttttaatcatgg ctggctcaaaacccaccacacattcagttttgctaactattacaatccgg aaagaatccatttcggagccttgcgagtgctgaatgatgacagtgtagac ccgtcgatgggatttgatactcatccacataaaaatatggaagtaatttc cattccgttgaaagggtatctgagacatggcgacagtgtacaaaatacga aaacgattactcccggtgatatccaagtgatgagtacgggcagtggtatc tatcatagtgagtataacgacagcaaggaagaacaattggaattcctgca aatatgggtattcccccgaatcgagaatacgaaaccgaatataacaatt tcgatatacgtccgctgctgaaaccgaacgagttatctctgttcatttca ccgaacggcaagacaccggcctccatcaaacaggatgcctggttctctat gggagacttcgatacggaaagaaccatcgaatattgtatgcatcaggaag gtaacggagcttatctgtttgtgatagaaggagagatcagcgtggccgat gaacatctggccaaacgtgacggcatcggaatatgggataccaaaagctt
```

```
ctctatccgtgctactaaagggaccaaacttctggtaatggaagtaccca tgtaa
```

SEQ ID NO 1 encodes SEQ ID NO 2 which is deposited with GenBank under accession number AAO75294.1.

The polynucleotide sequence of SEQ ID NO 1 was codon optimised for expression in *E. coli*. This codon optimised sequence is shown as SEQ ID NO 3. This sequence may also be referred herein as "Rec 1 HP" or "recombinant 1 HP".

SEQ ID NO 3 has the following sequence:

```
ggtaccatgaaaaaagtgattgatcgtgcgagcagccgtggctatttttaa ccatggctggctgaaaacccatcatacctttagcttcgcgaactattata atccggaacgcattcattttggcgcgctgcgtgtgctgaacgatgatagc gtggatccgagcatgggctttgatacccatccgcacaaaaacatggaagt gattagcattccgctgaaaggctatctgcgtcatggcgatagcgtgcaga acaccaaaaccattaccccgggtgatattcaggtgatgagcaccggcagc ggcatttatcatagcgaatacaacgatagcaaagaagaacagctggaatt tctgcagatttgggtgtttccgcgtattgaaaacaccaaaccggaatata acaactttgatattcgcccgctgctgaaaccgaacgaactgagcctgttt attagcccgaacggcaaaacccggcgagcattaaacaggatgcgtggtt tagcatgggcgatttgataccgaacgcaccattgaatattgcatgcatc aggaaggcaacggcgcgtacctgtttgtgattgaaggcgaaattagcgtg gcggatgaacatctggccaaacgtgatggcattggcatttgggataccaa aagcttcagcattcgtgcgaccaaaggcaccaaactgctggtgatggaag tgccgatgtaataagagctc
```

The polypeptide sequence encoded by SEQ ID NO 3 is shown as SEQ ID NO 4. SEQ ID NO 4 has the following sequence:

```
GTMKKVIDRASSRGYFNHGWLKTHHTFSFANYYNPERIHFGALRVLNDDS

VDPSMGFDTHPHKNMEVISIPLKGYLRHGDSVQNTKTITPGDIQVMSTGS

GIYHSEYNDSKEEQLEFLQIWVFPRIENTKPEYNNFDIRPLLKPNELSLF

ISPNGKTPASIKQDAWFSMGDFDTERTIEYCMHQEGNGAYLFVIEGEISV

ADEHLAKRDGIGIWDTKSFSIRATKGTKLLVMEVPM EL
```

The polynucleotide sequence of SEQ ID NO 1 was codon optimised for expression in *Lactococcus lactis*. This codon optimised sequence is shown as SEQ ID NO 5. This sequence may also be referred to as "Rec 2 HP" or "recombinant 2 HP".

SEQ ID NO 5 has the following sequence:

```
ggtaccatgaaaaaagttattgatcgtgcttcatcacgtggatattttaa tcatggatggcttaaaactcatcatacatttagttttgccaattattata atccagaacgtattcattttggtgctcttcgtgttcttaatgatgattca gttgatccatcaatgggatttgatacacatccacataaaaatatggaagt tatttcaattccacttaaaggatatcttcgtcatggtgattcagttcaaa atacaaaaacaattacacctggagatattcaagttatgtctacaggatca ggaatttatcattcagaatataatgattcaaaagaagaacaacttgaatt tcttcaaatttgggtctttccacgtattgaaaatacaaaaccagaatata ataatttcgacattcgtccacttcttaaaccaaatgaactttcactttttt atctcaccaaatggaaaaacaccagcttcaattaaacaagatgcttggtt ttcaatgggagattttgatacagaacgtacaattgaatattgtatgcatc aagaaggtaacggcgcttatcttttttgttattgaaggtgaaatttcagtt gctgatgaacatcttgctaaacgtgatggaattggaatttgggatacaaa atcattttcaattcgtgctacaaaaggtacaaaacttcttgttatggaag ttccaatgtaataagagctc
```

The polypeptide sequence encoded by SEQ ID NO 5 is shown as SEQ ID NO 6. SEQ ID NO 6 has the following sequence:

```
GTMKKVIDRASSRGYFNHGWLKTHHTFSFANYYNPERIHFGALRVLNDDS

VDPSMGFDTHPHKNMEVISIPLKGYLRHGDSVQNTKTITPGDIQVMSTGS

GIYHSEYNDSKEEQLEFLQIWVFPRIENTKPEYNNFDIRPLLKPNELSLF

ISPNGKTPASIKQDAWFSMGDFDTERTIEYCMHQEGNGAYLFVIEGEISV

ADEHLAKRDGIGIWDTKSFSIRATKGTKLLVMEVPM EL
```

In one embodiment, the polynucleotide sequence encoding polypeptide HP has at least 75%, 80%, 85%, 90%, 95%, 97%, 98%, or 99% identity to the polynucleotide sequence shown as SEQ ID NO 1, SEQ ID NO 3 or SEQ ID NO 5 or to variants, homologues, fragments or derivatives thereof.

In one embodiment, the polynucleotide sequence encoding polypeptide HP encodes a polypeptide shown as SEQ ID NO 2, SEQ ID NO 4 or SEQ ID NO 6 or a polypeptide having at least 75%, 80%, 85%, 90%, 95%, 97%, 98%, or 99% identity to the polypeptide shown as SEQ ID NO 2, SEQ ID NO 4 or SEQ ID NO 6 or to variants, homologues, fragments or derivatives thereof.

In one embodiment, the polypeptide HP is a truncated HP polypeptide. For example, the truncated polypeptide comprises at least 20, 30, 40, 50, 75, 100, 125, 150, 175 or 200 amino acids of polypeptide shown as SEQ ID NO 2, SEQ ID NO 4 or SEQ ID NO 6.

In one embodiment, the polynucleotide sequence encoding the polypeptide HP encodes a truncated HP polypeptide.

In one embodiment, the polypeptide HP is a fusion polypeptide. For example, the polypeptide is fused to glutathione S-transferase (GST).

Host Cell

In one aspect, a host cell as described herein comprises a polynucleotide sequence encoding polypeptide HP.

In another aspect, a host cell as described herein comprises an expression vector comprising a polynucleotide sequence encoding polypeptide HP.

In a further aspect, a host cell as described herein has been transformed with a nucleotide sequence that causes the host cell to overexpress HP. For example, a promoter is inserted into the genome of a host cell which enables the host cell to overexpress a polynucleotide sequence HP (such as an endogenous polynucleotide sequence)—i.e. the promoter is capable of overexpressing the polynucleotide sequence encoding HP.

As used herein, the term "overexpress" in the phrase "a nucleotide sequence that causes the host cell to overexpress HP" and "promoter capable of overexpressing the polynucleotide sequence encoding HP" refers to an increase in expression from zero to a level of expression or going from a lower level of expression to a higher level of expression (e.g. upregulation) when the transformed host cell is compared to the equivalent host cell prior to transformation.

In one embodiment, the level of mRNA encoding HP in a transformed host cell which overexpresses HP is increased (i.e. upregulated) such that the level of mRNA is at least 10%, 20%, 30%, 40% or 50% higher in a transformed host cell when compared to the equivalent host cell prior to transformation.

Examples of host cells overexpressing HP include: (i) host cells transformed with an expression vector encoding HP (prior to transformation said host cell was not capable of expressing HP); and (ii) host cells transformed to upregulate the expression of an endogenous HP (prior to transformation said host cell was capable of expressing said HP for a given set of culture conditions but after transformation said host cell is capable of expressing said HP at a higher level, in the same culture conditions).

The polynucleotide sequence encoding polypeptide HP may be codon optimised for the host cell. For instance, the polypeptide sequence may be codon optimised for expression in *E. coli* (such as SEQ ID NO 3) or the polynucleotide sequence may be codon optimised for expression in *Lactococcus lactis* (such as SEQ ID NO 5).

The term "host cell"—in relation to the present invention—includes any cell that comprises either the polynucleotide sequence encoding HP as described herein or an expression vector comprising said polynucleotide sequence as described herein. The host cell may be used in the recombinant production of a protein having the specific properties as defined herein. The host cell may contain a heterologous polynucleotide sequence coding for HP or may be a cell expressing its natural HP polynucleotide. For example, the host cell may be from *Bacteroides* spp such as *Bacteroides thetaiotaomicron*.

The term "host cell" as used herein may be interchangably used with "host organism" and "host microorganism".

Thus, there is provided host cells transformed or transfected with a polynucleotide sequence encoding HP as described herein or an expression vector comprising said polynucleotide sequence as described herein.

The term "transfected cell" or "transfected host cell" as used herein means a host cell transfected so that it comprises a polynucleotide sequence encoding HP as described herein or an expression vector comprising said polynucleotide sequence as described herein. In addition or alternatively, the host cell has been transformed with a nucleotide sequence that causes the host cell to overexpress a polynucleotide sequence encoding HP. For example, a promoter is inserted into the genome of a host cell which enables the host cell to overexpress an endogenous poly nucleotide sequence encoding HP.

The term "transformed cell" or "transformed host cell" as used herein means a host cell having a modified genetic structure.

The term "host cell" includes any cell which a vector is capable of transfecting or transducing.

Host cells will be chosen to be compatible with the vector and may for example be prokaryotic (for example bacterial), fungal, yeast or plant cells.

Host cells comprising polynucleotide sequences encoding polypeptide HP or an expression vector comprising said polynucleotide sequence may be used to express the polypeptide HP under in vitro, in vivo and ex vivo conditions.

In one embodiment, the host cell is a microorganism, such as a bacterium. Typically, the microorganism which inhabits the alimentary canal, or a section of the alimentary canal. Examples of suitable bacterial host cells are gram positive or gram negative bacterial species. For instance, the host cell may be selected from the group consisting of *Bacteroides* spp (such as *Bacteroides thetaiotaomicron*), *E. coli*, *Lactococcus* spp (such as *L. lactis*), *Lactobacillus* spp, *Bifidobacterium* spp, and *Streptococcus* spp (such as *Streptococcus thermophilus*).

In one embodiment, the host cell comprises an exogenous polynucleotide sequence encoding HP.

In another embodiment, the host cell comprises an endogenous polynucleotide sequence encoding HP. For example, the endogenous polynucleotide sequence under the control of a non-native promoter (such as a constitutive promoter). In a further example, the host cell comprises multiple copies of the endogenous polynucleotide sequence.

The term "host cell" does not cover native nucleotide coding sequences in their natural environment when they are under the control of their native promoter which is also in its natural environment. An example of a host cell which has a native nucleotide sequence which is not in its natural environment is a *Bacteroides thetaiotaomicron* VPI-5482 comprising SEQ ID NO 1 in which SEQ ID NO 1 under the control of a non-native promoter (such as a constitutive promoter). In another example, a *Bacteroides thetaiotaomicron* VPI-5482 comprising SEQ ID NO 1 has multiple copies of SEQ ID NO 1.

Depending on the nature of the nucleotide sequence, and/or the desirability for further processing of the expressed protein, eukaryotic hosts such as yeasts or other fungi or insect cells (such as insect Sf9 cells) may be used. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on the polypeptide described herein.

Host cells may be cultured under suitable conditions which allow expression of the polypeptide.

In some embodiments, the polypeptide can be extracted from host cells by a variety of techniques known in the art, including enzymatic, chemical and/or osmotic lysis and physical disruption. The polypeptide may be purified and isolated in a manner known per se.

Transformation of Host Cells

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host cell may be a fungus—such as a mould. Examples of suitable such hosts include any member belonging to the genera *Thermomyces, Acremonium, Aspergillus, Penicillium, Mucor, Neurospora, Trichoderma* and the like.

In one embodiment, the host cell may be a filamentous fungus.

Transforming filamentous fungi is discussed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings which may also be utilised in transforming filamentous fungi are reviewed in U.S. Pat. No. 5,674,707.

In addition, gene expression in filamentous fungi is taught in Punt et al. (2002) Trends Biotechnol 2002 May; 20(5): 200-6, Archer & Peberdy Crit Rev Biotechnol (1997) 17(4): 273-306.

The present description encompasses the production of transgenic filamentous fungi according to the present description prepared by use of these standard techniques.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus:* 50 years on. Progress in industrial microbiology vol 29. Elsevier Amsterdam 1994. pp. 641-666).

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

Transformed Plants/Plant Cells

A host cell suitable for the present invention may be a plant. In this respect, the basic principle in the construction of genetically modified plants is to insert genetic information in the plant genome so as to obtain a stable maintenance of the inserted genetic material. A review of the general techniques may be found in articles by Potrykus (*Annu Rev Plant Physiol Plant Mol Biol* [1991] 42:205-225) and Christou (Agro-Food-Industry Hi-Tech March/April 1994 17-27).

Direct infection of plant tissues by *Agrobacterium* is a simple technique which has been widely employed and which is described in Butcher D. N. et al., (1980), *Tissue Culture Methods for Plant Pathologists*, eds.: D. S. Ingrams and J. P. Helgeson, 203-208.

Other techniques for transforming plants include ballistic transformation, the silicon whisker carbide technique (see Frame B R, Drayton P R, Bagnaall S V, Lewnau C J, Bullock W P, Wilson H M, Dunwell J M, Thompson J A & Wang K (1994) Production of fertile transgenic maize plants by silicon carbide whisker-mediated transformation, *The Plant Journal* 6: 941-948) and viral transformation techniques (e.g. see Meyer P, Heidmann I & Niedenhof I (1992) The use of cassava mosaic virus as a vector system for plants, *Gene* 110: 213-217).

Further teachings on plant transformation may be found in EP-A-0449375.

Plant cells may be grown and maintained in accordance with well-known tissue culturing methods such as by culturing the cells in a suitable culture medium supplied with the necessary growth factors such as amino acids, plant hormones, vitamins, etc.

In a further aspect, the present description relates to a vector system which carries a nucleotide sequence or construct according to the present description and which is capable of introducing the nucleotide sequence or construct into the genome of an organism, such as a plant. The vector system may comprise one vector, but it may comprise two vectors. In the case of two vectors, the vector system is normally referred to as a binary vector system. Binary vector systems are described in further detail in Gynheung An et al., (1980), Binary Vectors, *Plant Molecular Biology Manual* A3, 1-19.

One extensively employed system for transformation of plant cells uses the Ti plasmid from *Agrobacterium tumefaciens* or a Ri plasmid from *Agrobacterium rhizogenes* An et al., (1986), *Plant Physiol.* 81, 301-305 and Butcher D. N. et al., (1980), *Tissue Culture Methods for Plant Pathologists*, eds.: D. S. Ingrams and J. P. Helgeson, 203-208. After each introduction method of the desired promoter or construct or nucleotide sequence according to the present invention in the plants, the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., *Crit. Rev. Plant Sci.*, 4:1-46; and An et al., *EMBO J.* (1985) 4:277-284.

Culturing and Production

Host cells transformed with the nucleotide sequence descred herein may be cultured under conditions conducive to the production of the encoded polypeptide and which facilitate recovery of the polypeptide from the cells and/or culture medium.

The medium used to cultivate the cells may be any conventional medium suitable for growing the host cell in questions and obtaining expression of the polypeptide.

The protein produced by a recombinant cell may be displayed on the surface of the cell.

The protein may be secreted from the host cells and may conveniently be recovered from the culture medium using well-known procedures.

Secretion

Often, it is desirable for the protein to be secreted from the expression host cell into the culture medium from where the protein may be more easily recovered. According to the present description, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

By way of example, the secretion of heterologous proteins in *E. coli* is reviewed in Methods Enzymol (1990) 182:132-43.

Expression Vectors

The term "expression vector" means a construct capable of in vivo, ex vivo or in vitro expression.

The term "construct"—which is synonymous with terms such as "conjugate", "cassette" and "hybrid"—includes a nucleotide sequence as described herein which optionally may be directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, the construct comprises at least the nucleotide sequence described herein operably linked to a promoter.

The nucleotide sequence of the present description may be present in a vector in which the nucleotide sequence is operably linked to regulatory sequences capable of providing for the expression of the nucleotide sequence by a suitable host cell.

In some embodiments, the polynucleotide sequence encoding polypeptide HP of an expression vector may be codon optimised for the host cell which will be or has been transformed or transfected with the polynucleotide sequence.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences. For example, a promoter is operably linked to a coding sequence if it controls the transcription of the coding sequence.

The term "regulatory sequences" includes promoters and enhancers and other expression regulation signals.

The term "promoter" is used in the normal sense of the art, e.g. an RNA polymerase binding site. The promoter may be heterologous or homologous to the nucleotide sequence.

Enhanced expression of the nucleotide sequence described herein may also be achieved by the selection of heterologous regulatory regions, e.g. promoter, secretion leader and terminator regions.

In one embodiment, the nucleotide sequence as described herein is operably linked to at least a promoter.

Other promoters may even be used to direct expression of the polypeptide described herein.

Examples of suitable promoters for directing the transcription of the nucleotide sequence in a bacterial, fungal or yeast host are well known in the art.

The promoter can additionally include features to ensure or to increase expression in a suitable host. For example, the features can be conserved regions such as a Pribnow Box or a TATA box.

Once transformed into a suitable host, the vector may replicate and function independently of the host genome, or may, in some instances, be incorporated into the genome into the genome of a suitable host cell. In some instances, the term "incorporated" covers stable incorporation into the genome.

The vectors for use in the present invention may be transformed into a suitable host cell as described herein to provide for expression of a polypeptide of the present description.

The vector may be a plasmid, a phage particle, or simply a potential genomic insert.

The choice of vector e.g. a plasmid, cosmid, or phage vector will often depend on the host cell into which it is to be introduced.

The vectors for use in the present invention may contain one or more selectable marker genes-such as a gene, which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

In one embodiment, an expression vector comprises one or more polynucleotide sequences according to the present invention. The polynucleotide sequence may be heterologous or homologous to a host cell transformed or transfected with the expression vector.

Disorders

Polypeptide HP or a polynucleotide sequence encoding polypeptide HP or a host cell comprising said polynucleotide sequence, or a host cell comprising an expression vector comprising said polynucleotide sequence may be used for the treatment and/or prevention of a disorder in a subject, wherein said disorder is an inflammatory disorder and/or an autoimmune disorder. The disorder may also be of the CNS, including autism.

In one embodiment, the disorder affects the alimentary canal, a section of the alimentary canal, the liver, liver cells, epithelial cells, epidermal cells, neuronal cells, the pancreas, and/or pancreatic cells (such as the islets of Langerhans), kidneys, spleen, lungs and heart and/or cells thereof.

Examples of sections (i.e. parts) of the alimentary canal include the mouth, the oesophagus, the stomach and the intestine (such as the small intestine (e.g. the duodenum, the jejunum and the ileum) and/or the large intestine (e.g. the caecum, ascending colon, transverse colon, descending colon, and sigmoid colon)).

Examples of epithelial cells include intestinal, oral, lung, nasal, vaginal epithelial cells.

In one embodiment, the disorder is selected from the group consisting of inflammatory bowel disorder (IBD), colitis, rheumatoid arthritis, psoriasis, multiple sclerosis, type I diabetes, coeliac disease, atopic dermatitis, rhinitis, irritable bowel syndrome (IBS), ulcerative colitis, pouchitis, Crohn's disease, functional dyspepsia, atopic diseases, necrotising enterocolitis, non alcoholic fatty liver disease, gastrointestinal infection, Lupus, nephritis/glomerulonephritis, asthma, COPD, mycocarditis and combinations thereof.

In one aspect, the disorder affects the intestine.

In one aspect, the disorder is an inflammatory disorder. For example, the disorder is an inflammatory bowel disorder (IBD) such as Crohn's disease.

In one aspect, the disorder is an autoimmune disorder. For example, the autoimmune disorder is selected from the group consisting of ulcerative colitis, pouchitis, rheumatoid arthritis, psoriasis, multiple sclerosis, type I diabetes, allergies (including coeliac disease), atopic dermatitis, rhinitis, Lupus, nephritis/glomerulonephritis, asthma, COPD and mycocarditis.

Subject

In one embodiment, the subject is a monogastric animal.

Examples of monogastric animals include poultry, humans, rats, pigs, dogs, cats, horses and rabbits.

In another embodiment, the subject is a mammal such as a monogastric mammal.

Examples of monogastric mammals include omnivores (such as humans, rats, and pigs), carnivores (such as dogs and cats), and herbivores (such as horses and rabbits).

In one embodiment, the subject is a human.

In one aspect, the subject has a disorder is selected from the group consisting of inflammatory bowel disorder (IBD), colitis, rheumatoid arthritis, psoriasis, multiple sclerosis, type I diabetes, coeliac disease, atopic dermatitis, rhinitis, irritable bowel syndrome (IBS), ulcerative colitis, pouchitis, Crohn's disease, functional dyspepsia, atopic diseases, necrotising enterocolitis, non alcoholic fatty liver disease, gastrointestinal infection Lupus, nephritis/glomerulonephritis, asthma, COPD, mycocarditis and combinations thereof. For example, the subject has IBD.

Modulation/Regulation

The terms "modulation" and "regulation" may be used interchangeably herein.

In one embodiment polypeptide HP, or a polynucleotide sequence encoding polypeptide HP, or a host cell comprising said polynucleotide sequence, or a host cell comprising an expression vector comprising said polynucleotide sequence, is used to modulate the inflammation of a cell, a tissue or an organ in a subject.

In one embodiment, the term "modulation" refers to an increase and/or induction and/or promotion and/or activation. In an alternative embodiment, the term "modulation" refers to a decrease and/or reduction and/or inhibition.

In one embodiment, the term "regulation" refers to an upregulation. In an alternative embodiment, the term "regulation" refers to a downregulation.

In one embodiment, the polypeptide HP or the polynucleotide sequence encoding polypeptide HP or the host cell as described herein reduces the inflammation of a cell, a tissue or an organ. For example, inflammation of the alimentary canal, a section (i.e. part) of the alimentary canal (such as the intestine), the liver, liver cells, epithelial cells, epidermal cells, neuronal cells, the pancreas, and/or pancreatic cells (such as the islets of Langerhans), kidneys, spleen, lungs and heart and/or cells thereof is reduced.

In one example, inflammation of the alimentary canal or part thereof (such as the intestine) is reduced.

In another example, inflammation by epithelial cells of the tissue or the organ is reduced.

The term "inflammation" as used herein refers to one or more of the following: redness, swelling, pain, tenderness, heat, and disturbed function of a cell, a tissue or organ due to an inflammatory process triggered by over-reaction of the immune system.

In one embodiment, the numbers of cells which are inflamed in a subject is at least 10%, 20%, 30%, 40% or 50% lower after administration of the polypeptide or polynucleotide or host cell as described herein when compared to the numbers of cells which are inflamed in a subject before the polypeptide HP or the polynucleotide sequence encoding HP or a host cell as described herein is administered to the subject.

In one embodiment, the amount of a tissue or organ which is inflamed in a subject is at least 10%, 20%, 30%, 40% or 50% lower after administration of the polypeptide or polynucleotide or host cell as described herein when compared to the amount of tissue or organ which is inflamed in a subject before the polypeptide HP or the polynucleotide sequence encoding HP or a host cell as described herein is administered to the subject.

In one embodiment, the polypeptide HP or the polynucleotide sequence encoding polypeptide HP or the host cells as described herein reduces the inflammation by epithelial cells of the tissue or the organ.

For example, the epithelial cells are epithelial cells of the alimentary canal or part thereof (such as the intestine).

Without wishing to be bound by theory, the polypeptide HP or the polynucleotide sequence encoding polypeptide HP or the host cell as described herein increases the production of T cells (such as regulatory T cells which may also be referred to as Tregs) in a subject. This increase in Treg numbers may combat the effects of other effector T cells (also referred to as Teffs), such as Th1, Th17 and Th2 which drive inflammation, autoimmunity and allergic/atopic conditions. In Crohn's disease and ulcerative colitis the Teff/Treg cell balance is lost.

In one embodiment, the production of T cells in a subject is increased such that there are at least 10%, 20%, 30%, 40% or 50% more T cells, or greater than 100% more T cells after administration of the polypeptide or polynucleotide or host cell as described herein when compared to the number of T cells in the subject before the polypeptide HP or the polynucleotide sequence encoding HP or the host cell as described herein is administered to the subject.

Intestine Barrier Integrity

In one embodiment, the polypeptide HP, or a polynucleotide sequence encoding polypeptide HP, or a host cell comprising said polynucleotide sequence, or a host cell comprising an expression vector comprising said polynucleotide sequence, is used to improve intestine barrier integrity in a subject.

The term "improving intestine barrier integrity" as used herein refers to a reduction in the numbers and/or types of microorganisms which spread from the intestine into other cells in a subject after administration of the polypeptide or polynucleotide or host cells as described herein when compared to the numbers and/or types of microorganisms which spread from the intestine into other cells in a subject before administration of the polypeptide or polynucleotide or host cell as described herein.

In one embodiment, the numbers of microorganisms which spread from the intestine into other cells in a subject are at least 10%, 20%, 30%, 40% or 50% lower after administration of the polypeptide or polynucleotide or host cell as described herein when compared to the numbers of microorganisms which spread from the intestine into other cells in a subject before the polypeptide HP or the polynucleotide sequence encoding HP or the host cell as described herein is administered to the subject.

In one embodiment, there are at least 5%, 10%, 15% or 20% fewer types of microorganisms which spread from the intestine into other cells in a subject after administration of the polypeptide or polynucleotide or host cell as described herein when compared to the types of microorganisms which spread from the intestine into other cells in a subject before the polypeptide HP or the polynucleotide sequence encoding HP or a host cell as described herein is administered to the subject.

Levels of Bacteria

In one embodiment polypeptide HP, or a polynucleotide sequence encoding polypeptide HP, or a host cell comprising said polynucleotide sequence, or a host cell comprising an expression vector comprising said polynucleotide sequence, is used to modify the bacterial composition in a tissue or organ to provide a more beneficial microbiota. For example, the invention can be used to reduce the level of one or more types of lactose fermenting bacteria (such as *E. coli*) in a tissue or an organ in a subject and/or reduce the level of one or more types of non-lactose fermenting bacteria in a tissue or an organ in a subject.

The term "reduce the level of one or more types of lactose fermenting bacteria" as used herein refers to a reduction in the numbers of lactose fermenting bacteria in a tissue or organ in a subject after administration of the polypeptide or polynucleotide or host cell as described herein when compared to the numbers of lactose fermenting bacteria in a tissue or organ in a subject before administration of the polypeptide or polynucleotide or host cell as described herein.

In one embodiment, the numbers of lactose fermenting bacteria in a tissue or organ in a subject are at least 10%, 20%, 30%, 40% or 50% lower after administration of the polypeptide or polynucleotide or host cell as described herein when compared to the numbers of lactose fermenting bacteria in a tissue or organ in a subject before the polypeptide HP or the polynucleotide sequence encoding HP or the host cell as described herein is administered to the subject.

Examples of lactose fermenting bacteria include *E. coli*, *Enterobacter* and *Klebsiella*.

The term "reduce the level of one or more types of non-lactose fermenting bacteria" as used herein refers to a reduction in the numbers of non-lactose fermenting bacteria in a tissue or organ in a subject after administration of the polypeptide or polynucleotide or host cells when compared to the numbers of non-lactose fermenting bacteria in a tissue or organ in a subject before administration of the polypeptide or polynucleotide or host cell as described herein.

In one embodiment, the numbers of non-lactose fermenting bacteria in a tissue or organ in a subject are at least 10%, 20%, 30%, 40% or 50% lower after administration of the polypeptide or polynucleotide or host cell as described herein when compared to the numbers of non-lactose fermenting bacteria in a tissue or organ in a subject before the polypeptide HP or the polynucleotide sequence encoding HP or the host cell as described herein is administered to the subject.

Examples of non-lactose fermenting bacteria include as *Salmonella*, *Proteus* species, *Pseudomonas aeruginosa* and *Shigella*.

In one embodiment the tissue or organ is selected from the group consisting of mesenteric lymph nodes, liver, pancreas, spleen and combinations thereof.

Regulating Appetite and/or Weight

In one embodiment, polypeptide HP or a polynucleotide sequence encoding said polypeptide or a host cell comprising said polynucleotide sequence, or a host cell comprising an expression vector comprising said polynucleotide sequence is used to regulate the appetite (e.g. food intake) in a subject (such as a subject with IBD).

As used herein, the term "regulate appetite" or "regulating appetite" refers to the ability to modulate (e.g. increase or decrease) the desire for a subject to eat food.

In one embodiment, the term "regulate" or "regulation" refers to an increase in appetite (e.g. food intake). In an alternative embodiment, the term "regulate" or "regulation" refers to a decrease in appetite (e.g. food intake).

For example, the polypeptide or polynucleotide or host cell as described herein maintains or stimulates the appetite in the subject.

In one embodiment, polypeptide HP or a polynucleotide sequence encoding said polypeptide or a host cell comprising said polynucleotide sequence, or a host cell comprising an expression vector comprising said polynucleotide sequence is used to regulate the weight of a subject (such as a subject with IBD).

In one embodiment, the term "regulate" or "regulation" refers to an increase in weight. In an alternative embodiment, the term "regulate" or "regulation" refers to a decrease in weight.

For example, the polypeptide or polynucleotide or host cell as described herein maintains the weight of a subject or increases the weight of a subject.

Without wishing to be bound by theory, the polypeptide HP or the polynucleotide sequence encoding HP or the host cell as described herein exerts a stimulatory effect on the appetite of a subject by downregulating the expression of genes associated with the suppression of appetite (such as genes encoding satiety hormones). Agt, Cartpt, Cck, Cxcl12 and Gcg are examples of genes associated with regulating appetite and the downregulation of one or more of these genes is associated with the suppression of appetite.

Cholecystokinin (Cck) and glucagon (Gcg) are examples of satiety hormones.

In one aspect, the polypeptide HP or the polynucleotide sequence encoding HP or the host cell as described herein stimulates the appetite in the subject such that the subject consumes at least 5%, 10%, or 15% more food after administration of the polypeptide or polynucleotide or host cell as described herein when compared to the subject before the polypeptide HP or the polynucleotide sequence encoding HP or the host cell as described herein is administered to the subject. In addition, or alternatively, the polypeptide HP or the polynucleotide sequence encoding HP or the host cell as described herein stimulates the appetite in the subject such that after 1 month from first administration of the polypeptide or polynucleotide or host cell as described herein the weight of the subject is at least 2%, 5%, or 10% higher when compared to the subject before the polypeptide HP or the polynucleotide sequence encoding HP or the host cell as described herein is administered to the subject.

In one embodiment, the polypeptide HP or the polynucleotide sequence encoding HP or the host cell as described herein reduces the level of cholecystokinin (Cck) and/or glucagon (Gcg) in the blood of a subject.

In one aspect, the polypeptide HP or the polynucleotide sequence encoding HP or the host cell as described herein reduces the level of cholecystokinin (Cck) and/or glucagon (Gcg) in the blood of a subject by at least 5%, 10%, 15% or 20% after administration of the polypeptide or polynucleotide or host cell as described herein when compared to the subject before the polypeptide HP or the polynucleotide sequence encoding HP or the host cell as described herein is administered to the subject.

In one embodiment, the polypeptide HP or the polynucleotide sequence encoding HP or the host cell as described herein downregulates the expression of the gene encoding cholecystokinin (Cck) and/or the expression of the gene encoding glucagon (Gcg) in a cell or cells of a subject.

In one aspect, the polypeptide HP or the polynucleotide sequence encoding HP or the host cell as described herein decreases the expression of the gene encoding cholecystokinin (Cck) such that the expression level (e.g. mRNA level) is at least 5%, 10%, 15% or 20% lower after administration of the polypeptide or polynucleotide or host cell as described herein when compared to the expression level in the subject before the polypeptide HP or the polynucleotide sequence encoding HP or the host cell as described herein is administered to the subject.

In one aspect, the polypeptide HP or the polynucleotide sequence encoding HP or the host cell as described herein decreases the expression of the gene encoding glucagon (Gcg) such that the expression level (e.g. mRNA level) is at least 5%, 10%, 15% or 20% lower after administration of the polypeptide or polynucleotide or host cell as described herein when compared to the expression level in the subject before the polypeptide HP or the polynucleotide sequence encoding HP or the host cell as described herein is administered to the subject.

Maintaining the Length of Part of the Intestine

In one embodiment polypeptide HP, or a polynucleotide sequence encoding polypeptide HP, or a host cell comprising said polynucleotide sequence, or a host cell comprising an expression vector comprising said polynucleotide sequence, is used to maintain the length of part of the intestine (such as the large intestine and/or small intestine) of a subject.

Examples of sections (i.e. parts) of the intestine include the small intestine (e.g. the duodenum, the jejunum and the ileum) and/or the large intestine (e.g. the caecum, ascending colon, transverse colon, descending colon, and sigmoid colon).

The term "maintains the length" as used herein refers to there being no or only a small change in the length of part of the intestine after administration of the polypeptide or polynucleotide or host cell as described herein when compared to the length of that part of the intestine before administration of the polypeptide or polynucleotide or host cell as described herein.

In one embodiment, the polypeptide or polynucleotide sequence or host cell as described herein prevents a reduction in the length of large intestine. In addition or alternatively, the polypeptide or polynucleotide sequence or host cell as described herein prevents an increase in the length of the small intestine.

In one embodiment, a small change in the length of the large intestine of a subject is a reduction in length of less than 5%, 2% or 1% after administration of the polypeptide or polynucleotide or host cell as described herein when compared to the length of the large intestine in a subject before the polypeptide HP or the polynucleotide sequence encoding HP or the host cell as described herein is administered to the subject.

In one embodiment, a small change in the length of the small intestine of a subject is an increase in length of less than 1%, 2%, 5%, 7% or 10% after administration of the polypeptide or polynucleotide or host cell as described herein when compared to the length of the small intestine in a subject before the polypeptide HP or the polynucleotide sequence encoding HP or the host cell as described herein is administered to the subject.

Intestine Disruption

In one embodiment, polypeptide HP, or a polynucleotide sequence encoding polypeptide HP, or a host cell comprising said polynucleotide sequence, or a host cell comprising an expression vector comprising said polynucleotide sequence, is used to reduce disruption to the intestine (e.g. large intestine) of a subject (such as a subject with IBD).

The term "disruption to the intestine of a subject" as used herein refers to an affect on the integrity of the mucosal epithelium and/or an affect on the number of goblet cells in the epithelium and/or an affect on the number of immune cells infiltrating the lamina propria.

In one embodiment, the polypeptide or polynucleotide sequence or host cell of the description reduces or prevents disruption to the integrity of the mucosal epithelium and/or reduces or prevents a reduction in the number of goblet cells in the epithelium and/or reduces or prevents the infiltration of immune cells into the lamina propria.

In one embodiment, a reduction in disruption to the integrity of the mucosal epithelium is a reduction of at least 5%, 10%, 15% or 20% in the numbers of bacteria crossing from the intestinal lumen into intestinal cells after administration of the polypeptide or polynucleotide or host cell as described herein when compared to the numbers of bacteria crossing from the intestinal lumen into intestinal cells in a subject before the polypeptide HP or the polynucleotide sequence encoding HP or the host cell as described herein is administered to the subject.

In one embodiment, an increase in the number of goblet cells in the epithelium is an increase of at least 2%, 5%, 10%, 15% or 20% in the numbers of goblet cells in the epithelium of a subject after administration of the polypeptide or polynucleotide or host cell as described herein when compared to the number goblet cells in the epithelium of a subject before the polypeptide HP or the polynucleotide sequence encoding HP or the host cell as described herein is administered to the subject.

In one embodiment, the reduction in the infiltration of immune cells into the lamina propria is such that over a fixed time period (such as 24 hours) there is a reduction of at least 5%, 10%, 15%, 20% or 30% in the numbers of immune cells (e.g. T cells) crossing into lamina propria after administration of the polypeptide or polynucleotide or host cell as described herein when compared to the numbers of immune cells (e.g. T cells) crossing from the into lamina propria cells in a subject before the polypeptide HP or the polynucleotide sequence encoding HP or the host cell as described herein is administered to the subject.

Pro-Inflammatory Genes and Barrier Integrity Genes

In one embodiment, polypeptide HP, or a polynucleotide sequence encoding polypeptide HP, or a host cell comprising said polynucleotide sequence, or a host cell comprising an expression vector comprising said polynucleotide sequence, is used to regulate the expression of one or more pro-inflammatory genes and/or anti-inflammatory genes and/or one or more barrier integrity genes in a cell or cells of a subject.

In one embodiment, the term "regulate" refers to an upregulation in the expression of one or more pro-inflammatory genes or anti-inflammatory genes. In an alternative embodiment, the term "regulate" refers to a downregulation in the expression of one or more pro-inflammatory genes or anti-inflammatory genes.

In one embodiment, the polypeptide HP or the polynucleotide sequence encoding polypeptide HP or the host cell as described herein downregulates the expression of one or more pro-inflammatory genes in a cell or cells of a subject.

The term "pro-inflammatory gene" as used herein refers to a gene which, when expressed, promotes inflammation. Examples of pro-inflammatory genes include genes encoding but not limited to IL1-β, IL4, IL5, IL6, IL8, IL12, IL13, IL17, IL21, IL22, IL23, IL27, IFNγ, CCL2, CCL3, CCL5, CCL20, CXCL5, CXCL10, CXCL12, CXCL13, and TNF-α.

In one embodiment, the pro-inflammatory gene is selected from the group consisting of IL6, CXCL10, and TNF-α.

In one embodiment, the expression level (e.g. mRNA level) of one or more pro-inflammatory genes is decreased (i.e. downregulated) such that the level is at least 10%, 20%, 30%, 40% or 50% lower after administration of the polypeptide or polynucleotide or host cell as described herein when compared to the level in the subject before polypeptide HP or the polynucleotide sequence encoding polypeptide HP or the host cell as described herein is administered to the subject.

The term "barrier integrity genes" as used herein refers to a gene which, when expressed, has a role in the function of the barrier of the intestine such as the repair of the barrier and the prevention of microorganisms crossing the barrier. Examples of barrier integrity genes include genes encoding Retnlg|Retnlb, Si, Defa24, Hsd11b2, Hsd17b2, and Nr1d1|Thra.

In one embodiment, the term "regulate" refers to an upregulation in the expression of one or more barrier integrity genes. In an alternative embodiment, the term "regulate" refers to a downregulation in the expression of one or more barrier integrity genes.

In one embodiment, the polypeptide HP or the polynucleotide sequence encoding polypeptide HP or the host cell as described herein upregulates the expression of barrier integrity genes in a cell or cells of a subject In one embodiment, the barrier integrity gene is selected from the group consisting of Retnlg|Retnlb, Si, Defa24, Hsd11b2, Hsd17b2, and Nr1d1|Thra.

In one embodiment, the expression level (e.g. mRNA level) of one or more barrier integrity genes is increased (i.e. upregulated) such that the level is at least 10%, 20%, 30%, 40% or 50% higher after administration of the polypeptide or polynucleotide or host cell as described herein when compared to the level in the subject before polypeptide HP or the polynucleotide sequence encoding polypeptide HP or the host cell as described herein is administered to the subject.

In one embodiment, the polypeptide HP or the polynucleotide sequence encoding polypeptide HP or the host cell as described herein upregulates the expression of anti-inflammatory genes.

Regulating Gene Expression

In one embodiment, the polypeptide HP, or a polynucleotide sequence encoding polypeptide HP, or a host cell comprising said polynucleotide sequence, or a host cell comprising an expression vector comprising said polynucleotide sequence, is used in regulating the expression in a cell or cells of a subject (such as a subject with IBD) of one or more genes selected from the group consisting of regenerating islet-derived 3 beta gene (Reg3b), resistin-like gamma resistin like beta gene (Retnlg|Retnlb), sucrase-isomaltase (alpha-glucosidase) gene (Si), defensin alpha 24 gene (Defa24), hydroxysteroid 11-beta dehydrogenase 2 gene (Hsd11b2), hydroxysteroid (17-beta) dehydrogenase 2 gene (Hsd17b2), resistin-Like Molecule-beta (RELMb), and nuclear receptor 1D1 thyroid hormone receptor alpha gene (Nr1d1|Thra).

The terms "Reg", "Reg3" and "Reg3b" as used herein are interchangeable.

The terms "Hsd", "Hsd17b2" or "Hsd17b2" as used herein are interchangeable.

In one embodiment, the term "regulate" refers to an upregulation in the expression of the genes. In an alternative embodiment, the term "regulate" refers to a downregulation in the expression of the genes.

The present invention is useful in regulating the expression of pro-inflammatory genes and/or barrier integrity genes.

For the avoidance of doubt, pro-inflammatory genes include IL-β, IL4, IL5, IL6, IL8, IL12, IL13, IL17, IL21, IL22, IL23, IL27, IFNα, CCL2, CCL3, CCL5, CCL20, CXCL5, CXCL10, CXCL12, CXCL13 and TNF-α.

For the avoidance of doubt, barrier integrity genes include Retnlg/Retnlb, Si, Defa24, Hsd11b2, Hsd17b2, and Nrd1\Thra.

In one embodiment, the polypeptide or polynucleotide sequence or host cell as described herein decreases the expression of one or more genes selected from the group consisting of regenerating islet-derived 3 beta gene (Reg3b); resistin-like gamma resistin like beta gene (Retnlg|Retnlb); resistin-Like Molecule-beta (RELMb), sucrase-isomaltase (alpha-glucosidase) gene (Si); and defensin alpha 24 gene (Defa24). For example, the expression level (e.g. mRNA level) of one or more genes selected from the group is decreased (i.e. downregulated) such that the level is at least 10%, 20%, 30%, 40% or 50% lower after administration of the polypeptide or polynucleotide or host cell as described herein when compared to the level in the subject before polypeptide HP or the polynucleotide sequence encoding polypeptide HP or the host cell as described herein is administered to the subject.

In one embodiment, the polypeptide or polynucleotide sequence or host cell as described herein increases the expression of one or more genes selected from the group consisting of hydroxysteroid 11-beta dehydrogenase 2 gene (Hsd11b2); hydroxysteroid (17-beta) dehydrogenase 2 gene (Hsd17b2); and nuclear receptor 1D1 thyroid hormone receptor alpha gene (Nr1d1|Thra). For example, the expression level (e.g. mRNA level) of one or more genes selected from the group is increased (i.e. upregulated) such that the level is at least 10%, 20%, 30%, 40% or 50% higher after administration of the polypeptide or polynucleotide or host cell as described herein when compared to the level in the subject before polypeptide HP or the polynucleotide sequence encoding polypeptide HP or the host cell as described herein is administered to the subject.

Proinflammatory Pathways

In one embodiment, polypeptide HP or a polynucleotide sequence encoding polypeptide HP, or a host cell comprising said polynucleotide sequence, or a host cell comprising an expression vector comprising said polynucleotide sequence, is used to reduce the activation of pro-inflammatory pathways in a cell or cells of a subject.

The reduction in the activation of pro-inflammatory pathways can be determined by determining the inflammation in a subject.

Inflammation in a subject can be determined by determining the levels of pro-inflammatory cytokines and chemokines in tissue, serum and/or faecal samples in a subject before, and after, the polypeptide or polynucleotide or host cell as described herein is administered to the subject. For example, the levels of one or more of the following can be monitored: IL-1, IL-4, IL5, IL6, IL-8, IL-12, IL-13, IL-17, IL-21, IL-22, IL23, TNFα, IFNγ, CXCL1, CXCL10, CCL20 serum and faecal calprotectin, SA1009/SA1008 calcium binding proteins, and Type 1 interferons, CD markers such as CD163, CD14, inflammatory transcription factors such as NF-κβ, STAT, and MAPkinases, c-reactive protein (CRP), erythrocyte sedimentation rate (ESR), complement proteins, serum albumin, histological evaluation of target tissues and organs, disease activity indices.

In one embodiment, polypeptide HP, or a polynucleotide sequence encoding polypeptide HP, or a host cell comprising said polynucleotide sequence, or a host cell comprising an expression vector comprising said polynucleotide sequence, is used to reduce the activity and/or expression of NF-κβ in a cell or cells (such as epithelial cells, epidermal cells, neuronal cells, liver, spleen, kidney, lung, heart and/or pancreatic cells) of a subject.

For example, the activity of NF-κβ is decreased such that the activity of NF-κβ is at least 10%, 20%, 30%, 40% or 50% lower after administration of the polypeptide or polynucleotide or host cell as described herein when compared to the level in the subject before the polypeptide HP or the polynucleotide sequence encoding polypeptide HP or the host cell as described herein is administered to the subject.

For example, the expression level (e.g. mRNA) of NF-κβ is decreased (i.e. downregulated) such that the level is at least 10%, 20%, 30%, 40% or 50% lower after administration of the polypeptide or polynucleotide or host cell as described herein when compared to the level in the subject before the polypeptide HP or the polynucleotide sequence encoding polypeptide HP or the host cell as described herein is administered to the subject.

Alimentary Canal

Parts of the alimentary canal include the mouth, the oesophagus, the stomach and the intestine (such as the small intestine (e.g. the duodenum, the jejunum and the ileum) and/or the large intestine (e.g. the caecum, ascending colon, transverse colon, descending colon, and sigmoid colon).

Herein, the term "large intestine" may be used interchangeably with the term "colon".

In one embodiment, polypeptide HP, or a polynucleotide sequence encoding polypeptide HP, or a host cell comprising said polynucleotide sequence, or a host cell comprising an expression vector comprising said polynucleotide sequence, is used for improving alimentary canal health in a subject.

The term "improving alimentary canal health" as used herein refers to reducing the level of inflammation in the alimentary canal or part thereof and/or improving intestinal microbiota.

In one embodiment, the level of inflammation in the alimentary canal is at least 10%, 20%, 30%, 40% or 50% lower after administration of the polypeptide or polynucleotide or host cell as described herein when compared to the level of inflammation in the alimentary canal of a subject before the polypeptide or polynucleotide or host cell as described herein is administered to the subject.

In one embodiment, polypeptide HP, or a polynucleotide sequence encoding polypeptide HP, or a host cell comprising said polynucleotide sequence, or a host cell comprising an expression vector comprising said polynucleotide sequence, is used for improving intestinal microbiota in a subject.

The term "intestinal microbiota" as used herein refers to microorganisms that live in the digestive tract of the host animals. These microorganisms perform a wide variety of metabolic, structural, protective and other beneficiary functions.

As used herein, the term "improving intestinal microbiota" refers to increasing the number and/or type of desirable microorganisms present in the intestine of a subject (e.g. the host), and/or increasing the activity of said desirable microorganisms in terms of their metabolic, structural, protective and other beneficiary functions. The term "improving intestinal microbiota" may also refer to decreasing the number and/or type of undesirable microorganisms present in the intestine of a subject (e.g. the host), and/or decreasing the activity of said undesirable microorganisms in terms of their metabolic, structural, protective and other beneficiary functions.

Microorganisms which are desirable in the intestine of a host are those microorganisms which have a protective and beneficiary function. Firmicutes and/or Bacteroidetes bacteria are examples of desirable microorganisms in the intestine of a host.

Microorganisms which are undesirable in the intestine of a host are those microorganisms which can interfere with the metabolic, structural, protective and other beneficiary functions of desirable microorganisms in the intestine have a protective and beneficiary function. In addition or alternatively, undesirable microorganisms are those which cause, for example, inflammation and/or diarrhoea. *E. coli* (ETEC, EPEC, EIEC, EHEC and/or EAEC) is an example of an undesirable microorganism in the intestine of a host.

For example, the numbers (i.e. levels) of Firmicutes and/or Bacteroidetes bacteria are increased and the numbers of *E. coli* are reduced; such an improvement in intestinal microbiota may occur in subjects with inflammatory bowel disease (IBD) once the polypeptide HP or the polynucleotide sequence encoding polypeptide HP or a host cell comprising said polynucleotide sequence or a host cell comprising an expression vector comprising said polynucleotide sequence has been administered to the subject.

In one embodiment, the number of desirable microorganisms (such as Firmicutes and/or Bacteroidetes bacteria) present in the intestine of a subject (e.g. the host), is increased such that the number of microorganisms is at least 10%, 20%, 30%, 40% or 50% higher, or greater than 100% higher after administration of the polypeptide or polynucleotide or host cell as described herein when compared to the level in the subject before the polypeptide or polynucleotide or host cell as described herein is administered to the subject. In addition, or alternatively, the types of desirable microorganisms (such as *Clostridium* cluster XIVa bacteria) present in the intestine of a subject (e.g. the host), are increased such that there are at least 2%, 5%, 10%, or 15% more types of microorganisms after administration of the polypeptide or polynucleotide or host cell as described herein when compared to the types in the subject before the polypeptide or polynucleotide or host cell as described herein is administered to the subject.

In one embodiment, the protein of the invention modifies the bacterial composition in the intestine of a subject to provide a beneficial microbiota. For example, the number of undesirable microorganisms (such as *E. coli* (ETEC, EPEC, EIEC, EHEC and/or EAEC)) present in the intestine of a subject (e.g. the host), is decreased such that the number of microorganisms is at least 10%, 20%, 30%, 40% or 50% lower after administration of the polypeptide or polynucleotide or host cell as described herein when compared to the level in the subject before the polypeptide or polynucleotide or host cell as described herein is administered to the subject. In addition, or alternatively, the types of undesirable microorganisms (such as *E. coli*) present in the intestine of a subject (e.g. the host), are decreased such that there are at least 1%, 2%, 5%, or 10%, fewer types of undesirable microorganisms after administration of the polypeptide or polynucleotide or host cell as described herein when compared to the types in the subject before the polypeptide or polynucleotide or host cell as described herein is administered to the subject.

Encapsulation

In one embodiment, the polynucleotide sequence encoding polypeptide HP or a host cell comprising said polynucleotide sequence or a host cell comprising an expression vector comprising said polynucleotide sequence is encapsulated.

In a further embodiment, a pharmaceutical composition comprising the polynucleotide sequence encoding polypeptide HP or a host cell comprising said polynucleotide sequence or a host cell comprising an expression vector comprising said polynucleotide sequence is encapsulated.

In another embodiment, a nutritional supplement comprising the polynucleotide sequence encoding polypeptide HP or a host cell comprising said polynucleotide sequence or a host cell comprising an expression vector comprising said polynucleotide sequence encoding said polypeptide is encapsulated.

In a further embodiment, a feedstuff, food product, dietary supplement, or food additive as described herein is encapsulated.

The term "encapsulated" as used herein refers to a means for protecting the polypeptide or polynucleotide or host cell as described herein from an incompatible environment by physical separation so that it can be delivered to the target site (e.g. the intestine) without degradation or significant degradation in order that the polypeptide or polynucleotide or host cell can have an effect on the target site. An example is an enteric coated capsule or an enterically-resistant capsule.

Even when the objective of the encapsulation is the isolation of the polypeptide or polynucleotide or host cell from its surroundings, the protective coating or shell must be ruptured at the time of desired action. The rupturing of the protective coating or shell is typically brought about through the application of chemical and physical stimuli such as pressure, enzyme attack, chemical reaction and physical disintegration.

For example, encapsulation ensures that the polypeptide or polynucleotide or host cell can be ingested so that the polypeptide or polynucleotide or host cell can be delivered to the target site (e.g. the intestine) in an amount which is effective to produce an effect at the target site.

Pharmaceutical Composition

In one embodiment, a pharmaceutical composition comprises polypeptide HP, or a polynucleotide sequence encoding polypeptide HP, or a host cell comprising said polynucleotide sequence, or a host cell comprising an expression vector comprising said polynucleotide sequence, and optionally a pharmaceutically acceptable excipient, carrier or diluent.

The pharmaceutical composition may be any pharmaceutical composition. In one aspect, the pharmaceutical composition is to be administered orally, enterally or rectally. For example, the composition may be an edible composition. "Edible" means a material that is approved for human or animal consumption.

The pharmaceutical compositions may be for human or animal usage in human and veterinary medicine.

Examples of such suitable excipients for the various different forms of pharmaceutical compositions described herein may be found in the "Handbook of Pharmaceutical Excipients, 2nd Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like.

Examples of suitable diluents include one or more of: water, ethanol, glycerol, propylene glycol and glycerin, and combinations thereof.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

In one aspect, the polypeptide or polynucleotide sequence or host cell of the pharmaceutical composition is encapsulated.

In another aspect, the polypeptide of the pharmaceutical composition is a recombinant polypeptide.

In a further aspect, the polynucleotide sequence of the pharmaceutical composition encodes a recombinant polypeptide.

In another aspect, the host cell of the pharmaceutical composition produces or is capable of producing a recombinant polypeptide.

In a further aspect, an expression vector comprises said polynucleotide sequence of the pharmaceutical composition.

The pharmaceutical may be in the form of a solution or as a solid—depending on the use and/or the mode of application and/or the mode of administration.

As used herein, the term "medicament" encompasses medicaments for both human and animal usage in human and veterinary medicine. In addition, the term "medicament" as used herein means any substance, which provides a therapeutic and/or beneficial effect. The term "medicament" as used herein is not necessarily limited to substances, which need Marketing Approval, but may include substances which, can be used in cosmetics, nutraceuticals, food (including feeds and beverages for example), probiotic cultures, nutritional supplements and natural remedies. In addition, the term "medicament" as used herein encompasses a product designed for incorporation in animal feed, for example livestock feed and/or pet food.

Nutritional Supplements

Nutritionally acceptable carriers, diluents and excipients include those suitable for human or animal consumption and that are used as standard in the food industry. Typical nutritionally acceptable carriers, diluents and excipients will be familiar to the skilled person in the art.

In one embodiment, a nutritional supplement comprises polypeptide HP, or a polynucleotide sequence encoding polypeptide HP, or a host cell comprising said polynucleotide sequence, or a host cell comprising an expression vector comprising said polynucleotide sequence, and a nutritional acceptable excipient, carrier or diluent.

In one example, the polypeptide or polynucleotide sequence or host cell of the nutritional supplement is encapsulated.

In another example, the polypeptide of the nutritional supplement is a recombinant polypeptide.

In a further aspect, the polynucleotide sequence of the nutritional supplement encodes a recombinant polypeptide.

In another aspect, the host cell of the nutritional supplement produces or is capable of producing a recombinant polypeptide.

In a further example, the polynucleotide of the nutritional supplement is comprised in an expression vector.

Feedstuff/Products

A further aspect of the invention relates to feedstuffs, food products, dietary supplements and food additives comprising polypeptide HP or a polynucleotide sequence encoding polypeptide HP or a host cell comprising said polynucleotide sequence or a host cell comprising an expression vector comprising said polynucleotide sequence.

The terms "feedstuff", "food product" "food additive" and "dietary supplement" as used herein are intended to cover all consumable products that can be solid, jellied or liquid.

The term "food product" is used in a broad sense—and covers food for humans as well as food for animals (i.e. a feed). In one aspect, the food product is for human consumption. Examples of food products include diary products (such as milk, cheese, beverages comprising whey protein, milk drinks, lactic acid bacteria drinks, yoghurt, drinking yoghurt), bakery products, beverages and beverage powders.

The "feedstuff", "food product" "food additive" and "dietary supplement" may be in the form of a solution or as a solid—depending on the use and/or the mode of application and/or the mode of administration.

As used herein the term "dietary supplement" includes a formulation which is or can be added to a food product or feedstuff as a nutritional supplement. The term "dietary supplement" as used here also refers to formulations which can be used at low levels in a wide variety of products that require gelling, texturising, stabilising, suspending, film-forming and structuring, retention of juiciness and improved mouthfeel, without adding viscosity.

Suitable food products may include, for example, functional food products, food compositions, pet food, livestock feed, health foods, feedstuffs and the like. In one aspect, the food product is a health food.

As used herein, the term "functional food product" means food that is capable of providing not only a nutritional effect, but is also capable of delivering a further beneficial effect to the consumer. Accordingly, functional foods are ordinary foods that have components or ingredients (such as those described herein) incorporated into them that impart to the food a specific functional—e.g. medical or physiological benefit—other than a purely nutritional effect.

Examples of specific food products that are applicable to the present invention include milk-based products, ready to eat desserts, powders for re-constitution with, e.g., milk or water, chocolate milk drinks, malt drinks, ready-to-eat dishes, instant dishes or drinks for humans or food compositions representing a complete or a partial diet intended for pets or livestock.

In one aspect, the feedstuff, food product, dietary supplement or food additive according to the present invention are intended for humans, pets or livestock such as monogastric animals. The feedstuff, food product, dietary supplement or food additive may be intended for animals selected from the group consisting of dogs, cats, pigs, horses, or poultry. In a further embodiment, the food product, dietary supplement or food additive is intended for adult species, in particular human adults.

The term "milk-based product" as used herein means any liquid or semi-solid milk or whey based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

The feedstuffs, food products, dietary supplements or food additives of the present invention may be—or may be added to—food supplements, also referred to herein as dietary or nutritional supplements or food additives.

The feedstuffs, food products, dietary supplements or food additives according to the invention may also be used in animal nutrition (e.g. in pig nutrition), particularly in the early-weaned period and growing fattening period. The feedstuffs, food products, dietary supplements or food additives are expected to enhance immune function reduce and prevent infectious diseases, beneficially alter the microbiota composition, and improve growth and performance of animals, for example, through increased feed conversion efficiency.

In one embodiment the feedstuff, food product, dietary supplement, or food additive is encapsulated.

In one embodiment, the polypeptide of the feedstuff, food product, dietary supplement, or food additive is a recombinant polypeptide.

In one example, the polynucleotide of the feedstuff, food product, dietary supplement, or food additive is comprised in an expression vector.

Administration

The pharmaceutical compositions, the nutritional supplements, feedstuffs, food products, dietary supplements or food additives of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

In one aspect, the pharmaceutical compositions, the nutritional supplements, feedstuffs, food products, dietary supplements or food additives of the present invention are adapted for oral, rectal, vaginal, parenteral, nasal, buccal or sublingual routes of administration.

In a further aspect, the pharmaceutical compositions, the nutritional supplements, feedstuffs, food products, dietary supplements or food additives of the present invention are adapted for oral administration.

For oral administration, particular use is made of compressed tablets, pills, tablets, gellules, drops, and capsules. Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. In another example, the active ingredient can also be incorporated into an ointment consisting of a white wax or white soft paraffin base together with such stabilisers and preservatives as may be required.

Pharmaceutical compositions, the nutritional supplements, feedstuffs, food products, dietary supplements or food additives may be formulated in unit dosage form, i.e., in the form of discrete portions containing a unit dose, or a multiple or sub-unit of a unit dose.

Dosage

A person of ordinary skill in the art can easily determine an appropriate dose of polypeptide HP or a polynucleotide sequence or a host cell as described herein to administer to a subject without undue experimentation. Typically, a physician will determine the actual dosage which will be most suitable for an individual patient and it will depend on a variety of factors including the activity of the specific bacterial strain employed, the metabolic stability and length of action of that strain, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Combinations

In one aspect, polypeptide HP or a polynucleotide sequence encoding polypeptide HP or a host cell comprising said polynucleotide sequence or a host cell comprising an expression vector comprising said polynucleotide sequence are administered in combination with one or more other active agents. In such cases, polypeptide HP or a polynucleotide sequence encoding polypeptide HP or a host cell comprising said polynucleotide sequence or a host cell comprising an expression vector comprising said polynucleotide sequence may be administered consecutively, simultaneously or sequentially with the one or more other active agents.

For instance, at least two of the polypeptide HP, the polynucleotide sequence and the host cell as described herein are administered to the subject.

For example, one type of host cell according the present invention (e.g. a L. lactis transformed with a polynucleotide sequence encoding HP) may be combined with another type of host cell according to the present invention (e.g. a Lactobacillus spp transformed with a polynucleotide sequence encoding HP).

In another example, one type of host cell according the present invention (e.g. a L. lactis transformed with a polynucleotide sequence encoding HP) may be combined with another microorganism such as Bacteroides spp (such as Bacteroides thetaiotaomicron), Lactococcus spp (such as L. lactis), Lactobacillus spp, Bifidobacterium spp, and Streptococcus spp (such as Streptococcus thermophilus).

Polynucleotide Sequence

The scope of the present description encompasses polynucleotide sequences encoding HP polypeptides.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present description includes genomic DNA, cDNA, synthetic DNA, and RNA. In one embodiment it means cDNA sequence.

In one embodiment, the nucleotide sequence when relating to and when encompassed by the per se scope of the present description does not include the native nucleotide sequence when in its natural environment and when it is linked to its naturally associated sequence(s) that is/are also in its/their natural environment. For ease of reference, herein this embodiment is called the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present description can be isolated and/or purified post expression of a nucleotide sequence in its native organism. In one embodiment, however, the amino acid sequence encompassed by scope of the present description may be expressed by a nucleotide sequence in its native organism but wherein the nucleotide sequence is not under the control of the promoter with which it is naturally associated within that organism.

Typically, the nucleotide sequence encompassed by the scope of the present description is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

The polynucleotide encompassed in the present description may be used in conjunction with other polynucleotide sequences. Thus the present description also covers a combination of polynucleotide sequences wherein the combination comprises the polynucleotide sequence encoding HP and another polynucleotide sequence, which may be another polynucleotide sequence encoding HP.

Preparation of the Nucleotide Sequence

A nucleotide sequence encoding either a peptide of the present description may be identified and/or isolated and/or purified from any cell or organism producing said peptide. Various methods are well known within the art for the identification and/or isolation and/or purification of nucleotide sequences. By way of example, DNA amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the peptide. If the amino acid sequence is known, labelled oligonucleotide probes may be synthesised and used to identify clones from the genomic library prepared from the organism. Alternatively, a labelled oligonucleotide probe containing sequences homologous to a similar known gene could be used to identify clones. In the latter case, hybridisation and washing conditions of lower stringency are used.

Alternatively, clones comprising the peptides of the present description could be identified by inserting fragments of genomic DNA into an expression vector, such as a plasmid, transforming bacteria with the resulting genomic DNA library, and then plating the transformed bacteria onto agar plates containing a substrate for the peptide thereby allowing clones expressing the peptide to be identified.

In a yet further alternative, the nucleotide sequence encoding the peptide may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

Amino Acid Sequences

The scope of the present description also encompasses HP polypeptides as defined herein.

The amino acid sequence may be prepared/isolated from a suitable source, or it may be made synthetically or it may be prepared by use of recombinant DNA techniques.

The polypeptide encompassed in the present description may be used in conjunction with other peptides. Thus the present description also covers a combination of peptides wherein the combination comprises the polypeptide HP and another peptide, which may be another HP polypeptide.

The amino acid sequence when relating to and when encompassed by the per se scope of the present invention is not a native peptide. In this regard, the term "native peptide" means an entire peptide that is in its native environment and when it has been expressed by its native nucleotide sequence.

Recombinant Polypeptide

In one aspect the polypeptide sequence for use in the present invention is a recombinant sequence—i.e. a sequence that has been prepared using recombinant DNA techniques (such as the expression of the polypeptide using a host cell comprising an expression vector encoding the polypeptide).

These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

Fusion Proteins

The polypeptide sequence for use according to the present invention may be produced as a fusion protein, for example to aid in extraction and purification. Examples of fusion protein partners include glutathione-S-transferase (GST), 6xHis, GAL4 (DNA binding and/or transcriptional activation domains) and (δ-galactosidase). It may also be convenient to include a proteolytic cleavage site between the fusion protein partner and the protein sequence of interest to allow removal of fusion protein sequences.

Typically, the fusion protein will not hinder the activity of the protein sequence.

Gene fusion expression systems in *E. coli* have been reviewed in *Curr Opin Biotechnol* (1995) 6(5):501-6.

In another embodiment of the description, the polypeptide sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Sequence Identity or Sequence Homology

The terms "polypeptide", "polypeptide sequence", "peptide", "protein" and "amino acid sequence" are used interchangeably herein.

The terms "polynucleotide sequence" and "nucleotide sequence" are used interchangeably herein.

The present invention also encompasses the use of sequences having a degree of sequence identity or sequence homology with amino acid sequence(s) of a polypeptide described herein (e.g. variants, homologues and derivatives) or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

In the present context, a homologous sequence is taken to include an amino acid or a nucleotide sequence which may be at least 50, 60, 70, 75, 80, 85 or 90% identical, in some embodiments at least 95, 96, 97, 98 or 99% identical to the subject sequence. Although homology can also be considered in terms of similarity (i.e. amino acid residues having similar chemical properties/functions), in the context of the present invention it is preferred to express homology in terms of sequence identity.

In some embodiments, a homologous sequence is taken to include an amino acid sequence or nucleotide sequence which has one or several additions, deletions and/or substitutions compared with the subject sequence.

In some embodiments, the present invention relates to the use of a protein whose amino acid sequence is represented herein or a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

In some embodiments, the present invention relates to the use of a nucleic acid sequence (or gene) encoding a protein whose amino acid sequence is represented herein or encoding a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

In the present context, a homologous sequence is taken to include a nucleotide sequence which may be at least 50, 60, 70, 75, 85 or 90% identical, in some embodiments at least 95, 96, 97, 98 or 99% identical to a nucleotide sequence encoding a polypeptide described herein (the subject sequence). Typically, the homologues will comprise the same or equivalent sequences that code for the domain(s) etc. as the subject sequence. Although homology can also be considered in terms of similarity (i.e. amino acid residues having similar chemical properties/functions), in the context of the present invention it is preferred to express homology in terms of sequence identity.

The homologous amino acid sequence and/or nucleotide sequence may provide and/or encode a polypeptide which retains the functional activity and/or enhances the activity of the polypeptide.

In some aspects, an amino acid sequence as described herein has at least 50, 60, 70, 75, 80, 85 or 90% identity, in some embodiments at least 95, 96, 97, 98 or 99% identity to the subject sequence.

In some aspects, a nucleotide sequence as described herein has at least 50, 60, 70, 75, 80, 85 or 90% identity, in some embodiments at least 95, 96, 97, 98 or 99% identity to the subject sequence.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximize local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimized alignments with fewer gaps. Most alignment programs allow the gap penalties to be modified. Typically the default values are used when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate homology, for example % sequence identity. The software typically does this as part of the sequence comparison and generates a numerical result.

Should Gap Penalties be used when determining sequence identity, then the following parameters can be used for pairwise alignment for example:

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above.

In one embodiment, the degree of identity with regard to a nucleotide sequence is determined over at least 20 contiguous nucleotides, for example over at least 30 contiguous nucleotides, for example over at least 40 contiguous nucleotides, for example over at least 50 contiguous nucleotides, for example over at least 60 contiguous nucleotides, for example over at least 100 contiguous nucleotides, for example over at least 200 contiguous nucleotides, for example over at least 300 contiguous nucleotides.

In one embodiment, the degree of identity with regard to a nucleotide sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
|---|---|---|
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, ß-alanine*, L-α-amino butyric acid*, L-γ-amino butyric acid*, L-α-amino isobutyric acid*, L-ε-amino caproic acid#, 7-amino heptanoic acid*, L-methionine sulfone#, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol*. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative or fragment thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Recombinant Polynucleotide Sequence

In one aspect the polynucleotide sequence for use in the present invention is a recombinant polypeptide sequence—i.e. a sequence that has been prepared using recombinant DNA techniques (such as the expression of the polypeptide using a host cell comprising an expression vector encoding the polypeptide). Examples of recombinant polynucleotide sequences include codon optimised sequences and polynucleotide sequences encoding fusion polypeptide.

These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

Synthetic

In one aspect the sequence for use in the present invention is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

The present invention is further described by way of the following non-limiting examples.

EXAMPLES

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequenc-* ing: *Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; and E. M. Shevach and W. Strober, 1992 and periodic supplements, *Current Protocols in Immunology*, John Wiley & Sons, New York, N.Y. Each of these general texts is herein incorporated by reference.

*Bacteroides thetaiotaomicron* HP (BT0187, a pirin-related protein) was shown in an NF-κB luciferase reporter assay, to greatly reduce NF-κB activity stimulated in epithelial cells in culture by flagellin-, PMA- or IL-1.

For large scale production, HP (referred to as HP in FIGS. 1A and 1B with FIG. 1A showing the polynucleotide sequence and FIG. 1B showing the polypeptide sequence) was expressed in *E. coli* or *L. lactis*.

The sequence was codon optimised for expression in (i) *E. coli* (referred to as Rec 1 HP in FIG. 1B) and (ii) *L. lactis* (referred to as Rec 2 HP in FIG. 1B).

Isolated recombinant HP was tested in vitro and encapsulated.

The efficacy of the encapsulated product was evaluated in a rat model of inflammatory bowel disease (Dextran Sodium Sulphate [DSS]-induced colitis).

Example 1—the Effect of HP on Inflammatory Bowel Disease

Rat study: Hooded-Lister rats (Rowett strain; 6 month-old; ~480 g) were reared, housed and managed under standard high quality conditions within the Bioresources of the Rowett Institute of Nutrition and Health. They had free access to sterile distilled water containing Dextran sodium sulphate (MP Biomedicals UK, Cambridge; DSS; 36000-50000 mol. wt.) for 7 days [days 1-5, 40 g DSS/I and days 6-7, 20 g DSS/I]. Half of the DSS-treated rats were dosed daily (day 1-7) with HP protein and the remaining six DSS-treated rats were dosed daily (day 1-7) with placebo. Untreated controls had free access to sterile distilled water but were not dosed. Untreated controls had access to sterile distilled water. All rats had free access to high quality rodent chow. Food intake, water intake and body weight were measured daily.

The rats were euthanased (isoflurane overdose and exsanguination) and dissected on day 8. The total length of the colon was measured and a piece of ascending colon 3-6 cm from the caecal/colon junction was collected in OCT or fixed in neutral buffered formalin, 2-3 cm from the caecal/colon junction was placed in RNAlater and a piece 0-2 cm from the caecal/colon junction was snap frozen. A piece of descending colon 3-6 cm from the rectum was collected in OCT or fixed in neutral buffered formalin, 2-3 cm from the rectum was placed in RNAlater and a piece 0-2 cm from the rectum was snap frozen. The small intestine was measured, a piece of ileal tissue 5-7 cm from the ileocaecal junction was collected in OCT or fixed in neutral buffered formalin, 7-9 cm from the ileocaecal junction was collected for microbiology, 9-10 cm from the ileocaecal junction was placed in RNAlater and a piece 9-17 cm from the ileocaecal junction was snap frozen. Transverse colon was collected for microbiology as were mesenteric lymph nodes, liver and spleen. Lactose-fermenting and non-lactose fermenting bacteria in tissues were evaluated using MacConkey no 3 agar.

Fixed colon samples were embedded in 8100 Technovit resin. 4 μm sections were cut and stained with hematoxylin and eosin. Whole transverse cross-sectional areas were imaged and digitised using a Zeiss Axioskop microscope connected to a QImaging camera controlled by ImagePro-Plus software. These were examined in a blinded manner by 2 independent individuals and the severity of intestinal damage was graded based on the method of Berg et al. (1996) and data expressed as percentage of fields of view with pathology of 0 [no pathology] through to grade 3 [major pathology].

The rats treated with Dextran Sodium Sulphate (DSS) and rats treated with both DSS and HP (DSS/HP) had comparable water intake and so, the intake of DSS was also same between the treatment groups. At the same time, it was observed that the food intake by DSS rats was at a slightly lower rate than that of DSS/HP treated rats and controls. The DSS treated rats also tended to lose weight, while at the same time, the DSS/HP and control rats maintained their weight (FIGS. 2A-2C).

Rat colon length was reduced due to intake of DSS, a reported feature of DSS colitis. However, this change in the colon was prevented when rats were also treated with HP (FIG. 3). In contrast, small intestine length was increased with intake of DSS but unaltered in rats given DSS/HP (FIG. 3).

Mesenteric lymph nodes, liver and spleen of rats given DSS were sub-clinically infected with lactose (predominantly *E. coli*)-fermenting and non-lactose-fermenting bacteria (FIG. 4). This was not evident with DSS/HP. Spread of bacteria to these systemic tissues is likely to be result of loss of gut barrier integrity due to damage caused by DSS. HP appeared to prevent this loss of gut barrier integrity.

Histological analysis of ascending and descending colon was carried out (FIGS. 5A-5B & 6). The severity of intestinal damage was graded based on the method of Berg et al. (1996) and data expressed as percentage of fields of view with pathology of 0 [no pathology] through to grade 3 [major pathology] or as mean histopathology score. Disruption to the tissue caused by DSS was moderate and patchy, with varying degrees of damage (from little or none to severe) localised throughout the tissue sections. Overall, the integrity of the mucosal epithelium was impaired, there was a reduced number of goblet cells in the epithelium and infiltration of immune cells into the lamina propria. In contrast, overall disruption to the colon caused by DSS was greatly reduced by co-treatment of rats with HP. It was therefore protective in the DSS-induced colitis model.

Affymetrix Analysis

Principal component analysis (PCA) was performed on the microarray data to separate the samples in a 3-dimensional way. Control and DSS/HP clustered together, and DSS were separate from this cluster. This PCA therefore indicated that DSS transcriptome profile was very different from the control and DSS/HP profiles, which were very similar. In turn, this indicated that HP was effective in treating the inflammation, as these animals seemed similar to healthy animals.

ANOVA with unequal variance (Welch), P<0.05, asymptotic, all against single condition, Tukey HSD post-hoc was carried out to get a list of differentially expressed genes. This generated a table of 377 genes with differential expression (Table 1 and Table 3).

TABLE 1

Genes with differential expression between DSS and Control and DSS/HP and control in rats given Dextran Sodium Sulphate in water with or without co-treatment with hypothetical protein (HP).

| Gene description | Gene symbol | Fold change | | p-value |
|---|---|---|---|---|
| | | DSS vs Control | DSS/HP vs Control | |
| Regenerating islet-derived 3 beta | Reg3b | 11.400 | 2.107 | 0.016 |
| Resistin-like gamma \| resistin like beta | Retnlg\| Retnlb | 3.957 | 1.556 | 0.020 |
| Sucrase-isomaltase (alpha-glucosidase) | Si | 3.903 | 1.347 | 0.040 |
| Defensin, alpha, 24 | Defa24 | 3.045 | 1.552 | 0.026 |
| Hydroxysteroid 11-beta dehydrogenase 2 | Hsd11b2 | −2.002 | 1.001 | 0.041 |
| Hydroxysteroid (17-beta) dehydrogenase 2 | Hsd17b2 | −2.530 | −1.603 | 0.040 |
| Nuclear receptor subfamily 3, group C, member 2 | Nr3c2 | −1.447 | −1.092 | 0.009 |

| Gene description | GO_biological_process (up to first 10) |
|---|---|
| Regenerating islet-derived 3 beta | GO:0006953 acute-phase response; GO:0006954 inflammatory response |
| Resistin-like gamma \| resistin like beta | |
| Sucrase-isomaltase (alpha-glucosidase) | GO:0005975 carbohydrate metabolic process; GO:0007568 aging; GO:0007584 response to nutrient; GO:0008152 metabolic process; GO:0009744 response to sucrose stimulus; GO:0009750 response to fructose stimulus; GO:0032868 response to insulin stimulus; GO:0033189 response to vitamin A; GO:0042594 response to starvation; GO:0051384 response to glucocorticoid stimulus |
| Defensin, alpha, 24 | GO:0006952 defense response; GO:0042742 defense response to bacterium |
| Hydroxysteroid 11-beta dehydrogenase 2 | GO:0001666 response to hypoxia; GO:0002017 regulation of blood volume by renal aldosterone; GO:0006950 response to stress; GO:0007565 female pregnancy; GO:0008152 metabolic process; GO:0008211 glucocorticoid metabolic process; GO:0032094 response to food; GO:0032868 response to insulin stimulus; GO:0042493 response to drug; GO:0048545 response to steroid hormone stimulus |
| Hydroxysteroid (17-beta) dehydrogenase 2 | GO:0006694 steroid biosynthetic process; GO:0032526 response to retinoic acid; GO:0055114 |
| Nuclear receptor subfamily 1, group D, member 1 \| thyroid hormone receptor alpha | GO:0006355 regulation of transcription, DNA-dependent; GO:0007623 circadian rhythm; GO:0001502 cartilage condensation; GO:0001503 ossification; GO:0001822 kidney development; GO:0001889 liver development; GO:0002155 regulation of thyroid hormone mediated signaling pathway; GO:0006950 |

TABLE 1-continued

Genes with differential expression between DSS and Control and DSS/HP and control in rats given Dextran Sodium Sulphate in water with or without co-treatment with hypothetical protein (HP).

response to stress; GO:0007420 brain development; GO:0007611 learning or memory

A heatmap was created of the subset of 377 genes (FIG. 7). This heatmap showed clear clustering of the DSS animals away from the Control and DSS/HP animals, which themselves also clustered separately, albeit not as distant from each other. The overall colour pattern of control and DSS/HP was very similar, while the DSS animals mostly showed inverse fold changes for this gene subset to the other two groups.

Seven of these genes showed comparatively high fold changes compared to controls. Of these seven genes, 4 were up regulated and the other 3 were down regulated with respect to control (Table 1). These fold changes were generally higher for the DSS animals than for the DSS/HP animals. The most affected genes were regenerating islet-derived 3 beta (Reg3b), resistin-like gamma|resistin like beta (Retnlg|Retnlb), sucrase-isomaltase (alpha-glucosidase) (Si) and defensin alpha 24 (Defa24), which were up regulated and hydroxysteroid 11-beta dehydrogenase 2 (Hsd11b2), hydroxysteroid (17-beta) dehydrogenase 2 (Hsd17b2), and nuclear receptor 1D1|thyroid hormone receptor alpha (Nr1d1|Thra), which were down regulated with respect to the control (Table 1).

Realtime PCR

Expression of inflammation-associated genes in the ascending colon was generally lower in rats treated with DSS and HP than in tissue from rats treated with DSS alone (FIG. 8; Table 2). Reg3 and RELMb expression were in particular greatly reduced as a result of treatment with HP.

TABLE 2

Statistical analysis of inflammation-associated genes (Realtime PCR) in ascending colons from rats given Dextran Sodium Sulphate in water with or without co-treatment with hypothetical protein (HP).

| | DSS vs Control | | DSS/HP vs Control | | DSS vs DSS/HP | |
|---|---|---|---|---|---|---|
| | Fold change | p-value | Fold change | p-value | Fold change | p-value |
| RELM-b | 6.61 | 0.03 | 1.2 | 0.17 | 5.49 | 0.04 |
| Reg3 | 61.25 | 0.04 | 4.04 | 0.24 | 15.15 | 0.01 |
| Defa24 | 23.08 | 0.01 | 6.37 | 0.01 | 3.62 | 0.22 |
| CXCL10 | 1.1 | 0.91 | 1.78 | 0.48 | −1.63 | 0.39 |
| TNF | −1.16 | 0.9 | 2.19 | 0.54 | −2.55 | 0.11 |
| Hsd | −3.17 | 0.01 | −2.28 | 0.01 | −1.39 | 0.36 |
| IL6 | 3.2 | 0.43 | 1.35 | 0.81 | 2.37 | 0.11 |

SUMMARY

Hypothetical protein ameliorated moderate DSS-induced colitis. This protection was, in part, linked with reduced expression of pro-inflammatory markers in the gut tissue.

TABLE 3 details all genes with differential expression between DSS and Control and DSS/HP and control in rats given
Dextran Sodium Sulphate in water with or without co-treatment with hypothetical protein (HP).

| Gene description | Gene symbol | Fold change DSS vs Control | Fold change DSS/HP vs Control | p-value | GO_biological_process (up to first 10) |
|---|---|---|---|---|---|
| Regenerating islet-derived 3 beta | Reg3b | 11.400 | 2.107 | 0.016 | GO:0006953 acute-phase response; GO:0006954 inflammatory response |
| Resistin-like gamma | resistin like beta | Retnlg|Retnlb | 3.957 | 1.556 | 0.020 | |
| Sucrase-isomaltase (alpha-glucosidase) | Si | 3.903 | 1.347 | 0.040 | GO:0005975 carbohydrate metabolic process; GO:0007568 aging; GO:0007584 response to nutrient; GO:0008152 metabolic process; GO:0009744 response to sucrose stimulus; GO:0009750 response to fructose stimulus; GO:0032868 response to insulin stimulus; GO:0033189 response to vitamin A; GO:0042594 response to starvation; GO:0051384 response to glucocorticoid stimulus |
| Defensin, alpha, 24 | Defa24 | 3.045 | 1.552 | 0.026 | GO:0006952 defense response; GO:0042742 defense response to bacterium |
| Matrix Gla protein | Mgp | 2.223 | 1.176 | 0.048 | GO:0001503 ossification; GO:0006461 protein complex assembly; GO:0007275 multicellular organismal development; GO:0007584 response to nutrient; GO:0009612 response to mechanical stimulus; GO:0009725 response to hormone stimulus; GO:0030154 cell differentiation; GO:0030324 lung development; GO:0030500 regulation of bone mineralization; GO:0042221 response to chemical stimulus |
| Phospholipase A2, group IIA (platelets, synovial fluid) | Pla2g2a | 2.006 | 1.262 | 0.027 | GO:0006644 phospholipid metabolic process; GO:0008285 negative regulation of cell proliferation; GO:0016042 lipid catabolic process; GO:0035019 somatic stem cell maintenance; GO:0042127 regulation of cell proliferation; GO:0046473 phosphatidic acid metabolic process; GO:0050678 regulation of epithelial cell proliferation; GO:0050680 negative regulation of epithelial cell proliferation |
| Gremlin 1, cysteine knot superfamily, homolog (Xenopus laevis) | Grem1 | 1.982 | 1.338 | 0.010 | GO:0001658 branching involved in ureteric bud morphogenesis; GO:0002689 negative regulation of leukocyte chemotaxis; GO:0006915 apoptosis; GO:0007267 cell-cell signaling; GO:0009887 organ morphogenesis; GO:0009954 proximal/distal pattern formation; GO:0010717 regulation of epithelial to mesenchymal transition; GO:0030308 negative regulation of cell growth; GO:0030326 emrnyonic limb morphogenesis; GO:0030514 negative regulation of BMP signaling pathway |
| Ribosomal protein L10A | similar to ribosomal protein L10a | Rpl10a|RGD1559639|RGD1566137 | 1.958 | 1.086 | 0.033 | GO:0006396 RNA processing; GO:0006412 translation; GO:0006414 translational elongation |
| Hydroxysteroid 11-beta dehydrogenase 1 | Hsd11b1 | 1.907 | 1.233 | 0.000 | GO:0006278 RNA-dependent DNA replication; GO:0006694 steroid biosynthetic process; GO:0006704 glucocorticoid biosynthetic process; GO:0006713 glucocorticoid catabolic process; GO:0008152 metabolic process GO:0030324 lung development; GO:0043456 regulation of pentose-phosphate shunt |
| Carbamoyl-phosphate synthetase 1 | Cps1 | 1.858 | 1.245 | 0.020 | GO:0000050 urea cycle; GO:0005980 glycogen catabolic process; GO:0006541 glutamine metabolic process; GO:0006807 nitrogen compound metabolic process; GO:0014075 response to amine stimulus; GO:0019433 triglyceride catabolic process; GO:0032496 response to lipopolysaccharide; GO:0033762 response to glucagon stimulus; GO:0034201 response to oleic acid; GO:0042493 response to drug |
| Paraoxonase 3 | Pon3 | 1.816 | 1.358 | 0.033 | GO:0019439 aromatic compound catabolic process; GO:0046395 carboxylic acid catabolic process |
| Ornithine carbamoyltransferase | Otc | 1.816 | 1.190 | 0.032 | GO:0000050 urea cycle; GO:0006526 arginine biosynthetic process; GO:0006591 ornithine metabolic process; GO:0008652 cellular amino acid biosynthetic process; GO:0051259 protein oligomerization; GO:0055081 anion homeostasis |
| Leukocyte immunoglobulin-like receptor, subfamily B, member 4 | Lilrb4 | 1.769 | 1.185 | 0.013 | |
| Cadherin 19, type 2 | Cdh19 | 1.732 | 1.328 | 0.001 | GO:0007155 cell adhesion; GO:0007156 homophilic cell adhesion |
| Complement factor H | Cfh | 1.723 | 1.509 | 0.031 | GO:0006956 complement activation GO:0030449 regulation of complement activation |
| Vomeronasal 1 receptor, E14 | V1re14 | 1.715 | 1.369 | 0.004 | GO:0007186 G-protein coupled receptor protein signaling pathway |
| Solute carrier family 25 (mitochondrial carrier; adenine nucleotide translocator), member 4 | Slc25a4 | 1.701 | 1.228 | 0.010 | GO:0015866 ADP transport; GO:0015867 ATP transport; GO:0051935 glutamate uptake involved in synaptic transmission; GO:0055085 transmembrane transport; GO:0060547 negative regulation of necrotic cell death |
| Immediate early response 3 | Ier3 | 1.692 | 1.227 | 0.037 | |
| ST3 beta-galactoside alpha-2,3-sialyltransferase 4 | St3gal4 | 1.666 | −1.069 | 0.047 | GO:0006486 protein amino acid glycosylation |
| Fc fragment of IgG, low affinity IIa, receptor (CD32) | Fc fragment of IgG, low affinity IIb, receptor | Fcgr2a|Fcgr2b|LOC498276| | 1.652 | 1.150 | 0.013 | GO:0001788 antibody-dependent cellular cytotoxicity; GO:0001798 positive regulation of type IIa hypersensitivity; GO:0001805 positive regulation of type III hypersensitivity; |

TABLE 3-continued details all genes with differential expression between DSS and Control and DSS/HP and control in rats given
Dextran Sodium Sulphate in water with or without co-treatment with hypothetical protein (HP).

| | | Fold change | | | |
|---|---|---|---|---|---|
| Gene description | Gene symbol | DSS vs Control | DSS/HP vs Control | p-value | GO_biological_process (up to first 10) |
| (CD32) | Fc gamma receptor II beta | Low affinity immunoglobulin gamma Fc region receptor III-like | LOC100362543 | | | | GO:0001812 positive regulation of type I hypersensitivity; GO:0001820 serotonin secretion; GO:0006910 phagocytosis, recognition; GO:0006911 phagocytosis, engulfment; GO:0007166 cell surface receptor linked signaling pathway; GO:0021675 nerve development; GO:0030593 neutrophil chemotaxis |
| Eukaryotic translation initiation factor 3, subunit E | Eif3e | 1.647 | 1.287 | 0.025 | GO:0000184 nuclear-transcribed mRNA catabolic process, nonsense-mediated decay; GO:0006413 translational initiation |
| Family with sequence similarity 96, member A | Fam96a | 1.641 | 1.277 | 0.014 | GO:0008150 biological_process |
| Peroxisomal membrane protein 3 | Pxmp3 | 1.631 | 1.093 | 0.007 | GO:0001764 neuron migration; GO:0006699 bile acid biosynthetic process GO:0007031 peroxisome organization; GO:0007399 nervous system development; GO:0008150 biological_process; GO:0042632 cholesterol homeostasis; GO:0045540 regulation of cholesterol biosynthetic process; GO:0001764 neuron migration; GO:0006699 bile acid biosynthetic process; GO:0007031 peroxisome organization |
| Fibroblast growth factor 15 | Fgf15 | 1.618 | 1.045 | 0.005 | GO:0001755 neural crest cell migration; GO:0007507 heart development; GO:0008284 positive regulation of cell proliferation; GO:0008543 fibroblast growth factor receptor signaling pathway; GO:0046326 positive regulation of glucose import; GO:0046330 positive regulation of JNK cascade; GO:0070374 positive regulation of ERK1 and ERK2 cascade; GO:0070858 negative regulation of bile acid biosynthetic process |
| Phospholamban | Pln | 1.616 | 1.194 | 0.021 | GO:0002026 regulation of the force of heart contraction; GO:0006816 calcium ion transport // non-traceable author statement; GO:0006874 cellular calcium ion homeostasis; GO:0045822 negative regulation of heart contraction; GO:0048738 cardiac muscle tissue development; GO:0051924 regulation of calcium ion transport |
| Suppressor of cytokine signaling 3 | Socs3 | 1.613 | 1.157 | 0.007 | GO:0001558 regulation of cell growth; GO:0001666 response to hypoxia; GO:0001932 regulation of protein amino acid phosphorylation; GO:0007165 signal transduction; GO:0007243 intracellular protein kinase cascade; GO:0007259 JAK-STAT cascade; GO:0007568 aging; GO:0009408 response to heat; GO:0009617 response to bacterium; GO:0009725 response to hormone stimulus |
| PQ loop repeat containing 3 | Pqlc3 | 1.608 | 1.073 | 0.037 | |
| Midkine | Mdk | 1.600 | 1.032 | 0.045 | GO:0000087 M phase of mitotic cell cycle; GO:0007275 multicellular organismal development; GO:0009611 response to wounding; GO:0009725 response to hormone stimulus; GO:0016477 cell migration; GO:0030154 cell differentiation; GO:0030325 adrenal gland development; GO:0042493 response to drug; GO:0051384 response to glucocorticoid stimulus; GO:0051781 positive regulation of cell division |
| MOB1, Mps One Binder kinase activator-like 3 (yeast) | Mobkl3 | 1.593 | 1.310 | 0.047 | GO:0006810 transport |
| Nuclear factor, interleukin 3 regulated | Nfil3 | 1.589 | 1.579 | 0.041 | GO:0006355 regulation of transcription, DNA-dependent; GO:0048511 rhythmic process |
| Alpha-2u globulin PGCL1 | alpha-2u-globulin (L type) | alpha-2u globulin PGCL2 | alpha2u globulin | alpha-2u globulin PGCL3 | alpha 2U globulin | LOC259246| LOC298116| LOC298109| LOC298111| LOC259244| LOC366380 | 1.586 | −1.100 | 0.021 | GO:0006810 transport |
| Tp53rk binding protein | Tprkb | 1.580 | 1.187 | 0.018 | |
| Similar to protein C33A12.3 | RGD1359508 | 1.574 | 1.141 | 0.013 | |
| V-ral simian leukemia viral oncogene homolog A (ras related) | Rala | 1.563 | 1.175 | 0.005 | GO:0000910 cytokinesis; GO:0007165 signal transduction; GO:0007264 small GTPase mediated signal transduction; GO:0007265 Ras protein signal transduction; GO:0017157 regulation of exocytosis; GO:0031532 actin cytoskeleton reorganization; GO:0051491 positive regulation of filopodium assembly; GO:0051665 membrane raft localization |
| Hematopoietic prostaglandin D synthase | Hpgds | 1.539 | 1.220 | 0.009 | GO:0001516 prostaglandin biosynthetic process; GO:0006633 fatty acid biosynthetic process; GO:0006693 prostaglandin metabolic process |
| Forkhead box E3 | Foxe3 | 1.519 | 1.131 | 0.024 | GO:0001654 eye development; GO:0006350 transcription; GO:0006355 regulation of transcription, DNA-dependent; GO:0006366 transcription from RNA polymerase II promoter; |

TABLE 3-continued details all genes with differential expression between DSS and Control and DSS/HP and control in rats given
Dextran Sodium Sulphate in water with or without co-treatment with hypothetical protein (HP).

| | | Fold change | | | |
|---|---|---|---|---|---|
| Gene description | Gene symbol | DSS vs Control | DSS/HP vs Control | p-value | GO_biological_process (up to first 10) |
| Complement component 1, s subcomponent | C1s | 1.513 | 1.170 | 0.006 | GO:0008150 biological_process; GO:0045449 regulation of transcription; GO:0048468 cell development; GO:0050679 positive regulation of epithelial cell proliferation GO:0006508 proteolysis; GO:0006958 complement activation, classical pathway; GO:0010001 glial cell differentiation; GO:0045087 innate immune response; GO:0051591 response to cAMP |
| Reticulocalbin 2, EF-hand calcium binding domain | Rcn2 | 1.512 | 1.223 | 0.035 | |
| Solute carrier family 7 (cationic amino acid transporter, y+ system), member 9 | Slc7a9 | 1.500 | 1.047 | 0.046 | GO:0006865 amino acid transport; GO:0055085 transmembrane transport; GO:0015804 neutral amino acid transport |
| Butyrylcholinesterase | Bche | 1.488 | 1.042 | 0.019 | GO:0007584 response to nutrient; GO:0007612 learning; GO:0019695 choline metabolic process; GO:0042493 response to drug; GO:0043279 response to alkaloid; GO:0050805 negative regulation of synaptic transmission; GO:0051384 response to glucocorticoid stimulus; GO:0051593 response to folic acid |
| SFT2 domain containing 1 | Sft2d1 | 1.487 | 1.125 | 0.023 | GO:0015031 protein transport; GO:0016192 vesicle-mediated transport |
| TCF3 (E2A) fusion partner | Tfpt | 1.475 | 1.165 | 0.002 | GO:0006917 induction of apoptosis |
| UDP-Gal:betaGlcNAc beta 1,4-galactosyltransferase, polypeptide 4 | B4galt4 | 1.466 | 1.188 | 0.008 | GO:0005975 carbohydrate metabolic process |
| Somatostatin | Sst | 1.460 | 1.139 | 0.020 | GO:0001101 response to acid; GO:0006972 hyperosmotic response; GO:0007186 G-protein coupled receptor protein signaling pathway; GO:0009408 response to heat; GO:0010243 response to organic nitrogen; GO:0030334 regulation of cell migration; GO:0042493 response to drug; GO:0043200 response to amino acid stimulus; GO:0048545 response to steroid hormone stimulus |
| Lin-7 homolog C (C. elegans) | Lin7c | 1.459 | 1.195 | 0.005 | GO:0006887 exocytosis; GO:0007269 neurotransmitter secretion |
| Glycoprotein (transmembrane) nmb | Gpnmb | 1.452 | 1.100 | 0.036 | GO:0001649 osteoblast differentiation; GO:0007155 cell adhesion; GO:0030282 bone mineralization |
| Coiled-coil-helix-coiled-coil-helix domain containing 4 \| similar to coiled-coil-helix-coiled-coil-helix domain containing 4 | Chchd4\|LOC685505 | 1.449 | 1.121 | 0.033 | GO:0015031 protein transport; GO:0055085 transmembrane transport |
| Olfactory receptor 63 | Olr63 | 1.445 | 1.147 | 0.029 | GO:0007165 signal transduction; GO:0007186 G-protein coupled receptor protein signaling pathway; GO:0050911 detection of chemical stimulus involved in sensory perception of smell |
| Proline-rich acidic protein 1 | Prap1 | 1.444 | 1.055 | 0.035 | |
| Immunoglobulin superfamily, member 6 | Igsf6 | 1.443 | 1.108 | 0.045 | |
| Ly49 inhibitory receptor 9 \| hypothetical protein LOC497796 \| killer cell lectin-like receptor, subfamily A, member 17 \| similar to immunoreceptor Ly49si3 | Ly49i9\|LOC497796\|Klra17\|RGD1561306 | 1.440 | 1.026 | 0.034 | |
| Allograft inflammatory factor 1 | Aif1 | 1.431 | 1.107 | 0.010 | GO:0001934 positive regulation of protein amino acid phosphorylation; GO:0010629 negative regulation of gene expression; GO:0014739 positive regulation of muscle hyperplasia; GO:0030335 positive regulation of cell migration; GO:0031668 cellular response to extracellular stimulus; GO:0032870 cellular response to hormone stimulus; GO:0034097 response to cytokine stimulus; GO:0042116 macrophage activation; GO:0043066 negative regulation of apoptosis; GO:0045429 positive regulation of nitric oxide biosynthetic process |
| Legumain | Lgmn | 1.427 | 1.268 | 0.003 | GO:0006508 proteolysis; GO:0040015 negative regulation of multicellular organism growth |
| Brain expressed X-linked 2 \| brain expressed gene 1 \| brain expressed gene 4 | Bex2\|Bex1\|Bex4 | 1.420 | 1.194 | 0.043 | GO:0006915 apoptosis; GO:0007049 cell cycle; GO:0002052 positive regulation of neuroblast proliferation; GO:0007275 multicellular organismal development; GO:0007399 nervous system development; GO:0030154 cell differentiation GO:0045665 negative regulation of neuron differentiation; GO:0048011 nerve growth factor receptor signaling pathway |
| Tumor suppressor candidate 3 | Tusc3 | 1.419 | 1.145 | 0.049 | GO:0045454 cell redox homeostasis |
| ATP synthase, H+ transporting, | Atp5h\| | 1.415 | 1.072 | 0.036 | GO:0006811 ion transport; GO:0015986 ATP synthesis coupled |

TABLE 3-continued details all genes with differential expression between DSS and Control and DSS/HP and control in rats given
Dextran Sodium Sulphate in water with or without co-treatment with hypothetical protein (HP).

| | | Fold change | | | |
|---|---|---|---|---|---|
| Gene description | Gene symbol | DSS vs Control | DSS/HP vs Control | p-value | GO_biological_process (up to first 10) |
| mitochondrial F0 complex, subunit d | ATP synthase, H+ transporting, mitochondrial F0 complex, subunit d-like 1 | Atp5hl1 | | | | proton transport; GO:0015992 proton transport; GO:0046034 ATP metabolic process |
| C-type lectin domain family 10, member A | Clec10a | 1.413 | −1.051 | 0.034 | |
| Sodium channel, voltage-gated, type VII, alpha | Scn7a | 1.412 | 1.274 | 0.017 | GO:0006811 ion transport; GO:0006814 sodium ion transport; GO:0055085 transmembrane transport |
| | Cd55 | 1.412 | 1.065 | 0.015 | GO:0007204 elevation of cytosolic calcium ion concentration |
| Galactokinase 2 | Galk2 | 1.409 | 1.182 | 0.000 | GO:0006012 galactose metabolic process; GO:0008152 metabolic process; GO:0046835 carbohydrate phosphorylation |
| Necdin homolog (mouse) | Ndn | 1.402 | 1.174 | 0.004 | GO:0001764 neuron migration; GO:0006355 regulation of transcription, DNA-dependent; GO:0007409 axonogenesis; GO:0007413 axonal fasciculation; GO:0007417 central nervous system development; GO:0007585 respiratory gaseous exchange; GO:0008347 glial cell migration; GO:0019233 sensory perception of pain; GO:0048011 nerve growth factor receptor signaling pathway; GO:0048666 neuron development |
| BUD31 homolog (S. cerevisiae) | pentatricopeptide repeat domain 1 | Bud31|Ptcd1 | 1.401 | 1.098 | 0.047 | |
| Proenkephalin | Penk | 1.394 | 1.073 | 0.017 | GO:0001662 behavioral fear response; GO:0007186 G-protein coupled receptor protein signaling pathway; GO:0007218 neuropeptide signaling pathway; GO:0007610 behavior; GO:0019233 sensory perception of pain |
| Musculoskeletal, embryonic nuclear protein 1 | Mustn1 | 1.394 | 1.074 | 0.031 | GO:0030326 embryonic limb morphogenesis; GO:0042060 wound healing; GO:0042246 tissue regeneration |
| EGF-like module containing, mucin-like, hormone receptor-like sequence 4 | Emr4 | 1.380 | 1.175 | 0.025 | GO:0007218 neuropeptide signaling pathway |
| Testis specific X-linked gene | Tsx | 1.378 | 1.245 | 0.000 | |
| Lecithin-retinol acyltransferase (phosphatidylcholine-retinol-O-acyltransferase) | Lrat | 1.369 | 1.058 | 0.004 | GO:0006776 vitamin A metabolic process; GO:0007601 visual perception; GO:0009790 embryonic development; GO:0042572 retinol metabolic process; GO:0050896 response to stimulus |
| Integrin, alpha 1 | Itga1 | 1.366 | 1.089 | 0.013 | GO:0000187 activation of MAPK activity; GO:0006936 muscle contraction; GO:0007155 cell adhesion; GO:0007229 integrin-mediated signaling pathway; GO:0030593 neutrophil chemotaxis; GO:0042311 vasodilation; GO:0043525 positive regulation of neuron apoptosis; GO:0045123 cellular extravasation; GO:0048812 neuron projection morphogenesis; GO:0060326 cell chemotaxis |
| Stathmin-like 3 | Stmn3 | 1.355 | 1.164 | 0.005 | GO:0007019 microtubule depolymerization; GO:0031122 cytoplasmic microtubule organization; GO:0031175 neuron projection development; GO:0032314 regulation of Rac GTPase activity; GO:0035021 negative regulation of Rac protein signal transduction; GO:0051493 regulation of cytoskeleton organization |
| Family with sequence similarity 12, member B (epididymal) | Fam12b | 1.344 | 1.134 | 0.003 | |
| Mitochondrial ribosomal protein L13 | Mrpl13 | 1.344 | 1.089 | 0.022 | GO:0006412 translation |
| Similar to RIKEN cDNA 1700023M03 | RGD1305457 | 1.344 | 1.078 | 0.000 | |
| Growth differentiation factor 9 | Gdf9 | 1.343 | 1.019 | 0.029 | GO:0001555 oocyte growth; GO:0030308 negative regulation of cell growth |
| Olfactory receptor 826 | olfactory receptor 825 | olfactory receptor 829 | Olr826|Olr825|Olr829 | 1.334 | 1.264 | 0.001 | GO:0007186 G-protein coupled receptor protein signaling pathway; GO:0050911 detection of chemical stimulus involved in sensory perception of smell; GO:0007165 signal transduction |
| Oxidized low density lipoprotein (lectin-like) receptor 1 | Olr1 | 1.333 | 1.081 | 0.022 | GO:0006954 inflammatory response; GO:0006955 immune response; GO:0007155 cell adhesion; GO:0007159 leukocyte cell-cell adhesion; GO:0008219 cell death; GO:0042157 lipoprotein metabolic process; GO:0042542 response to hydrogen peroxide |
| Heat shock protein alpha 2 | Hspa2 | 1.325 | 1.044 | 0.023 | GO:0006950 response to stress; GO:0007275 multicellular organismal development; GO:0007283 spermatogenesis; GO:0030154 cell differentiation |
| Membrane-spanning 4-domains, subfamily A, member 2 (Fc fragment of IgE, high affinity I, receptor for; beta polypeptide) | Ms4a2 | 1.321 | 1.129 | 0.031 | GO:0006954 inflammatory response; GO:0007165 signal transduction; GO:0007166 cell surface receptor linked signaling pathway; GO:0007202 activation of phospholipase C activity; GO:0007205 activation of protein kinase C activity by G-protein coupled receptor protein signaling pathway; GO:0043306 positive regulation of mast cell degranulation; GO:0050663 cytokine secretion; GO:0051279 regulation of release of sequestered calcium ion into cytosol |

TABLE 3-continued details all genes with differential expression between DSS and Control and DSS/HP and control in rats given Dextran Sodium Sulphate in water with or without co-treatment with hypothetical protein (HP).

| | | Fold change | | | |
|---|---|---|---|---|---|
| Gene description | Gene symbol | DSS vs Control | DSS/ HP vs Control | p-value | GO_biological_process (up to first 10) |
| Mesenchyme homeobox 2 | Meox2 | 1.320 | 1.087 | 0.013 | GO:0001525 angiogenesis; GO:0001757 somite specification; GO:0006355 regulation of transcription, DNA-dependent; GO:0007275 multicellular organismal development; GO:0007519 skeletal muscle tissue development; GO:0060021 palate development; GO:0060173 limb development |
| Angiopoietin-like 3 | Angptl3 | 1.319 | 1.166 | 0.002 | GO:0006071 glycerol metabolic process; GO:0006631 fatty acid metabolic process; GO:0006644 phospholipid metabolic process; GO:0007160 cell-matrix adhesion; GO:0007165 signal transduction; GO:0008203 cholesterol metabolic process; GO:0009395 phospholipid catabolic process; GO:0009725 response to hormone stimulus; GO:0010519 negative regulation of phospholipase activity; GO:0019915 lipid storage |
| Phosphotriesterase related | Pter | 1.318 | 1.091 | 0.008 | GO:0009056 catabolic process |
| G protein-coupled receptor 119 | Gpr119 | 1.317 | 1.164 | 0.036 | GO:0007165 signal transduction; GO:0007186 G-protein coupled receptor protein signaling pathway; GO:0030073 insulin secretion |
| Similar to 14-3-3 protein sigma | stratifin | LOC298795| Sfn | 1.309 | 1.084 | 0.036 | GO:0000079 regulation of cyclin-dependent protein kinase activity; GO:0001836 release of cytochrome c from mitochondria; GO:0008285 negative regulation of cell proliferation; GO:0008630 DNA damage response, signal transduction resulting in induction of apoptosis; GO:0030216 keratinocyte differentiation; GO:0030307 positive regulation of cell growth; GO:0043154 negative regulation of caspase activity; GO:0043588 skin development; GO:0043616 keratinocyte proliferation; GO:0000079 regulation of cyclin-dependent protein kinase activity |
| Serpine1 mRNA binding protein 1 | Serbp1 | 1.307 | 1.136 | 0.041 | GO:0045767 regulation of anti-apoptosis |
| Granzyme F | Gzmf | 1.300 | 1.043 | 0.027 | GO:0006508 proteolysis |
| Tissue factor pathway inhibitor (lipoprotein-associated coagulation inhibitor) | Tfpi | 1.298 | 1.198 | 0.000 | GO:0007596 blood coagulation; GO:0007598 blood coagulation, extrinsic pathway |
| Fibroblast growth factor 3 | Fgf3 | 1.294 | 1.138 | 0.036 | GO:0001759 induction of an organ; GO:0008284 positive regulation of cell proliferation; GO:0008543 fibroblast growth factor receptor signaling pathway; GO:0048538 thymus development |
| Secreted and transmembrane 1A | Sectm1a | 1.292 | 1.096 | 0.003 | GO:0043123 positive regulation of I-kappaB kinase/NF-kappaB cascade |
| Ubiquitin-conjugating enzyme | RGD69425 | 1.288 | 1.059 | 0.040 | GO:0008150 biological_process; GO:0043687 post-translational protein modification; GO:0051246 regulation of protein metabolic process |
| Neuropeptide W | Npw | 1.287 | 1.009 | 0.029 | GO:0007186 G-protein coupled receptor protein signaling pathway; GO:0007218 neuropeptide signaling pathway; GO:0007631 feeding behavior |
| | LOC362526 | 1.282 | 1.026 | 0.014 | |
| Olfactory receptor 1075 | Olr1075 | 1.279 | −1.179 | 0.027 | GO:0007186 G-protein coupled receptor protein signaling pathway; GO:0050911 detection of chemical stimulus involved in sensory perception of smell |
| Myelin protein zero-like 1 | Mpzl1 | 1.278 | 1.269 | 0.001 | |
| Keratin 18 | Krt18 | 1.276 | 1.124 | 0.048 | GO:0006915 apoptosis; GO:0008150 biological_process; GO:0033209 tumor necrosis factor-mediated signaling pathway; GO:0043000 Golgi to plasma membrane CFTR protein transport; GO:0043066 negative regulation of apoptosis |
| Choline phosphotransferase 1 | Chpt1 | 1.273 | 1.198 | 0.033 | GO:0006656 phosphatidylcholine biosynthetic process; GO:0006663 platelet activating factor biosynthetic process; GO:0008654 phospholipid biosynthetic process |
| Neurogenic differentiation 1 | Neurod1 | 1.271 | 1.152 | 0.020 | GO:0003326 pancreatic A cell fate commitment; GO:0003329 pancreatic PP cell fate commitment; GO:0006355 regulation of transcription, DNA-dependent; GO:0007263 nitric oxide mediated signal transduction; GO:0007275 multicellular organismal development; GO:0007399 nervous system development; GO:0009749 response to glucose stimulus; GO:0009952 anterior/posterior pattern formation; GO:0021549 cerebellum development; GO:0030073 insulin secretion |
| Fibroblast growth factor 2 | Fgf2 | 1.264 | 1.032 | 0.042 | GO:0000186 activation of MAPKK activity; GO:0000189 nuclear translocation of MAPK; GO:0001525 angiogenesis; GO:0001658 branching involved in ureteric bud morphogenesis; GO:0001759 induction of an organ; GO:0001934 positive regulation of protein amino acid phosphorylation; GO:0002042 cell migration involved in sprouting angiogenesis; GO:0006355 regulation of transcription, DNA-dependent; GO:0006700 C21-steroid hormone biosynthetic process; GO:0006915 apoptosis |

TABLE 3-continued details all genes with differential expression between DSS and Control and DSS/HP and control in rats given
Dextran Sodium Sulphate in water with or without co-treatment with hypothetical protein (HP).

| | | Fold change | | | |
|---|---|---|---|---|---|
| Gene description | Gene symbol | DSS vs Control | DSS/ HP vs Control | p-value | GO_biological_process (up to first 10) |
| Fin bud initiation factor homolog (zebrafish) | Fibin | 1.264 | 1.014 | 0.001 | |
| Olfactory receptor 7 | Olr7 | 1.261 | 1.228 | 0.011 | GO:0007186 G-protein coupled receptor protein signaling pathway; GO:0050911 detection of chemical stimulus involved in sensory perception of smell |
| Sterol O-acyltransferase 2 | Soat2 | 1.256 | −1.037 | 0.016 | GO:0007584 response to nutrient; GO:0008202 steroid metabolic process; GO:0008203 cholesterol metabolic process; GO:0033344 cholesterol efflux; GO:0034379 veiy-low-density lipoprotein particle assembly; GO:0034435 cholesterol esterification |
| Neurexin 1 | Nrxn1 | 1.256 | 1.071 | 0.022 | GO:0007268 synaptic transmission; GO:0007269 neurotransmitter secretion; GO:0007416 synapse assembly; GO:0051290 protein heterotetramerization |
| MARCKS-like 1 | Marcksl1 | 1.251 | 1.104 | 0.033 | GO:0008284 positive regulation of cell proliferation; GO:0016192 vesicle-mediated transport |
| Calcium/calmodulin-dependent protein kinase II inhibitor 1 | Camk2n1 | 1.251 | 1.151 | 0.024 | GO:0007268 synaptic transmission |
| Armadillo repeat containing, X-linked 1 | Armcx1 | 1.247 | 1.042 | 0.003 | |
| Protocadherin beta 2 | Pcdhb2 | 1.244 | 1.090 | 0.037 | GO:0007155 cell adhesion GO:0007156 homophilic cell adhesion |
| ELAV (embryonic lethal, abnormal vision, *Drosophila*)-like 2 (Hu antigen B) | Elavl2 | 1.242 | −1.022 | 0.041 | |
| DNA-damage regulated autophagy modulator 2 \| similar to CG4025-PA | Dram2\| LOC689412 | 1.239 | 1.088 | 0.013 | GO:0006915 apoptosis; GO:0006917 induction of apoptosis |
| Proteolipid protein 1 | Plp1 | 1.238 | 1.183 | 0.019 | GO:0007229 integrin-mediated signaling pathway; GO:0008366 axon ensheathment; GO:0010001 glial cell differentiation; GO:0022010 myelination in the central nervous system; GO:0042552 myelination GO:0042759 long-chain fatty acid biosynthetic process; GO:0048469 cell maturation |
| Aspartoacylase | Aspa | 1.237 | 1.012 | 0.036 | GO:0008152 metabolic process; GO:0022010 myelination in the central nervous system; GO:0048714 positive regulation of oligodendrocyte differentiation |
| First gene upstream of Nt5dc3 | LOC362863 | 1.232 | 1.198 | 0.037 | |
| PRKC, apoptosis, WT1, regulator | Pawr | 1.232 | 1.140 | 0.049 | GO:0006915 apoptosis; GO:0030889 negative regulation of B cell proliferation; GO:0042094 interleukin-2 biosynthetic process; GO:0042130 negative regulation of T cell proliferation; GO:0042986 positive regulation of amyloid precursor protein biosynthetic process; GO:0045449 regulation of transcription; GO:0050860 negative regulation of T cell receptor signaling pathway |
| Glutamate receptor, ionotropic, AMPA4 | Gria4 | 1.231 | 1.181 | 0.036 | GO:0007268 synaptic transmission |
| Fumarylacetoacetate hydrolase domain containing 1 | Fahd1 | 1.229 | 1.152 | 0.039 | GO:0008152 metabolic process |
| McKusick-Kaufman syndrome | Mkks | 1.225 | 1.178 | 0.010 | GO:0007286 spermatid development; GO:0007608 sensory perception of smell; GO:0008150 biological_process; GO:0009296 flagellum assembly; GO:0021756 striatum development; GO:0021766 hippocampus development; GO:0021987 cerebral cortex development; GO:0035058 sensory cilium assembly; GO:0035176 social behavior; GO:0042384 cilium assembly |
| Protein kinase inhibitor, gamma | Pkig | 1.223 | 1.226 | 0.017 | GO:0000122 negative regulation of transcription from RNA polymerase II promoter; GO:0006469 negative regulation of protein kinase activity; GO:0007165 signal transduction; GO:0042308 negative regulation of protein import into nucleus |
| Cholecystokinin B receptor | Cckbr | 1.222 | 1.103 | 0.036 | GO:0001821 histamine secretion; GO:0002209 behavioral defense response; GO:0006915 apoptosis; GO:0007165 signal transduction; GO:0007186 G-protein coupled receptor protein signaling pathway; GO:0007204 elevation of cytosolic calcium ion concentration; GO:0007586 digestion; GO:0008284 positive regulation of cell proliferation; GO:0032230 positive regulation of synaptic transmission, GABAergic; GO:0032868 response to insulin stimulus |
| RAS-like family 11 member B | Rasl11b | 1.221 | 1.156 | 0.028 | GO:0007165 signal transduction; GO:0007264 small GTPase mediated signal transduction |
| Galanin receptor 1 | Galr1 | 1.219 | 1.117 | 0.047 | GO:0007165 signal transduction; GO:0007186 G-protein coupled receptor protein signaling pathway; GO:0007189 activation of adenylate cyclase activity by G-protein signaling pathway |
| Potassium voltage gated channel, Shab-related subfamily, member 1 | Kcnb1 | 1.217 | 1.040 | 0.038 | GO:0006811 ion transport; GO:0006813 potassium ion transport; GO:0051259 protein oligomerization; GO:0055085 transmembrane transport |

TABLE 3-continued details all genes with differential expression between DSS and Control and DSS/HP and control in rats given
Dextran Sodium Sulphate in water with or without co-treatment with hypothetical protein (HP).

| | | Fold change | | | |
|---|---|---|---|---|---|
| Gene description | Gene symbol | DSS vs Control | DSS/ HP vs Control | p-value | GO_biological_process (up to first 10) |
| Protein disulfide isomerase family A, member 4 | Pdia4 | 1.216 | 1.159 | 0.037 | GO:0045454 cell redox homeostasis |
| Myosin, light polypeptide 1 | Myl1 | 1.215 | 1.128 | 0.024 | GO:0060048 cardiac muscle contraction |
| Persephin | Pspn | 1.213 | 1.255 | 0.006 | GO:0001658 branching involved in ureteric bud morphogenesis |
| Tumor necrosis factor (ligand) superfamily, member 13 | Tnfsf13 | 1.212 | 1.228 | 0.001 | GO:0002426 immunoglobulin production in mucosal tissue; GO:0002636 positive regulation of germinal center formation; GO:0006955 immune response; GO:0008150 biological_process; GO:0008284 positive regulation of cell proliferation; GO:0016064 immunoglobulin mediated immune response; GO:0048298 positive regulation of isotype switching to IgA isotypes; GO:0050776 regulation of immune response |
| ADP-ribosylation factor interacting protein 1 | Arfip1 | 1.211 | 1.039 | 0.027 | GO:0006886 intracellular protein transport; GO:0050708 regulation of protein secretion |
| Zinc finger, MYND-type containing 19 | Zmynd19 | 1.211 | 1.043 | 0.035 | |
| Centrosomal protein 70 kDa | Cep70 | 1.210 | 1.158 | 0.024 | |
| Ribosomal L24 domain containing 1 | Rsl24d1 | 1.210 | 1.139 | 0.035 | GO:0006412 translation; GO:0042254 ribosome biogenesis |
| Ring finger protein 133 | Rnf133 | 1.209 | 1.157 | 0.018 | GO:0051865 protein autoubiquitination |
| Plasma glutamate carboxypeptidase | Pgcp | 1.205 | 1.147 | 0.044 | GO:0006508 proteolysis; GO:0042246 tissue regeneration |
| DnaJ (Hsp40) homolog, subfamily A, member 1 | Dnaja1 | 1.199 | 1.320 | 0.014 | GO:0006457 protein folding; GO:0007283 spermatogenesis; GO:0009408 response to heat; GO:0030317 sperm motility; GO:0030521 androgen receptor signaling pathway; GO:0042769 DNA damage response, detection of DNA damage |
| Transmembrane and coiled-coil domains 1 | Tmco1 | 1.198 | 1.057 | 0.011 | GO:0008150 biological process |
| Arrestin, beta 1 | Arrb1 | 1.196 | 1.204 | 0.002 | GO:0000187 activation of MAPK activity; GO:0002031 G-protein coupled receptor internalization; GO:0002032 desensitization of G-protein coupled receptor protein signaling pathway by arrestin; GO:0006366 transcription from RNA polymerase II promoter; GO:0006892 post-Golgi vesicle-mediated transport; GO:0006897 endocytosis; GO:0007165 signal transduction; GO:0007186 G-protein coupled receptor protein signaling pathway; GO:0007188 G-protein signaling, coupled to cAMP nucleotide second messenger //; GO:0007600 sensory perception |
| Dystonia 1 | Dyt1 | 1.193 | 1.043 | 0.002 | GO:0006457 protein folding; GO:0006979 response to oxidative stress; GO:0051085 chaperone mediated protein folding requiring cofactor |
| Latrophilin 3 | Lphn3 | 1.191 | 1.172 | 0.025 | GO:0007218 neuropeptide signaling pathway; GO:0007420 brain development |
| FK506 binding protein 14 | Fkbp14 | 1.190 | 1.332 | 0.022 | GO:0006457 protein folding |
| Nitric oxide synthase 2, inducible | Nos2 | 1.188 | 1.001 | 0.021 | GO:0001542 ovulation from ovarian follicle; GO:0001666 response to hypoxia; GO:0001935 endothelial cell proliferation; GO:0001974 blood vessel remodeling; GO:0006527 arginine catabolic process; GO:0006801 superoxide metabolic process; GO:0006809 nitric oxide biosynthetic process; GO:0007165 signal transduction; GO:0007199 G-protein signaling, coupled to cGMP nucleotide second messenger; GO:0007243 intracellular protein kinase cascade |
| Olfactory receptor 1105 | Olr1105 | 1.187 | −1.050 | 0.026 | GO:0007186 G-protein coupled receptor protein signaling pathway; GO:0050911 detection of chemical stimulus involved in sensory perception of smell |
| Heat shock protein beta 2 | Hspb2 | 1.186 | −1.117 | 0.041 | GO:0007525 somatic muscle development; GO:0009408 response to heat |
| Uncoupling protein 1 (mitochondrial, proton carrier) | Ucp1 | 1.185 | 1.100 | 0.009 | GO:0006091 generation of precursor metabolites and energy; GO:0006839 mitochondrial transport; GO:0015992 proton transport; GO:0032870 cellular response to hormone stimulus; GO:0044253 positive regulation of multicellular organismal metabolic process; GO:0048545 response to steroid hormone stimulus; GO:0050873 brown fat cell differentiation; GO:0055085 transmembrane transport |
| Ankyrin repeat and SOCS box-containing 2 | Asb2 | 1.182 | 1.117 | 0.037 | |
| WD repeat domain 31 | Wdr31 | 1.182 | 1.041 | 0.036 | |
| Neurexophilin 4 | Nxph4 | 1.180 | −1.046 | 0.047 | |
| Keratin 82 | Krt82 | 1.178 | 1.063 | 0.043 | |
| Feline leukemia virus subgroup C cellular receptor family, member 2 | Flvcr2 | 1.177 | −1.071 | 0.028 | GO:0055085 transmembrane transport |
| Alpha-2u globulin PGCL4 \| major urinary protein 4 \| alpha-2u globulin PGCL3 \| alpha-2u globulin PGCL1 \| alpha2u globulin \| alpha-2u globulin | Obp3\|Mup4\| LOC259244\| LOC259246\| LOC298111\| | 1.176 | −1.185 | 0.030 | GO:0006810 transport |

TABLE 3-continued details all genes with differential expression between DSS and Control and DSS/HP and control in rats given Dextran Sodium Sulphate in water with or without co-treatment with hypothetical protein (HP).

| | | Fold change | | | |
|---|---|---|---|---|---|
| Gene description | Gene symbol | DSS vs Control | DSS/ HP vs Control | p-value | GO_biological_process (up to first 10) |
| PGCL2 \| alpha 2U globulin | LOC298109\|LOC366380 | | | | |
| Reelin | Reln | 1.176 | 1.055 | 0.037 | GO:0000904 cell morphogenesis involved in differentiation; GO:0001764 neuron migration; GO:0007411 axon guidance; GO:0007417 central nervous system development; GO:0007420 brain development; GO:0007626 locomotory behavior; GO:0010001 glial cell differentiation; GO:0018108 peptidyl-tyrosine phosphorylation; GO:0021511 spinal cord patterning; GO:0021800 cerebral cortex tangential migration |
| Vesicle-associated membrane protein 7 | Vamp7 | 1.175 | 1.049 | 0.048 | GO:0006888 ER to Golgi vesicle-mediated transport; GO:0006906 vesicle fusion; GO:0006911 phagocytosis, engulfment; GO:0008333 endosome to lysosome transport; GO:0015031 protein transport; GO:0016044 cellular membrane organization; GO:0016192 vesicle-mediated transport; GO:0017156 calcium ion-dependent exocytosis; GO:0043308 eosinophil degranulation; GO:0043312 neutrophil degranulation |
| Plasminogen | Plg | 1.175 | −1.022 | 0.037 | GO:0006915 apoptosis; GO:0006917 induction of apoptosis; GO:0007596 blood coagulation; GO:0042246 tissue regeneration; GO:0045445 myoblast differentiation; GO:0046716 muscle cell homeostasis; GO:0048771 tissue remodeling; GO:0051603 proteolysis involved in cellular protein catabolic process; GO:0051918 negative regulation of fibrinolysis; GO:0051919 positive regulation of fibrinolysis |
| Family with sequence similarity 131, member B | Fam131b | 1.173 | 1.085 | 0.020 | |
| Cholinergic receptor, nicotinic, beta 2 (neuronal) | Chrnb2 | 1.169 | 1.112 | 0.004 | GO:0001508 regulation of action potential; GO:0001661 conditioned taste aversion; GO:0001666 response to hypoxia; GO:0006811 ion transport; GO:0006816 calcium ion transport; GO:0006939 smooth muscle contraction; GO:0007165 signal transduction; GO:0007271 synaptic transmission, cholinergic; GO:0007601 visual perception; GO:0007605 sensory perception of sound |
| Dynein light chain LC8-type 1 | Dynll1 | 1.169 | 1.153 | 0.033 | GO:0006809 nitric oxide biosynthetic process; GO:0007017 microtubule-based process; GO:0008633 activation of pro-apoptotic gene products; GO:0042133 neurotransmitter metabolic process; GO:0042326 negative regulation of phosphorylation |
| Kinesin family member 27 | Kif27 | 1.167 | 1.078 | 0.005 | GO:0007018 microtubule-based movement |
| LOC362793 | RGD1307315 | 1.165 | 1.033 | 0.021 | |
| Unc-50 homolog (C. elegans) | Unc50 | 1.163 | 1.035 | 0.044 | GO:0007166 cell surface receptor linked signaling pathway; GO:0015031 protein transport |
| Sonic hedgehog | Shh | 1.163 | 1.202 | 0.010 | GO:0001525 angiogenesis; GO:0001569 patterning of blood vessels; GO:0001570 vasculogenesis; GO:0001656 metanephros development; GO:0001658 branching involved in ureteric bud morphogenesis; GO:0001666 response to hypoxia; GO:0001708 cell fate specification; GO:0001755 neural crest cell migration; GO:0001822 kidney development; GO:0001841 neural tube formation |
| Histidine decarboxylase | Hdc | 1.162 | 1.041 | 0.044 | GO:0001692 histamine metabolic process; GO:0006519 cellular amino acid and derivative metabolic process; GO:0006547 histidine metabolic process; GO:0006548 histidine catabolic process; GO:0019752 carboxylic acid metabolic process; GO:0042423 catecholamine biosynthetic process |
| Olfactory receptor 1593 | Olr1593 | 1.162 | 1.083 | 0.037 | GO:0007186 G-protein coupled receptor protein signaling pathway; GO:0050911 detection of chemical stimulus involved in sensory perception of smell |
| Zinc finger protein 354A | Zfp354a | 1.160 | 1.051 | 0.007 | GO:0000122 negative regulation of transcription from RNA polymerase II promoter; GO:0001666 response to hypoxia; GO:0001822 kidney development; GO:0006355 regulation of transcription, DNA-dependent; GO:0007275 multicellular organismal development; GO:0007576 nucleolar fragmentation; GO:0051593 response to folic acid |
| Tumor protein p63 | Tp63 | 1.157 | 1.048 | 0.026 | GO:0000122 negative regulation of transcription from RNA polymerase II promoter; GO:0001302 replicative cell aging; GO:0001501 skeletal system development; GO:0001736 establishment of planar polarity; GO:0001738 morphogenesis of a polarized epithelium; GO:0001942 hair follicle development; GO:0002053 positive regulation of mesenchymal cell proliferation; GO:0002064 epithelial cell development; GO:0006915 apoptosis; GO:0006916 anti-apoptosis |

TABLE 3-continued details all genes with differential expression between DSS and Control and DSS/HP and control in rats given
Dextran Sodium Sulphate in water with or without co-treatment with hypothetical protein (HP).

| | | Fold change | | | |
|---|---|---|---|---|---|
| Gene description | Gene symbol | DSS vs Control | DSS/HP vs Control | p-value | GO_biological_process (up to first 10) |
| Histone cluster 1, H1t | Hist1h1t | 1.155 | 1.034 | 0.015 | GO:0006334 nucleosome assembly; GO:0007275 multicellular organismal development; GO:0007283 spermatogenesis; GO:0007339 binding of sperm to zona pellucida; GO:0030154 cell differentiation; GO:0030317 sperm motility |
| Disabled homolog 1 (*Drosophila*) | Dab1 | 1.154 | −1.073 | 0.018 | GO:0001764 neuron migration; GO:0007162 negative regulation of cell adhesion; GO:0007264 small GTPase mediated signal transduction; GO:0007275 multicellular organismal development; GO:0007399 nervous system development; GO:0007420 brain development; GO:0021589 cerebellum structural organization; GO:0021795 cerebral cortex cell migration; GO:0021799 cerebral cortex radially oriented cell migration; GO:0021813 cell-cell adhesion involved in neuronal-glial interactions involved in cerebral cortex radial glia guided migration |
| Leucine rich repeat containing 66 | Lrrc66 | 1.154 | 1.139 | 0.045 | |
| Neuronal PAS domain protein 4 | Npas4 | 1.154 | 1.095 | 0.015 | GO:0007165 signal transduction; GO:0045941 positive regulation of transcription; GO:0045944 positive regulation of transcription from RNA polymerase II promoter, GO:0045944 positive regulation of transcription from RNA polymerase II promoter |
| N-acetylneuraminic acid phosphatase | Nanp | 1.154 | 1.165 | 0.042 | GO:0005975 carbohydrate metabolic process; GO:0008152 metabolic process; GO:0046380 N-acetylneuraminate biosynthetic process |
| MAD2L1 binding protein | Mad2l1bp | 1.152 | 1.111 | 0.004 | GO:0007093 mitotic cell cycle checkpoint; GO:0007096 regulation of exit from mitosis |
| Neuromedin S | NMS | 1.152 | −1.015 | 0.045 | GO:0006940 regulation of smooth muscle contraction; GO:0007218 neuropeptide signaling pathway; GO:0045475 locomotor rhythm |
| Transmembrane protease, serine 8 (intestinal) | Tmprss8 | 1.149 | 1.203 | 0.035 | GO:0006508 proteolysis; GO:0006811 ion transport; GO:0006814 sodium ion transport |
| Myoglobin | Mb | 1.149 | 1.036 | 0.015 | GO:0001666 response to hypoxia; GO:0006810 transport; GO:0007507 heart development; GO:0009725 response to hormone stimulus; GO:0015671 oxygen transport; GO:0031444 slow-twitch skeletal muscle fiber contraction; GO:0042542 response to hydrogen peroxide; GO:0043353 enucleate erythrocyte differentiation; GO:0050873 brown fat cell differentiation |
| Similar to RIKEN cDNA 1500031L02 | RGD621352 | 1.145 | 1.411 | 0.006 | |
| Dehydrogenase/reductase (SDR family) member 7 | Dhrs7 | 1.145 | −1.013 | 0.046 | GO:0055114 oxidation reduction |
| Nuclear pore associated protein | Npap60 | 1.143 | −1.073 | 0.033 | GO:0001841 neural tube formation; GO:0015031 protein transport; GO:0046907 intracellular transport; GO:0051028 mRNA transport; GO:0055085 transmembrane transport |
| Olfactory receptor 484 | Olr484 | 1.141 | 1.355 | 0.016 | GO:0007186 G-protein coupled receptor protein signaling pathway; GO:0050911 detection of chemical stimulus involved in sensory perception of smell |
| Torsin family 3, member A | Tor3a | 1.140 | 1.088 | 0.020 | GO:0051085 chaperone mediated protein folding requiring cofactor |
| Similar to Protein C20orf103 precursor | RGD1306991 | 1.139 | −1.041 | 0.041 | |
| Similar to RAN protein | RGD1306195 | 1.138 | 1.112 | 0.014 | GO:0006886 intracellular protein transport; GO:0006913 nucleocytoplasmic transport; GO:0007165 signal transduction |
| Natriuretic peptide receptor A/ guanylate cyclase A (atrionatriuretic peptide receptor A) | Npr1 | 1.138 | 1.050 | 0.034 | GO:0006182 cGMP biosynthetic process; GO:0006468 protein amino acid phosphorylation; GO:0007166 cell surface receptor linked signaling pathway; GO:0007168 receptor guanylyl cyclase signaling pathway; GO:0008217 regulation of blood pressure; GO:0030828 positive regulation of cGMP biosynthetic process; GO:0042417 dopamine metabolic process |
| Olfactory receptor 174 | Olr174 | 1.138 | 1.294 | 0.040 | GO:0007186 G-protein coupled receptor protein signaling pathway; GO:0050911 detection of chemical stimulus involved in sensory perception of smell |
| NADH dehydrogenase (ubiquinone) 1 alpha subcomplex, assembly factor 3 | Ndufaf3 | 1.131 | −1.084 | 0.042 | GO:0032981 mitochondrial respiratory chain complex I assembly I assembly |
| Interleukin 6 signal tiansducer | Il6st | 1.128 | 1.061 | 0.001 | GO:0005977 glycogen metabolic process; GO:0006642 triglyceride mobilization; GO:0007165 signal transduction; GO:0007259 JAK-STAT cascade; GO:0007584 response to nutrient; GO:0008284 positive regulation of cell proliferation; GO:0008593 regulation of Notch signaling pathway; GO:0014911 positive regulation of smooth muscle cell migration; GO:0019221 cytokine-mediated signaling pathway; GO:0030307 positive regulation of cell growth |
| Synuclein, alpha (non A4 component of amyloid precursor) | Snca | 1.127 | 1.096 | 0.005 | GO:0001774 microglial cell activation; GO:0001921 positive regulation of receptor recycling; GO:0001956 positive regulation |

TABLE 3-continued details all genes with differential expression between DSS and Control and DSS/HP and control in rats given Dextran Sodium Sulphate in water with or without co-treatment with hypothetical protein (HP).

| Gene description | Gene symbol | Fold change DSS vs Control | Fold change DSS/HP vs Control | p-value | GO_biological_process (up to first 10) |
|---|---|---|---|---|---|
| | | | | | of neurotransmitter secretion; GO:0001963 synaptic transmission, dopaminergic; GO:0006631 fatty acid metabolic process; GO:0006638 neutral lipid metabolic process; GO:0006644 phospholipid metabolic process; GO:0006916 anti-apoptosis; GO:0007006 mitochondrial membrane organization; GO:0008344 adult locomotory behavior |
| Interferon regulatory factor 3 | Irf3 | 1.127 | 1.166 | 0.011 | GO:0006355 regulation of transcription, DNA-dependent; GO:0007249 I-kappaB kinase/NF-kappaB cascade; GO:0009617 response to bacterium; GO:0031663 lipopolysaccharide-mediated signaling pathway; GO:0032496 response to lipopolysaccharide; GO:0043330 response to exogenous dsRNA; GO:0045351 type I interferon biosynthetic process |
| Asialoglycoprotein receptor 1 | Asgr1 | 1.121 | 1.051 | 0.028 | GO:0006897 endocytosis; GO:0031668 cellular response to extracellular stimulus |
| Heat shock 105 kDa/110 kDa protein 1 | Hsph1 | 1.120 | 1.358 | 0.036 | GO:0006950 response to stress; GO:0051085 chaperone mediated protein folding requiring cofactor |
| Actin, gamma 2, smooth muscle, enteric | Actg2 | 1.117 | 1.070 | 0.008 | GO:0006936 muscle contraction |
| Similar to putative protein, with at least 9 transmembrane domains, of eukaryotic origin (43.9 kD) (2G415) | RGD1309228 | 1.111 | 1.099 | 0.007 | |
| Transient receptor potential cation channel, subfamily V, member 2 | Trpv2 | 1.111 | 1.060 | 0.018 | GO:0006811 ion transport; GO:0006816 calcium ion transport; GO:0009266 response to temperature stimulus; GO:0009408 response to heat; GO:0055085 transmembrane transport |
| Glutathione S-transferase, theta 2 | Gstt2 | 1.108 | 1.123 | 0.033 | GO:0006749 glutathione metabolic process |
| Adenosine A3 receptor | Adora3 | 1.099 | −1.150 | 0.048 | GO:0001973 adenosine receptor signaling pathway; GO:0002553 histamine secretion by mast cell; GO:0002687 positive regulation of leukocyte migration; GO:0007165 signal transduction; GO:0007186 G-protein coupled receptor protein signaling pathway; GO:0014061 regulation of norepinephrine secretion; GO:0014068 positive regulation of phosphoinositide 3-kinase cascade; GO:0043306 positive regulation of mast cell degranulation; GO:0050729 positive regulation of inflammatory response; GO:0050850 positive regulation of calcium-mediated signaling |
| Sarcolipin | Sln | 1.087 | 1.355 | 0.038 | GO:0051924 regulation of calcium ion transport |
| N-myc downstream regulated gene 4 | Ndrg4 | 1.087 | 1.105 | 0.010 | |
| Gypsy retrotransposon integrase 1 | Gin1 | 1.086 | 1.054 | 0.025 | GO:0015074 DNA integration |
| ATP-binding cassette, sub-family G (WHITE), member 3-like 1 \| ATP-binding cassette, sub-family G (WHITE), member 3-like 2 \| similar to ATP-binding cassette, sub-family G (WHITE), member 3 | Abcg3l1\|Abcg3l2\|RGD1564709\|LOC360997 | 1.084 | 1.064 | 0.043 | |
| Oxytocin prepropeptide \| arginine vasopressin | Oxt\|Avp | 1.084 | −1.112 | 0.013 | GO:0001696 gastric acid secretion; GO:0001975 response to amphetamine; GO:0002027 regulation of heart rate; GO:0002125 maternal aggressive behavior; GO:0003077 negative regulation of diuresis; GO:0003079 positive regulation of natriuresis; GO:0006950 response to stress; GO:0007204 elevation of cytosolic calcium ion concentration; GO:0007507 heart development; GO:0007565 female pregnancy |
| Thimet oligopeptidase 1 | Thop1 | 1.080 | −1.013 | 0.049 | GO:0006508 proteolysis; GO:0006518 peptide metabolic process; GO:0007243 intracellular protein kinase cascade |
| cAMP responsive element binding protein 3 | Creb3 | 1.078 | 1.137 | 0.021 | GO:0006355 regulation of transcription, DNA-dependent |
| Peroxisomal biogenesis factor 12 | Pex12 | 1.071 | 1.149 | 0.001 | GO:0007031 peroxisome organization. GO:0015031 protein transport; GO:0016558 protein import into peroxisome matrix |
| Endothelin receptor type A \| endothelin-1 receptor-like | Ednra\|LOC100366209 | 1.071 | 1.130 | 0.009 | GO:0001569 patterning of blood vessels; GO:0001666 response to hypoxia; GO:0001701 in utero embryonic development; GO:0001934 positive regulation of protein amino acid phosphorylation; GO:0007165 signal transduction; GO:0007204 elevation of cytosolic calcium ion concentration; GO:0007205 activation of protein kinase C activity by G-protein coupled receptor protein signaling pathway; GO:0007507 heart development; GO:0007585 respiratory gaseous exchange; GO:0008217 regulation of blood pressure |
| | Mkl | 1.068 | −1.152 | 0.038 | GO:0030036 actin cytoskeleton organization |
| Protein geranylgeranyltransferase type I, beta subunit | Pggt1b | 1.062 | 1.162 | 0.039 | GO:0008284 positive regulation of cell proliferation; GO:0018348 protein amino acid geranylgeranylation; GO:0034097 response to cytokine stimulus; GO:0045787 positive regulation of cell cycle; |

TABLE 3-continued details all genes with differential expression between DSS and Control and DSS/HP and control in rats given
Dextran Sodium Sulphate in water with or without co-treatment with hypothetical protein (HP).

| Gene description | Gene symbol | Fold change DSS vs Control | Fold change DSS/HP vs Control | p-value | GO_biological_process (up to first 10) |
|---|---|---|---|---|---|
| Olfactory receptor 1356 | Olr1356 | 1.061 | 1.323 | 0.021 | GO:0051774 negative regulation of nitric-oxide synthase 2 biosynthetic process; GO:0051789 response to protein stimulus GO:0007186 G-protein coupled receptor protein signaling pathway; GO:0050911 detection of chemical stimulus involved in sensory perception of smell |
| Immunity-related GTPase family, cinema 1 | Irgc1 | 1.060 | −1.124 | 0.017 | |
| Distal-less homeobox 5 | Dlx5 | 1.050 | −1.140 | 0.008 | GO:0001649 osteoblast differentiation; GO:0001958 endochondial ossification; GO:0006355 regulation of transcription, DNA-dependent; GO:0007275 multicellular organismal development; GO:0007399 nervous system development; GO:0007409 axonogenesis; GO:0007411 axon guidance; GO:0008283 cell proliferation; GO:0030326 embryonic limb morphogenesis; GO:0030855 epithelial cell differentiation |
| RELT-like 2 \| FCH and double SH3 domains 1 | Rell2\|Fchsd1 | 1.047 | −1.088 | 0.041 | GO:0010811 positive regulation of cell-substrate adhesion |
| Membrane magnesium transporter 2 | Mmgt2 | 1.047 | 1.171 | 0.025 | GO:0006810 transport; GO:0006824 cobalt ion transport; GO:0006825 copper ion transport; GO:0006828 manganese ion transport; GO:0015674 di-, tri-valent inorganic cation transport; GO:0015675 nickel ion transport; GO:0015693 magnesium ion transport |
| STEAP family member 3 | Steap3 | 1.046 | 1.177 | 0.004 | GO:0006811 ion transport; GO:0006826 iron ion transport; GO:0006915 apoptosis; GO:0006917 induction of apoptosis; GO:0007049 cell cycle; GO:0009306 protein secretion; GO:0055114 oxidation reduction |
| Sialidase 2 (cytosolic sialidase) | Neu2 | 1.030 | 1.134 | 0.023 | GO:0008152 metabolic process; GO:0010831 positive regulation of myotube differentiation; GO:0045471 response to ethanol; GO:0045663 positive regulation of myoblast differentiation |
| Spermatogenesis associated 6 | Spata6 | 1.028 | 1.057 | 0.045 | GO:0007275 multicellular organismal development; GO:0007283 spermatogenesis; GO:0030154 cell differentiation |
| Fibroblast growth factor 20 | Fgf20 | 1.027 | −1.096 | 0.044 | GO:0008284 positive regulation of cell proliferation; GO:0008543 fibroblast growth factor receptor signaling pathway; GO:0016049 cell growth; GO:0030154 cell differentiation; GO:0060113 inner ear receptor cell differentiation |
| Cholinergic receptor, nicotinic, alpha 9 | Chrna9 | 1.022 | −1.124 | 0.006 | GO:0006812 cation transport; GO:0006816 calcium ion transport; GO:0007204 elevation of cytosolic calcium ion concentration; GO:0007605 sensory perception of sound; GO:0042472 inner ear morphogenesis; GO:0050910 detection of mechanical stimulus involved in sensory perception of sound |
| Coagulation factor II (thrombin) receptor | F2r | 1.005 | 1.345 | 0.007 | GO:0000186 activation of MAPKK activity; GO:0002248 connective tissue replacement during inflammatory response; GO:0006919 activation of caspase activity; GO:0006954 inflammatory response; GO:0007165 signal transduction; GO:0007186 G-protein coupled receptor protein signaling pathway; GO:0007205 activation of protein kinase C activity by G-protein coupled receptor protein signaling pathway; GO:0007260 tyrosine phosphorylation of STAT protein; GO:0007262 STAT protein nuclear translocation; GO:0007529 establishment of synaptic specificity at neuromuscular junction |
| Potassium channel, subfamily K, member 1 | Kcnk1 | 1.004 | 1.241 | 0.015 | GO:0006811 ion transport; GO:0006813 potassium ion transport; GO:0035094 response to nicotine |
| Ameloblastin | Ambn | −1.000 | −1.046 | 0.025 | |
| Adhesion molecule with Ig like domain 3 | Amigo3 | −1.023 | 1.147 | 0.022 | GO:0007155 cell adhesion; GO:0007157 heterophilic cell-cell adhesion; GO:0007399 nervous system development |
| Ankyrin repeat and SOCS box-containing 6 | Asb6 | −1.028 | −1.072 | 0.015 | |
| ATPase, H transporting, lysosomal V1 subunit B2 | Atp6v1b2 | −1.039 | 1.046 | 0.011 | GO:0006811 ion transport; GO:0007035 vacuolar acidification; GO:0015986 ATP synthesis coupled proton transport; GO:0015992 proton transport; GO:0030641 regulation of cellular pH; GO:0046034 ATP metabolic process |
| Myeloid/lymphoid or mixed-lineage leukemia (trithorax homolog, *Drosophila*); translocated to, 10 | Mllt10 | −1.041 | −1.001 | 0.023 | GO:0008150 biological_process |
| Phosphorylase kinase, beta | Phkb | −1.042 | 1.078 | 0.009 | GO:0005976 polysaccharide metabolic process; GO:0005977 glycogen metabolic process |
| Olfactory receptor 1409 | Olr1409 | −1.059 | −1.105 | 0.038 | GO:0007186 G-protein coupled receptor protein signaling pathway; GO:0050911 detection of chemical stimulus involved in sensory perception of smell |
| MIF4G domain containing | Mif4gd | −1.063 | −1.109 | 0.002 | GO:0006417 regulation of translation; GO:0016070 RNA metabolic process |

TABLE 3-continued details all genes with differential expression between DSS and Control and DSS/HP and control in rats given
Dextran Sodium Sulphate in water with or without co-treatment with hypothetical protein (HP).

| | | Fold change | | | |
|---|---|---|---|---|---|
| Gene description | Gene symbol | DSS vs Control | DSS/ HP vs Control | p-value | GO_biological_process (up to first 10) |
| Olfactory receptor 44 | Olr44 | −1.073 | −1.122 | 0.039 | GO:0007186 G-protein coupled receptor protein signaling pathway; GO:0050911 detection of chemical stimulus involved in sensory perception of smell |
| Sulfatase modifying factor 2 | Sumf2 | −1.077 | −1.088 | 0.034 | |
| WD repeat domain 45 | Wdr45 | −1.078 | 1.120 | 0.049 | |
| Synclecan binding protein | Sdcbp | −1.080 | 1.170 | 0.008 | GO:0007265 Ras protein signal transduction |
| Bernardinelli-Seip congenital lipodystrophy 2 homolog (human) | Bscl2 | −1.082 | −1.006 | 0.047 | GO:0008150 biological_process |
| Dehydrogenase/reductase (SDR family) member 1 | Dhrs1 | −1.083 | 1.116 | 0.006 | GO:0055114 oxidation reduction |
| Polymerase (DNA directed), gamma | Polg | −1.089 | −1.102 | 0.029 | GO:0006264 mitochondrial DNA replication; GO:0006287 base-excision repair, gap-filling; GO:0007568 aging |
| Protein O-fucosyltransferase 1 | Pofut1 | −1.091 | 1.03 | 0.026 | GO:0001525 angiogenesis; GO:0001756 somitogenesis; GO:0005975 carbohydrate metabolic process; GO:0006004 fucose metabolic process; GO:0006493 protein amino acid O-linked glycosylation; GO:0007219 Notch signaling pathway; GO:0007399 nervous system development; GO:0007507 heart development; GO:0008150 biological_process |
| Outer dense fiber of sperm tails 2 | Odf2 | −1.098 | −1.005 | 0.044 | GO:0007286 spermatid development |
| Nuclear prelamin A recognition factor-like | Narfl | −1.099 | −1.006 | 0.017 | GO:0001666 response to hypoxia; GO:0016226 iron-sulfur cluster assembly; GO:0032364 oxygen homeostasis; GO:0045449 regulation of transcription |
| Solute carrier family 6 (neurotransmitter transporter, serotonin), member 4 | Slc6a4 | −1.105 | −1.065 | 0.038 | GO:0001504 neurotransmitter uptake; GO:0006837 serotonin transport; GO:0007626 locomotory behavior; GO:0009636 response to toxin; GO:0015844 monoamine transport; GO:0021794 thalamus development; GO:0051610 serotonin uptake |
| Acyl-Coenzyme A oxidase 3, pristanoyl | Acox3 | −1.106 | −1.081 | 0.001 | GO:0006629 lipid metabolic process; GO:0006631 fatty acid metabolic process; GO:0006635 fatty acid beta-oxidation; GO:0033540 fatty acid beta-oxidation using acyl-CoA oxidase; GO:0055114 oxidation reduction |
| Shroom family member 2 | Shroom2 | −1.115 | 1.191 | 0.035 | GO:0000902 cell morphogenesis; GO:0007275 multicellular organismal development; GO:0016477 cell migration; GO:0030835 negative regulation of actin filament depolymerization; GO:0032438 melanosome organization GO:0045217 cell-cell junction maintenance; GO:0051017 actin filament bundle assembly |
| Similar to RIKEN cDNA A730011L01 gene | LOC498029 | −1.115 | −1.077 | 0.023 | GO:0006281 DNA repair |
| Neuropeptide FF receptor 1 | Npffr1 | −1.117 | −1.111 | 0.024 | GO:0007165 signal transduction; GO:0007186 G-protein coupled receptor protein signaling pathway |
| Kelch-like 36 (*Drosophila*) | Klhl36 | −1.119 | −1.021 | 0.014 | |
| Phosphatidylinositol glycan anchor biosynthesis, class S | Pigs | −1.128 | 1.007 | 0.033 | GO:0006506 GPI anchor biosynthetic process; GO:0016255 attachment of GPI anchor to protein |
| PDZ and LIM domain 1 | Pdlim1 | −1.131 | 1.111 | 0.049 | GO:0001666 response to hypoxia; GO:0045449 regulation of transcription |
| Alpha-1-B glycoprotein | A1bg | −1.132 | −1.048 | 0.005 | |
| WD repeat domain 7 | Wdr7 | −1.133 | −1.041 | 0.017 | |
| Protein O-linked mannose beta1,2-N-acetylglucosaminyltransferase | Pomgnt1 | −1.135 | −1.056 | 0.012 | GO:0006487 protein amino acid N-linked glycosylation; GO:0006493 protein amino acid O-linked glycosylation; GO:0008150 biological process |
| Fibroblast growth factor 11 | Fgf11 | −1.135 | −1.162 | 0.016 | |
| DEAD (Asp-Glu-Ala-Asp) box polypeptide 24 | Ddx24 | −1.139 | 1.006 | 0.027 | |
| Heterogeneous nuclear ribonucleoprotein H1 | Hnrph1 | −1.143 | 1.100 | 0.040 | GO:0006396 RNA processing |
| Rho-related BTB domain containing 2 | Rhobtb2 | −1.145 | −1.024 | 0.013 | GO:0007264 small GTPase mediated signal transduction |
| Ring finger protein 135 | Rnf135 | −1.147 | −1.045 | 0.013 | GO:0006270 DNA-dependent DNA replication initiation; GO:0007264 small GTPase mediated signal transduction; GO:0047497 mitochondrion transport along microtubule |
| Vaccinia related kinase 3 | Vrk3 | −1.150 | 1.011 | 0.046 | GO:0006468 protein amino acid phosphorylation; GO:0032516 positive regulation of phosphoprotein phosphatase activity; GO:0070373 negative regulation of ERK1 and ERK2 cascade |
| Cardiotrophin-like cytokine factor 1 | Clcf1 | −1.150 | −1.144 | 0.029 | GO:0007166 cell surface receptor linked signaling pathway; GO:0007259 JAK-STAT cascade; GO:0030183 B cell differentiation |
| Prostate tumor overexpressed 1 | Ptov1 | −1.154 | −1.014 | 0.050 | GO:0045449 regulation of transcription |
| Mitogen activated protein kinase kinase kinase 1 | Map3k1 | −1.158 | −1.106 | 0.008 | GO:0000165 MAPKKK cascade; GO:0000186 activation of MAPKK activity; GO:0000209 protein polyubiquitination; GO:0006468 protein amino acid phosphorylation; GO:0006970 |

TABLE 3-continued details all genes with differential expression between DSS and Control and DSS/HP and control in rats given
Dextran Sodium Sulphate in water with or without co-treatment with hypothetical protein (HP).

| | | Fold change | | | |
|---|---|---|---|---|---|
| Gene description | Gene symbol | DSS vs Control | DSS/HP vs Control | p-value | GO_biological_process (up to first 10) |
| | | | | | response to osmotic stress; GO:0007179 transforming growth factor beta receptor signaling pathway; GO:0007249 I-kappaB kinase/NF-kappaB cascade; GO:0007254 JNK cascade; GO:0007256 activation of JNKK activity; GO:0007257 activation of JUN kinase activity |
| Calcium homeostasis endoplasmic reticulum protein | similar to 1700030K09Rik protein | Cherp| RGD1311847 | −1.160 | −1.040 | 0.018 | GO:0006396 RNA processing; GO:0006874 cellular calcium ion homeostasis; GO:0008285 negative regulation of cell proliferation |
| Progestin and adipoQ receptor family member III | Paqr3 | −1.161 | −1.063 | 0.016 | |
| Glioma tumor suppressor candidate region gene 2 | Gltscr2 | −1.162 | −1.123 | 0.012 | |
| Poly(rC) binding protein 2 | Pcbp2 | −1.162 | −1.015 | 0.014 | GO:0008380 RNA splicing |
| THO complex 5 | Thoc5 | −1.163 | −1.025 | 0.036 | GO:0006397 mRNA processing; GO:0006406 mRNA export from nucleus; GO:0006810 transport; GO:0008150 biological_process; GO:0008380 RNA splicing; GO:0030154 cell differentiation; GO:0045650 negative regulation of macrophage differentiation; GO:0046784 intronless viral mRNA export from host nucleus; GO:0051028 mRNA transport |
| Glycine-, glutamate-, thienylcyclohexylpiperidine-binding protein | LOC246295 | −1.165 | 1.035 | 0.045 | |
| Family with sequence similarity 113, member A | Fam113a | −1.171 | 1.022 | 0.049 | |
| Leucine rich repeat (in FLII) interacting protein 1 | Lrrfip1 | −1.175 | 1.000 | 0.048 | GO:0045449 regulation of transcription |
| AlkB, alkylation repair homolog 3 (E. coli) | Alkbh3 | −1.177 | −1.138 | 0.001 | GO:0006281 DNA repair; GO:0055114 oxidation reduction |
| Amyloid beta (A4) precursor protein-binding, family B, member 3 | Apbb3 | −1.181 | 1.016 | 0.018 | |
| Cyclin-dependent kinase inhibitor 2B (p15, inhibits CDK4) | Cdkn2b | −1.185 | −1.104 | 0.017 | GO:0000079 regulation of cyclin-dependent protein kinase activity; GO:0000086 G2/M transition of mitotic cell cycle; GO:0007050 cell cycle arrest; GO:0008285 negative regulation of cell proliferation; GO:0014070 response to organic cyclic substance; GO:0030219 megakalyocyte differentiation; GO:0030511 positive regulation of transforming growth factor beta receptor signaling pathway; GO:0030858 positive regulation of epithelial cell differentiation; GO:0031575 G1/S transition checkpoint; GO:0031668 cellular response to extracellular stimulus |
| CD2-associated protein | Cd2ap | −1.189 | −1.089 | 0.039 | GO:0016337 cell-cell adhesion; GO:0016477 cell migration; GO:0043161 proteasomal ubiquitin-dependent protein catabolic process; GO:0048259 // regulation of receptor-mediated endocytosis |
| ATPase, Na+/K+transporting, beta 1 polypeptide | Atp1b1 | −1.192 | −1.020 | 0.036 | GO:0001666 response to hypoxia; GO:0006754 ATP biosynthetic process; GO:0006811 ion transport; GO:0006813 potassium ion transport; GO:0006814 sodium ion transport; GO:0030001 metal ion transport |
| Ring finger protein 114 | Rnf114 | −1.193 | 1.005 | 0.050 | GO:0007275 multicellular organismal development; GO:0007283 spermatogenesis; GO:0030154 cell differentiation |
| Inositol polyphosphate phosphatase-like 1 | Inppl1 | −1.198 | −1.022 | 0.046 | GO:0006006 glucose metabolic process; GO:0007420 brain development; GO:0008156 negative regulation of DNA replication; GO:0008285 negative regulation of cell proliferation; GO:0009791 post-embryonic development; GO:0010629 negative regulation of gene expression; GO:0010642 negative regulation of platelet-derived growth factor receptor signaling pathway; GO:0010977 negative regulation of neuron projection development; GO:0032868 response to insulin stimulus; GO:0032957 inositol trisphosphate metabolic process |
| TAO kinase 2 | Taok2 | −1.200 | −1.058 | 0.010 | GO:0000186 activation of MAPKK activity; GO:0006468 protein amino acid phosphorylation; GO:0006950 response to stress; GO:0008360 regulation of cell shape; GO:0030036 actin cytoskeleton organization; GO:0046330 positive regulation of JNK cascade; GO:0048041 focal adhesion assembly; GO:0000186 activation of MAPKK activity |
| Dynamin 2 | Dnm2 | −1.200 | −1.085 | 0.036 | GO:0006892 post-Golgi vesicle-mediated transport; GO:0006897 endocytosis; GO:0006898 receptor-mediated endocytosis; GO:0016044 cellular membrane organization; GO:0031623 receptor internalization; GO:0033572 transferrin transport |
| Calcium channel, voltage-dependent, beta 3 subunit | Cacnb3 | −1.200 | 1.009 | 0.029 | GO:0006811 ion transport; GO:0006816 calcium ion transport; GO:0050852 T cell receptor signaling pathway |

TABLE 3-continued details all genes with differential expression between DSS and Control and DSS/HP and control in rats given
Dextran Sodium Sulphate in water with or without co-treatment with hypothetical protein (HP).

| | | Fold change | | | |
|---|---|---|---|---|---|
| Gene description | Gene symbol | DSS vs Control | DSS/HP vs Control | p-value | GO_biological_process (up to first 10) |
| Similar to chromosome 1 open reading frame 172 | RGD1303271 | −1.201 | −1.049 | 0.048 | |
| Pre-B-cell leukemia homeobox 2 | Pbx2 | −1.202 | −1.007 | 0.019 | GO:0006355 regulation of transcription, DNA-dependent; GO:0009954 proximal/distal pattern formation; GO:0030326 embryonic limb morphogenesis; GO:0045944 positive regulation of transcription from RNA polymerase II promoter |
| SCY1-like 1 (*S. cerevisiae*) | latent transforming growth factor beta binding protein 3 | Scyl1|Ltbp3 | −1.204 | 1.032 | 0.034 | GO:0006468 protein amino acid phosphorylation; GO:0006890 retrograde vesicle-mediated transport, Golgi to ER; GO:0016192 vesicle-mediated transport |
| Olfactory receptor 1765 | Olr1765 | −1.206 | −1.436 | 0.003 | GO:0007186 G-protein coupled receptor protein signaling pathway; GO:0050911 detection of chemical stimulus involved in sensory perception of smell |
| Transmembrane BAX inhibitor motif containing 6 | Tmbim6 | −1.209 | −1.048 | 0.006 | GO:0007283 spermatogenesis; GO:0030324 lung development; GO:0043066 negative regulation of apoptosis |
| Solute carrier organic anion transporter, family member 2b1 | Slco2b1 | −1.210 | 1.027 | 0.030 | GO:0001889 liver development; GO:0006811 ion transport; sGO:0015721 bile acid and bile alt transport; GO:0071718 sodium-independent icosanoid transport |
| Trace amine-associated receptor 8c | Taar8c | −1.210 | 1.130 | 0.011 | GO:0007165 signal transduction; GO:0007186 G-protein coupled receptor protein signaling pathway |
| Transmembrane protein, adipocyte asscociated 1 | Tpra1 | −1.211 | −1.019 | 0.033 | |
| DiGeorge syndrome critical region gene 2 | Dgcr2 | −1.211 | −1.046 | 0.036 | GO:0042493 response to drug |
| Casein kinase 1, delta | solute carrier family 16, member 3 (monocarboxylic acid transporter 4) | Csnk1d|Slc16a3 | −1.211 | −1.042 | 0.021 | GO:0000278 mitotic cell cycle; GO:0006468 protein amino acid phosphorylation; GO:0032436 positive regulation of proteasomal ubiquitin-dependent protein catabolic process; GO:0032922 circadian regulation of gene expression; GO:0042752 regulation of circadian rhythm; GO:0006090 pyruvate metabolic process; GO:0015711 organic anion transport; GO:0055085 transmembrane transport |
| Scaffold attachment factor B | Safb | −1.219 | −1.003 | 0.016 | GO:0006355 regulation of transcription, DNA-dependent; GO:0030520 estrogen receptor signaling pathway; GO:0040007 growth; GO:0042445 hormone metabolic process; GO:0050684 regulation of mRNA processing |
| MAP/microtubule affinity-regulating kinase 2 | Mark2 | −1.219 | −1.025 | 0.044 | GO:0006468 protein amino acid phosphorylation; GO:0006979 response to oxidative stress; GO:0007243 intracellular protein kinase cascade; GO:0007275 multicellular organismal development; GO:0030154 cell differentiation; GO:0045197 establishment or maintenance of epithelial cell apical/basal polarity |
| Era (G-protein)-like 1 (*E. coli*) | Eral1 | −1.219 | 1.006 | 0.040 | |
| RT1 class I, locus CE12 | RT1 class I, locus1 | RT1 class I, locus CE14 | RT1-CE12|RT1-CE14 | −1.220 | −1.156 | 0.002 | GO:0002474 antigen processing and presentation of peptide antigen via MHC class I; GO:0006955 immune response; GO:0019882 antigen processing and presentation |
| Serine incorporator 3 | Serinc3 | −1.220 | 1.055 | 0.021 | GO:0006658 phosphatidylserine metabolic process; GO:0006665 sphingolipid metabolic process; GO:0006917 induction of apoptosis; GO:0015825 L-serine transport; GO:0051347 positive regulation of transferase activity |
| Cancer susceptibility candidate 3 | Casc3 | −1.225 | −1.024 | 0.048 | GO:0000184 nuclear-transcribed mRNA catabolic process, nonsense-mediated decay; GO:0006397 mRNA processing; GO:0006417 regulation of translation; GO:0006810 transport; GO:0006950 response to stress; GO:0008298 intracellular mRNA localization; GO:0008380 RNA splicing; GO:0051028 mRNA transport |
| DAB2 interacting protein | Dab2ip | −1.233 | −1.016 | 0.038 | GO:0007165 signal transduction; GO:0051056 regulation of small GTPase mediated signal transduction |
| Gamma-glutamyl transferase 6 | Ggt6 | −1.233 | −1.024 | 0.018 | GO:0006750 glutathione biosynthetic process |
| Fatty acid desaturase 1 | Fads1 | −1.233 | −1.192 | 0.021 | GO:0006636 unsaturated fatty acid biosynthetic process; GO:0006810 transport; GO:0006950 response to stress; GO:0007568 aging; GO:0007584 response to nutrient; GO:0009267 cellular response to starvation; GO:0009744 response to sucrose stimulus; GO:0010033 response to organic substance; GO:0014070 response to organic cyclic substance; GO:0019369 arachidonic acid metabolic process |
| PTK2B protein tyrosine kinase 2 beta | Ptk2b | −1.233 | −1.101 | 0.009 | GO:0000165 MAPKKK cascade; GO:0000302 response to reactive oxygen species; GO:0001525 angiogenesis; GO:0001556 oocyte maturation; GO:0001666 response to hypoxia; GO:0006468 protein amino acid phosphorylation; GO:0006800 oxygen and reactive oxygen species metabolic process; GO:0006950 response to stress; GO:0006970 response to osmotic stress; GO:0007015 actin filament organization |

TABLE 3-continued details all genes with differential expression between DSS and Control and DSS/HP and control in rats given
Dextran Sodium Sulphate in water with or without co-treatment with hypothetical protein (HP).

| | | Fold change | | | |
|---|---|---|---|---|---|
| Gene description | Gene symbol | DSS vs Control | DSS/HP vs Control | p-value | GO_biological_process (up to first 10) |
| RAD23 homolog A (*S. cerevisiae*) | Rad23a | −1.234 | −1.089 | 0.008 | GO:0006289 nucleotide-excision repair; GO:0006974 response to DNA damage stimulus; GO:0043161 proteasomal ubiquitin-dependent protein catabolic process |
| GDP dissociation inhibitor 1 | Gdi1 | −1.235 | −1.013 | 0.025 | GO:0007264 small GTPase mediated signal transduction; GO:0015031 protein transport; GO:0043087 regulation of GTPase activity |
| Solute carrier family 15, member 4 | Slc15a4 | −1.237 | −1.100 | 0.029 | GO:0006857 oligopeptide transport; GO:0015031 protein transport; GO:0015817 histidine transport |
| DALR anticodon binding domain containing 3 | Dalrd3 | −1.242 | 1.008 | 0.026 | GO:0006420 arginyl-tRNA aminoacylation |
| Axin 1 | Axin1 | −1.244 | −1.077 | 0.006 | GO:0007275 multicellular organismal development; GO:0007605 sensory perception of sound; GO:0010800 positive regulation of peptidyl-threonine phosphorylation; GO:0016055 Wnt receptor signaling pathway; GO:0030163 protein catabolic process; GO:0030178 negative regulation of Wnt receptor signaling pathway; GO:0031398 positive regulation of protein ubiquitination; GO:0033138 positive regulation of peptidyl-serine phosphorylation; GO:0046330 positive regulation of JNK cascade; GO:0060070 Wnt receptor signaling pathway through beta-catenin |
| ATG7 autophagy related 7 homolog (*S. cerevisiae*) | Atg7 | −1.247 | −1.107 | 0.010 | GO:0001889 liver development; GO:0006497 protein amino acid lipidation; GO:0006520 cellular amino acid metabolic process; GO:0006914 autophagy; GO:0006996 organelle organization; GO:0007628 adult walking behavior; GO:0008152 metabolic process; GO:0009791 post-embryonic development; GO:0015031 protein transport; GO:0016044 cellular membrane organization |
| General transcription factor II I | Gtf2i | −1.247 | 1.033 | 0.046 | GO:0009790 embryonic development GO:0051481 reduction of cytosolic calcium ion concentration |
| Phosphatidylinositol glycan anchor biosynthesis, class V | Pigv | −1.253 | 1.010 | 0.005 | GO:0006506 GPI anchor biosynthetic process; GO:0016254 preassembly of GPI anchor in ER membrane |
| Anterior pharynx defective 1 homolog A (*C. elegans*) | Aph1a | −1.255 | −1.029 | 0.046 | GO:0001656 metanephros development; GO:0006509 membrane protein ectodomain proteolysis; GO:0006915 apoptosis; GO:0007220 Notch receptor processing; GO:0008624 induction of apoptosis by extracellular signals; GO:0016485 protein processing; GO:0031293 membrane protein intracellular domain proteolysis; GO:0042987 amyloid precursor protein catabolic process; GO:0043085 positive regulation of catalytic activity |
| Purinergic receptor P2X, ligand-gated ion channel 4 | P2rx4 | −1.260 | −1.135 | 0.017 | GO:0002028 regulation of sodium ion transport; GO:0006809 nitric oxide biosynthetic process; GO:0006810 transport; GO:0006811 ion transport; GO:0006816 calcium ion transport; GO:0007165 signal transduction; GO:0008217 regulation of blood pressure; GO:0010524 positive regulation of calcium ion transport into cytosol; GO:0010614 negative regulation of cardiac muscle hypertrophy; GO:0019228 regulation of action potential in neuron |
| Secretory carrier membrane protein 2 | Scamp2 | −1.262 | 1.071 | 0.018 | GO:0006886 intracellular protein transport; GO:0006897 endocytosis; GO:0015031 protein transport |
| Bcl2-like 1 | Bcl2l1 | −1.264 | −1.205 | 0.024 | GO:0001541 ovarian follicle development; GO:0001666 response to hypoxia; GO:0001701 in utero embryonic development; GO:0001836 release of cytochrome c from mitochondria; GO:0006915 apoptosis; GO:0006916 anti-apoptosis; GO:0006950 response to stress; GO:0006979 response to oxidative stress; GO:0007281 germ cell development; GO:0007283 spermatogenesis |
| Olfactory receptor 1614 | Olr1614 | −1.267 | −1.411 | 0.004 | GO:0007186 G-protein coupled receptor protein signaling pathway; GO:0050911 detection of chemical stimulus involved in sensory perception of smell |
| LUC7-like (*S. cerevisiae*) | Luc7l | −1.270 | 1.061 | 0.043 | |
| Telomerase associated protein 1 | Tep1 | −1.271 | −1.012 | 0.016 | GO:0000722 telomere maintenance via recombination; GO:0000722 telomere maintenance via recombination; GO:0007004 telomere maintenance via telomerase |
| Serine/threonine kinase 39, STE20/SPS1 homolog (yeast) | Stk39 | −1.272 | −1.061 | 0.030 | GO:0006468 protein amino acid phosphorylation; GO:0043268 positive regulation of potassium ion transport |
| CREB binding protein | Crebbp | −1.272 | −1.102 | 0.002 | GO:0006355 regulation of transcription, DNA-dependent; GO:0008283 cell proliferation; GO:0016573 histone acetylation; GO:0018076 N-terminal peptidyl-lysine acetylation; GO:0030718 germ-line stem cell maintenance; GO:0033261 regulation of S phase; GO:0045449 regulation of transcription; GO:0045893 positive regulation of transcription, DNA-dependent; |

TABLE 3-continued details all genes with differential expression between DSS and Control and DSS/HP and control in rats given Dextran Sodium Sulphate in water with or without co-treatment with hypothetical protein (HP).

| | | Fold change | | | |
|---|---|---|---|---|---|
| Gene description | Gene symbol | DSS vs Control | DSS/ HP vs Control | p-value | GO_biological_process (up to first 10) |
| | | | | | GO:0045941 positive regulation of transcription; GO:0045944 positive regulation of transcription from RNA polymerase II promoter |
| Serine/threonine kinase 40 | Stk40 | −1.272 | −1.073 | 0.016 | GO:0006468 protein amino acid phosphorylation |
| Protein kinase N1 | Pkn1 | −1.274 | −1.095 | 0.035 | GO:0006468 protein amino acid phosphorylation; GO:0006972 hyperosmotic response; GO:0007165 signal transduction |
| Ligase III, DNA, ATP-dependent | Lig3 | −1.276 | −1.089 | 0.035 | GO:0006260 DNA replication; GO:0006281 DNA repair; GO:0006310 DNA recombination; GO:0033151 V(D)J recombination |
| Post-GPI attachment to proteins 2 | Pgap2 | −1.277 | 1.012 | 0.026 | GO:0006916 anti-apoptosis; GO:0006974 response to DNA damage stimulus; GO:0042770 DNA damage response, signal transduction |
| Glucagon | Gcg | −1.280 | −1.140 | 0.021 | GO:0006109 regulation of carbohydrate metabolic process; GO:0007186 G-protein coupled receptor protein signaling pathway; GO:0007188 G-protein signaling, coupled to cAMP nucleotide second messenger; GO:0009755 hormone-mediated signaling pathway; GO:0019216 regulation of lipid metabolic process; GO:0019538 protein metabolic process; GO:0032099 negative regulation of appetite; GO:0050796 regulation of insulin secretion |
| CDC42 small effector 1 | Cdc42se1 | −1.280 | −1.105 | 0.010 | GO:0006909 phagocytosis; GO:0008360 regulation of cell shape |
| Solute carrier family 25 (mitochondrial carrier, phosphate carrier), member 3 | Slc25a3 | −1.282 | 1.010 | 0.025 | GO:0055085 transmembrane transport |
| Ubiquitin-associated protein 1 | Ubap1 | −1.284 | −1.090 | 0.006 | |
| ATP citrate lyase | Acly | −1.292 | −1.138 | 0.025 | GO:0006084 acetyl-CoA metabolic processt assay; GO:0006085 acetyl-CoA biosynthetic process; GO:0006101 citrate metabolic process; GO:0006629 lipid metabolic process; GO:0006633 fatty acid biosynthetic process; GO:0008152 metabolic process; GO:0044262 cellular carbohydrate metabolic process |
| Potassium channel, subfamily K, member 6 | CWC15 spliceosome-associated protein homolog (S. cerevisiae) | family with sequence similarity 35, member A | Kcnk6|Cwc15| Fam35a | −1.294 | 1.142 | 0.019 | GO:0006811 ion transport; GO:0006813 potassium ion transport; GO:0000398 nuclear mRNA splicing, via spliceosome; GO:0008150 biological_process; GO:0008380 RNA splicing |
| Inositol (myo)-1(or 4)-monophosphatase 2 | Impa2 | −1.294 | −1.024 | 0.018 | GO:0008150 biological process; GO:0046855 inositol phosphate dephosphorylation |
| Transmembrane protein 171 | Tmem171 | −1.296 | 1.129 | 0.022 | |
| Zinc finger, DHHC-type containing 23 | Zdhhc23 | −1.301 | −1.025 | 0.002 | |
| A kinase (PRKA) anchor protein 1 | Akap1 | −1.301 | 1.061 | 0.022 | GO:0010614 negative regulation of cardiac muscle hypertrophy; GO:0010738 regulation of protein kinase A signaling cascade; GO:0032869 cellular response to insulin stimulus; GO:0035308 negative regulation of protein amino acid dephosphorylation; GO:0051534 negative regulation of NFAT protein import into nucleus; GO:0070887 cellular response to chemical stimulus |
| Shisa homolog 5 (Xenopus laevis) | Shisa5 | −1.302 | 1.022 | 0.010 | GO:0006915 apoptosis; GO:0006917 induction of apoptosis; GO:0043123 positive regulation of I-kappaB kinase |
| Phosphatidic acid phosphatase type 2c | Ppap2c | −1.306 | −1.145 | 0.048 | |
| Nuclear RNA export factor 1 | Nxf1 | −1.307 | 1.174 | 0.026 | GO:0006405 RNA export from nucleus; GO:0006406 mRNA export from nucleus; GO:0006810 transport; GO:0016973 poly(A)+ mRNA export from nucleus; GO:0051028 mRNA transport |
| Fas-activated serine/threonine kinase | Fastk | −1.308 | −1.082 | 0.001 | GO:0006915 apoptosis |
| Ring finger protein 160 | Rnf160 | −1.317 | 1.091 | 0.042 | |
| PCTAIRE protein kinase 1 | Pctk1 | −1.318 | −1.126 | 0.029 | GO:0006468 protein amino acid phosphorylation |
| Prickle homolog 3 (Drosophila) | Prickle3 | −1.326 | −1.096 | 0.042 | |
| Solute carrier family 9 (sodium/hydrogen exchanger), member 3 | Slc9a3 | −1.333 | 1.233 | 0.025 | GO:0002028 regulation of sodium ion transport; GO:0006812 cation transport; GO:0006814 sodium ion transport; GO:0006885 regulation of pH; GO:0006898 receptor-mediated endocytosis; GO:0007623 circadian rhythm; GO:0051384 response to glucocorticoid stimulus; GO:0055085 transmembrane transport |
| CDP-diacylglycerol synthase 1 | Cds1 | −1.339 | −1.064 | 0.014 | GO:0008654 phospholipid biosynthetic process |
| Trinucleotide repeat containing 6B | Tnrc6b | −1.342 | −1.089 | 0.040 | |
| Cytochrome P450, family 2, subfamily d, polypeptide 4 | cytochrome P450, family 2, subfamily d, polypeptide 5 | Cyp2d4| Cyp2d5 | −1.347 | −1.127 | 0.001 | GO:0008202 steroid metabolic process; GO:0009804 coumarin metabolic process; GO:0009820 alkaloid metabolic process; GO:0009822 alkaloid catabolic process; GO:0009892 negative regulation of metabolic process; GO:0010033 response to organic substance; GO:0016098 monoterpenoid metabolic process; GO:0017144 drug metabolic process; GO:0019369 arachidonic |

TABLE 3-continued details all genes with differential expression between DSS and Control and DSS/HP and control in rats given
Dextran Sodium Sulphate in water with or without co-treatment with hypothetical protein (HP).

| | | Fold change | | | |
|---|---|---|---|---|---|
| Gene description | Gene symbol | DSS vs Control | DSS/ HP vs Control | p-value | GO_biological_process (up to first 10) |
| | | | | | acid metabolic process; GO:0033076 isoquinoline alkaloid metabolic process |
| Hypothetical protein MGC:72616 | RGD735175 | −1.347 | −1.059 | 0.021 | |
| Basic helix-loop-helix family, member e40 | Bhlhe40 | −1.347 | −1.158 | 0.022 | GO:0007399 nervous system development; GO:0007623 circadian rhythm; GO:0009416 response to light stimulus; GO:0009649 entrainment of circadian clock; GO:0045892 negative regulation of transcription, DNA-dependent; GO:0048168 regulation of neuronal synaptic plasticity |
| Phosphatidylinositol 4-kinase, catalytic, alpha | Pi4ka | −1.348 | −1.089 | 0.009 | GO:0046854 phosphoinositide phosphorylation; GO:0048015 phosphoinositide-mediated signaling |
| Similar to 2310044H10Rik protein | MGC93975 | −1.351 | −1.168 | 0.001 | |
| CDP-diacylglycerol synthase (phosphatidate cytidylyltransferase) 2 | Cds2 | −1.354 | 1.015 | 0.031 | GO:0008654 phospholipid biosynthetic process |
| Prolyl endopeptidase-like | Prepl | −1.354 | 1.006 | 0.045 | GO:0006508 proteolysis |
| B-cell translocation gene 1, anti-proliferative | Btg1 | −1.360 | −1.130 | 0.043 | GO:0006479 protein amino acid methylation; GO:0006979 response to oxidative stress; GO:0007283 spermatogenesis; GO:0007286 spermatid development; GO:0008285 negative regulation of cell proliferation; GO:0042981 regulation of apoptosis; GO:0043434 response to peptide hormone stimulus; GO:0045603 positive regulation of endothelial cell differentiation; GO:0045663 positive regulation of myoblast differentiation; GO:0045766 positive regulation of angiogenesis |
| Claudin 3 | Cldn3 | −1.373 | −1.030 | 0.031 | GO:0001666 response to hypoxia; GO:0016338 calcium-independent cell-cell adhesion |
| Serine/threonine kinase 38 | Stk38 | −1.375 | −1.058 | 0.006 | GO:0006464 protein modification process; GO:0006468 protein amino acid phosphorylation; GO:0007243 intracellular protein kinase cascade; GO:0008150 biological process |
| Mucin and cadherin like | Mucdhl | −1.375 | −1.064 | 0.009 | GO:0007155 cell adhesion |
| Thyroid hormone receptor interactor 10 | Trip10 | −1.377 | −1.103 | 0.011 | GO:0006897 endocytosis; GO:0042538 hyperosmotic salinity response |
| Solute carrier family 44, member 1 | Slc44a1 | −1.381 | −1.043 | 0.010 | GO:0015871 choline transport |
| Mitofusin 2 | Mfn2 | −1.382 | −1.103 | 0.034 | GO:0001825 blastocyst formation; GO:0006626 protein targeting to mitochondrion; GO:0007006 mitochondrial membrane organization; GO:0007050 cell cycle arrest; GO:0008053 mitochondrial fusion; GO:0008285 negative regulation of cell proliferation; GO:0046580 negative regulation of Ras protein signal transduction; GO:0048593 camera-type eye morphogenesis; GO:0048662 negative regulation of smooth muscle cell proliferation; GO:0051646 mitochondrion localization |
| Solute carrier family 9 (sodium/ hydrogen exchanger), member 3 regulator 1 | Slc9a3r1 | −1.388 | −1.041 | 0.037 | GO:0016055 Wnt receptor signaling pathway; GO:0030643 cellular phosphate ion homeostasis |
| ATP-binding cassette, sub-family B (MDR/TAP), member 6 | Abcb6 | −1.390 | 1.002 | 0.008 | GO:0006810 transport; GO:0055085 transmembrane transport |
| Spermatogenesis associated 2 | Spata2 | −1.390 | −1.165 | 0.039 | |
| Sphingomyelin synthase 2 | Sgms2 | −1.398 | −1.072 | 0.022 | GO:0006629 lipid metabolic process; GO:0006665 sphingolipid metabolic process; GO:0006686 sphingomyelin biosynthetic process |
| Ras homolog gene family, member T2 | Rhot2 | −1.404 | 1.018 | 0.049 | GO:0006915 apoptosis; GO:0007264 small GTPase mediated signal transduction; GO:0019725 cellular homeostasis; GO:0047497 mitochondrion transport along microtubule |
| V-erb-b2 erythroblastic leukemia viral oncogene homolog 2, neuro/ glioblastoma derived oncogene homolog (avian) | Erbb2 | −1.417 | −1.065 | 0.047 | GO:0001889 liver development; GO:0007165 signal transduction; GO:0007166 cell surface receptor linked signaling pathway; GO:0007169 transmembrane receptor protein tyrosine kinase signaling pathway; GO:0007399 nervous system development; GO:0007417 central nervous system development; GO:0007422 peripheral nervous system development; GO:0007507 heart development; GO:0007519 skeletal muscle tissue development; GO:0007528 neuromuscular junction development |
| Integrin alpha FG-GAP repeat containing 3 | Itfg3 | −1.420 | −1.003 | 0.039 | |
| Enclothelin 2 | Edn2 | −1.424 | −1.091 | 0.001 | GO:0001516 prostaglandin biosynthetic process; GO:0001543 ovarian follicle rupture; GO:0002690 positive regulation of leukocyte chemotaxis; GO:0003100 regulation of systemic arterial blood pressure by endothelin; GO:0007204 elevation of cytosolic calcium ion concentration; GO:0007205 activation of protein kinase C activity by G-protein coupled receptor protein signaling pathway; GO:0008217 regulation of blood pressure; GO:0008284 positive regulation of cell proliferation; GO:0010460 positive regulation of heart rate; GO:0014824 artery smooth muscle |

TABLE 3-continued details all genes with differential expression between DSS and Control and DSS/HP and control in rats given Dextran Sodium Sulphate in water with or without co-treatment with hypothetical protein (HP).

| | | Fold change | | | |
|---|---|---|---|---|---|
| Gene description | Gene symbol | DSS vs Control | DSS/ HP vs Control | p-value | GO_biological_process (up to first 10) |
| Ring finger protein 10 | Rnf10 | −1.440 | −1.069 | 0.013 | GO:0008150 biological process; GO:0045941 positive regulation of transcription |
| Aldolase A, fructose-bisphosphate | Aldoa | −1.442 | 1.024 | 0.016 | GO:0001666 response to hypoxia; GO:0006000 fructose metabolic process; GO:0006096 glycolysis; GO:0006754 ATP biosynthetic process; GO:0006941 striated muscle contraction; GO:0008152 metabolic process; GO:0008360 regulation of cell shape; GO:0009408 response to heat; GO:0030388 fructose 1,6-bisphosphate metabolic process; GO:0032496 response to lipopolysaccharide |
| Adenylate cyclase 6 | Adcy6 | −1.442 | −1.031 | 0.036 | GO:0006171 cAMP biosynthetic process; GO:0007193 inhibition of adenylate cyclase activity by G-protein signaling pathway; GO:0009755 hormone-mediated signaling pathway; GO:0034199 activation of protein kinase A activity |
| UDP-glucose ceramide glucosyltransferase | Ugcg | −1.443 | −1.257 | 0.001 | GO:0006665 sphingolipid metabolic process; GO:0008610 lipid biosynthetic process |
| Nuclear receptor subfamily 3, group C, member 2 | Nr3c2 | −1.447 | −1.092 | 0.009 | GO:0006883 cellular sodium ion homeostasis; GO:0007588 excretion; GO:0031959 mineralocorticoid receptor signaling pathway; GO:0042127 regulation of cell proliferation |
| Inositol polyphosphate-5-phosphatase J | Inpp5j | −1.455 | −1.112 | 0.023 | GO:0010977 negative regulation of neuron projection development; GO:0031115 negative regulation of microtubule polymerization; GO:0033137 negative regulation of peptidyl-serine phosphorylation |
| cytokine-like nuclear factor n-pac | N-pac | −1.456 | −1.106 | 0.032 | GO:0006098 pentose-phosphate shunt; GO:0055114 oxidation reduction |
| Glutamic-oxaloacetic transaminase 2, mitochondrial (aspartate aminotransferase 2) | Got2 | −1.458 | −1.135 | 0.017 | GO:0006103 2-oxoglutarate metabolic process; GO:0006107 oxaloacetate metabolic process; GO:0006520 cellular amino acid metabolic process; GO:0006531 aspartate metabolic process; GO:0006532 aspartate biosynthetic process; GO:0006533 aspartate catabolic process; GO:0006536 glutamate metabolic process; GO:0009058 biosynthetic process; GO:0015908 fatty acid transport; GO:0019550 glutamate catabolic process to aspartate |
| MAX interactor 1 | Mxi1 | −1.466 | −1.047 | 0.018 | GO:0000122 negative regulation of transcription from RNA polymerase II promoter; GO:0006355 regulation of transcription, DNA-dependent |
| Vacuolar protein sorting 52 homolog (S. cerevisiae) | Vps52 | −1.478 | −1.160 | 0.025 | GO:0015031 protein transport |
| Adenosylhomocysteinase | Ahcy | −1.487 | −1.135 | 0.008 | GO:0001666 response to hypoxia; GO:0002439 chronic inflammatory response to antigenic stimulus; GO:0006730 one-carbon metabolic process; GO:0007584 response to nutrient; GO:0008152 metabolic process; GO:0019510 S-adenosylhomocysteine catabolic process; GO:0042745 circadian sleep/wake cycle |
| Meprin 1 alpha | Mep1a | −1.502 | −1.200 | 0.037 | GO:0006508 proteolysis |
| Myosin IE | Myo1e | −1.516 | −1.229 | 0.004 | GO:0001570 vasculogenesis; GO:0001701 in utero embryonic development; GO:0001822 kidney development; GO:0006807 nitrogen compound metabolic process; GO:0030097 hemopoiesis; GO:0035166 post-embryonic hemopoiesis; GO:0048008 platelet-derived growth factor receptor signaling pathway |
| Lymphocyte antigen 6 complex, locus E | Ly6e | −1.541 | −1.316 | 0.001 | GO:0001701 in utero embryonic development; GO:0030325 adrenal gland development; GO:0035265 organ growth; GO:0042415 norepinephrine metabolic process; GO:0048242 epinephrine secretion; GO:0055010 ventricular cardiac muscle tissue morphogenesis |
| Aldehyde dehydrogenase 1 family, member A1 | Aldh1a1 | −1.553 | 1.170 | 0.023 | GO:0001822 kidney development; GO:0001889 liver development; GO:0002072 optic cup morphogenesis involved in camera-type eye development; GO:0006979 response to oxidative stress; GO:0007494 midgut development; GO:0014070 response to organic cyclic substance; GO:0032355 response to estradiol stimulus; GO:0032526 response to retinoic acid; GO:0042493 response to drug; GO:0042572 retinol metabolic process |
| Olfactory receptor 434 | Olr434 | −1.560 | −1.382 | 0.000 | GO:0007186 G-protein coupled receptor protein signaling pathway |
| Olfactory, receptor 1607 | Olr1607 | −1.578 | −1.370 | 0.043 | GO:0007186 G-protein coupled receptor protein signaling pathway; GO:0050911 detection of chemical stimulus involved in sensory perception of smell |
| Serine peptidase inhibitor, Kunitz type 1 | Spint1 | −1.611 | −1.093 | 0.011 | GO:0001763 morphogenesis of a branching structure; GO:0001892 embryonic placenta development; GO:0030198 extracellular matrix organization; GO:0060670 branching involved in embryonic placenta morphogenesis; GO:0060674 placenta blood vessel development |

TABLE 3-continued details all genes with differential expression between DSS and Control and DSS/HP and control in rats given
Dextran Sodium Sulphate in water with or without co-treatment with hypothetical protein (HP).

| Gene description | Gene symbol | Fold change DSS vs Control | Fold change DSS/HP vs Control | p-value | GO_biological_process (up to first 10) |
|---|---|---|---|---|---|
| D site of albumin promoter (albumin D-box) binding protein | Dbp | −1.647 | −1.918 | 0.000 | GO:0006355 regulation of transcription, DNA-dependent; GO:0042127 regulation of cell proliferation; GO:0048511 rhythmic process |
| Solute carrier family 5 (sodium-dependent vitamin transporter), member 6 | Slc5a6 | −1.650 | −1.222 | 0.021 | GO:0006811 ion transport; GO:0006814 sodium ion transport; GO:0015878 biotin transport; GO:0015887 pantothenate transmembrane transport; GO:0055085 transmembrane transport |
| Multiple inositol polyphosphate histidine phosphatase 1 | Minpp1 | −1.658 | −1.225 | 0.010 | GO:0048015 phosphoinositide-mediated signaling |
| Tsukushin | Tsku | −1.682 | 1.012 | 0.014 | |
| Solute carrier family 26, member 3 | Slc26a3 | −1.724 | −1.112 | 0.034 | GO:0006820 anion transport; GO:0008272 sulfate transport; GO:0055085 transmembrane transport |
| Cystathionase (cystathionine gamma-lyase) | Cth | −1.725 | −1.172 | 0.046 | GO:0006520 cellular amino acid metabolic process; GO:0006749 glutathione metabolic process; GO:0008285 negative regulation of cell proliferation; GO:0008652 cellular amino acid biosynthetic process; GO:0018272 protein-pyridoxal-5-phosphate linkage via peptidyl-N6-pyridoxal phosphate-L-lysine; GO:0019344 cysteine biosynthetic process; GO:0019346 transsulfuration // traceable author statement; GO:0030308 negative regulation of cell growth; GO:0050667 homocysteine metabolic process; GO:0051289 protein homotetramerization |
| Peripheral myelin protein 22 | Pmp22 | −1.955 | −1.443 | 0.042 | GO:0007049 cell cycle; GO:0007050 cell cycle arrest; GO:0008285 negative regulation of cell proliferation; GO:0030154 cell differentiation; GO:0032288 myelin assembly; GO:0042552 myelination |
| Hydroxysteroid 11-beta dehydrogenase 2 | Hsd11b2 | −2.002 | 1.001 | 0.041 | GO:0001666 response to hypoxia; GO:0002017 regulation of blood volume by renal aldosterone; GO:0006950 response to stress; GO:0007565 female pregnancy; GO:0008152 metabolic process; GO:0008211 glucocorticoid metabolic process; GO:0032094 response to food; GO:0032868 response to insulin stimulus; GO:0042493 response to drug; GO:0048545 response to steroid hormone stimulus |
| Hydroxysteroid (17-beta) dehydrogenase 2 | Hsd17b2 | −2.530 | −1.603 | 0.040 | GO:0006694 steroid biosynthetic process; GO:0032526 response to retinoic acid; GO:0055114 |
| Nuclear receptor subfamily 1, group D, member 1 \| thyroid hormone receptor alpha | Nr1d1\|Thra | −2.844 | −2.072 | 0.018 | GO:0006355 regulation of transcription, DNA-dependent; GO:0007623 circadian rhythm; GO:0001502 cartilage condensation; GO:0001503 ossification; GO:0001822 kidney development; GO:0001889 liver development; GO:0002155 regulation of thyroid hormone mediated signaling pathway; GO:0006950 response to stress; GO:0007420 brain development; GO:0007611 learning or memory |

REFERENCES

Kelly D, Campbell J I, King T P, Grant G, Jansson E A, Coutts A G, Pettersson S, Conway S. Commensal anaerobic gut bacteria attenuate inflammation by regulating nuclear-cytoplasmic shuttling of PPAR-gamma and RelA. Nat Immunol. 2004 January; 5(1):104-12.

Xu J, Bjursell M K, Himrod J, Deng S, Carmichael L K, Chiang H C, Hooper L V, Gordon J I. A genomic view of the human-*Bacteroides thetaiotaomicron* symbiosis. Science. 2003 Mar. 28; 299(5615):2074-6.

Wendler W M, Kremmer E, Förster R, Winnacker E L. Identification of pirin, a novel highly conserved nuclear protein. J Biol Chem. 1997 Mar. 28; 272(13):8482-9.

Berg, D. J., Davidson, N., Kuhn, R., Müller, W., Menon, S., Holland, G., Thompson-Snipes, L., Leach, M. W., Rennick, D. Enterocolitis and colon cancer in interleukin-10-deficient mice are associated with aberrant cytokine production and CD4+Th1-like responses (1996) Journal of Clinical Investigation, 98 (4), 1010-1020.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in biochemistry and molecular biology or related fields are intended to be within the scope of the following claims.

The invention claimed is:

1. A method of treating an inflammatory disorder or an autoimmune disorder in a mammalian subject comprising administering to said subject a pharmaceutical composition that comprises:

a pirin-related polypeptide of *Bacteroides thetaiotaomicron*, wherein said pirin-related polypeptide comprises an amino acid sequence having at least 95% identity to SEQ ID NO: 2, as determined by a sequence alignment performed using a Basic Local Alignment Search Tool algorithm with a gap open penalty of 0, a gap extension penalty of 0, and a Blocks Substitution Matrix of 62;

wherein said pirin-related polypeptide is functionally equivalent to SEQ ID NO: 2 and is present in an amount effective to reduce inflammation associated with said inflammatory disorder or said autoimmune disorder in said subject as compared to prior to said administering: and a pharmaceutically acceptable excipient, diluent or carrier.

2. The method of claim 1, wherein said pharmaceutical composition is a solid composition.

3. The method of claim 1, wherein said pharmaceutical composition is a liquid composition.

4. The method of claim 1, wherein said pirin-related polypeptide is encapsulated in a capsule.

5. The method of claim 4, wherein said capsule is an enterically resistant capsule for delivery to an intestine of said subject.

6. The method of claim 1, wherein said pirin-related polypeptide is Polypeptide Hypothetical Protein (HP).

7. The method of claim 1, wherein said pirin-related polypeptide comprises an amino acid sequence having at least 99% identity to SEQ ID NO: 2, as determined by said sequence alignment performed using said Basic Local Alignment Search Tool algorithm with said gap open penalty of 0, said gap extension penalty of 0, and said Blocks Substitution Matrix of 62.

8. The method of claim 1, wherein said pirin-related polypeptide comprises the amino acid sequence of SEQ ID NO: 2.

9. The method of claim 1, wherein said inflammatory disorder or said autoimmune disorder is selected from the group consisting of an inflammatory bowel disorder (IBD), colitis, rheumatoid arthritis, psoriasis, multiple sclerosis, type I diabetes, coeliac disease, atopic dermatitis, rhinitis, irritable bowel syndrome (IBS), pouchitis, functional dyspepsia, atopic diseases, necrotising enterocolitis, non-alcoholic fatty liver disease, gastrointestinal infection, Lupus, nephritis/glomerulonephritis, asthma, COPD, and myocarditis.

10. The method of claim 9, wherein said IBD is Crohn's disease or ulcerative colitis.

11. The method of claim 1, wherein said subject has colitis, and wherein said administering reduces the large intestine length or increases the small intestine length relative to a subject that has colitis and was not administered said pharmaceutical composition.

12. The method of claim 1, wherein said administering reduces the number of lactose fermenting bacteria or the number of non-lactose fermenting bacteria in an organ of said subject, relative to the number of said lactose fermenting bacteria or the number of said nonlactose fermenting bacteria prior to said administering.

13. The method of claim 12, wherein said organ is selected from the group consisting of a mesenteric lymph node, a liver, and a spleen.

14. The method of claim 1, wherein said administering reduces the level of at least one inflammatory marker, relative to the level of said at least one inflammatory marker prior to said administering.

15. The method of claim 14, wherein said at least one inflammatory marker is a marker of an NF-κβ pathway.

16. The method of claim 14, wherein said at least one inflammatory marker is Reg3 or RELMb.

17. The method of claim 8, wherein said administering decreases the level of a gene selected from the group consisting of Reg3b, Retnlg, Retnlb, sucrase-isomaltase glucosidase, and Defa24, relative to the level of said gene prior to said administering.

18. The method of claim 8, wherein said administering decreases the level of a gene selected from the group consisting of Hsdl1b2, Hsdl7b2, and Nr3c2, relative to the level of said gene prior to said administering.

19. The method of claim 1, wherein said administering is oral, parenteral, intramuscular, intraperitoneal, subcutaneous, intradermal, or intravenous.

* * * * *